US012780867B2

(12) United States Patent
Xu et al.

(10) Patent No.: US 12,780,867 B2
(45) Date of Patent: Nov. 3, 2026

(54) STEROL BASED IONIZABLE LIPIDS AND LIPID NANOPARTICLES COMPRISING THE SAME

(71) Applicants: Advanced RNA Vaccine (ARV) Technologies, Inc., North Bethesda, MD (US); SUZHOU VENCUBIO LTD., Suzhou (CN)

(72) Inventors: Jiangsheng Xu, Greenbelt, MD (US); Jiayi Zheng, Suzhou (CN); Ju Hyeong Jeon, Frederick, MD (US); Renhuan Xu, North Potomac, MD (US)

(73) Assignees: Advanced RNA Vaccine (ARV) Technologies, Inc.; SUZHOU VENCUBIO LTD., Suzhou (CN)

( * ) Notice: Subject to any disclaimer, the term of this patent is extended or adjusted under 35 U.S.C. 154(b) by 0 days.

(21) Appl. No.: 18/907,013

(22) Filed: Oct. 4, 2024

(65) Prior Publication Data

US 2025/0092083 A1 Mar. 20, 2025

Related U.S. Application Data

(63) Continuation of application No. PCT/US2023/029742, filed on Aug. 8, 2023.

(60) Provisional application No. 63/396,125, filed on Aug. 8, 2022.

(51) Int. Cl.
*C07J 7/00* (2006.01)

(52) U.S. Cl.
CPC .................................... *C07J 7/009* (2013.01)

(58) Field of Classification Search
CPC ...... C07J 7/009; C07J 43/003; C07J 41/0055; C12N 15/88
See application file for complete search history.

(56) References Cited

U.S. PATENT DOCUMENTS

2012/0027690 A1 2/2012 Lee et al.
2016/0090593 A1 3/2016 Sah et al.

FOREIGN PATENT DOCUMENTS

WO WO-2019232208 A1 * 12/2019 ............ A61K 38/45
WO 2021026358 A1 2/2021
WO 2021/174205 A1 9/2021
WO 2022/032154 A2 2/2022
WO 2022115645 A1 6/2022

OTHER PUBLICATIONS

Patel, S., Ashwanikumar, N., Robinson, E. et al. Naturally-occurring cholesterol analogues in lipid nanoparticles induce polymorphic shape and enhance intracellular delivery of mRNA. Nat Commun 11, 983 (2020). https://doi.org/10.1038/s41467-020-14527-2.
International Search Report and Written Opinion mailed Jan. 26, 2024, from International Application No. PCT/US2023/029742, 19 pages.
“Pubchem CID 58069296”, Create date: Aug. 19, 2012 (Aug. 19, 2012).
“Pubchem CID 139436903”, Create date: Nov. 2, 2019 (Nov. 2, 2019).
Extended European Search Report issued in Application No. 23853283.2, dated Jun. 29, 2026, 9 pages.

* cited by examiner

*Primary Examiner* — Rayna Rodriguez
(74) *Attorney, Agent, or Firm* — Meunier Carlin & Curfman LLC

(57) ABSTRACT

Described are compounds, compositions, and methods for delivery of therapeutic, diagnostic, or prophylactic agents (for example, a nucleic acid).

11 Claims, 21 Drawing Sheets

Target 1

Report

Signal ->: ELS1 A, ELSD Signal

| # | Meas. Ret. | Height | Width | Area | Area % |
|---|---|---|---|---|---|
| 1 | 3.971 | 217.967 | 0.087 | 1140.021 | 100.000 |

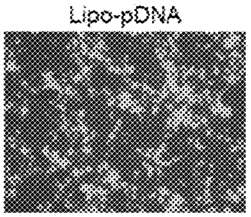
FIG. 9B FIG. 9C
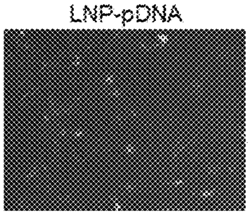
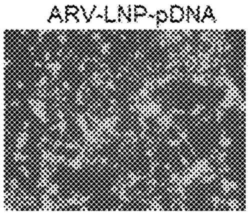
FIG. 9D FIG. 9E
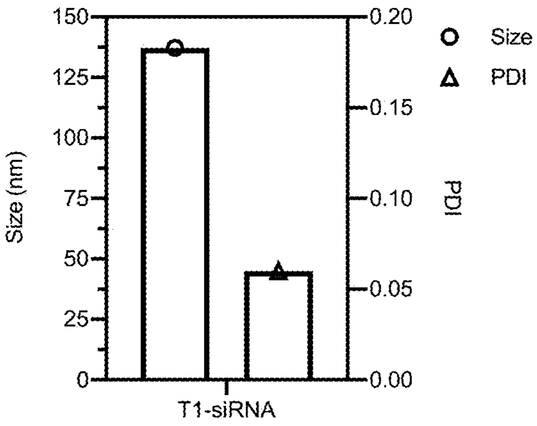
FIG. 10A
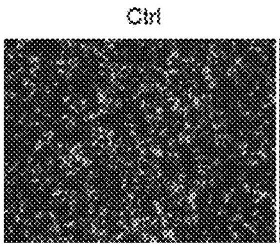
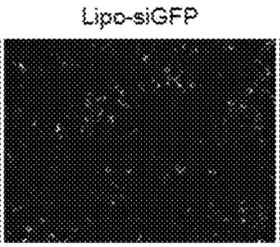
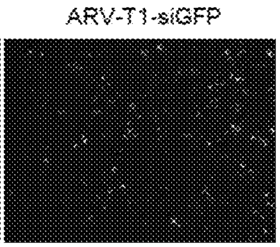
FIG. 10B FIG. 10C FIG. 10D Target 11

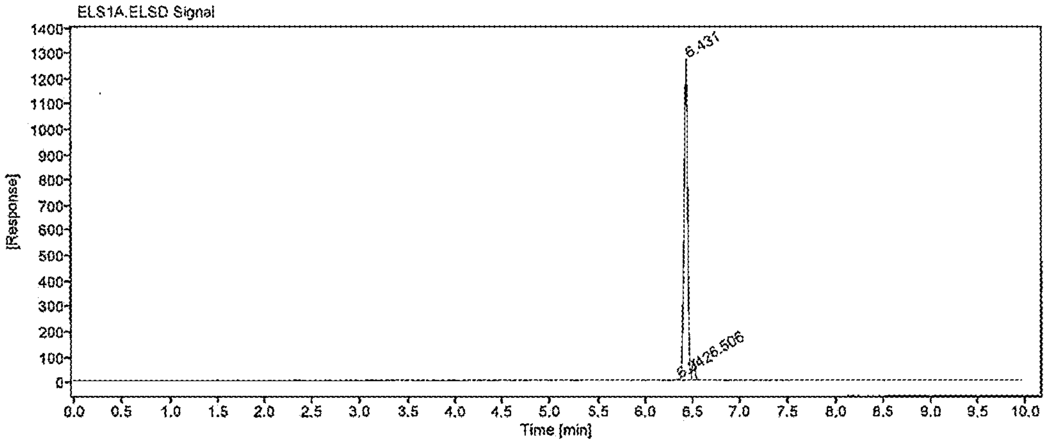
Signal: ELS1A,ELSD Signal
| RT [min] | Width [min] | Area | Height | Area% |
|---|---|---|---|---|
| 6.342 | 0.057 | 6.624 | 3.286 | 0.191 |
| 6.431 | 0.119 | 3299.043 | 1268.301 | 95.097 |
| 6.506 | 0.082 | 163.482 | 81.779 | 4.712 |
| | Sum | 3469.1495 | | |
FIG. 16C
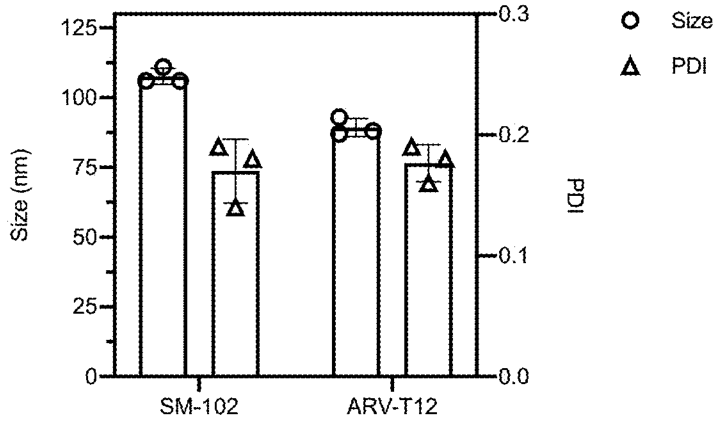
FIG. 17A
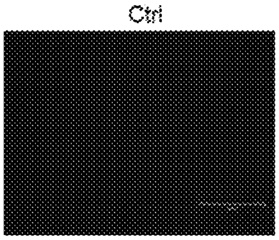
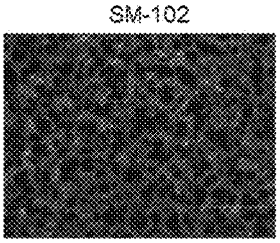
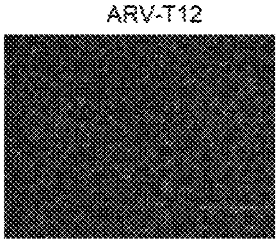
FIG. 17B FIG. 17C FIG. 17D Signal: ELS1A,ELSD Signal

| RT [min] | Width [min] | Area | Height | Area% |
|---|---|---|---|---|
| 3.796 | 0.191 | 456.851 | 179.583 | 100.000 |
| | Sum | 456.8513 | | |

STEROL BASED IONIZABLE LIPIDS AND LIPID NANOPARTICLES COMPRISING THE SAME

CROSS-REFERENCE TO RELATED APPLICATION

This application is a continuation of PCT/US2023/29742 filed Aug. 8, 2023, which claims priority to U.S. Provisional Application No. 63/396,125, filed on Aug. 8, 2022, the content of which is hereby incorporated in its entirety.

BACKGROUND

The effective targeted delivery of active agents such as diagnostic agents, small molecule drugs, proteins, and nucleic acids represents a continuing medical challenge. In particular, the delivery of nucleic acids to cells is made difficult by the relative instability and low cell permeability of such species.

Lipid-containing nanoparticle compositions, liposomes, and lipoplexes have proven effective as transport vehicles into cells and/or intracellular compartments for active agents.

Though a variety of such lipid-containing nanoparticle compositions have been demonstrated, improvements in safety, efficacy, and specificity are still lacking.

Thus, there is a need to develop methods and compositions to facilitate the delivery of therapeutic, diagnostics, and/or prophylactics such as nucleic acids to cells.

The compounds, compositions, and methods disclosed herein address these and other needs.

SUMMARY

The present disclosure provides compounds and uses thereof. Also provided are compositions including a compound of the invention and an agent. The present disclosure also provides methods of using the compositions for delivering an active agent to a subject.

In one aspect, described herein are compounds of Formula Y:

Formula Y

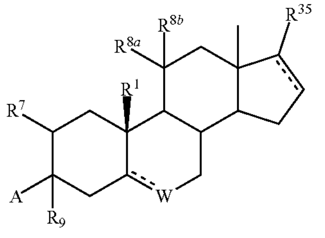

or pharmaceutically acceptable salts thereof, wherein:

$R^1$ is H or —$CH_3$;

 denotes carbon-carbon bond or carbon-carbon double bond;

$R^7$ is H or $OR^{16}$;

$R^{8a}$ and $R^{8b}$ are each independently, H or $OR^{16}$, or $R^{8a}$ and $R^{8b}$, together with the atom to which each is attached, combine to form a cycloalkyl, aryl, heterocycloalkyl, or heteroaryl;

$R^9$ is H, $C_1$-$C_6$ alkyl, $C_2$-$C_6$ alkenyl, or $C_2$-$C_6$ alkynyl;

W is $CR^{4a}$ or $CR^{4a}R^{4b}$, where if a double bond is present between W and the adjacent carbon, then W is $CR^{4a}$; and if a single bond is present between W and the adjacent carbon, then W is $CR^{4a}R^{4b}$; each of $R^{4a}$ and $R^{4b}$ is, independently, H, halogen, or $C_1$-$C_6$ alkyl;

A is

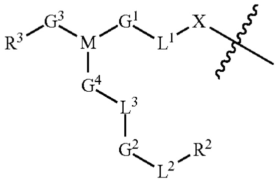

or

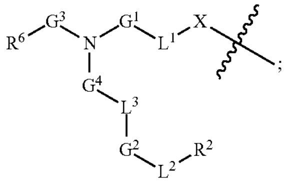

;

X is O or S;

$L^1$ is —O(C═O)—, —C(═O)—, —S(O)$_x$—, —C(═O)$R^a$C(═O)—, —N$R^a$C(═O)—, —NC(═O)$R^a$C(═O)—, or —C(═O)N$R^a$C(═O)—;

$L^2$ is —O(C═O)—, —(C═O)O—, —O(C═O)O—, —C(═O)—, —O—, —S(O)$_x$—, —S—S—, —N$R^a$C(═O)—, or —C(═O)$R^a$N—;

$L^3$ is absent, —O(C═O)—, —(C═O)O—, —O(C═O)O—, —C(═O)—, —O—, —N$R^a$C(═O)—, or —C(═O)$R^a$N—;

$R^a$ is

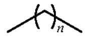

wherein n is an integer from 0 to 12;

x is 0, 1, or 2;

M is CH,

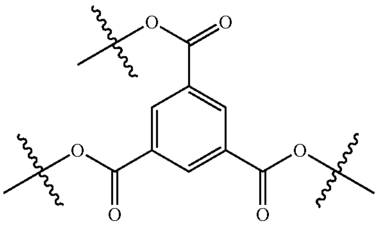

,

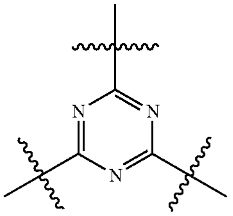

,

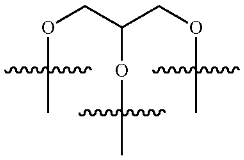

,

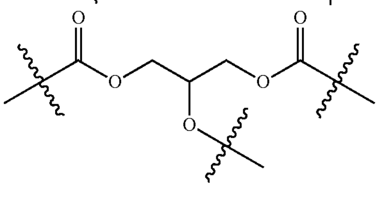

,

-continued

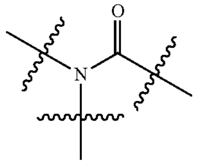,
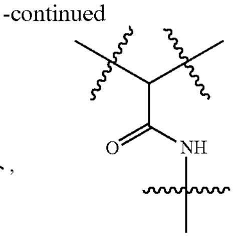, or
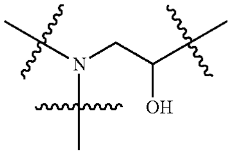;

$G^1$, $G^2$ and $G^3$ are each independently selected from $C_1$-$C_{12}$ alkyl or $C_1$-$C_{12}$ alkenyl;

$G^4$ is absent or selected from $C_1$-$C_{12}$ alkyl or $C_1$-$C_{12}$ alkenyl;

$R^2$ is —$CR^bR^c$, $C_6$-$C_{24}$ alkyl or $C_6$-$C_{24}$ alkenyl;

$R^3$ is

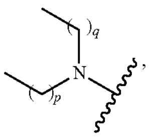,
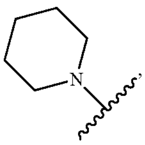,
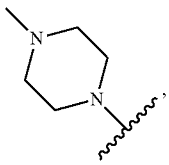,
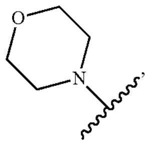,
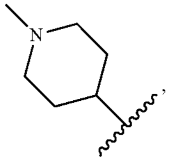,
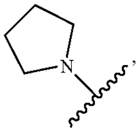, or
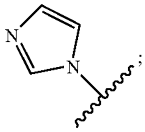;

$R^6$ is H, $OR^b$, CN, —C(═O)$OR^b$, —NC(═O)$R^b$, —C(═O)$NR^b$,

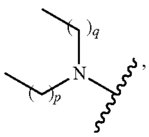,
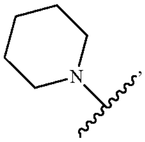,
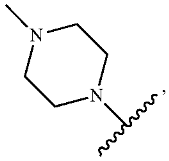,
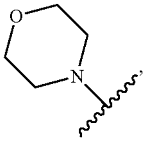,
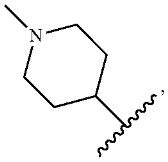,
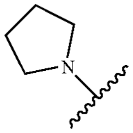, or
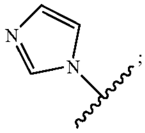;

$R^b$ and $R^c$ are independently H, $C_1$-$C_{12}$ alkyl or $C_1$-$C_{12}$ alkenyl;

p and q are independently 0, 1, 2, 3 or 4;

$R^{35}$ is

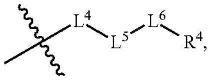,
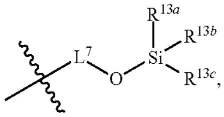,
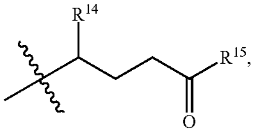,
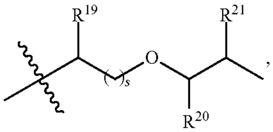,
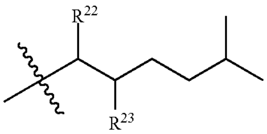,
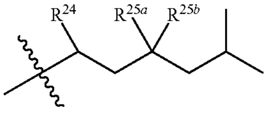,
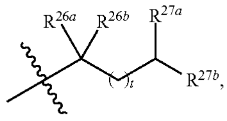,
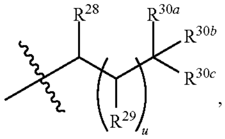,
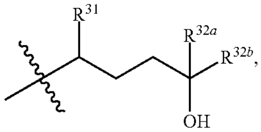,
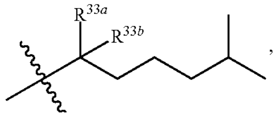,
or
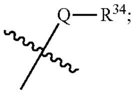;

$L^4$ is absent,

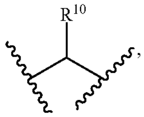, or
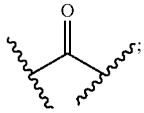;

$R^{10}$ is absent or $C_1$-$C_6$ alkyl;

$L^5$ is absent, or

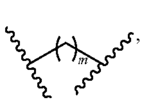, or
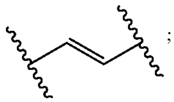;

m is an integer 1, 2, or 3;

$L^6$ is absent,

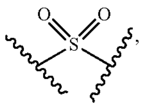, or
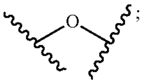;

$R^4$ is a $C_3$-$C_{10}$ alkyl, $C_3$-$C_{10}$ cycloalkyl, $C_3$-$C_{10}$ alkenyl, $C_3$-$C_{10}$ cycloalkenyl, $C_3$-$C_{10}$ alkynyl, $C_3$-$C_{10}$ aryl, $C_2$-$C_9$ heterocyclyl, or $C_2$-$C_9$ heteroaryl;

$L^7$ is $C_1$-$C_6$ alkylene;

$R^{13a}$, $R^{13b}$, and $R^{13c}$ are each independently $C_1$-$C_6$ alkyl or $C_6$-$C_{10}$ aryl;

$R^{14}$, $R^{16}$, $R^{19}$, $R^{21}$, $R^{22}$, $R^{24}$, $R^{28}$, $R^{29}$, and $R^{31}$ are each independently H or $C_1$-$C_6$ alkyl;

$R^{15}$ is —$OR^{16}$, —$NR^{17}R^{17}$, or

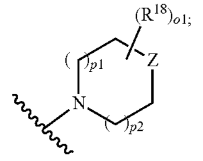

$R^{17}$ are each independently H, —$OR^{16}$, $C_6$-$C_{10}$ aryl, or $C_1$-$C_6$ alkyl;

$R^{18}$ are each independently halogen or $C_1$-$C_6$ alkyl;

o1 is an integer from 0 to 8;

p1 and p2 are each independently an integer from 0 to 2;

Z is $CH_2$, O, S, or $NR^{16}$;

s and t are each independently 0 or 1;

$R^{23}$ is halo, hydroxyl, $C_1$-$C_6$ alkyl, or $C_1$-$C_6$ heteroalkyl;

$R^{20}$, $R^{25a}$ and $R^{25b}$, $R^{30a}$, $R^{30b}$, $R^{30c}$, $R^{32a}$, $R^{32b}$, and $R^{34}$ are each independently $C_1$-$C_6$ alkyl;

$R^{26a}$ and $R^{26b}$ are each independently H, $C_1$-$C_6$ alkyl, or $R^{26a}$ and $R^{26b}$, together with the atom to which each is attached combine to form

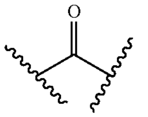

or

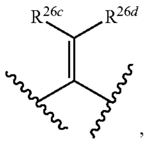

, were $R^{26c}$ and $R^{26d}$ are each independently H or substituted $C_1$-$C_6$ alkyl;

$R^{27a}$ and $R^{26b}$ are each independently H, hydroxyl, or $C_1$-$C_6$ alkyl;

u is 1, 2, or 3;

$R^{33a}$ and $R^{33b}$ are each independently $C_1$-$C_6$ alkyl, $C_1$-$C_6$ heteroalkyl, halogen, or hydroxyl;

Q is O, S, or $NR^{16}$; and or a pharmaceutically acceptable salt thereof.

In some embodiments, provided herein are methods for the delivery of agents (e.g., polynucleotides). In some embodiments, provided herein are methods for diagnosing, treating, or preventing diseases. In some embodiments, provided herein are methods for inducing an immune response against infection agents. In some embodiments, provided herein are methods for treating a cancer. In some embodiments, provided herein are methods to regulate the immune system for treating cancers and other immune disorders.

BRIEF DESCRIPTION OF THE DRAWINGS

The accompanying figures, which are incorporated in and constitute a part of this specification, illustrate several aspects described below.

FIGS. 9A-9E show in vitro delivery of GFP plasmid DNA using ARV-T1 LNP into 293T cells. (9A) is a graph showing the size and PDI characterization of GFP pDNA lipid nanoparticles (LNPs). (9B-9E) are images of in vivo transfection efficiency of GFP-expressing pDNA (500 ng DNA and 48 hours incubation). (9B) 293T only, (9C) Lipo-pDNA, (9D) LNP-pDNA, (9E) ARV-LNP-pDNA. LNP-pDNA is formulated using traditional formulation ratio of lipids, and ARV-LNP-pDNA is formulated using Target 1 lipid supplement with DOTAP.

FIGS. 10A-10F show in vitro delivery of small-size RNA (siRNA) and large-size RNA (saRNA), respectively, using ARV-T1 LNP into 293T cells. (10A) is a graph showing the size and PDI characterization of GFP siRNA lipid nanoparticles (LNPs). T1-siRNA is formulated using the same formulation as of mRNA. (10B-10D) are images of in vivo delivery of GFP siRNA (siGFP) using ARV-T1 LNP to inhibit the GFP expression (10B) control, (1° C.) Lipo-siGFP, and (10D) ARV-T1-siGFP. (10E-10F) are images of in vitro delivery of GFP self-amplifying RNA (saRNA) using ARV-T1 LNP, formulation of C12-200 used as control (10E) C12-200-saRNA and (10F) ARV-T1-saRNA.

FIGS. 16A-16C show $^1$H NMR spectra (16A), mass spectra (16B), and HPLC spectra (16C) for compound Target 12.

FIGS. 17A-17E show formulation of mRNA-LNP using ARV-T12 lipid and in vitro transfection efficiency of 1 μg GFP mRNA (1 μg/mL) using ARV-T12 LNP deliver into 293T cells after 24 hours. (17A) is a graph of size and PDI characterization of GFP mRNA ARV-T12 LNPs. (17B-17D) are representative fluorescent images of 293T cells after transfection (17B) control, (17C) SM-102, and (17D) ARV-T12. (17E) is a graph of the transfection efficacy analysis of GFP expression using flow cytometer.

DETAILED DESCRIPTION

Figure 1:
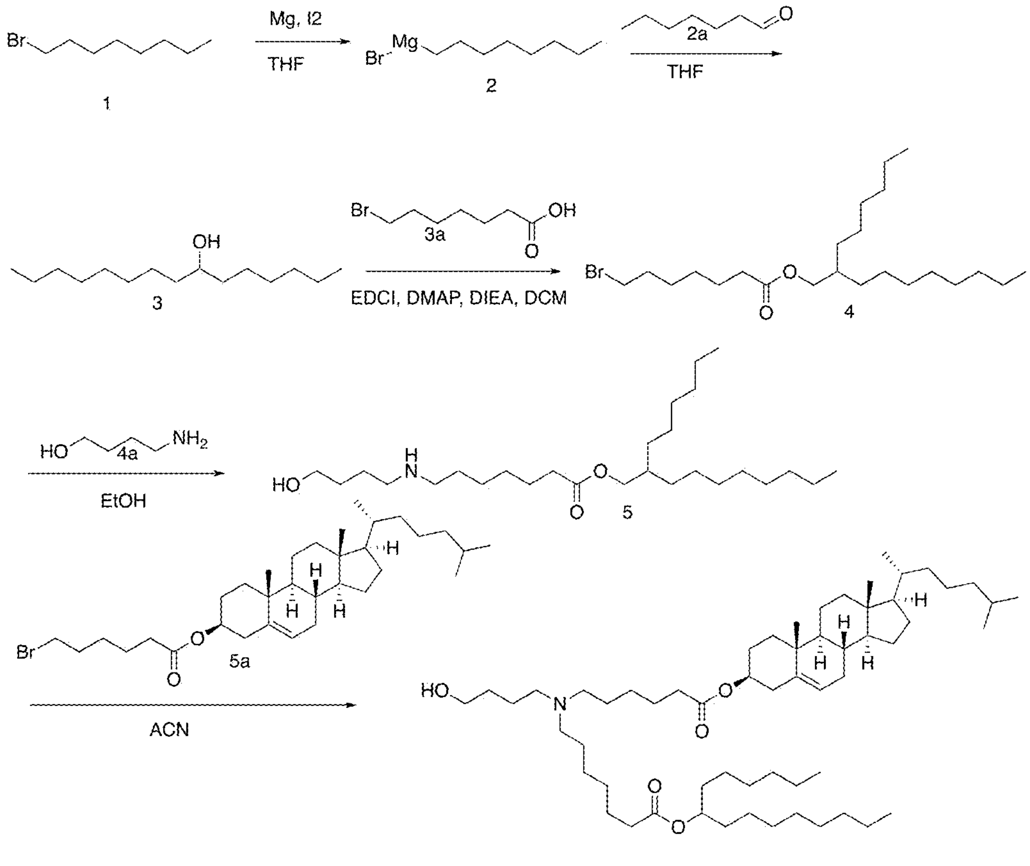
FIG. 1 illustrates a synthetic route for compound Target 1.

The present disclosure provides new compounds, nanomaterials, and uses thereof. Also provided are compositions including a compound of the invention and an agent. The present disclosure also provides methods using the compositions for delivering an agent to a subject. These nanomaterials are used in applications such as gene therapy and drug delivery.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Definitions

General Definitions

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. Other than where noted, all numbers expressing quantities of ingredients, reaction conditions, geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Accordingly, these terms are intended to not only cover the recited element(s) or step(s), but may also include other elements or steps not expressly recited. Furthermore, as used herein, the use of the terms "a", "an", and "the" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. A range may be construed to include the start and the end of the range. For example, a range of 10% to 20% (i.e., range of 10%-20%) can includes 10% and also includes 20%, and includes percentages in between 10% and 20%, unless explicitly stated otherwise herein.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein.

"Administration" to a subject includes any route of introducing or delivering to a subject an agent. Administration can be carried out by any suitable route, including oral, topical, transcutaneous, transdermal, intra-joint, intra-arteriole, intradermal, intraventricular, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

As used herein, the term "controlled-release" or "controlled-release drug delivery" or "extended release" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the term "therapeutic agent" is used, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Inactivate", "inactivating" and "inactivation" means to decrease or eliminate an activity, response, condition, disease, or other biological parameter due to a chemical (covalent bond formation) between the ligand and a its biological target.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented.

Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms. As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount". However, an appropriate "effective' amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)n\text{-}COOH$ where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

A "control" is an alternative subject or sample used in an experiment for comparison purposes. A control can be "positive" or "negative."

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, goats, sheep, pigs, dogs, cats, etc.), and birds (e.g., chickens, turkeys, songbirds, etc.). "Subject" can also include a mammal, such as a primate or a human. Thus, the subject can be a human or veterinary patient. The term "patient" refers to a subject under the treatment of a clinician, e.g., physician. Administration of the therapeutic agents can be carried out at dosages and for periods of time effective for treatment of a subject. In some embodiments, the subject is a human.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.,* 22:1859-1862 (1981), or by the triester method according to Matteucci, et al., *J. Am. Chem. Soc.,* 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6, H1, and T7 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, beta-globin promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It is appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

A nucleic acid sequence is "heterologous" to a second nucleic acid sequence if it originates from a foreign species, or, if from the same species, is modified by human action from its original form. For example, a heterologous promoter (or heterologous 5' untranslated region (5'UTR)) operably linked to a coding sequence refers to a coding sequence from a species different from that from which the promoter was derived, or, if from the same species, a coding sequence which is different from naturally occurring allelic variants (for example, the 5'UTR or 3'UTR from a different gene is operably linked to a nucleic acid encoding for a co-stimulatory molecule).

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or antigen binding fragment thereof" or "antibody or fragments thereof" encompasses chimeric antibodies and hybrid antibodies, with dual or multiple antigen or epitope specificities, and fragments, such as F(ab')2, Fab', Fab, Fv, sFv, scFv and the like, including hybrid fragments. Thus, fragments of the antibodies that retain the ability to bind their specific antigens are provided. For example, fragments of antibodies which maintain binding activity are included within the meaning of the term "antibody or antigen binding fragment thereof" Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual.* Cold Spring Harbor Publications, New York, (1988)).

Also included within the meaning of "antibody or antigen binding fragment thereof" are conjugates of antibody fragments and antigen binding proteins (single chain antibodies). Also included within the meaning of "antibody or antigen binding fragment thereof" are immunoglobulin single variable domains, such as for example a nanobody.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as $—OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C{=}C(Z^3Z^4)$ are intended to include both the E and Z isomers. This can be presumed in structural formulae herein wherein an asymmetric alkene is present, or it can be explicitly indicated by the bond symbol $C{=}C$. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C═O.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O.

The term "ester" as used herein is represented by the formula —$OC(O)Z^1$ or —$C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula OH.

The term "nitro" as used herein is represented by the formula —$NO_2$.

The term "silyl" as used herein is represented by the formula —$SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "phosphonyl" is used herein to refer to the phospho-oxo group represented by the formula —$P(O)(OZ^1)_2$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"$R^1$," "$R^2$," "$R^3$," "$R^a$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxyl group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As used herein, "ionizable lipid" refers to a lipid with a group or atom that can be charged (ionized) dependent upon the pH of the environment. Typically, the charge of a primary, secondary and tertiary amines is dependent upon the pH of the system. At low pH levels, these amines tend to be strongly cationic. At high pH levels these amines do not ionize.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Described herein are compounds of Formula Y:

Formula Y

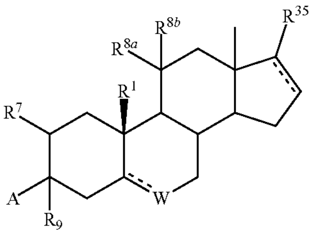

or pharmaceutically acceptable salts thereof, wherein:

$R^1$ is H or —$CH_3$;

 denotes carbon-carbon bond or carbon-carbon double bond;

$R^7$ is H or $OR^{16}$;

$R^{8a}$ and $R^{8b}$ are each independently, H or $OR^{16}$, or $R^{8a}$ and $R^{8b}$, together with the atom to which each is attached, combine to form a cycloalkyl, aryl, heterocycloalkyl, or heteroaryl;

$R^9$ is H, $C_1$-$C_6$ alkyl, $C_2$-$C_6$ alkenyl, or $C_2$-$C_6$ alkynyl;

W is $CR^{4a}$ or $CR^{4a}R^{4b}$, where if a double bond is present between W and the adjacent carbon, then W is $CR^{4a}$; and if a single bond is present between W and the adjacent carbon, then W is $CR^{4a}R^{4b}$; each of $R^{4a}$ and $R^{4b}$ is, independently, H, halogen, or $C_1$-$C_6$ alkyl;

A is

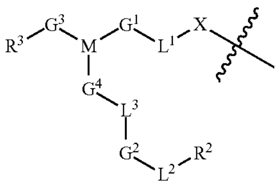

or

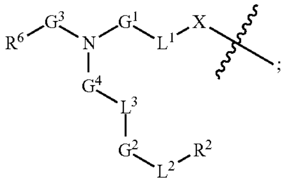

;

X is O or S;

$L^1$ is —O(C═O)—, —C(═O)—, —$S(O)_x$—, —C(═O)$R^a$C(═O)—, —$NR^a$C(═O)—, —NC(═O)$R^a$C(═O)—, or —C(═O)$NR^a$C(═O)—;

$L^2$ is —O(C═O)—, —(C═O)O—, —O(C═O)O—, —C(═O)—, —O—, —$S(O)_x$—, —S—S—, —$NR^a$C(═O)—, or —C(═O)$R^a$N—;

$L^3$ is absent, —O(C═O)—, —(C═O)O—, —O(C═O)O—, —C(═O)—, —O—, —$NR^a$C(═O)—, or —C(═O)$R^a$N—;

$R^a$ is

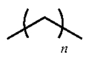

wherein n is an integer from 0 to 12;

x is 0, 1, or 2;

M is CH,

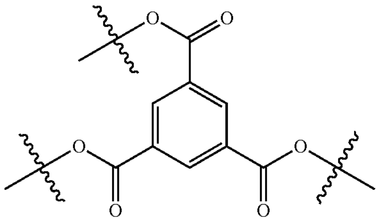

,

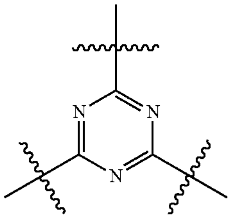

,

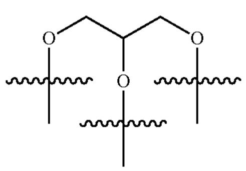

,

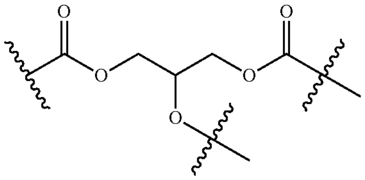

,

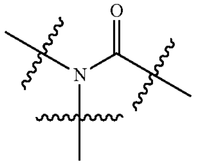

,

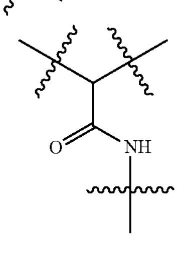

, or

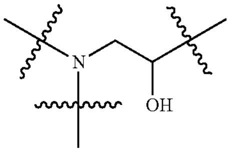

;

$G^1$, $G^2$ and $G^3$ are each independently selected from $C_1$-$C_{12}$ alkyl or $C_1$-$C_{12}$ alkenyl;

$G^4$ is absent or selected from $C_1$-$C_{12}$ alkyl or $C_1$-$C_{12}$ alkenyl;

$R^2$ is —$CR^bR^c$, $C_6$-$C_{24}$ alkyl or $C_6$-$C_{24}$ alkenyl;

$R^3$ is

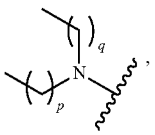,
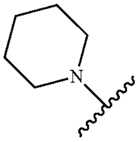,
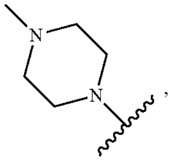,
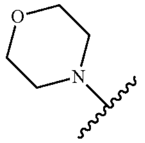,
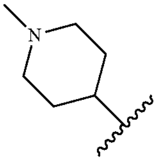,
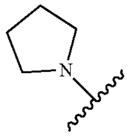, or
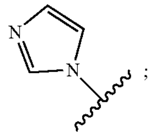;

$R^6$ is H, $OR^b$, CN, —C(═O)$OR^b$, —NC(═O)$R^b$, —C(═O)$NR^b$,

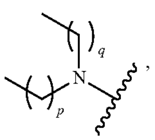,
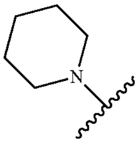,
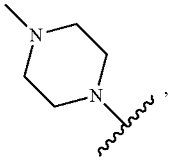,
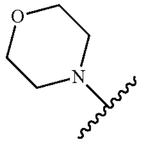,
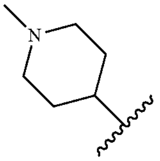,
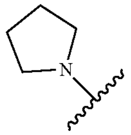, or
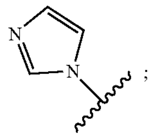;

$R^b$ and $R^c$ are independently H, $C_1$-$C_{12}$ alkyl or $C_1$-$C_{12}$ alkenyl;

p and q independently 0, 1, 2, 3 or 4;

$R^{35}$ is

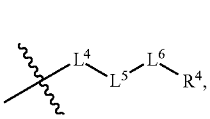
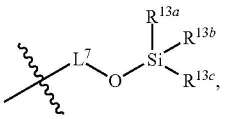
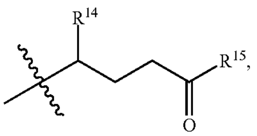
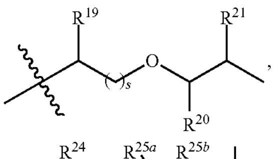
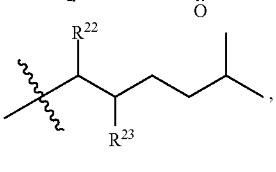
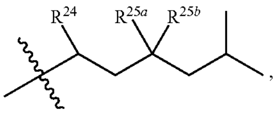

-continued

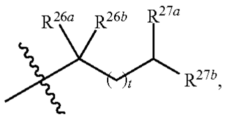
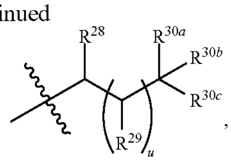
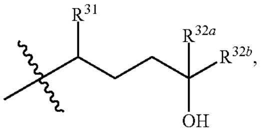
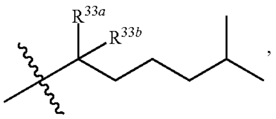
or
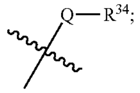

$L^4$ is absent,

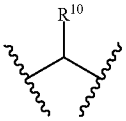, or
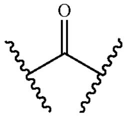;

$R^{10}$ is absent or $C_1$-$C_6$ alkyl;

$L^6$ is absent, or

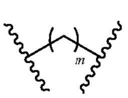, or
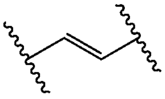;

m is an integer 1, 2, or 3;

$L^6$ is absent,

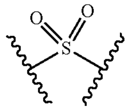, or
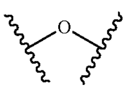;

$R^4$ is a $C_3$-$C_{10}$ alkyl, $C_3$-$C_{10}$ cycloalkyl, $C_3$-$C_{10}$ alkenyl, $C_3$-$C_{10}$ cycloalkenyl, $C_3$-$C_{10}$ alkynyl, $C_3$-$C_{10}$ aryl, $C_2$-$C_9$ heterocyclyl, or $C_2$-$C_9$ heteroaryl;

$L^7$ is $C_1$-$C_6$ alkylene;

$R^{13a}$, $R^{13b}$, and $R^{13c}$ are each independently $C_1$-$C_6$ alkyl or $C_6$-$C_{10}$ aryl;

$R^{14}$, $R^{16}$, $R^{19}$, $R^{21}$, $R^{22}$, $R^{24}$, $R^{28}$, $R^{29}$, and $R^{31}$ are each independently H or $C_1$-$C_6$ alkyl;

$R^{15}$ is —$OR^{16}$, —$NR^{17}R^{17}$, or

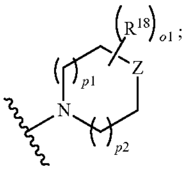;

$R^{17}$ are each independently H, —$OR^{16}$, $C_6$-$C_{10}$ aryl, or $C_1$-$C_6$ alkyl;

$R^{18}$ are each independently halogen or $C_1$-$C_6$ alkyl;

o1 is an integer from 0 to 8;

p1 and p2 are each independently an integer from 0 to 2;

Z is $CH_2$, O, S, or $NR^{16}$;

s and t are each independently 0 or 1;

$R^{23}$ is halo, hydroxyl, $C_1$-$C_6$ alkyl, or $C_1$-$C_6$ heteroalkyl;

$R^{20}$, $R^{25a}$ and $R^{25b}$, $R^{30a}$, $R^{30b}$, $R^{30c}$, $R^{32a}$, $R^{32b}$, and $R^{34}$ are each independently $C_1$-$C_6$ alkyl;

$R^{26a}$ and $R^{26b}$ are each independently H, $C_1$-$C_6$ alkyl, or $R^{26a}$ and $R^{26b}$, together with the atom to which each is attached combine to form

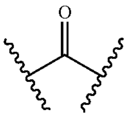
or
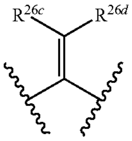
, were $R^{26c}$ and $R^{26d}$ are each independently H or substituted $C_1$-$C_6$ alkyl;

$R^{27a}$ and $R^{26b}$ are each independently H, hydroxyl, or $C_1$-$C_6$ alkyl;

u is 1, 2, or 3;

$R^{33a}$ and $R^{33b}$ are each independently $C_1$-$C_6$ alkyl, $C_1$-$C_6$ heteroalkyl, halogen, or hydroxyl;

Q is O, S, or $NR^{16}$; and or a pharmaceutically acceptable salt thereof.

In some embodiments, $R^{35}$ is

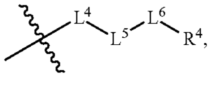

wherein $L^4$ is absent,

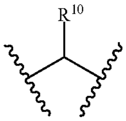
, or
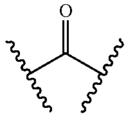
;

$R^{10}$ is absent or $C_1$-$C_6$ alkyl;

$L^5$ is absent, or

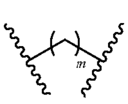
, or
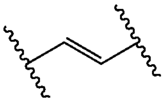
;

m is an integer 1, 2, or 3;

$L^6$ is absent,

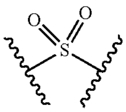
, or
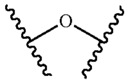
;

and $R^4$ is a $C_3$-$C_{10}$ alkyl, $C_3$-$C_{10}$ cycloalkyl, $C_3$-$C_{10}$ alkenyl, $C_3$-$C_{10}$ cycloalkenyl, $C_3$-$C_{10}$ alkynyl, $C_3$-$C_{10}$ aryl, $C_2$-$C_9$ heterocyclyl, or $C_2$-$C_9$ heteroaryl;

or a pharmaceutically acceptable salt thereof.

In one aspect, disclosed herein is a compound of Formula I:

Formula I

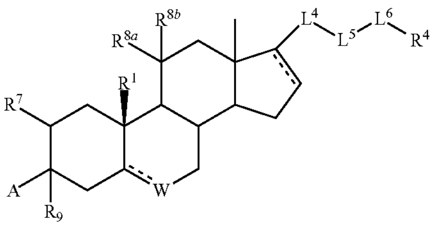

or pharmaceutically acceptable salts thereof, wherein:

$R^1$ is H or —$CH_3$;

denotes carbon-carbon bond or carbon-carbon double bond;

$L^4$ is absent

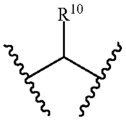
, or
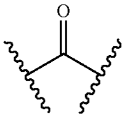
;

$R^{10}$ is absent or $C_1$-$C_6$ alkyl;

$L^5$ is absent, or

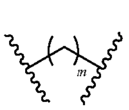
, or
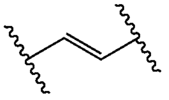
;

m is an integer 1, 2, or 3;

$L^6$ is absent,

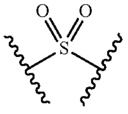
, or
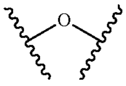
;

$R^4$ is a $C_3$-$C_{10}$ alkyl, $C_3$-$C_{10}$ cycloalkyl, $C_3$-$C_{10}$ alkenyl, $C_3$-$C_{10}$ cycloalkenyl, $C_3$-$C_{10}$ alkynyl, $C_3$-$C_{10}$ aryl, $C_2$-$C_9$ heterocyclyl, $C_2$-$C_9$ heteroaryl;

$R^7$ is H or $OR^{16}$;

$R^{8a}$ and $R^{8b}$ are each independently, H or $OR^{16}$, or $R^{8a}$ and $R^{8b}$, together with the atom to which each is attached, combine to form a cycloalkyl, aryl, heterocycloalkyl, or heteroaryl;

$R^{16}$ is H or $C_1$-$C_6$ alkyl;

$R^9$ is H, $C_1$-$C_6$ alkyl, $C_2$-$C_6$ alkenyl, or $C_2$-$C_6$ alkynyl;

W is $CR^{4a}$ or $CR^{4a}R^{4b}$, where if a double bond is present between W and the adjacent carbon, then W is $CR^{4a}$; and if a single bond is present between W and the adjacent carbon, then W is $CR^{4a}R^{4b}$; each of $R^{4a}$ and $R^{4b}$ is, independently, H, halogen, or $C_1$-$C_6$ alkyl;

A is

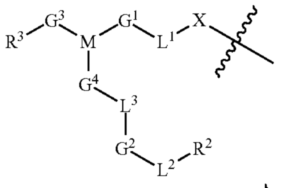

or

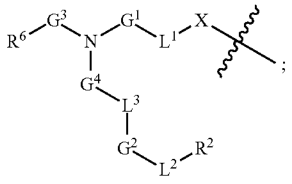

;

X is O or S;

$L^1$ is —O(C═O)—, —C(═O)—, —S(O)$_x$—, —C(═O)$R^a$C(═O)—, —N$R^a$C(═O)—, —NC(═O)$R^a$C(═O)—, or —C(═O)N$R^a$C(═O)—;

$L^2$ is —O(C═O)—, —(C═O)O—, —O(C═O)O—, —C(═O)—, —O—, —S(O)$_x$—, —S—S—, —N$R^a$C(═O)—, or —C(═O)$R^a$N—;

$L^3$ is absent, —O(C═O)—, —(C═O)O—, —O(C═O)O—, —C(═O)—, —O—, —N$R^a$C(═O)—, or —C(═O)$R^a$N—;

$R^a$ is

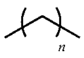

wherein n is an integer from 0 to 12;

x is 0, 1, or 2;

M is CH,

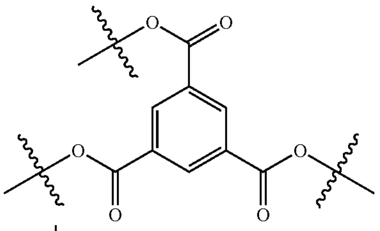

,

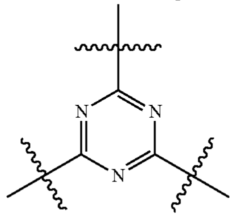

,

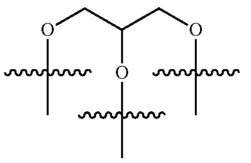

,

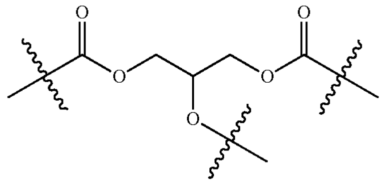

,

-continued

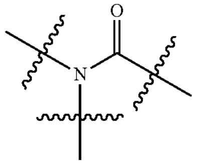

,

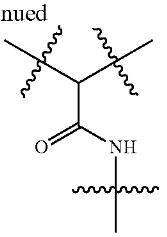

, or

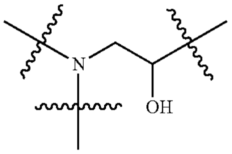

;

$G^1$, $G^2$ and $G^3$ are each independently selected from $C_1$-$C_{12}$ alkyl or $C_1$-$C_{12}$ alkenyl;

$G^4$ is absent or selected from $C_1$-$C_{12}$ alkyl or $C_1$-$C_{12}$ alkenyl;

$R^2$ is —C$R^bR^c$, $C_6$-$C_{24}$ alkyl or $C_6$-$C_{24}$ alkenyl;

$R^3$ is

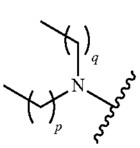

,

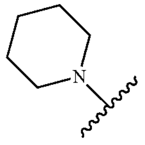

,

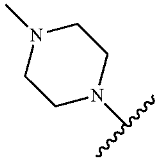

,

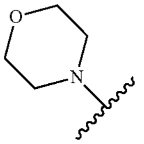

,

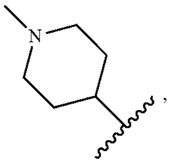

,

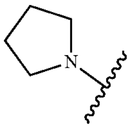

, or

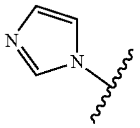

;

$R^6$ is H, O$R^b$, CN, —C(═O)O$R^b$, —NC(═O)$R^b$, —C(═O)N$R^b$,

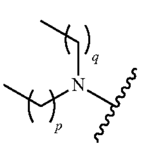

,

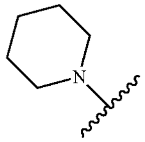

,

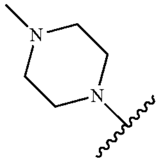

,

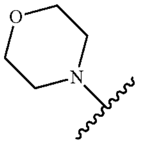

,

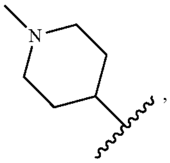

,

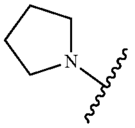

, or

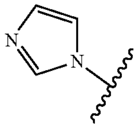

;

$R^b$ and $R^c$ are independently H, $C_1$-$C_{12}$ alkyl or $C_1$-$C_{12}$ alkenyl; and p and q are independently 0, 1, 2, 3 or 4;

or a pharmaceutically acceptable salt thereof.

In some embodiments, described herein are compounds of Formula Ia:

Formula Ia

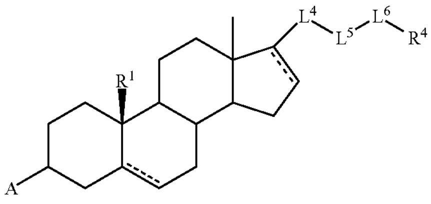

or pharmaceutically acceptable salts thereof, wherein:

$R^1$ is H or —$CH_3$;

⋱ denotes carbon-carbon bond or carbon-carbon double bond;

$L^4$ is absent,

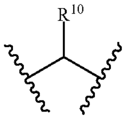 , or 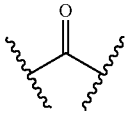 ;

$L^5$ is absent, or

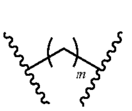 , or 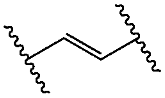 ;

wherein m is an integer 1, 2, or 3;

$L^6$ is absent,

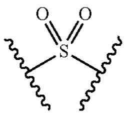 , or 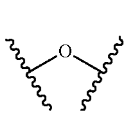 ;

$R^4$ is a $C_3$-$C_{10}$ alkyl, $C_3$-$C_{10}$ cycloalkyl, $C_3$-$C_{10}$ alkenyl, $C_3$-$C_{10}$ cycloalkenyl, $C_3$-$C_{10}$ alkynyl, $C_3$-$C_{10}$ aryl, $C_2$-$C_9$ heterocyclyl, $C_2$-$C_9$ heteroaryl;

$R^{10}$ is absent or $C_1$-$C_6$ alkyl;

A is

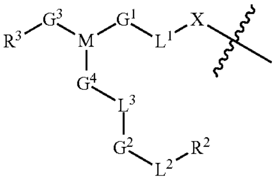 or

-continued

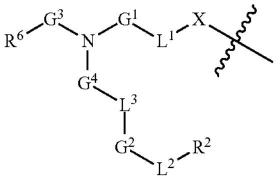 ;

X is O or S;

$L^1$ is —O(C═O)—, —C(═O)—, —S(O)$_x$—, —C(═O)$R^a$C(═O)—, —$NR^a$C(═O)—, —NC(═O)$R^a$C(═O)—, or —C(═O)$NR^a$C(═O)—;

$L^2$ is —O(C═O)—, —(C═O)O—, —O(C═O)O—, —C(═O)—, —O—, —S(O)$_x$—, —S—S—, —$NR^a$C(═O)—, or —C(═O)$R^a$N—;

$L^3$ is absent, —O(C═O)—, —(C═O)O—, —O(C═O)O—, —C(═O)—, —O—, —$NR^a$C(═O)—, or —C(═O)$R^a$N—;

$R^a$ is

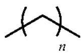

wherein n is an integer from 0 to 12;

x is 0, 1, or 2;

M is CH,

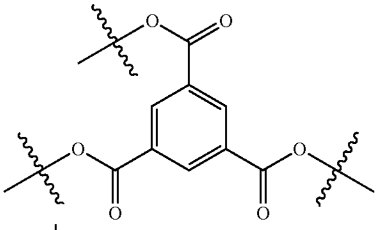 ,

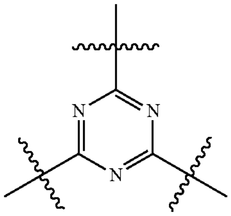 , 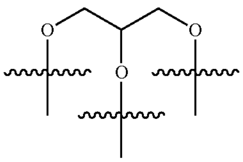 ,

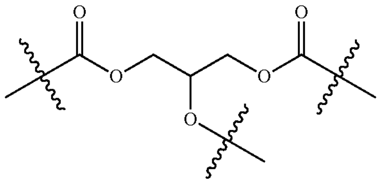 ,

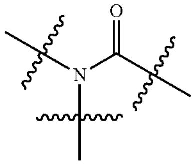 , 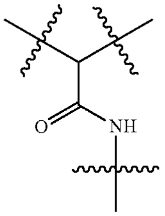 , or

-continued

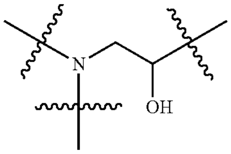 ;

$G^1$, $G^2$ and $G^3$ are each independently selected from $C_1$-$C_{12}$ alkyl or $C_1$-$C_{12}$ alkenyl;

$G^4$ is absent or selected from $C_1$-$C_{12}$ alkyl or $C_1$-$C_{12}$ alkenyl;

$R^2$ is —$CR^bR^c$, $C_6$-$C_{24}$ alkyl or $C_6$-$C_{24}$ alkenyl;

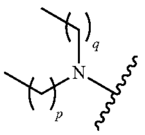 , 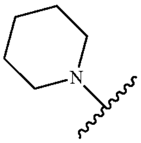 , 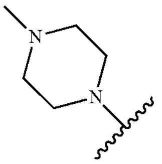 ,

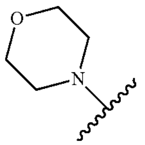 , 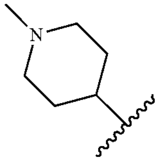 ,

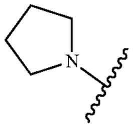 , or 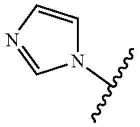 ;

$R^6$ is H, $OR^b$, CN, —C(=O)$OR^b$, —NC(=O)$R^b$, —C(=O)$NR^b$,

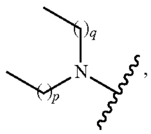 , 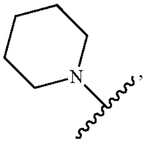 , 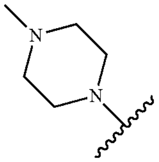 ,

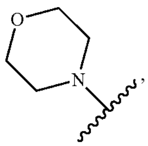 , 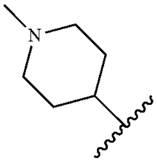 ,

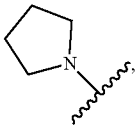 , or 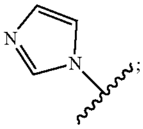 ;

$R^b$ and $R^c$ are independently H, $C_1$-$C_{12}$ alkyl or $C_1$-$C_{12}$ alkenyl; and p and q are independently 0, 1, 2, 3 or 4;

or a pharmaceutically acceptable salt thereof.

In some embodiments, compounds of Formula Y can be:

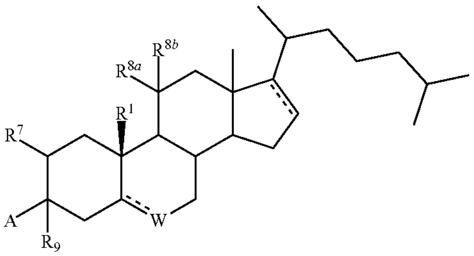 ,

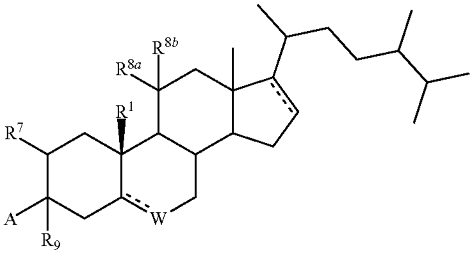 ,

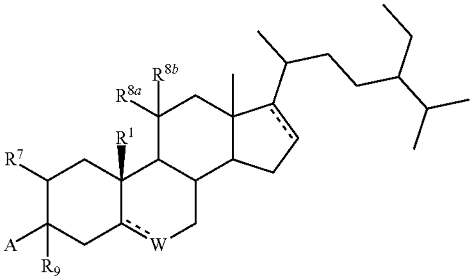 ,

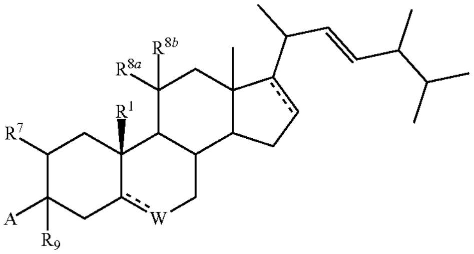 ,

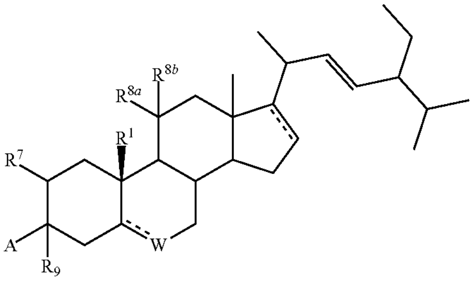 ,

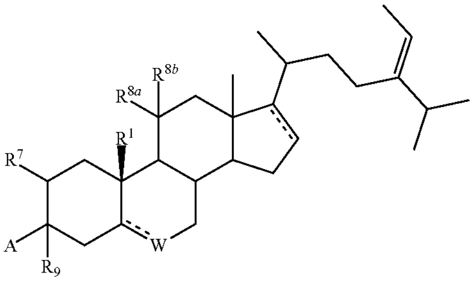 ,

-continued
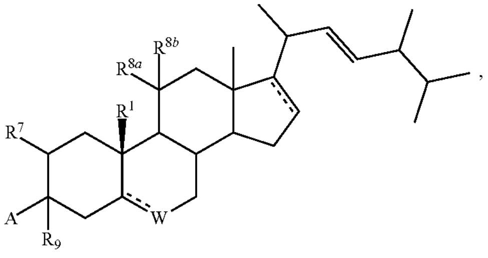
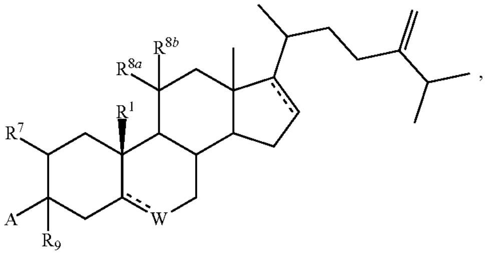
or a pharmaceutically acceptable salt thereof;
wherein A, $R^1$, $R^7$, $R^{8a}$, $R^{8b}$, $R^9$, W, are the same as for Formula Y.
In some embodiments, the compounds of Formula Y can be:
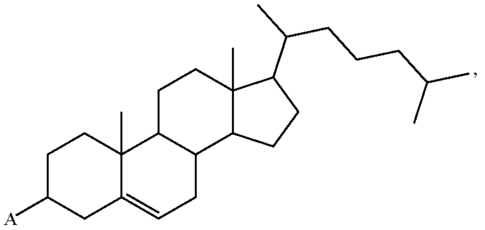
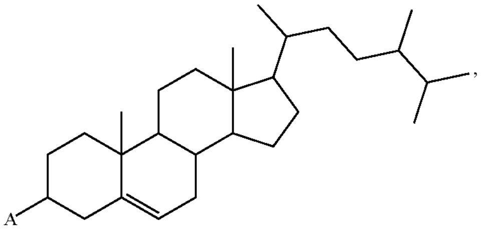
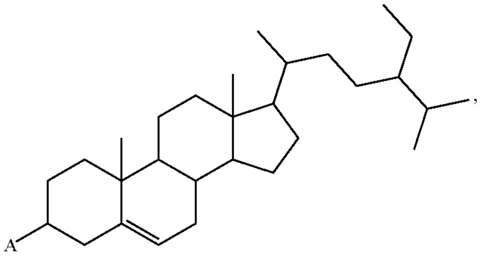
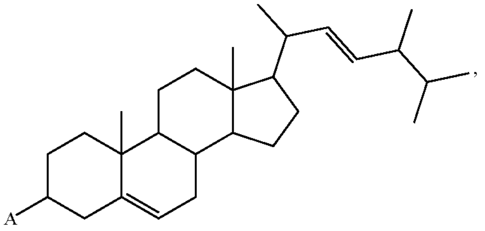
-continued
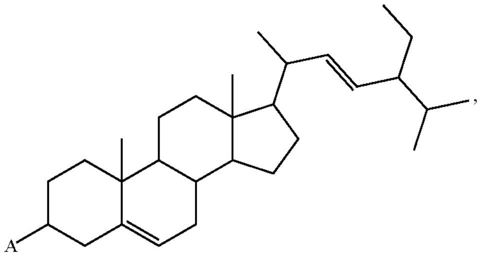
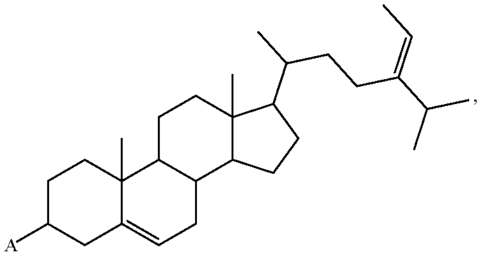
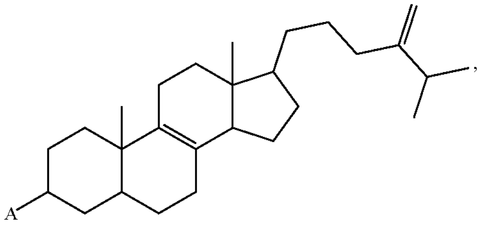
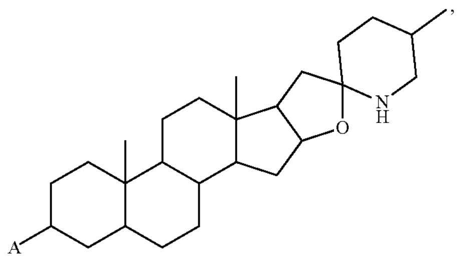
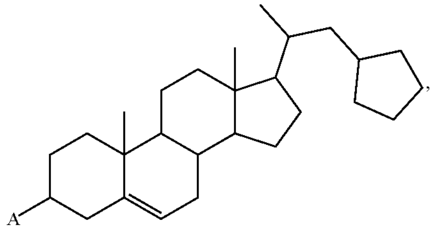
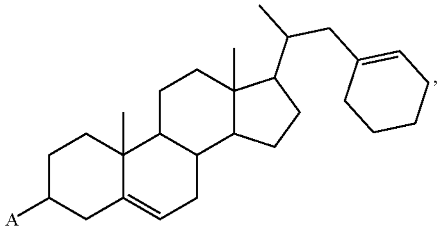
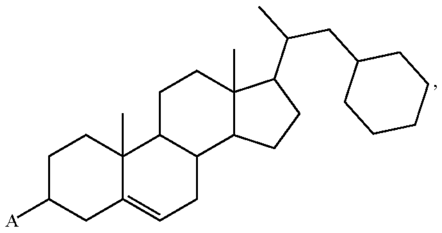

-continued
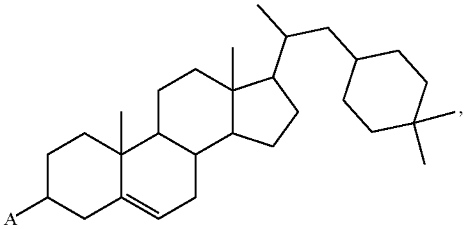,
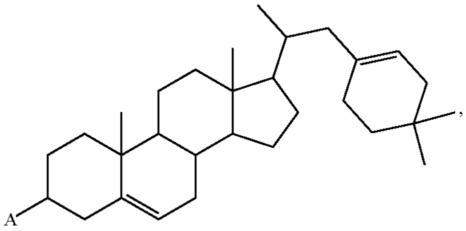,
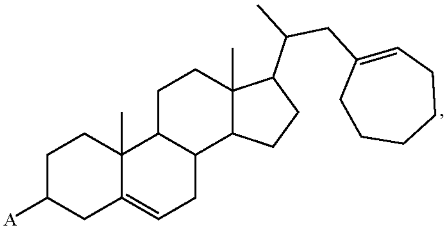,
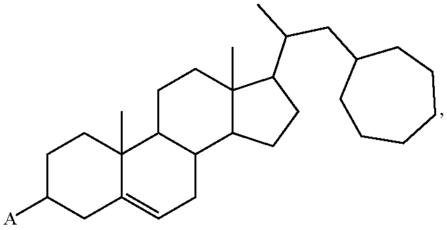,
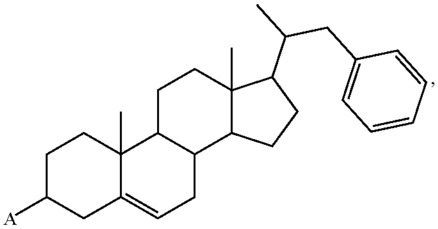,
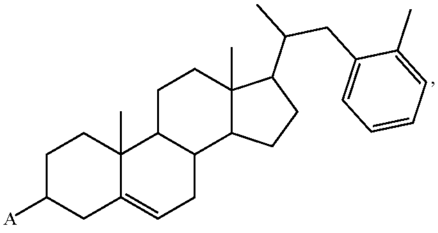,
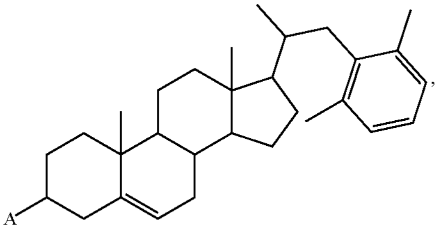,
-continued
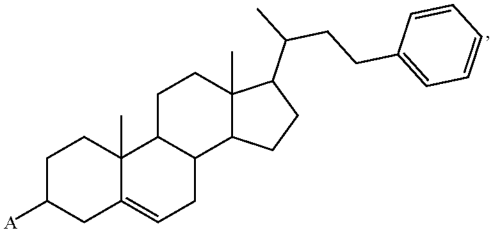,
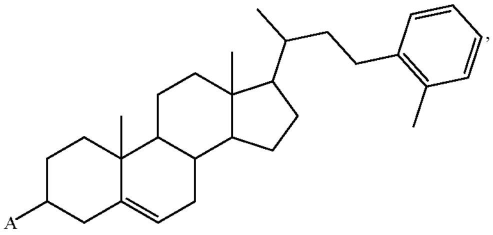,
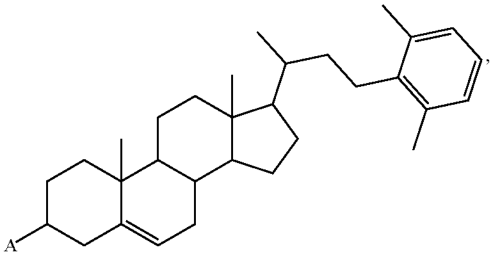,
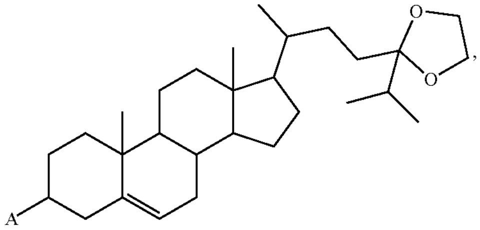,
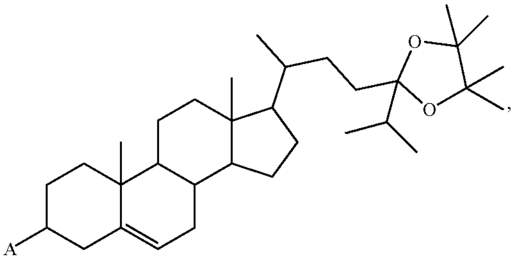,
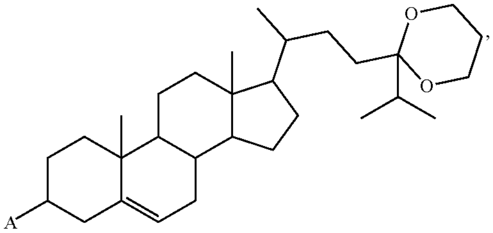,
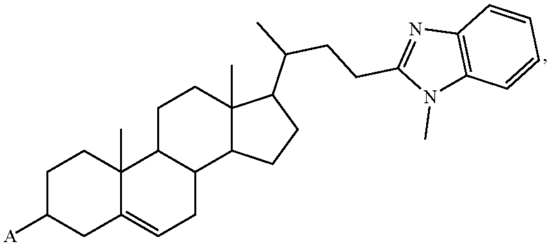, -continued
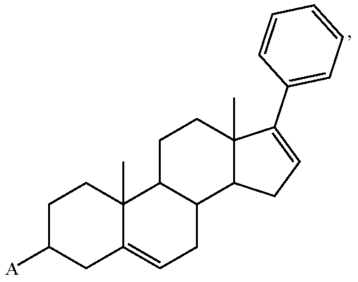
,
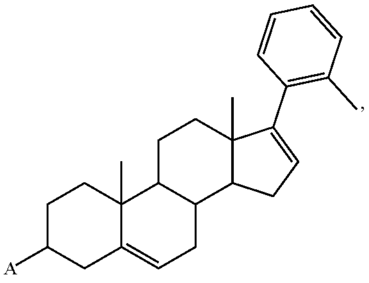
,
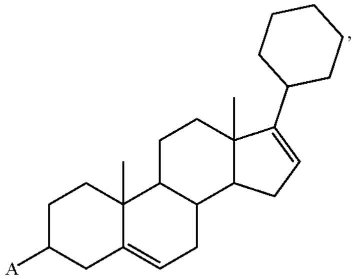
,
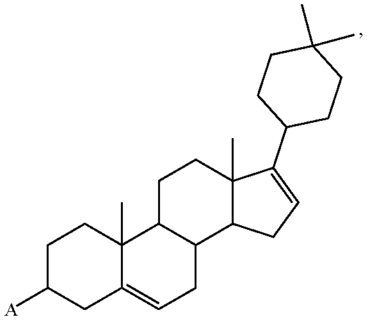
,
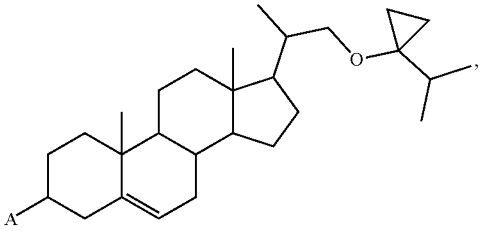
,
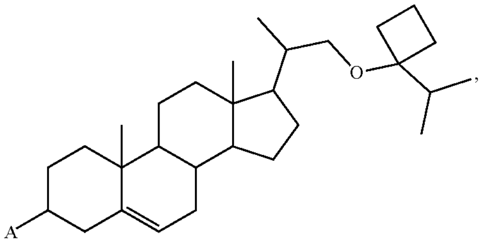
,
-continued
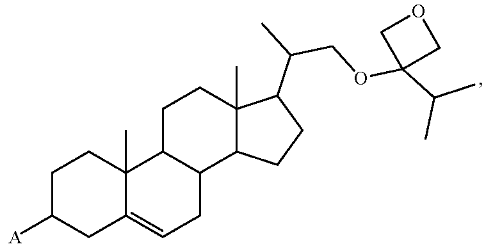
,
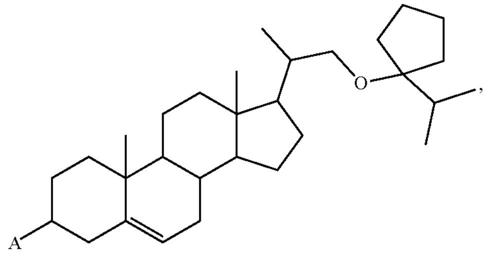
,
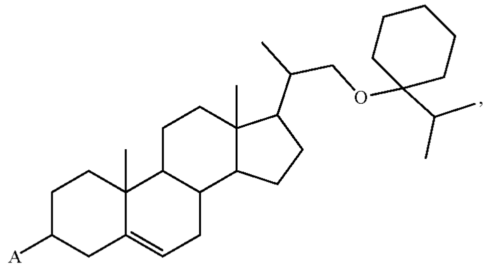
,
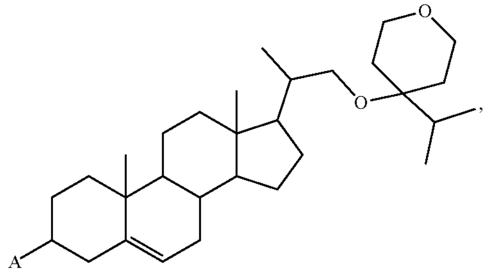
,
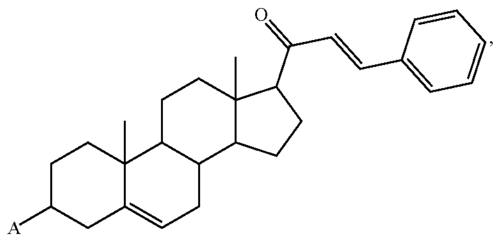
,
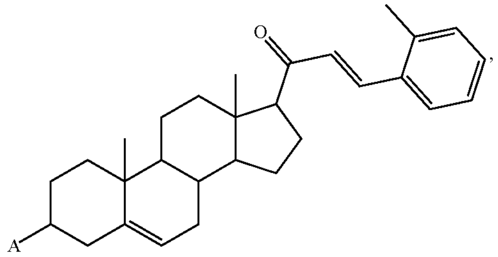
, -continued
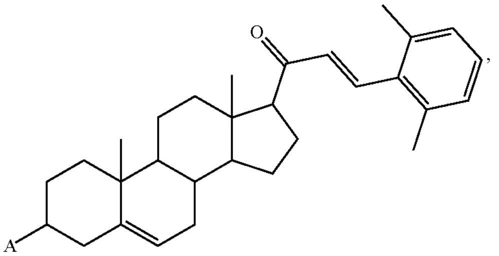
,
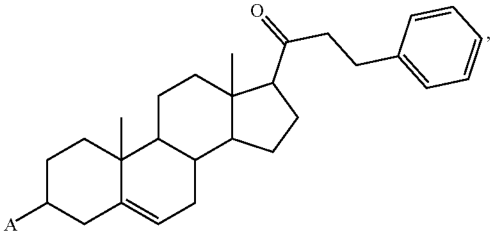
,
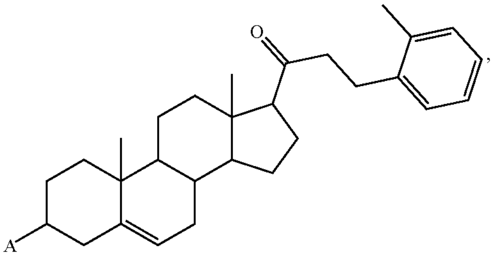
,
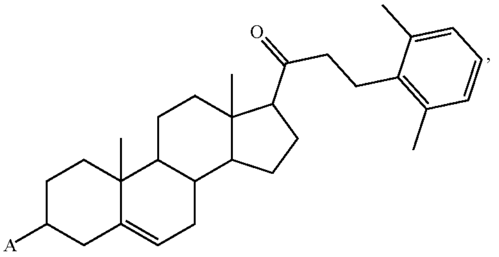
,
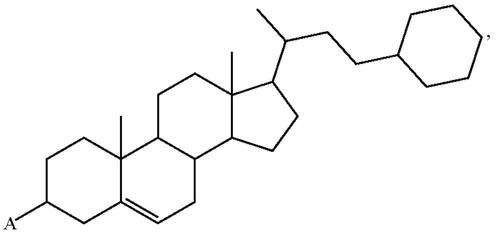
,
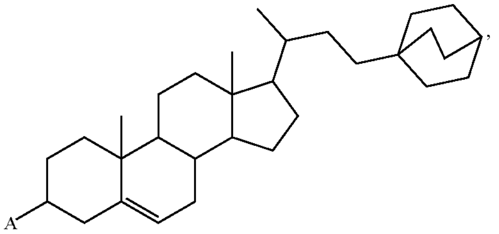
,
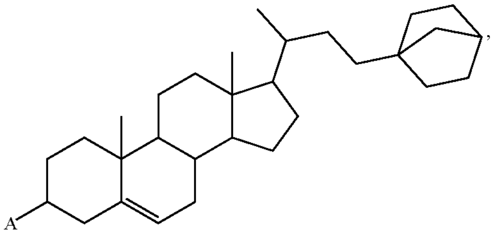
,
-continued
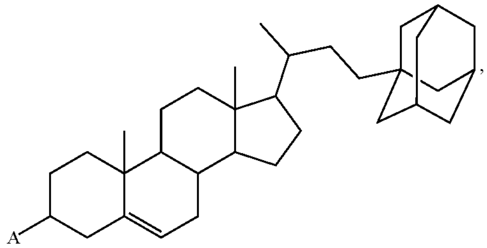
,
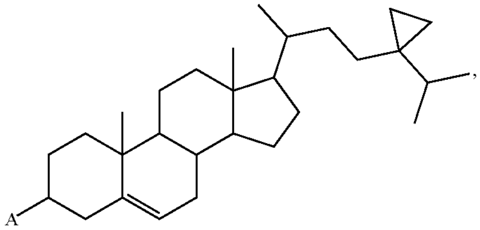
,
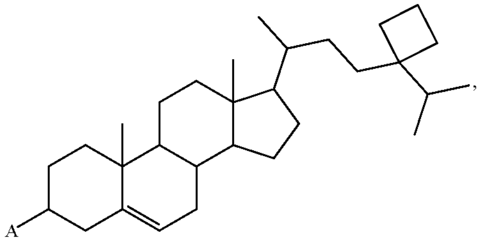
,
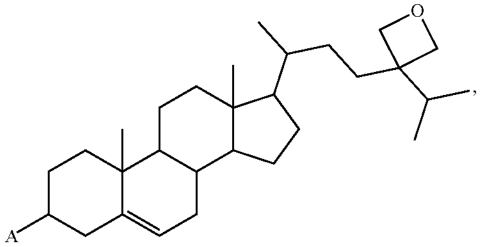
,
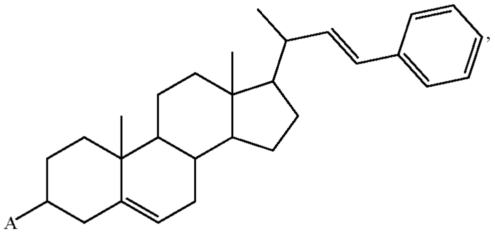
,
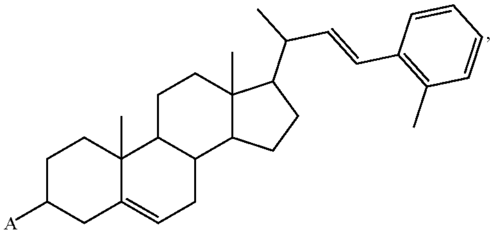
,
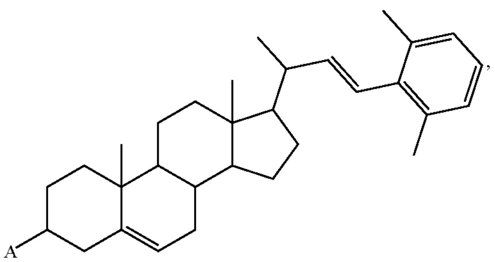
, -continued
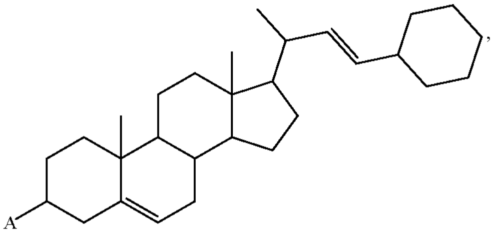
,
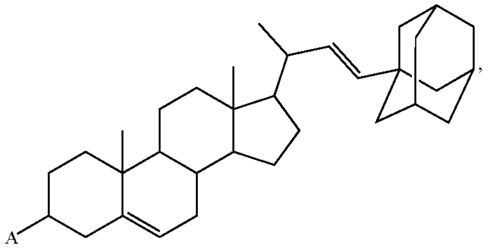
,
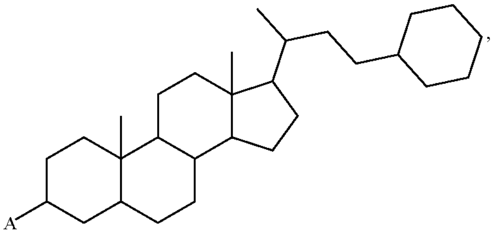
,
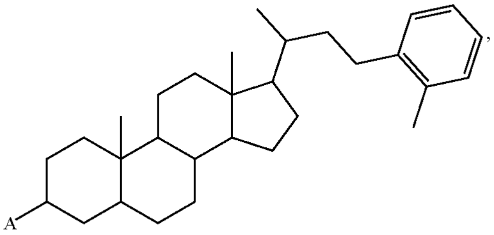
,
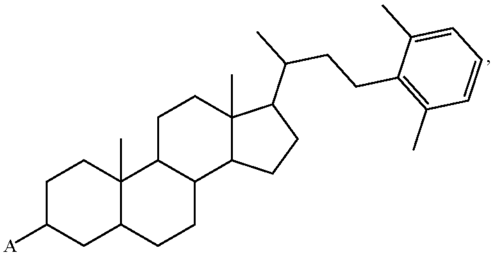
,
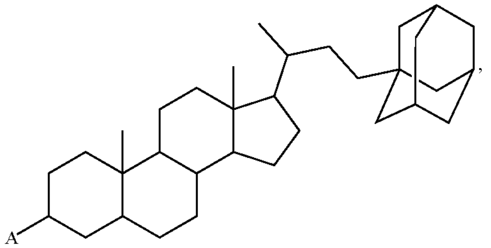
,
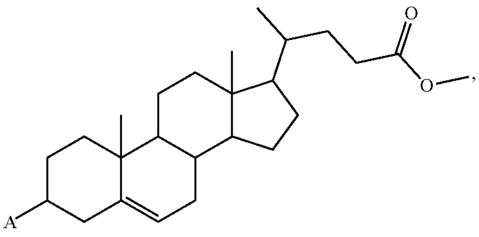
,
-continued
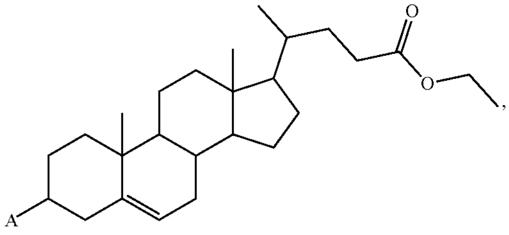
,
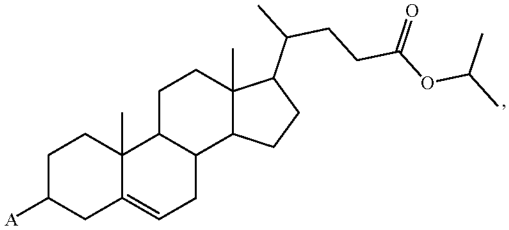
,
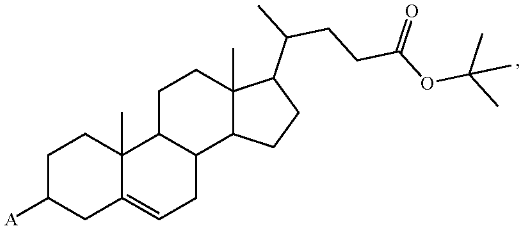
,
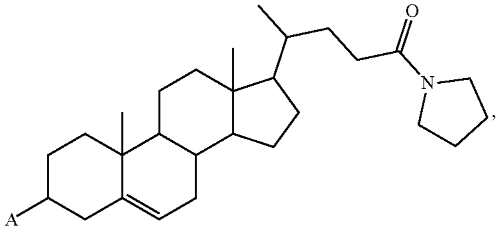
,
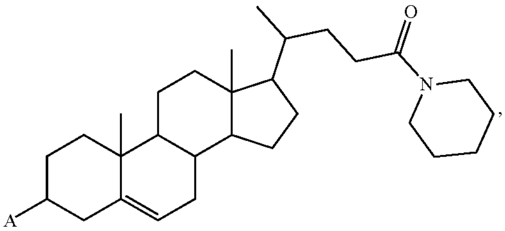
,
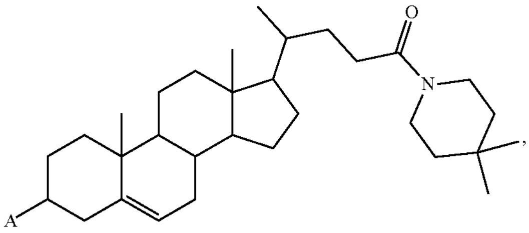
,
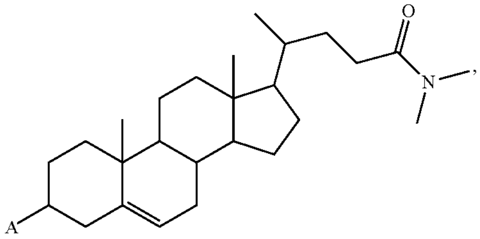
, -continued
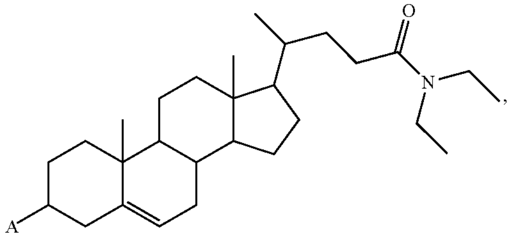
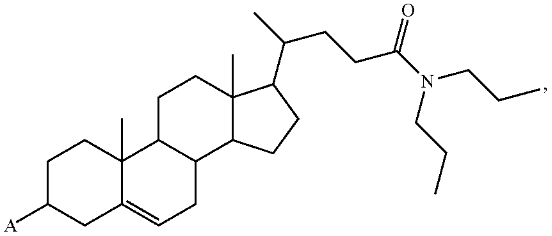
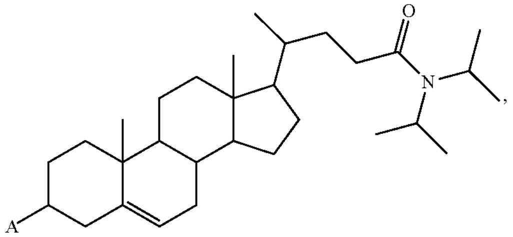
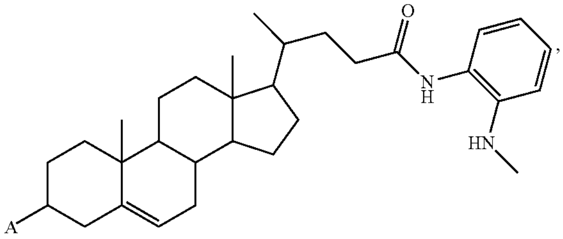
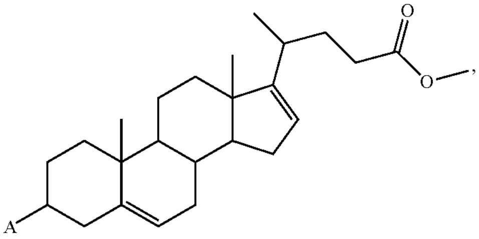
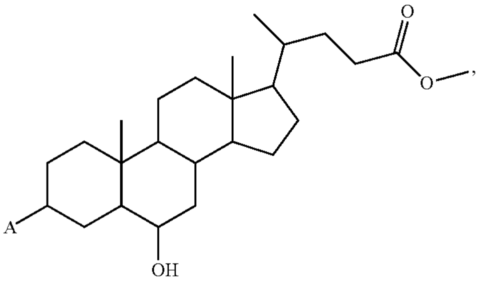
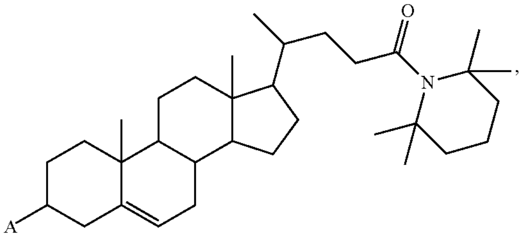
-continued
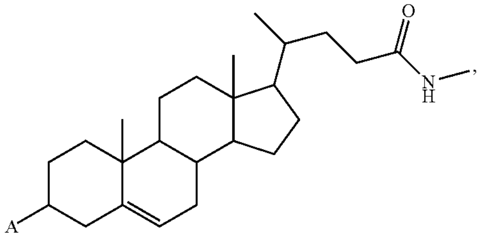
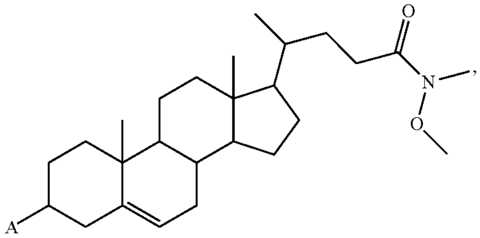
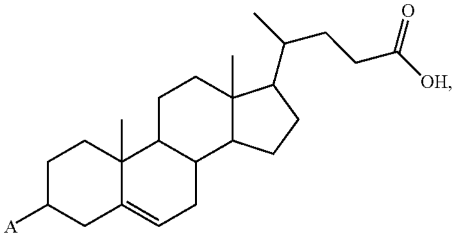
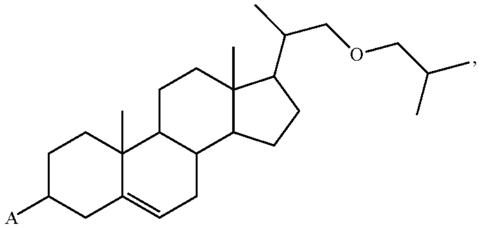
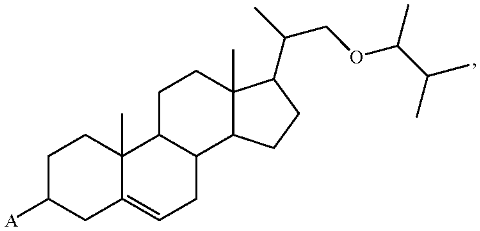
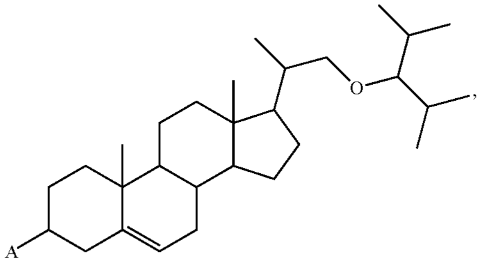
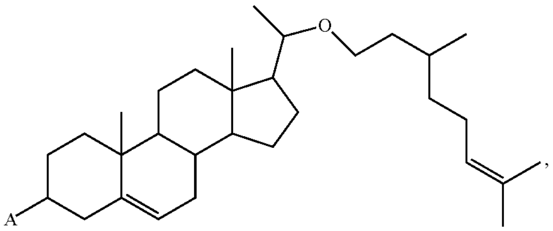

-continued
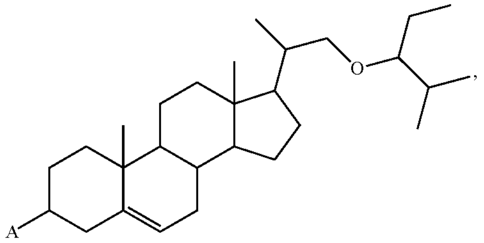
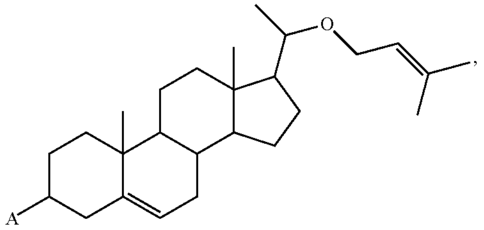
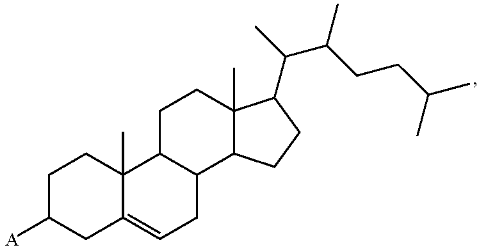
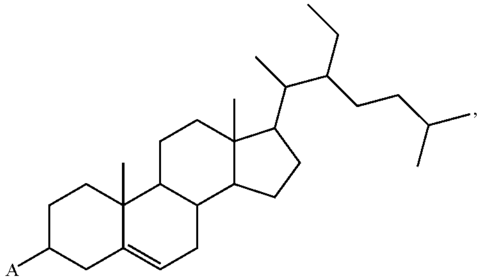
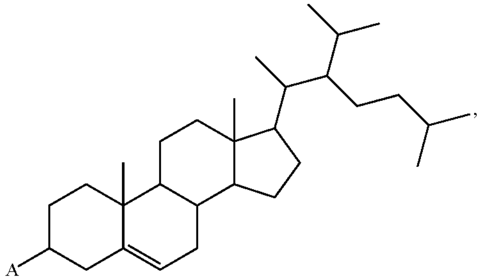
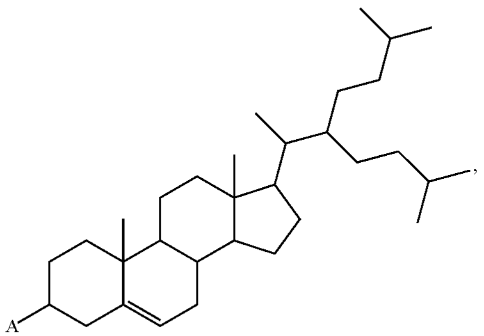
-continued
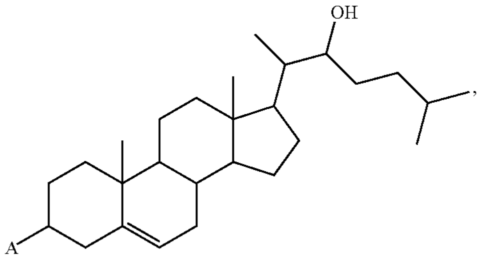
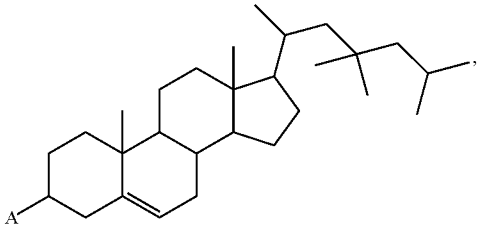
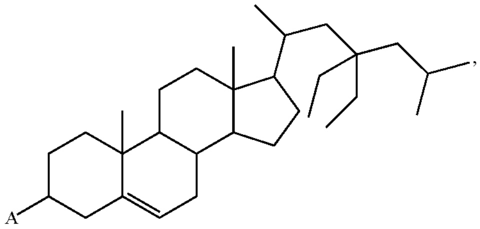
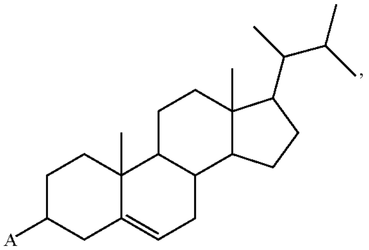
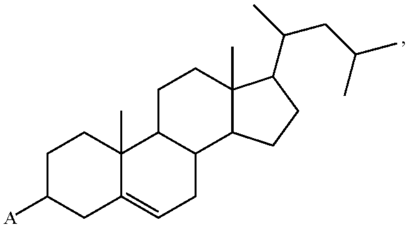
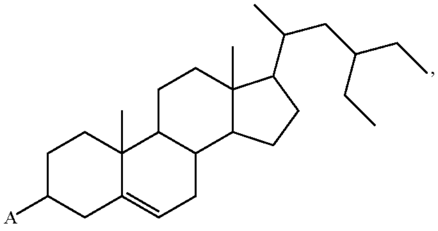
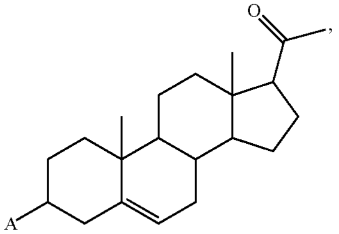

-continued
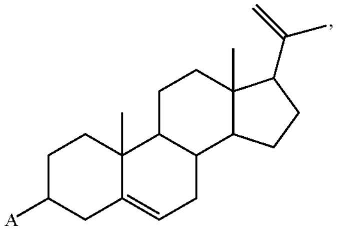
,
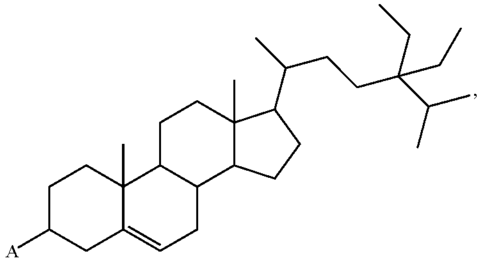
,
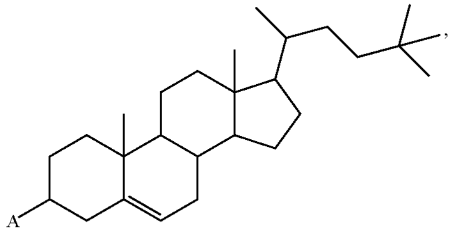
,
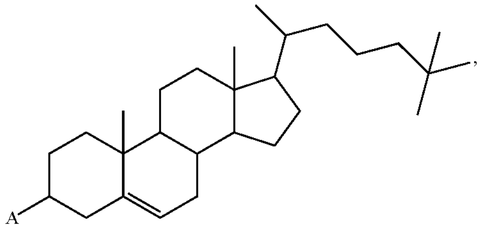
,
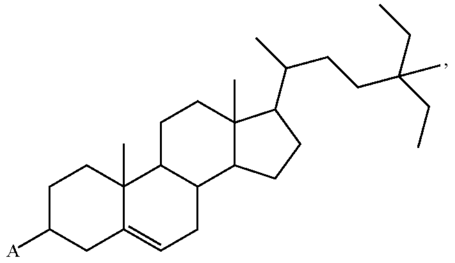
,
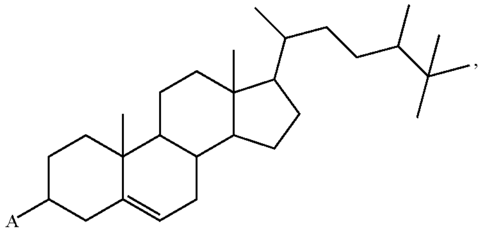
,
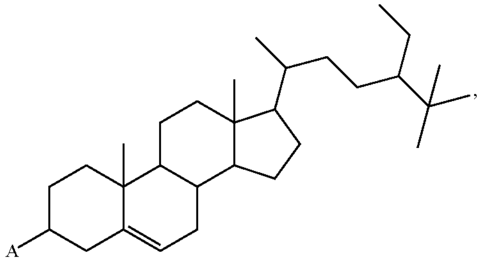
,
-continued
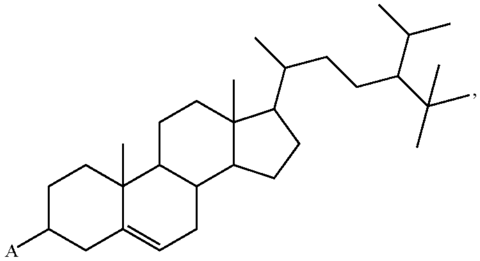
,
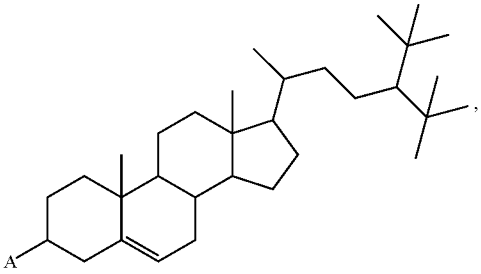
,
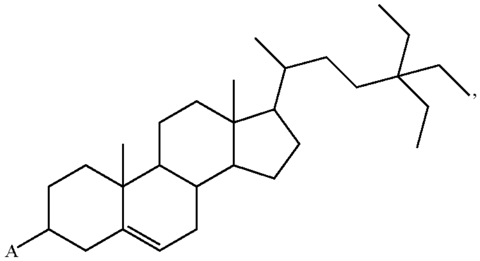
,
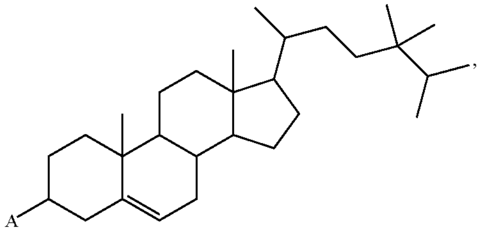
,
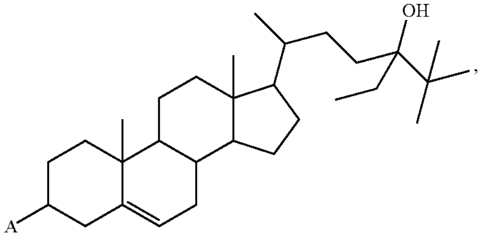
,
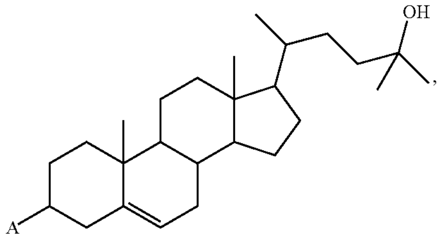
, -continued
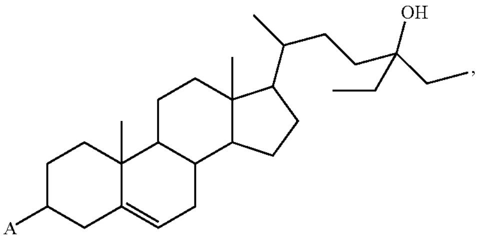
,
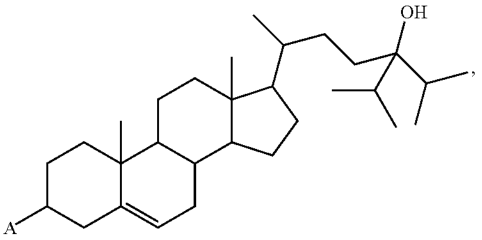
,
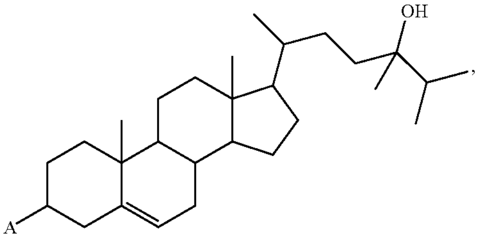
,
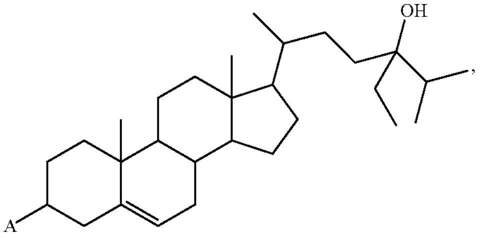
,
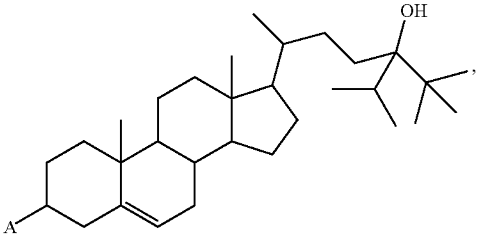
,
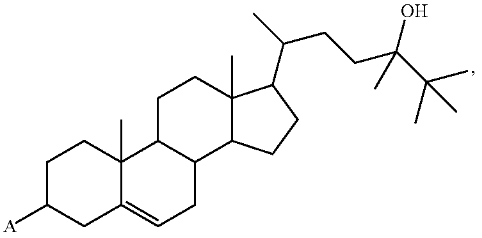
,
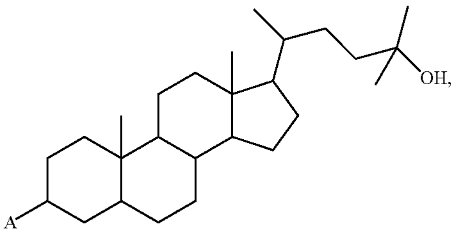
,
-continued
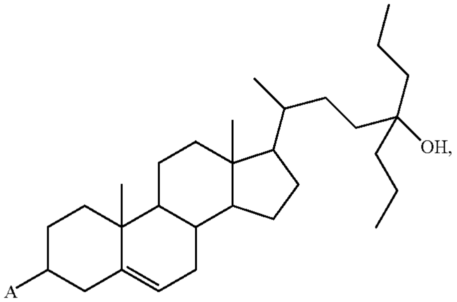
,
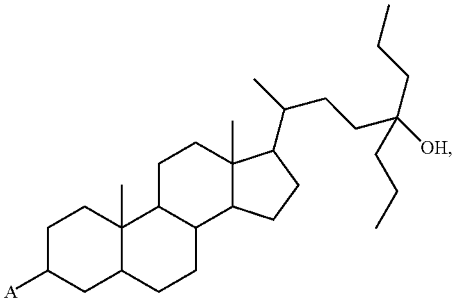
,
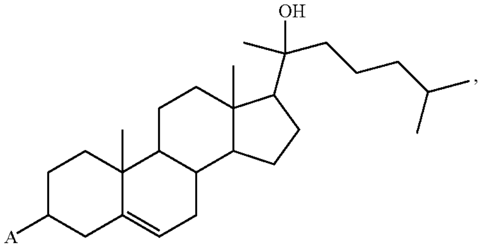
,
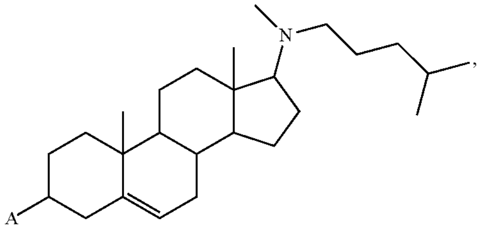
,
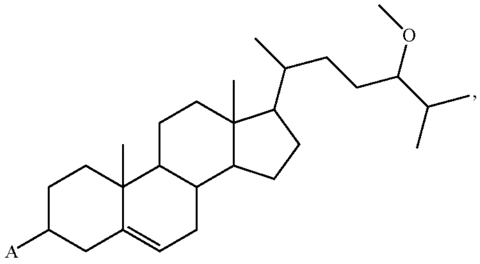
,
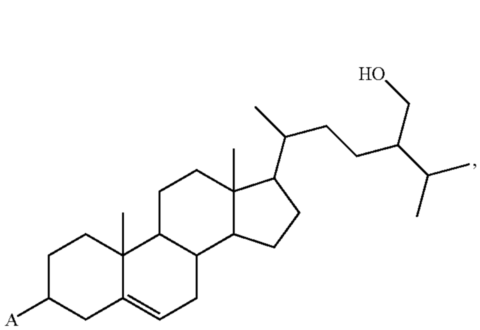
, -continued
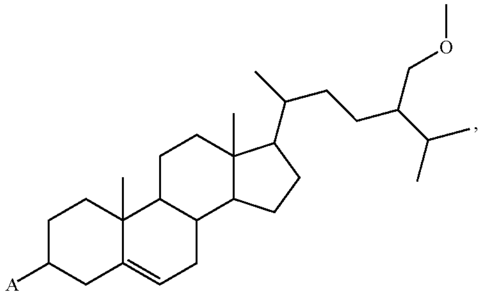
,
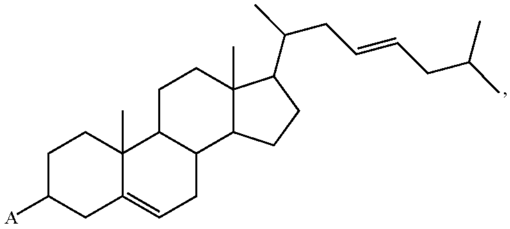
,
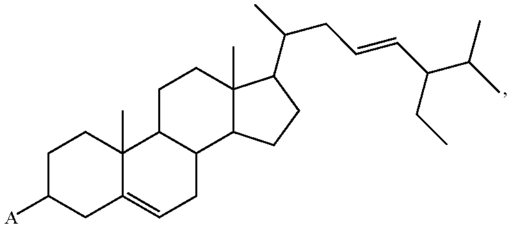
,
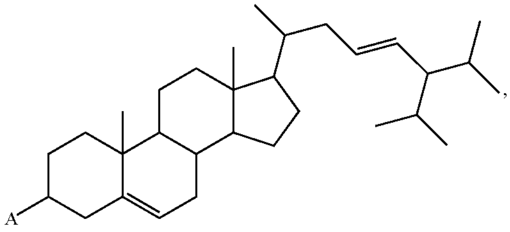
,
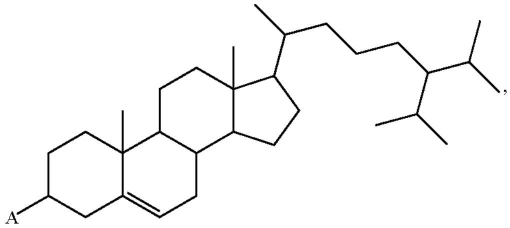
,
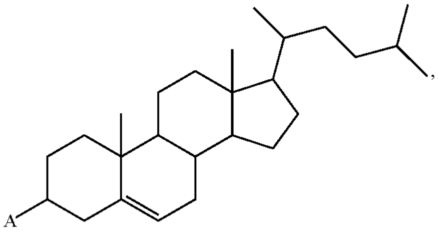
,
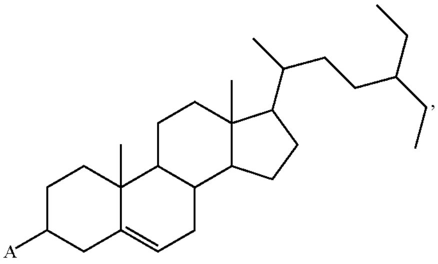
,
-continued
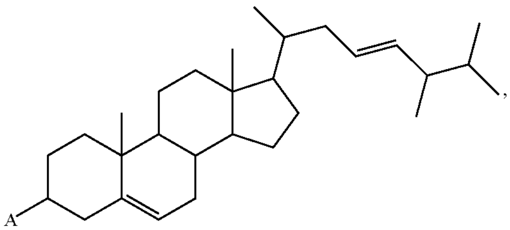
,
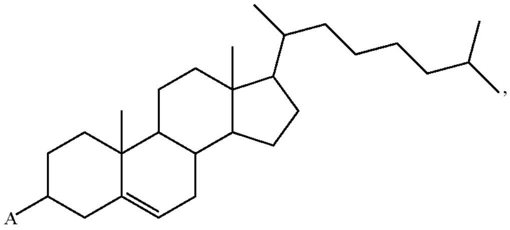
,
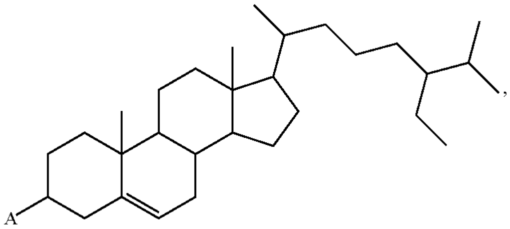
,
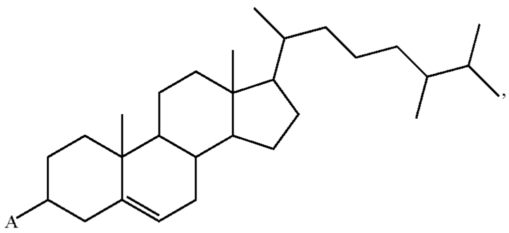
,
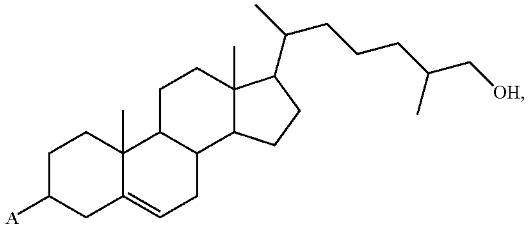
,
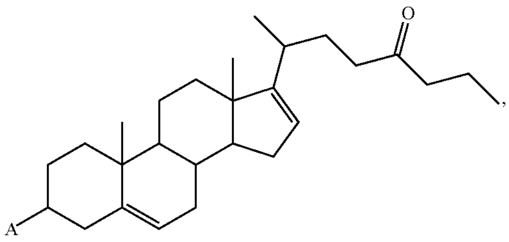
,
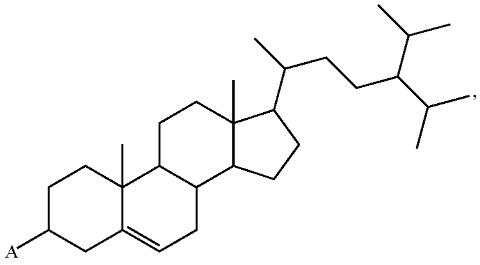
, -continued
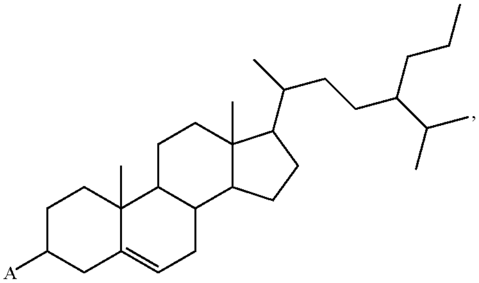
,
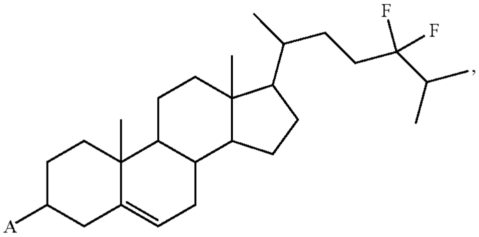
,
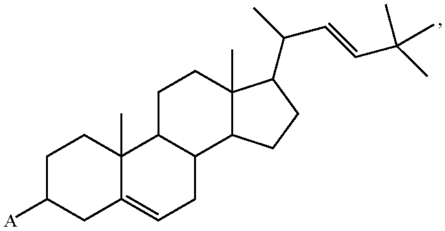
,
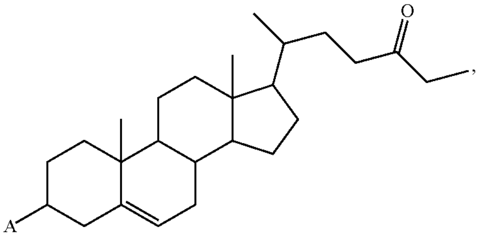
,
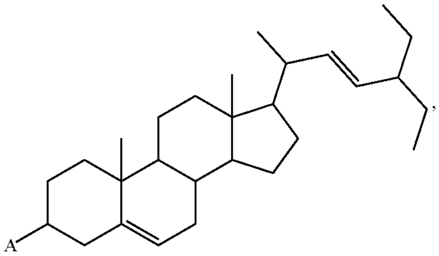
,
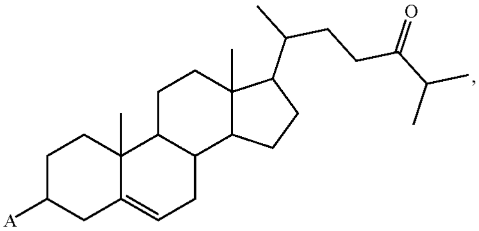
,
-continued
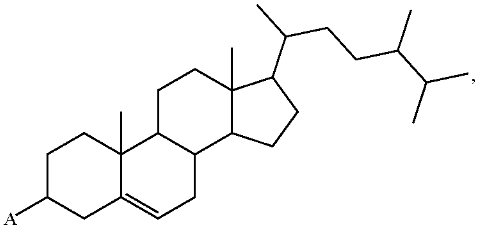
,
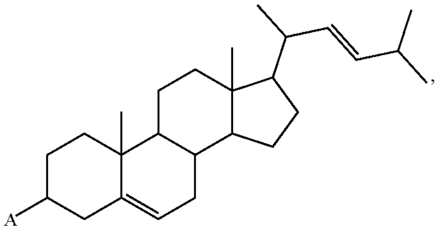
,
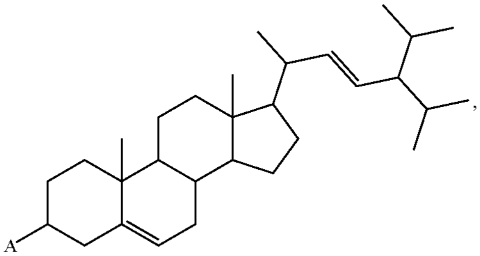
,
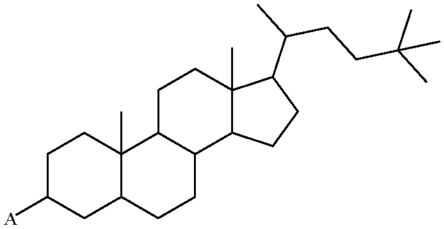
,
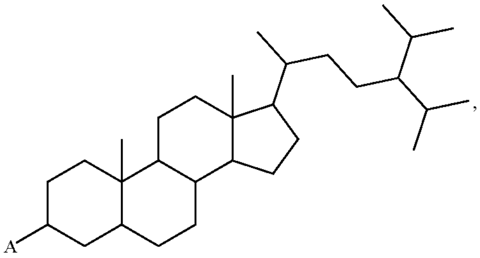
,
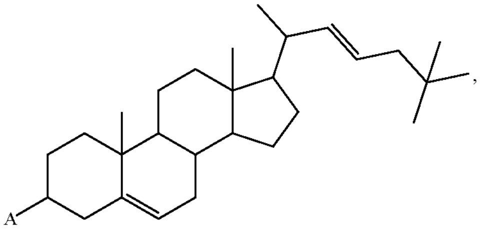
,
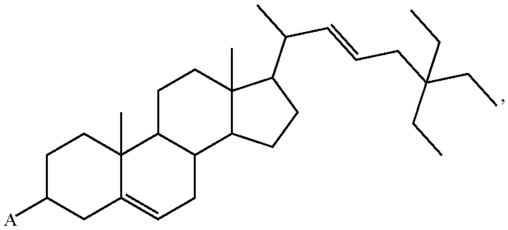
, -continued
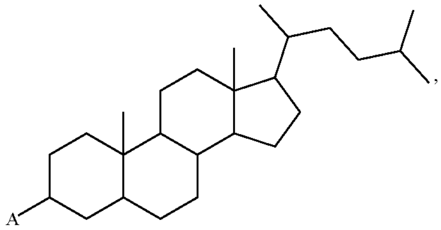
,
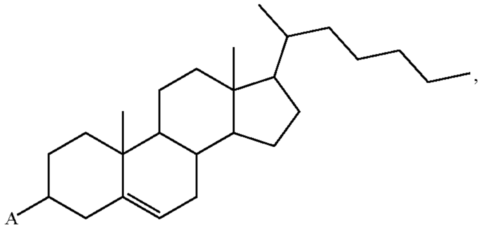
,
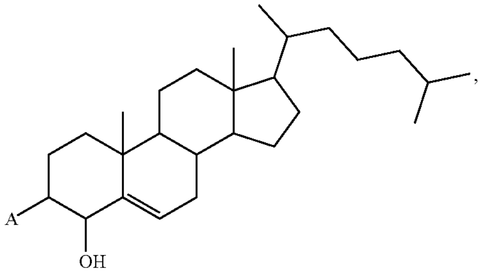
,
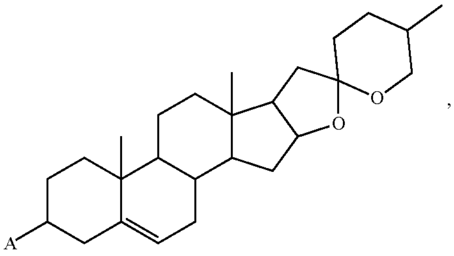
,
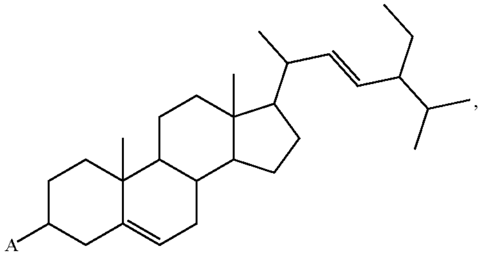
,
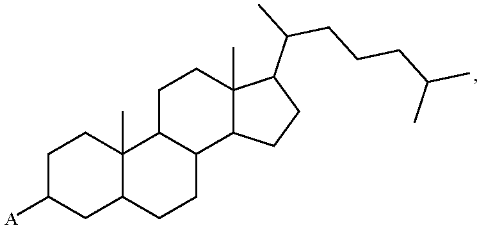
,
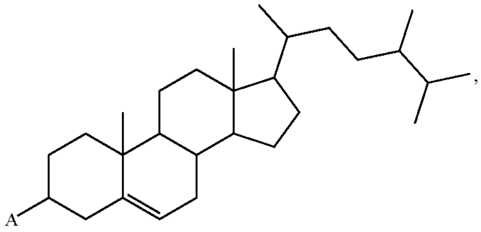
,
-continued
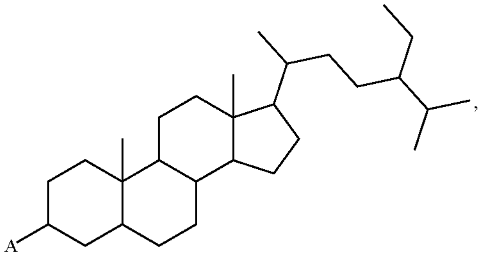
,
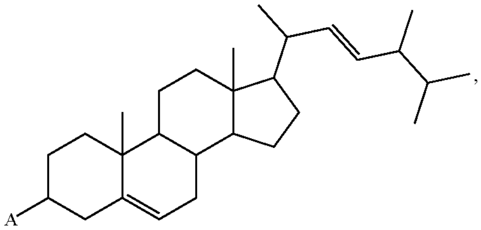
,
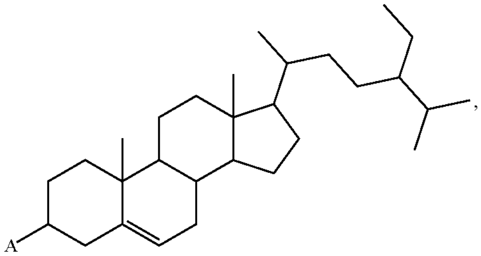
,
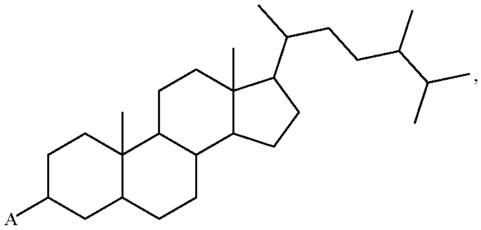
,
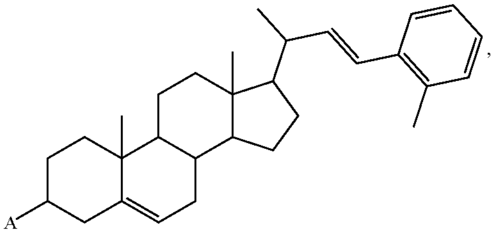
,
or a pharmaceutically acceptable salt thereof; wherein A is the same as for Formula Y.

In some embodiments, described herein are compounds of Formula II or Formula III:

Formula II

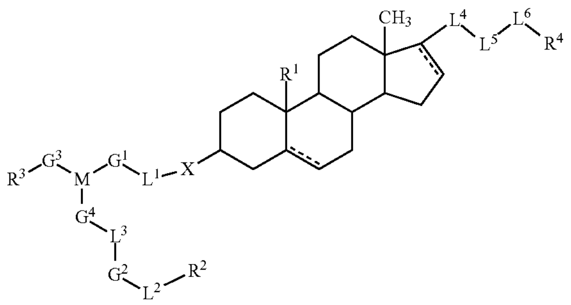

Formula III

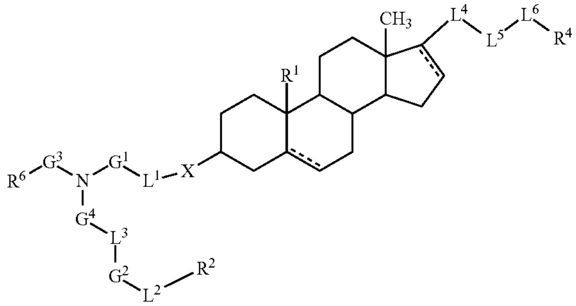

or pharmaceutically acceptable salts thereof, wherein:

$R^1$ is H or —$CH_3$;

X is O or S;

⋱ denotes carbon-carbon bond or carbon-carbon double bond;

$L^4$ is absent,

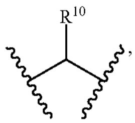, or 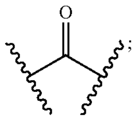;

$R^{10}$ is absent or $C_1$-$C_6$ alkyl;

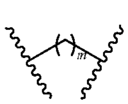 or 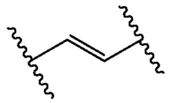;

$L^5$ is absent, or m is an integer 1, 2, or 3;

$L^6$ is absent,

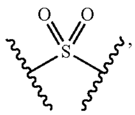, or 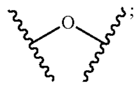;

$R^4$ is a $C_3$-$C_{10}$ alkyl, $C_3$-$C_{10}$ cycloalkyl, $C_3$-$C_{10}$ alkenyl, $C_3$-$C_{10}$ cycloalkenyl, $C_3$-$C_{10}$ alkynyl, or a derivative thereof;

$L^1$ is —O(C═O)—, —C(═O)—, —S(O)$_x$—, —C(═O)$R^a$C(═O)—, —N$R^a$C(═O)—, —NC(═O)$R^a$C(═O)—, or —C(═O)N$R^a$C(═O)—;

$L^2$ is —O(C═O)—, —(C═O)O—, —O(C═O)O—, —C(═O)—, —O—, —S(O)$_x$—, —S—S—, —N$R^a$C(═O)—, or —C(═O)$R^a$N—;

$L^3$ is absent, —O(C═O)—, —(C═O)O—, —O(C═O)O—, —C(═O)—, —O—, —N$R^a$C(═O)—, or —C(═O)$R^a$N—;

$R^a$ is

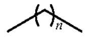

wherein n is an integer from 0 to 12;

x is 0, 1, or 2;

M is CH,

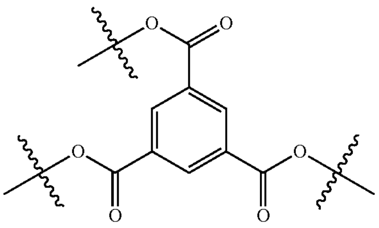,

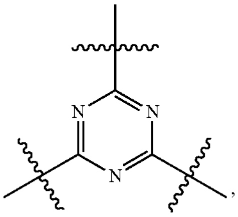, 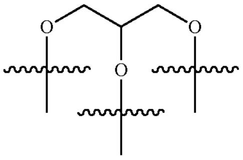,

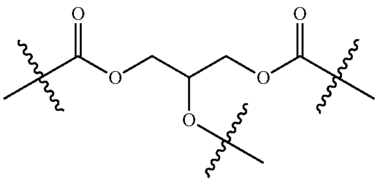,

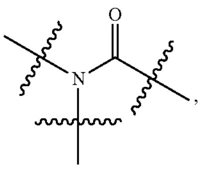, 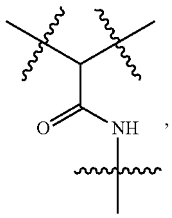, or

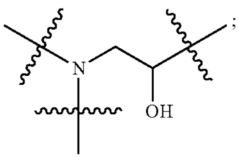;

$G^1$, $G^2$ and $G^3$ are each independently selected from $C_1$-$C_{12}$ alkyl or $C_1$-$C_{12}$ alkenyl;

$G^4$ is absent or selected from $C_1$-$C_{12}$ alkyl or $C_1$-$C_{12}$ alkenyl;

$R^2$ is —$CR^bR^c$, $C_6$-$C_{24}$ alkyl or $C_6$-$C_{24}$ alkenyl;

$R^3$ is

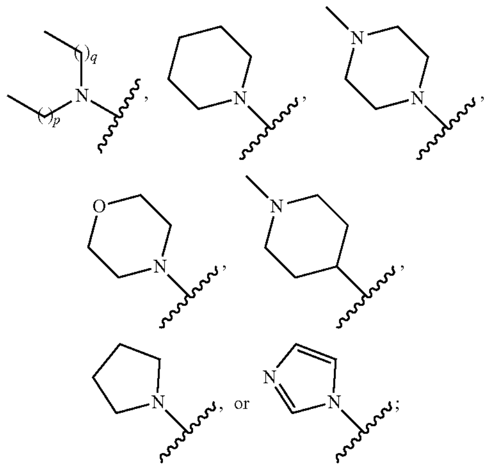

$R^6$ is H, $OR^b$, CN, —C(═O)$OR^b$, —NC(═O)$R^b$, —C(═O)$NR^b$,

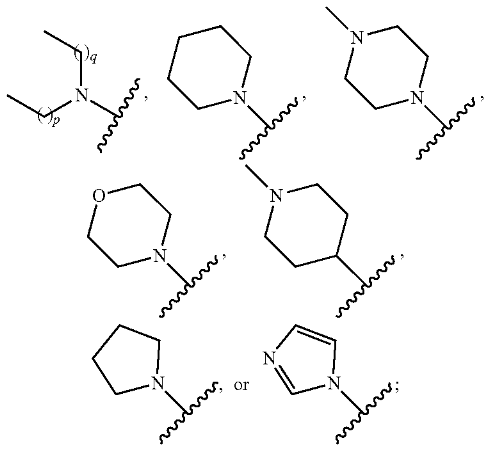

$R^b$ and $R^c$ are independently H, $C_1$-$C_{12}$ alkyl or $C_1$-$C_{12}$ alkenyl; and p and q are independently 0, 1, 2, 3 or 4;

or a pharmaceutically acceptable salt thereof.

In some embodiments, $R^1$ is —$CH_3$. In some embodiments, X is O. In some embodiments, $L^4$ is

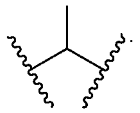 [SMILES: *C(*)C]

In some embodiments, $L^5$ is

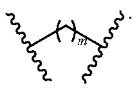

In some embodiments, $L^5$ is

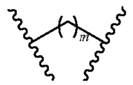

and m is 3. In some embodiments, $L^6$ is absent. In some embodiments, $R^4$ is methyl, ethyl, n-propyl, isopropyl, n-butyl, isobutyl, t-butyl, pentyl, hexyl, heptyl, octyl, nonyl, or decyl. In some embodiments, $R^4$ is isopropyl. In some embodiments, M is CH.

In some embodiments, $R^3$ is

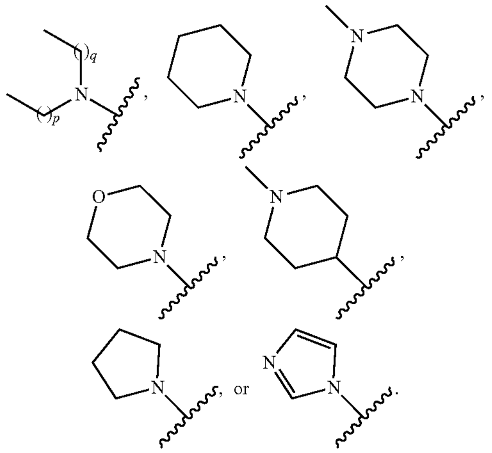

In some embodiments, $R^6$ is H, $OR^b$, CN, —C(═O)$OR^b$, —NC(═O)$R^b$, —C(═O)$NR^b$,

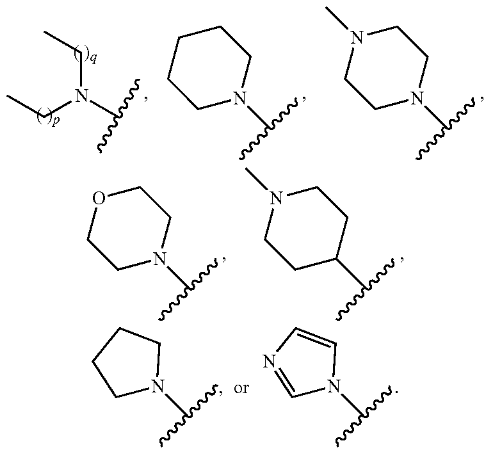

In some embodiments, described herein are compounds of Formula IV or Formula V:

Formula IV

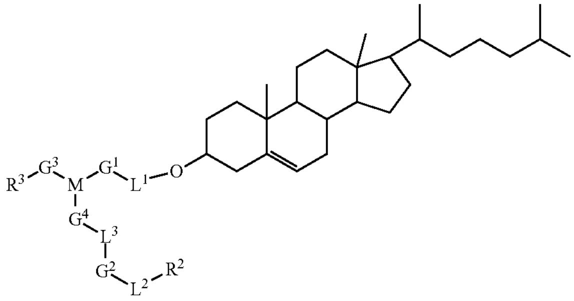

Formula V

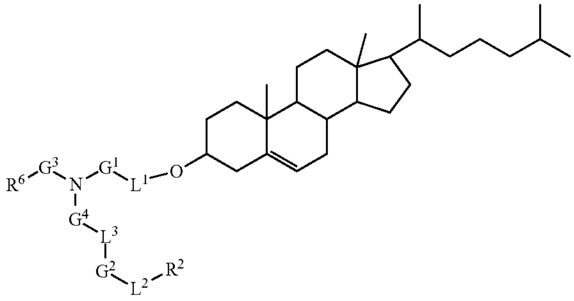

or a pharmaceutically acceptable salts thereof, wherein:

$L^1$ is —O(C=O)—, —C(=O)—, —$S(O)_x$—, —C(=O)$R^a$C(=O)—, —$NR^a$C(=O)—, —NC(=O)$R^a$C(=O)—, or —C(=O)$NR^a$C(=O)—;

$L^2$ is —O(C=O)—, —(C=O)O—, —O(C=O)O—, —C(=O)—, —O—, —$S(O)_x$—, —S—S—, —$NR^a$C(=O)—, or —C(=O)$R^a$N—;

$L^3$ is absent, —O(C=O)—, —(C=O)O—, —O(C=O)O—, —C(=O)—, —O—, —$NR^a$C(=O)—, or —C(=O)$R^a$N—;

$R^a$ is

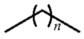

wherein n is an integer from 0 to 12;

x is 0, 1, or 2;

M is CH,

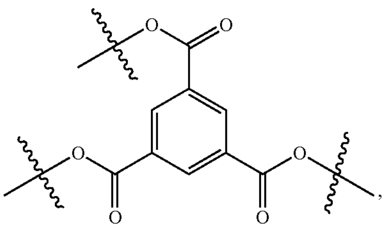,

-continued

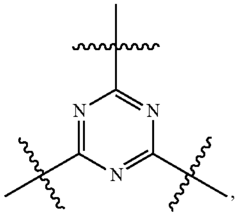,

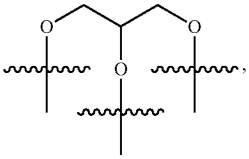,

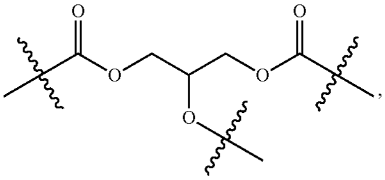,

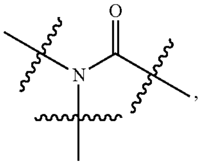, 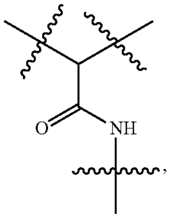, or

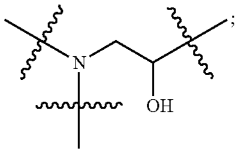;

$G^1$, $G^2$ and $G^3$ are each independently selected from $C_1$-$C_{12}$ alkyl or $C_1$-$C_{12}$ alkenyl;

$G^4$ is absent or selected from $C_1$-$C_{12}$ alkyl or $C_1$-$C_{12}$ alkenyl;

$R^2$ is —$CR^bR^c$, $C_6$-$C_{24}$ alkyl, or $C_6$-$C_{24}$ alkenyl;

$R^3$ is

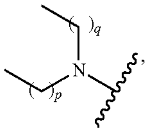, 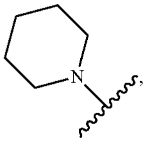, 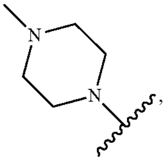,

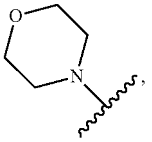, 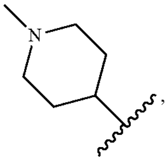,

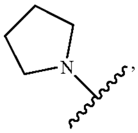, or 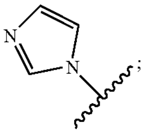;

$R^6$ is H, $OR^b$, CN, —C(=O)$OR^b$, —NC(=O)$R^b$, —C(=O)$NR^b$,

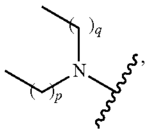, 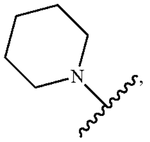, 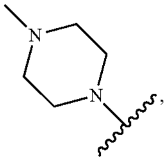, 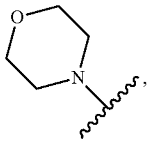, 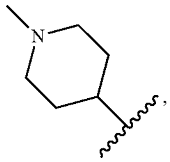, 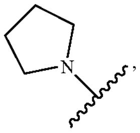, or 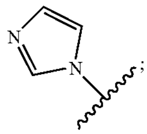;

$R^b$ and $R^c$ are independently H, $C_1$-$C_{12}$ alkyl, or $C_1$-$C_{12}$ alkenyl; and p and q are independently 0, 1, 2, 3 or 4.

In some embodiments, $L^1$ is —C(=O)—. In some embodiments, $L^2$ is —(C=O)O—. In some embodiments, $L^3$ is absent. In some embodiments, $G^1$ is $C_5$ alkyl. In some embodiments, $G^2$ is $C_6$ alkyl. In some embodiments, $G^3$ is $C_2$ alkyl. In some embodiments, $G^4$ is absent.

In some embodiments, $R^2$ is —$CR^bR^c$. In some embodiments, $R^b$ and $R^c$ are $C_2$ alkyl. In some embodiments, $R^b$ and $R^c$ are $C_4$ alkyl. In some embodiments, $R^b$ and $R^c$ are $C_6$ alkyl. In some embodiments, $R^b$ and $R^c$ are $C_8$ alkyl. In some embodiments, $R^2$ is —$CR^bR^c$ and $R^b$ and $R^c$ are $C_{10}$ alkyl. In some embodiments, $R^2$ is —$CR^bR^c$ and $R^b$ and $R^c$ are $C_{12}$ alkyl. In some embodiments, $R^2$ is —$CR^bR^c$ and $R^b$ is $C_{12}$ alkyl and $R^c$ is $C_{10}$ alkyl. In some embodiments, $R^2$ is —$CR^bR^c$ and $R^b$ is $C_{10}$ alkyl and $R^c$ is $C_{12}$ alkyl. In some embodiments, $R^2$ is —$CR^bR^c$ and $R^b$ is $C_8$ alkyl and $R^c$ is $C_{10}$ alkyl. In some embodiments, $R^2$ is —$CR^bR^c$ and $R^b$ is $C_6$ alkyl and $R^c$ is $C_{10}$ alkyl. In some embodiments, $R^2$ is —$CR^bR^c$ and $R^b$ is $C_4$ alkyl and $R^c$ is $C_{10}$ alkyl. In some embodiments, $R^2$ is —$CR^bR^c$ and $R^b$ is $C_2$ alkyl and $R^c$ is $C_{10}$ alkyl. In some embodiments, $R^2$ is —$CR^bR^c$ and $R^b$ is $C_1$ alkyl and $R^c$ is $C_{10}$ alkyl. In some embodiments, $R^2$ is —$CR^bR^c$ and $R^b$ is $C_{10}$ alkyl and $R^c$ is $C_8$ alkyl. In some embodiments, $R^2$ is —$CR^bR^c$ and $R^b$ is $C_{10}$ alkyl and $R^c$ is $C_6$ alkyl. In some embodiments, $R^2$ is —$CR^bR^c$ and $R^b$ is $C_{10}$ alkyl and $R^c$ is $C_4$ alkyl. In some embodiments, $R^2$ is —$CR^bR^c$ and $R^b$ is $C_{10}$ alkyl and $R^c$ is $C_2$ alkyl. In some embodiments, $R^2$ is —$CR^bR^c$ and $R^b$ is $C_{10}$ alkyl and $R^c$ is $C_1$ alkyl. In some embodiments, $R^2$ is —$CR^bR^c$ and $R^b$ is $C_8$ alkyl and $R^c$ is $C_8$ alkyl. In some embodiments, $R^2$ is —$CR^bR^c$ and $R^b$ is $C_6$ alkyl and $R^c$ is $C_8$ alkyl. In some embodiments, $R^2$ is —$CR^bR^c$ and $R^b$ is $C_4$ alkyl and $R^c$ is $C_8$ alkyl. In some embodiments, $R^2$ is —$CR^bR^c$ and $R^b$ is $C_2$ alkyl and $R^c$ is $C_8$ alkyl. In some embodiments, $R^2$ is —$CR^bR^c$ and $R^b$ is $C_1$ alkyl and $R^c$ is $C_8$ alkyl. In some embodiments, $R^2$ is —$CR^bR^c$ and $R^b$ is $C_8$ alkyl and $R^c$ is $C_6$ alkyl. In some embodiments, $R^2$ is —$CR^bR^c$ and $R^b$ is $C_8$ alkyl and $R^c$ is $C_4$ alkyl. In some embodiments, $R^2$ is —$CR^bR^c$ and $R^b$ is $C_8$ alkyl and $R^c$ is $C_2$ alkyl. In some embodiments, $R^2$ is —$CR^bR^c$ and $R^b$ is $C_8$ alkyl and $R^c$ is $C_1$ alkyl. In some embodiments, $R^2$ is —$CR^bR^c$ and $R^b$ is $C_8$ alkyl and $R^c$ is $C_6$ alkyl. In some embodiments, $R^2$ is —$CR^bR^c$ and $R^b$ is $C_6$ alkyl and $R^c$ is $C_6$ alkyl. In some embodiments, $R^2$ is —$CR^bR^c$ and $R^b$ is $C_4$ alkyl and $R^c$ is $C_6$ alkyl. In some embodiments, $R^2$ is —$CR^bR^c$ and $R^b$ is $C_2$ alkyl and $R^c$ is $C_6$ alkyl. In some embodiments, $R^2$ is —$CR^bR^c$ and $R^b$ is $C_1$ alkyl and $R^c$ is $C_6$ alkyl. In some embodiments, $R^2$ is —$CR^bR^c$ and $R^b$ is $C_6$ alkyl and $R^c$ is $C_8$ alkyl. In some embodiments, $R^2$ is —$CR^bR^c$ and $R^b$ is $C_6$ alkyl and $R^c$ is $C_4$ alkyl. In some embodiments, $R^2$ is —$CR^bR^c$ and $R^b$ is $C_6$ alkyl and $R^c$ is $C_2$ alkyl. In some embodiments, $R^2$ is —$CR^bR^c$ and $R^b$ is $C_6$ alkyl and $R^c$ is $C_1$ alkyl. In some embodiments, $R^2$ is —$CR^bR^c$ and $R^b$ is $C_8$ alkyl and $R^c$ is $C_4$ alkyl. In some embodiments, $R^2$ is —$CR^bR^c$ and $R^b$ is $C_6$ alkyl and $R^c$ is $C_4$ alkyl. In some embodiments, $R^2$ is —$CR^bR^c$ and $R^b$ is $C_4$ alkyl and $R^c$ is $C_4$ alkyl. In some embodiments, $R^2$ is —$CR^bR^c$ and $R^b$ is $C_2$ alkyl and $R^c$ is $C_4$ alkyl. In some embodiments, $R^2$ is —$CR^bR^c$ and $R^b$ is $C_1$ alkyl and $R^c$ is $C_4$ alkyl. In some embodiments, $R^2$ is —$CR^bR^c$ and $R^b$ is $C_4$ alkyl and $R^c$ is $C_8$ alkyl. In some embodiments, $R^2$ is —$CR^bR^c$ and $R^b$ is $C_4$ alkyl and $R^c$ is $C_6$ alkyl. In some embodiments, $R^2$ is —$CR^bR^c$ and $R^b$ is $C_4$ alkyl and $R^c$ is $C_4$ alkyl. In some embodiments, $R^2$ is —$CR^bR^c$ and $R^b$ is $C_4$ alkyl and $R^c$ is $C_2$ alkyl. In some embodiments, $R^2$ is —$CR^bR^c$ and $R^b$ is $C_4$ alkyl and $R^c$ is $C_1$ alkyl. In some embodiments, $R^2$ is —$CR^bR^c$ and $R^b$ is $C_8$ alkyl and $R^c$ is $C_2$ alkyl. In some embodiments, $R^2$ is —$CR^bR^c$ and $R^b$ is $C_6$ alkyl and $R^c$ is $C_2$ alkyl. In some embodiments, $R^2$ is —$CR^bR^c$ and $R^b$ is $C_4$ alkyl and $R^c$ is $C_2$ alkyl. In some embodiments, $R^2$ is —$CR^bR^c$ and $R^b$ is $C_2$ alkyl and $R^c$ is $C_2$ alkyl. In some embodiments, $R^2$ is —$CR^bR^c$ and $R^b$ is $C_1$ alkyl and $R^c$ is $C_2$ alkyl. In some embodiments, $R^2$ is —$CR^bR^c$ and $R^b$ is $C_2$ alkyl and $R^c$ is $C_8$ alkyl. In some embodiments, $R^2$ is —$CR^bR^c$ and $R^b$ is $C_2$ alkyl and $R^c$ is $C_6$ alkyl. In some embodiments, $R^2$ is —$CR^bR^c$ and $R^b$ is $C_2$ alkyl and $R^c$ is $C_4$ alkyl. In some embodiments, $R^2$ is —$CR^bR^c$ and $R^b$ is $C_2$ alkyl and $R^c$ is $C_1$ alkyl. In some embodiments, $R^2$ is —$CR^bR^c$ and $R^b$ is $C_8$ alkyl and $R^c$ is $C_1$ alkyl. In some embodiments, $R^2$ is —$CR^bR^c$ and $R^b$ is $C_6$ alkyl and $R^c$ is $C_1$ alkyl. In some embodiments, $R^2$ is —$CR^bR^c$ and $R^b$ is $C_4$ alkyl and $R^c$ is $C_1$ alkyl. In some embodiments, $R^2$ is —$CR^bR^c$ and $R^b$ is $C_2$ alkyl and $R^c$ is $C_1$ alkyl. In some embodiments, $R^2$ is —$CR^bR^c$ and $R^b$ is $C_1$ alkyl and $R^c$ is $C_1$ alkyl. In some embodiments, $R^2$ is —$CR^bR^c$ and $R^b$ is $C_1$ alkyl and $R^c$ is $C_8$ alkyl. In some embodiments, $R^2$ is —$CR^bR^c$ and $R^b$ is $C_1$ alkyl and $R^c$ is $C_6$ alkyl. In some embodiments, $R^2$ is —$CR^bR^c$ and $R^b$ is $C_1$ alkyl and $R^c$ is $C_4$ alkyl. In some embodiments, $R^2$ is —$CR^bR^c$ and $R^b$ is $C_1$ alkyl and $R^c$ is $C_2$ alkyl.

In some embodiments, $R^2$ is —$CR^bR^c$. In some embodiments, $R^b$ and $R^c$ are $C_2$ alkenyl. In some embodiments, $R^b$ and $R^c$ are $C_4$ alkenyl. In some embodiments, $R^b$ and $R^c$ are $C_6$ alkenyl. In some embodiments, $R^b$ and $R^c$ are $C_8$ alkenyl. In some embodiments, $R^2$ is —$CR^bR^c$ and $R^b$ and $R^c$ are $C_{10}$ alkenyl. In some embodiments, $R^2$ is —$CR^bR^c$ and $R^b$ and $R^c$ are $C_{12}$ alkenyl. In some embodiments, $R^2$ is —$CR^bR^c$ and $R^b$ is $C_{12}$ alkenyl and $R^c$ is $C_{10}$ alkenyl. In some embodiments, $R^2$ is —$CR^bR^c$ and $R^b$ is $C_{10}$ alkenyl and $R^c$ is $C_{12}$ alkenyl. In some embodiments, $R^2$ is —$CR^bR^c$ and $R^b$ is $C_8$ alkenyl and $R^c$ is $C_{10}$ alkenyl. In some embodiments, $R^2$ is —$CR^bR^c$ and $R^b$ is $C_6$ alkenyl and $R^c$ is $C_{10}$ alkenyl. In some embodiments, $R^2$ is —$CR^bR^c$ and $R^b$ is $C_4$ alkenyl and $R^c$ is $C_{10}$ alkenyl. In some embodiments, $R^2$ is —$CR^bR^c$ and $R^b$ is $C_2$ alkenyl and $R^c$ is $C_{10}$ alkenyl. In some embodiments, $R^2$ is —$CR^bR^c$ and $R^b$ is $C_1$ alkenyl and $R^c$ is $C_{10}$ alkenyl. In some embodiments, $R^2$ is —$CR^bR^c$ and $R^b$ is $C_{10}$ and $R^c$ is $C_8$ alkenyl. In some embodiments, $R^2$ is —$CR^bR^c$ and $R^b$ is $C_{10}$ alkenyl and $R^c$ is $C_6$ alkenyl. In some embodiments, $R^2$ is —$CR^bR^c$ and $R^b$ is $C_{10}$ alkenyl and $R^c$ is $C_4$ alkenyl. In some embodiments, $R^2$ is —$CR^bR^c$ and $R^b$ is $C_{10}$ alkenyl and $R^c$ is $C_2$ alkenyl. In some embodiments, $R^2$ is —$CR^bR^c$ and $R^b$ is $C_{10}$ alkenyl and $R^c$ is $C_1$ alkenyl. In some embodiments, $R^2$ is —$CR^bR^c$ and $R^b$ is $C_8$ alkenyl and $R^c$ is $C_8$ alkenyl. In some embodiments, $R^2$ is —$CR^bR^c$ and $R^b$ is $C_6$ alkenyl and $R^c$ is $C_8$ alkenyl. In some embodiments, $R^2$ is —$CR^bR^c$ and $R^b$ is $C_4$ alkenyl and $R^c$ is $C_8$ alkenyl. In some embodiments, $R^2$ is —$CR^bR^c$ and $R^b$ is $C_2$ alkenyl and $R^c$ is $C_8$ alkenyl. In some embodiments, $R^2$ is —$CR^bR^c$ and $R^b$ is $C_1$ alkenyl and $R^c$ is $C_8$ alkenyl. In some embodiments, $R^2$ is —$CR^bR^c$ and $R^b$ is $C_8$ alkenyl and $R^c$ is $C_6$ alkenyl. In some embodiments, $R^2$ is —$CR^bR^c$ and $R^b$ is $C_8$ alkenyl and $R^c$ is $C_4$ alkenyl. In some embodiments, $R^2$ is —$CR^bR^c$ and $R^b$ is $C_8$ alkenyl and $R^c$ is $C_2$ alkenyl. In some embodiments, $R^2$ is —$CR^bR^c$ and $R^b$ is $C_8$ alkenyl and $R^c$ is $C_1$ alkenyl. In some embodiments, $R^2$ is —$CR^bR^c$ and $R^b$ is $C_8$ alkenyl and $R^c$ is $C_6$ alkenyl. In some embodiments, $R^2$ is —$CR^bR^c$ and $R^b$ is $C_6$ alkenyl and $R^c$ is $C_6$ alkenyl. In some embodiments, $R^2$ is —$CR^bR^c$ and $R^b$ is $C_4$ alkenyl and $R^c$ is $C_6$ alkenyl. In some embodiments, $R^2$ is —$CR^bR^c$ and $R^b$ is $C_2$ alkenyl and $R^c$ is $C_6$ alkenyl. In some embodiments, $R^2$ is —$CR^bR^c$ and $R^b$ is $C_1$ alkenyl and $R^c$ is $C_6$ alkenyl. In some embodiments, $R^2$ is —$CR^bR^c$ and $R^b$ is $C_6$ and $R^c$ is $C_8$ alkenyl. In some embodiments, $R^2$ is —$CR^bR^c$ and $R^b$ is $C_6$ alkenyl and $R^c$ is $C_4$ alkenyl. In some embodiments, $R^2$ is —$CR^bR^c$ and $R^b$ is $C_6$ alkenyl and $R^c$ is $C_2$ alkenyl. In some embodiments, $R^2$ is —$CR^bR^c$ and $R^b$ is $C_6$ alkenyl and $R^c$ is $C_1$ alkenyl. In some embodiments, $R^2$ is —$CR^bR^c$ and $R^b$ is $C_8$ alkenyl and $R^c$ is $C_4$ alkenyl. In some embodiments, $R^2$ is —$CR^bR^c$ and $R^b$ is $C_6$ alkenyl and $R^c$ is $C_4$ alkenyl. In some embodiments, $R^2$ is —$CR^bR^c$ and $R^b$ is $C_4$ alkenyl and $R^c$ is $C_4$ alkenyl. In some embodiments, $R^2$ is —$CR^bR^c$ and $R^b$ is $C_2$ alkenyl and $R^c$ is $C_4$ alkenyl. In some embodiments, $R^2$ is —$CR^bR^c$ and $R^b$ is $C_1$ alkenyl and $R^c$ is $C_4$ alkenyl. In some embodiments, $R^2$ is —$CR^bR^c$ and $R^b$ is $C_4$ alkenyl and $R^c$ is $C_8$ alkenyl. In some embodiments, $R^2$ is —$CR^bR^c$ and $R^b$ is $C_4$ alkenyl and $R^c$ is $C_6$ alkenyl. In some embodiments, $R^2$ is —$CR^bR^c$ and $R^b$ is $C_4$ alkenyl and $R^c$ is $C_4$ alkenyl. In some embodiments, $R^2$ is —$CR^bR^c$ and $R^b$ is $C_4$ alkenyl and $R^c$ is $C_2$ alkenyl. In some embodiments, $R^2$ is —$CR^bR^c$ and $R^b$ is $C_4$ alkenyl and $R^c$ is $C_1$ alkenyl. In some embodiments, $R^2$ is —$CR^bR^c$ and $R^b$ is $C_8$ alkenyl and $R^c$ is $C_2$ alkenyl. In some embodiments, $R^2$ is —$CR^bR^c$ and $R^b$ is $C_6$ alkenyl and $R^c$ is $C_2$ alkenyl. In some embodiments, $R^2$ is —$CR^bR^c$ and $R^b$ is $C_4$ alkenyl and $R^c$ is $C_2$ alkenyl. In some embodiments, $R^2$ is —$CR^bR^c$ and $R^b$ is $C_2$ alkenyl and $R^c$ is $C_2$ alkenyl. In some embodiments, $R^2$ is —$CR^bR^c$ and $R^b$ is $C_1$ alkenyl and $R^c$ is $C_2$ alkenyl. In some embodiments, $R^2$ is —$CR^bR^c$ and $R^b$ is $C_2$ alkenyl and $R^c$ is $C_8$ alkenyl. In some embodiments, $R^2$ is —$CR^bR^c$ and $R^b$ is $C_2$ alkenyl and $R^c$ is $C_6$ alkenyl. In some embodiments, $R^2$ is —$CR^bR^c$ and $R^b$ is $C_2$ alkenyl and $R^c$ is $C_4$ alkenyl. In some embodiments, $R^2$ is —$CR^bR^c$ and $R^b$ is $C_2$ alkenyl and $R^c$ is $C_1$ alkenyl. In some embodiments, $R^2$ is —$CR^bR^c$ and $R^b$ is $C_8$ alkenyl and $R^c$ is $C_1$ alkenyl. In some embodiments, $R^2$ is —$CR^bR^c$ and $R^b$ is $C_6$ alkenyl and $R^c$ is $C_1$ alkenyl. In some embodiments, $R^2$ is —$CR^bR^c$ and $R^b$ is $C_4$ alkenyl and $R^c$ is $C_1$ alkenyl. In some embodiments, $R^2$ is —$CR^bR^c$ and $R^b$ is $C_2$ alkenyl and $R^c$ is $C_1$ alkenyl. In some embodiments, $R^2$ is —$CR^bR^c$ and $R^b$ is $C_1$ alkenyl and $R^c$ is $C_1$ alkenyl. In some embodiments, $R^2$ is —$CR^bR^c$ and $R^b$ is $C_1$ alkenyl and $R^c$ is $C_8$ alkenyl. In some embodiments, $R^2$ is —$CR^bR^c$ and $R^b$ is $C_1$ alkenyl and $R^c$ is $C_6$ alkenyl. In some embodiments, $R^2$ is —$CR^bR^c$ and $R^b$ is $C_1$ alkenyl and $R^c$ is $C_4$ alkenyl. In some embodiments, $R^2$ is —$CR^bR^c$ and $R^b$ is $C_1$ alkenyl and $R^c$ is $C_2$ alkenyl.

In some embodiments, $R^2$ is —$C_6H_{13}$, —$C_7H_{15}$, —$C_8H_{17}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{36}$, —$C_{19}H_{39}$, —$C_{20}H_{41}$, —$C_{21}H_{43}$, —$C_{22}H_{45}$, —$C_{23}H_{47}$, —$C_{24}H_{49}$, —$C_6H_{12}$, —$C_7H_{14}$, —$C_8H_{16}$, —$C_{10}H_{20}$, —$C_{11}H_{21}$, —$C_{12}H_{24}$, —$C_{13}H_{26}$, —$C_{14}H_{28}$, —$C_{15}H_{30}$, —$C_{16}H_{32}$, —$C_{17}H_{34}$, —$C_{18}H_{35}$, —$C_{19}H_{38}$, —$C_{20}H_{40}$, —$C_{21}H_{42}$, —$C_{22}H_{44}$, —$C_{23}H_{46}$, or —$C_{24}H_{48}$.

In some embodiments, $R^3$ is

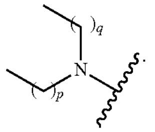

In some embodiments, p and q are 0. In some embodiments, p and q are 1. In some embodiments, p and q are 2. In some embodiments, p and q are 3. In some embodiments, p and q are 4. In some embodiments, p is 0 and q is 1. In some embodiments, p is 0 and q is 2. In some embodiments, p is 0 and q is 3. In some embodiments, p is 0 and q is 4. In some embodiments, p is 1 and q is 2. In some embodiments, p is 1 and q is 3. In some embodiments, p is 1 and q is 4. In some embodiments, p is 2 and q is 1. In some embodiments, p is 2 and q is 3. In some embodiments, p is 2 and q is 4. In some embodiments, p is 3 and q is 1. In some embodiments, p is 3 and q is 2. In some embodiments, p is 3 and q is 4. In some embodiments, p is 4 and q is 1. In some embodiments, p is 4 and q is 2. In some embodiments, p is 4 and q is 3.

In some embodiments, M is CH. In some embodiments, M is

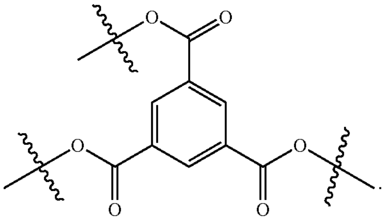 [SMILES: *OC(=O)c1cc(C(=O)O*)cc(C(=O)O*)c1]

In some embodiments, M is

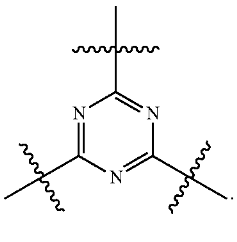 [SMILES: *c1nc(*)nc(*)n1]

In some embodiments, M is
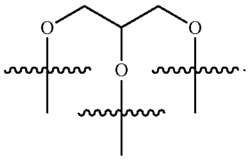 [SMILES: *OCC(CO*)O*]
In some embodiments, M is
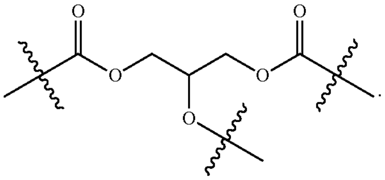 [SMILES: *OC(COC(*)=O)COC(*)=O]
In some embodiments, M is
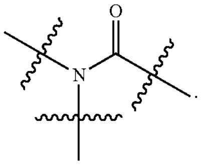 [SMILES: *C(=O)N(*)*]
In some embodiments, M is
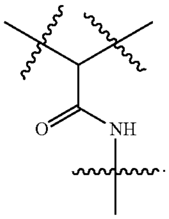 [SMILES: *NC(=O)C(*)*]
In some embodiments, M is
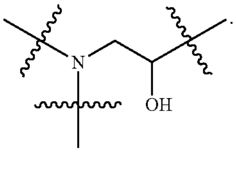 [SMILES: *C(O)CN(*)*]
In some embodiments, $R^3$ is
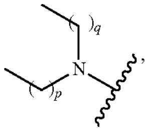, 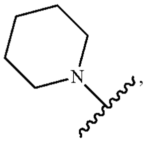, 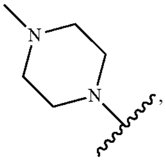, 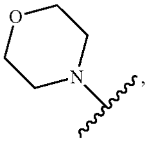, 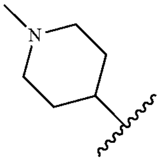, 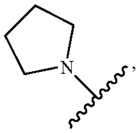, or 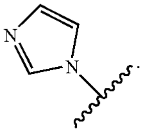.
In some embodiments, $R^6$ is H, $OR^b$, CN, $—C(=O)OR^b$, $—NC(=O)R^b$, $—C(=O)NR^b$,
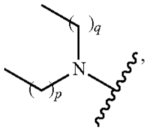, 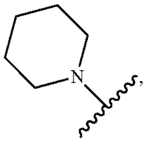, 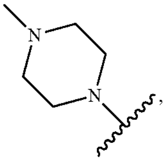, 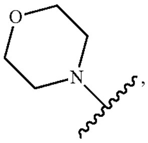, 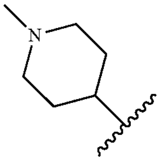, 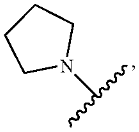, or 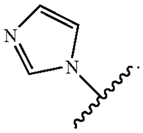.

In some embodiments, the compounds of Formula Y, I, Ia, or II-V can be selected from:
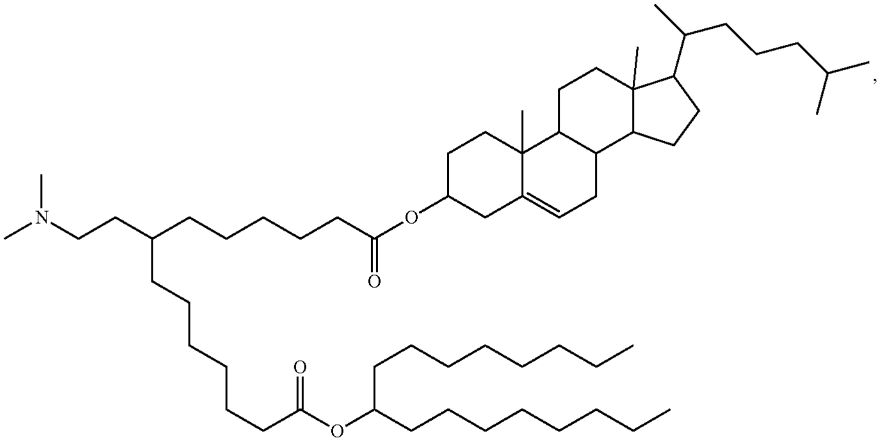
,
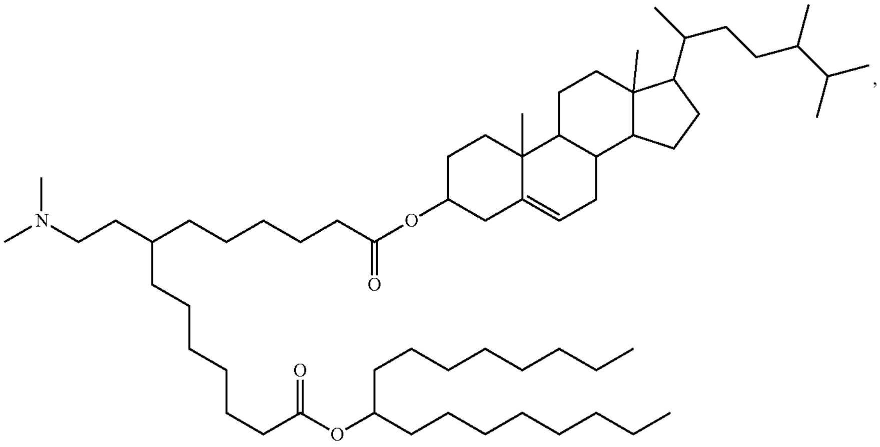
,
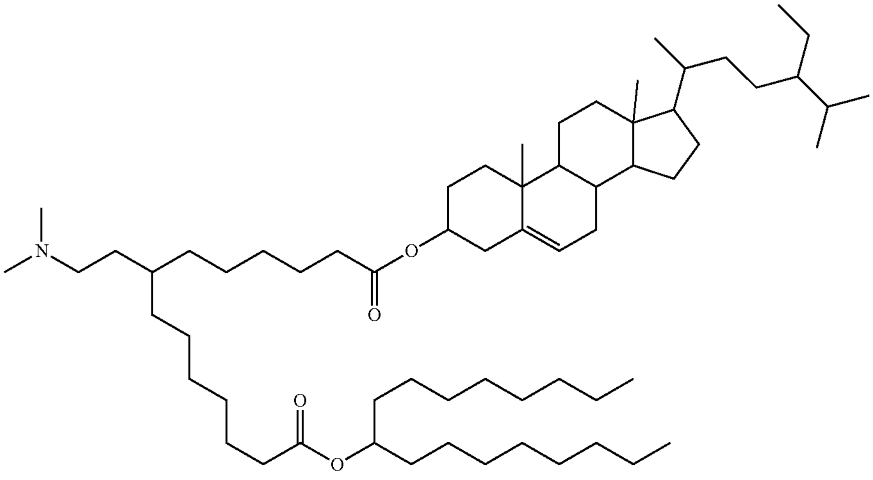
, -continued
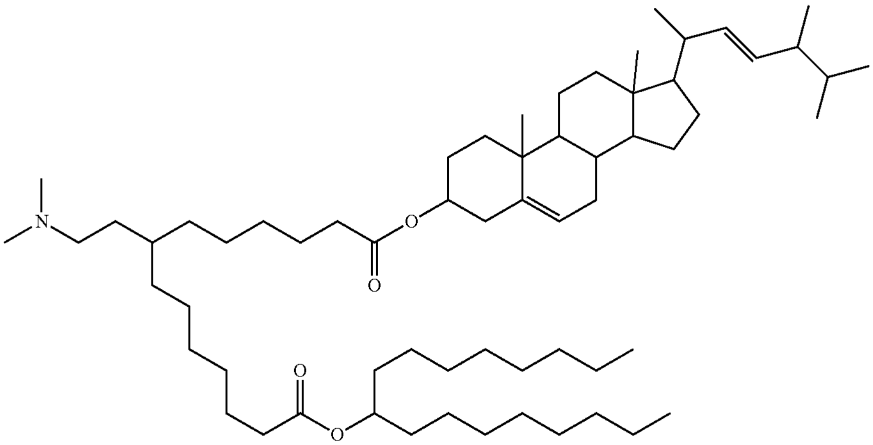
,
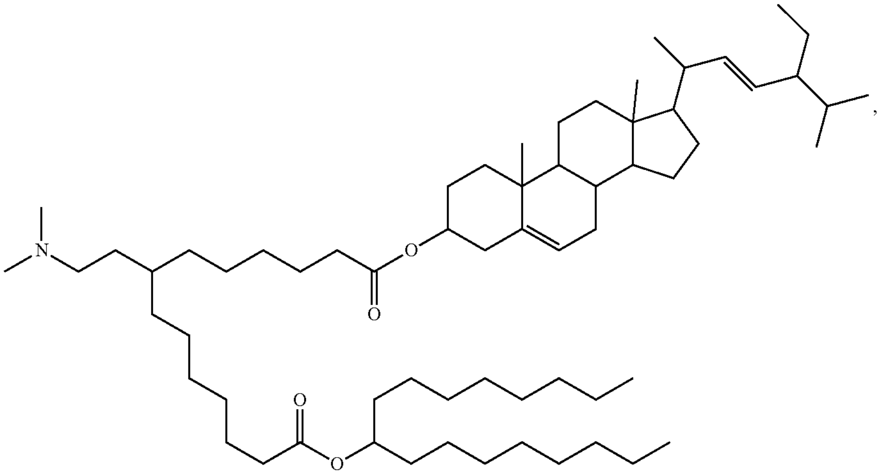
,
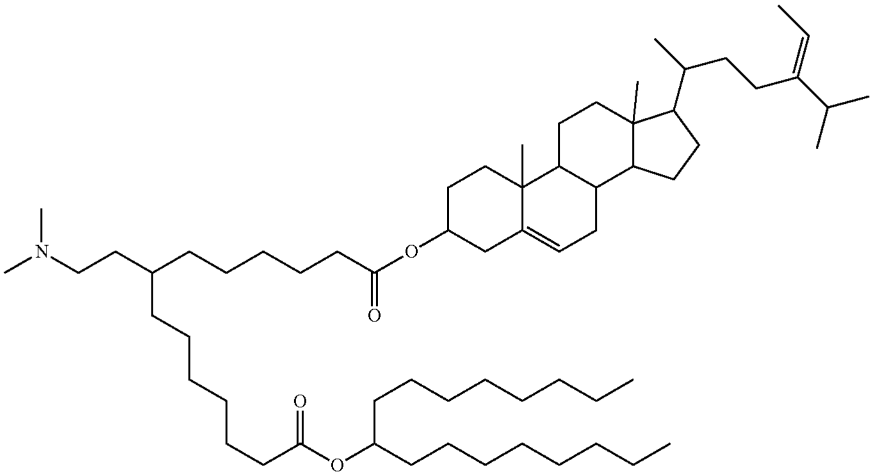
, -continued
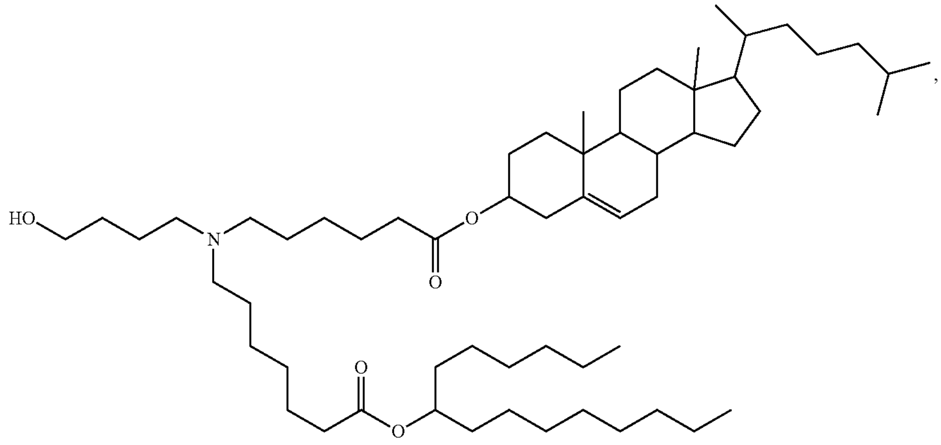
,
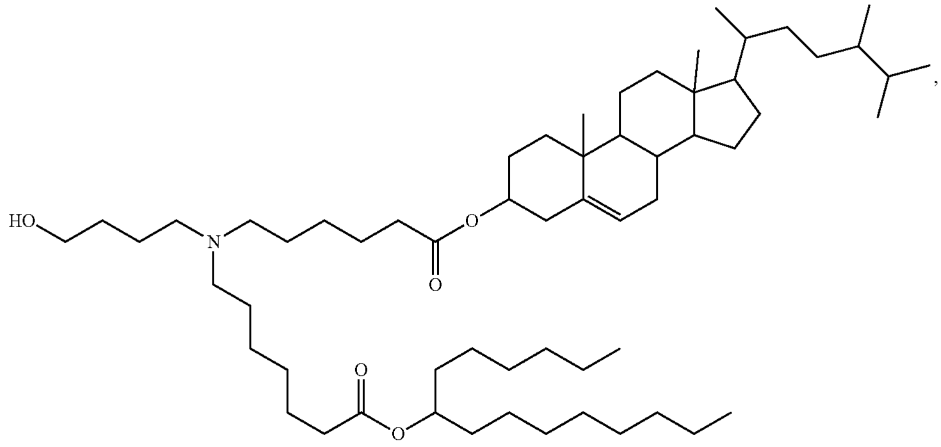
,
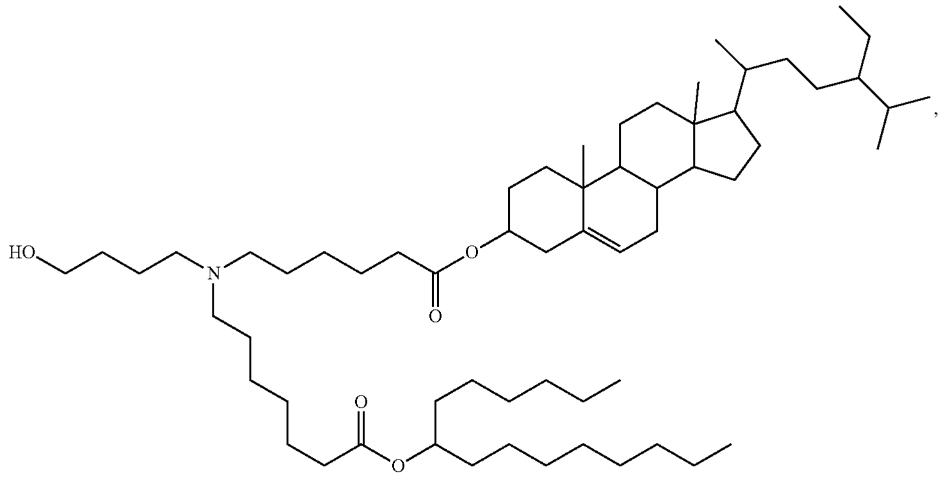
, -continued
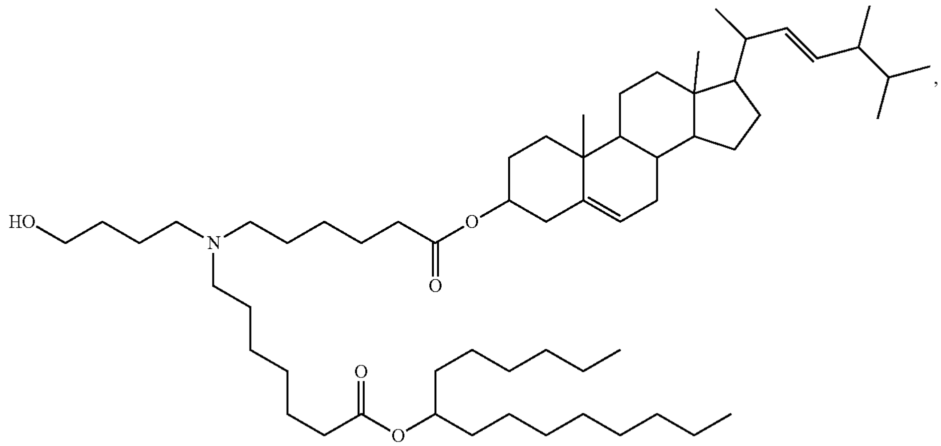
,
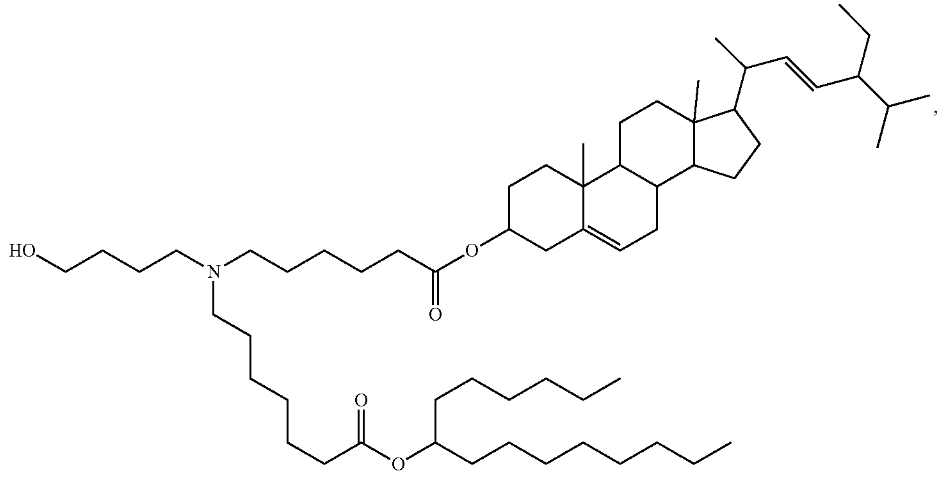
,
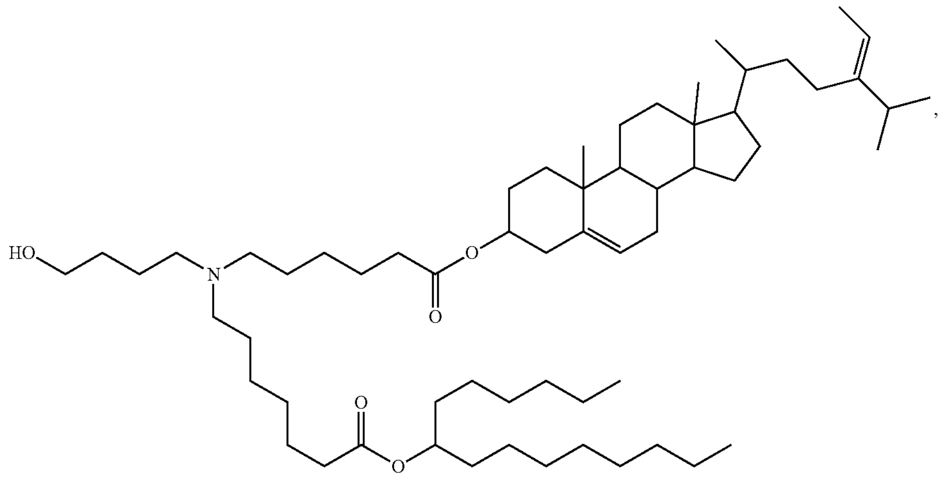
, -continued
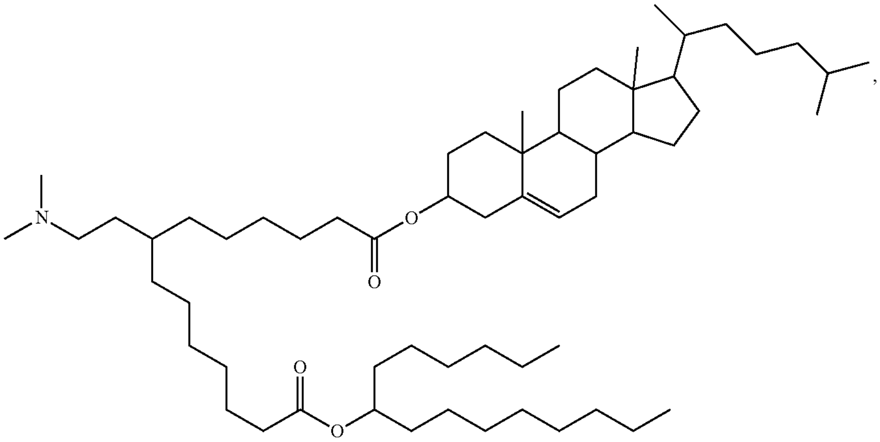
,
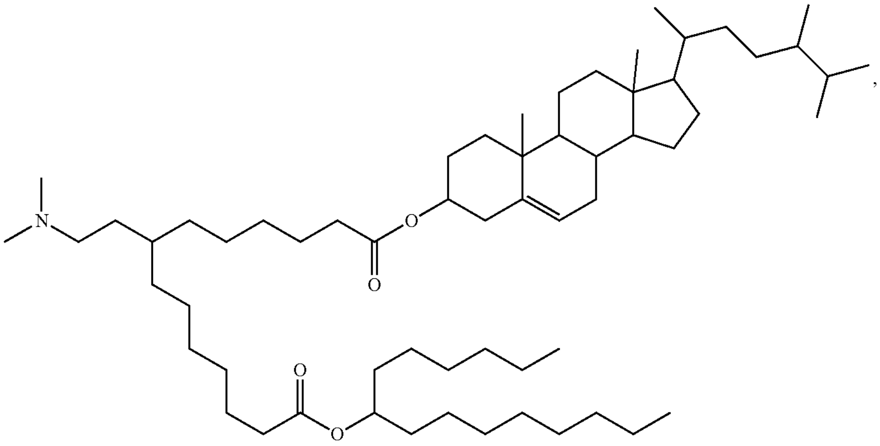
,
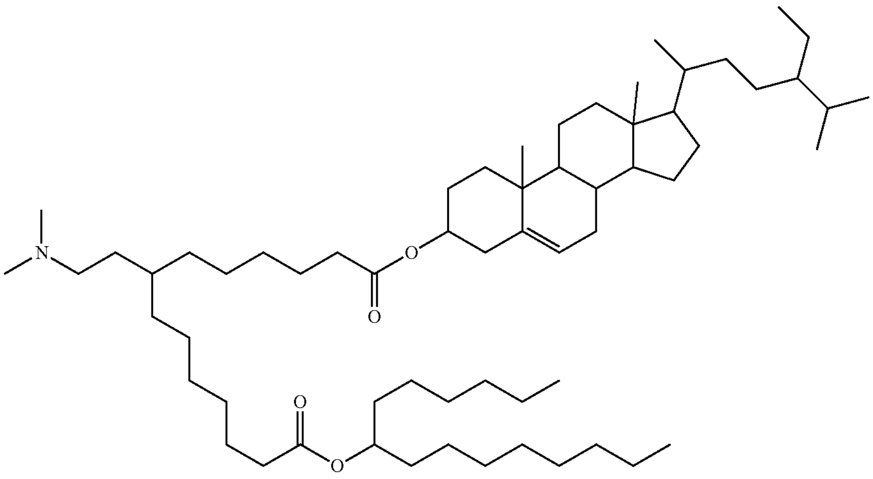
, -continued
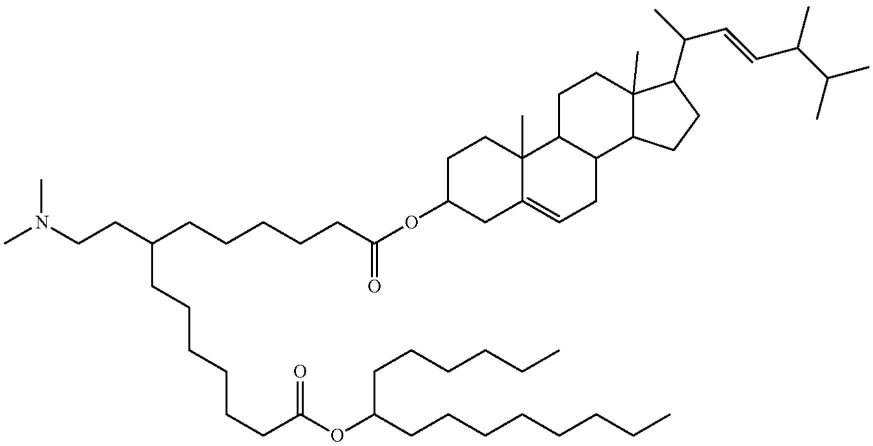
,
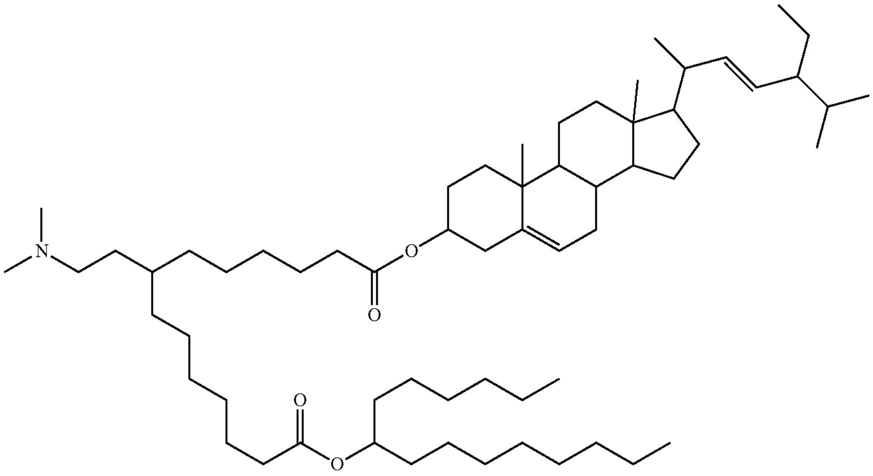
,
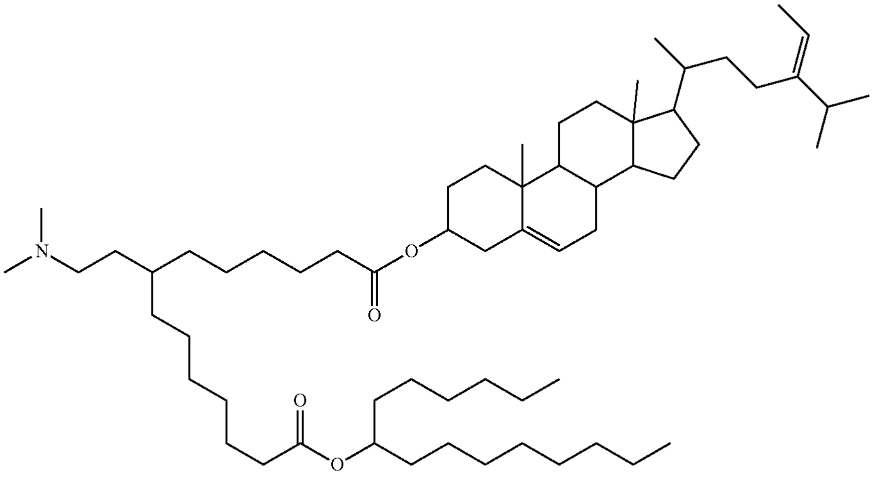
, -continued
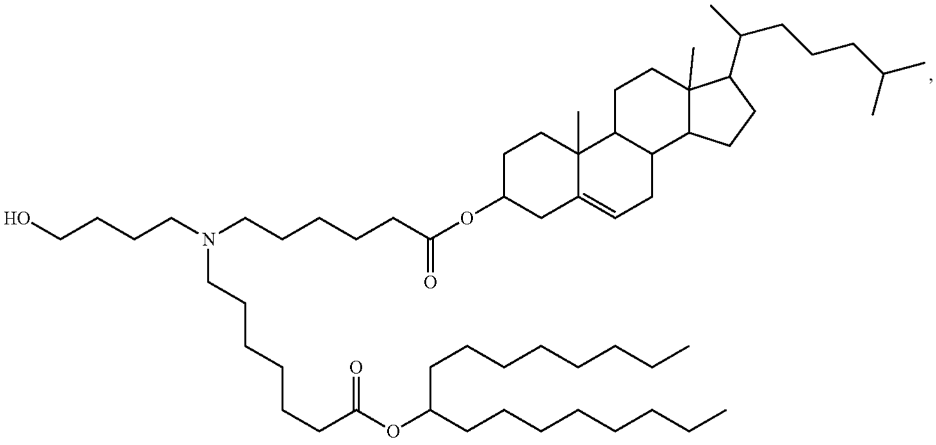
,
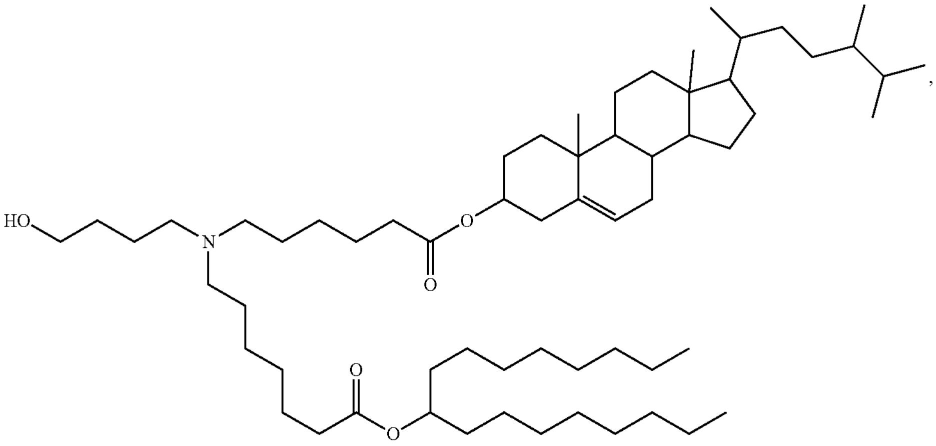
,
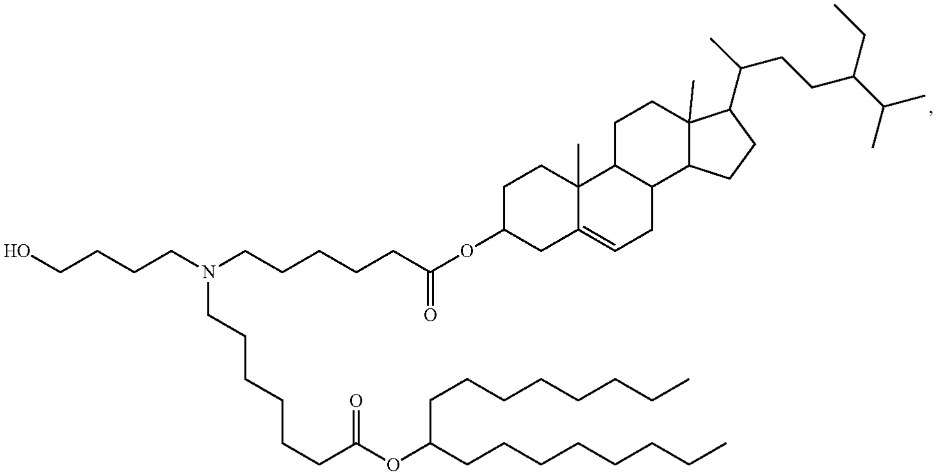
, -continued
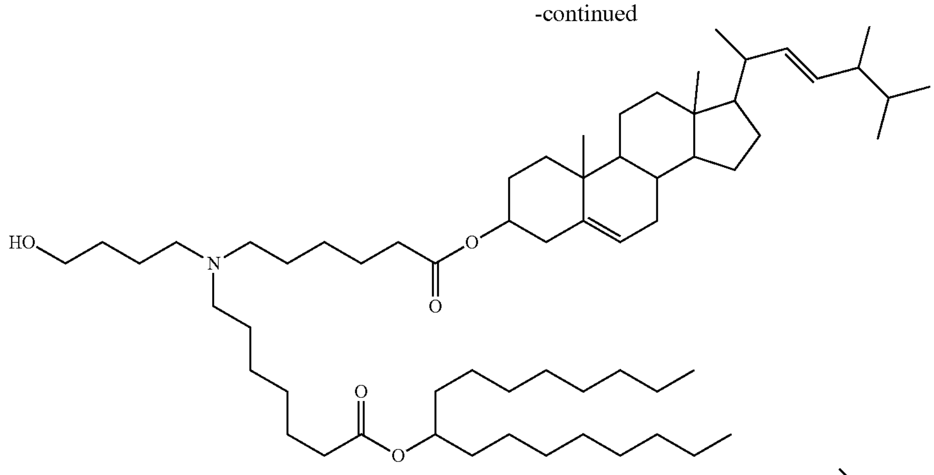
,
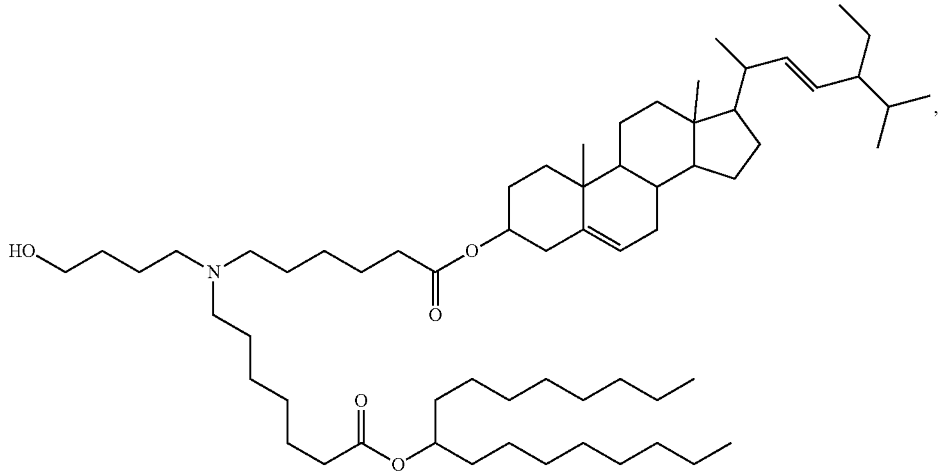
,
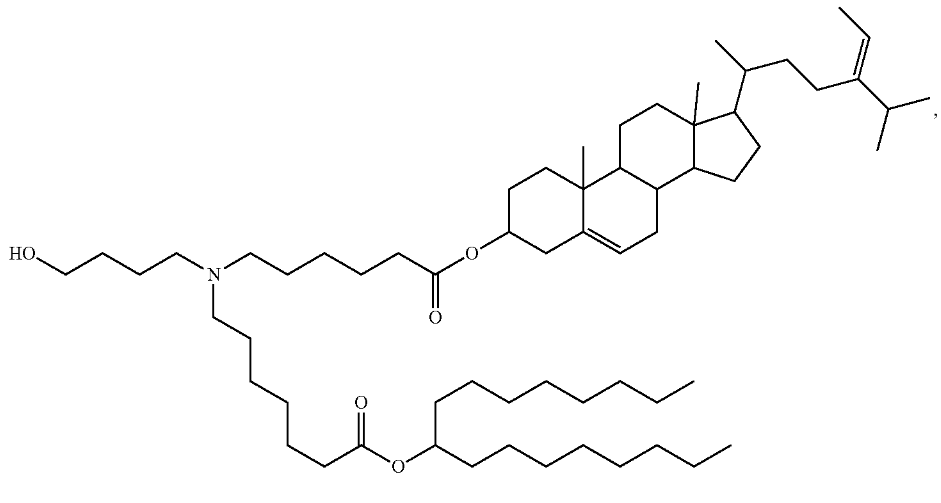
, -continued
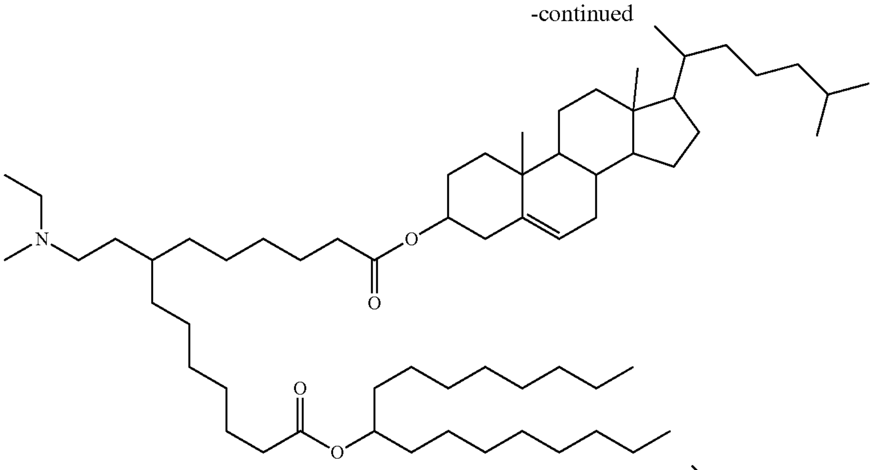
,
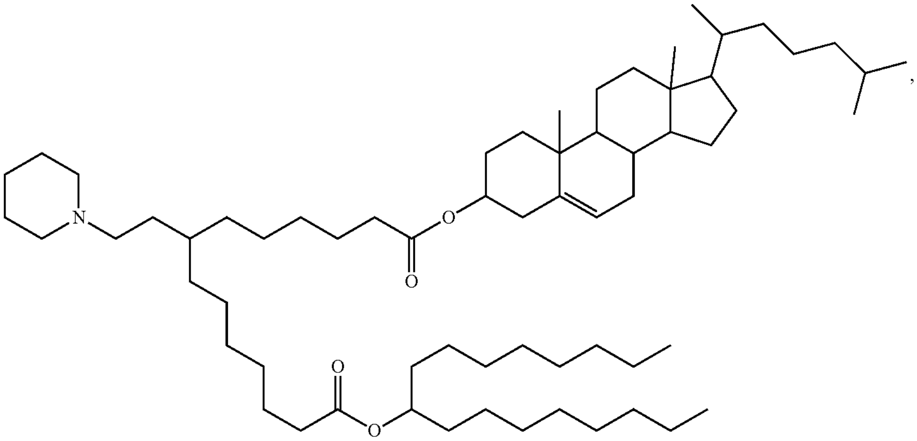
,
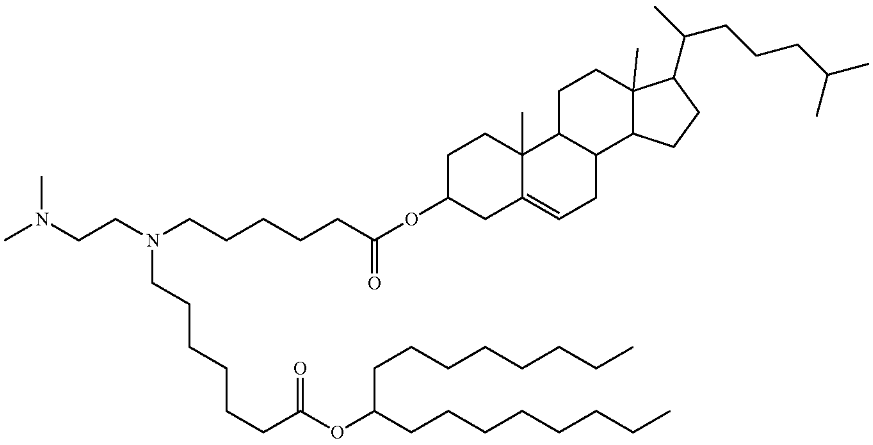
, -continued
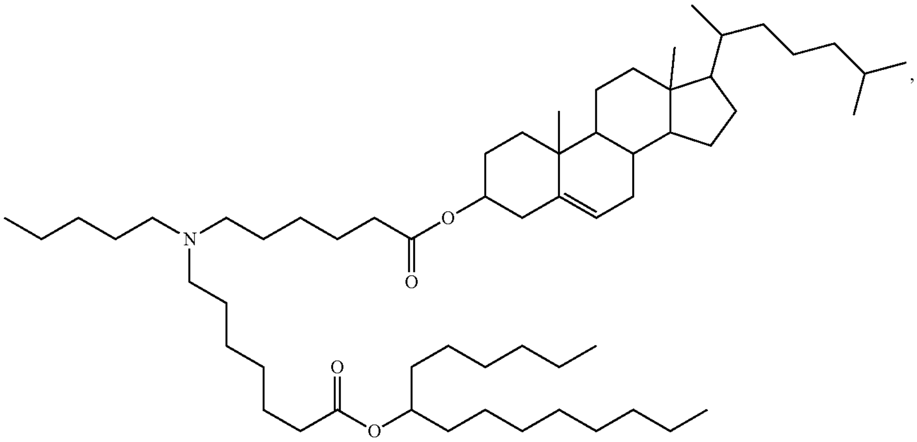
,
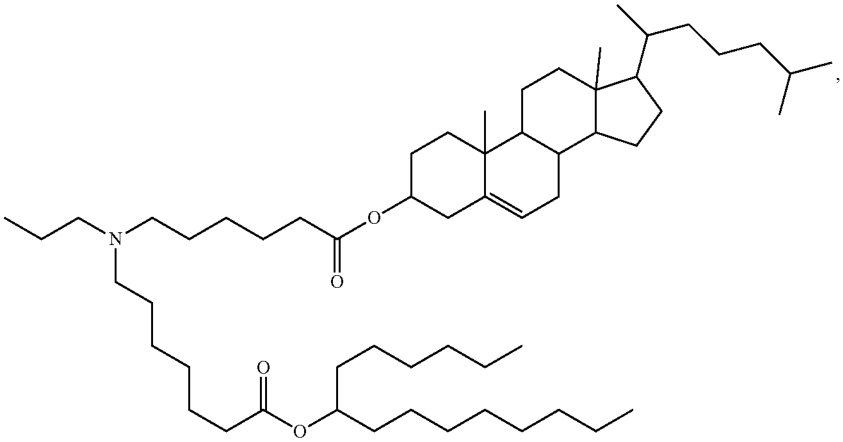
,
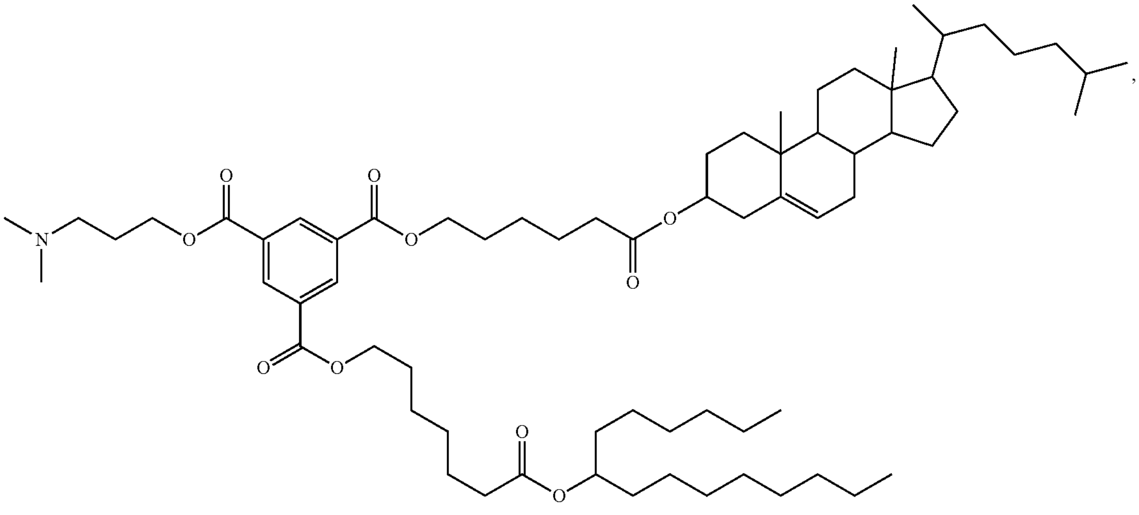
, -continued
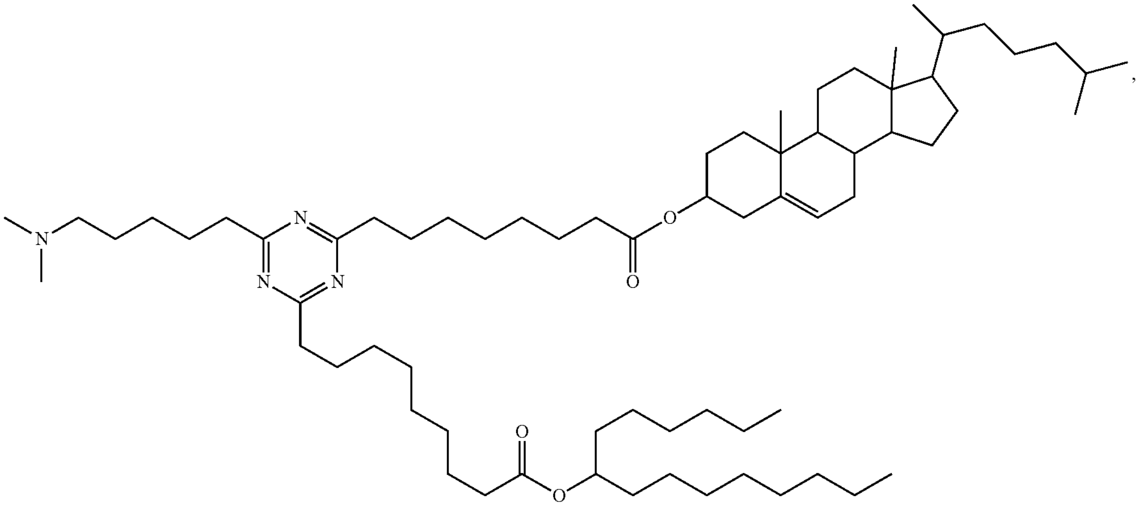
,
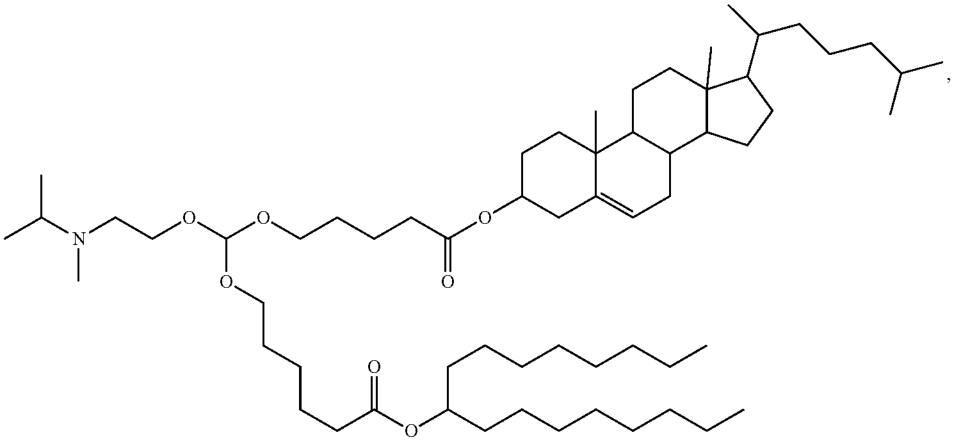
,
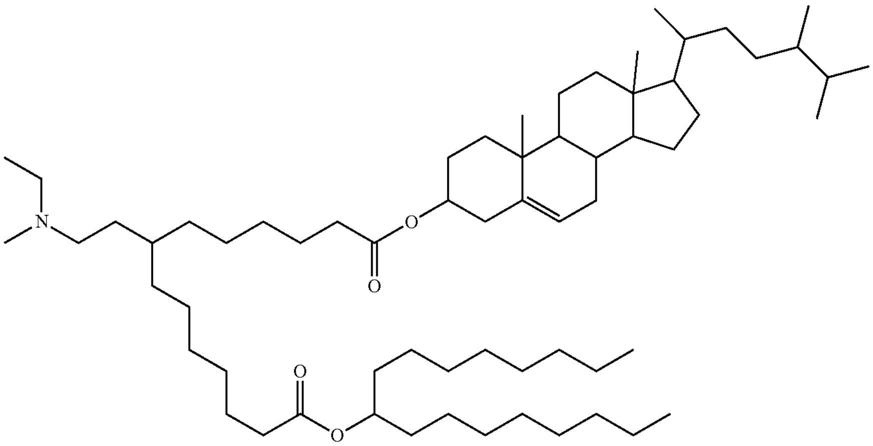
, -continued
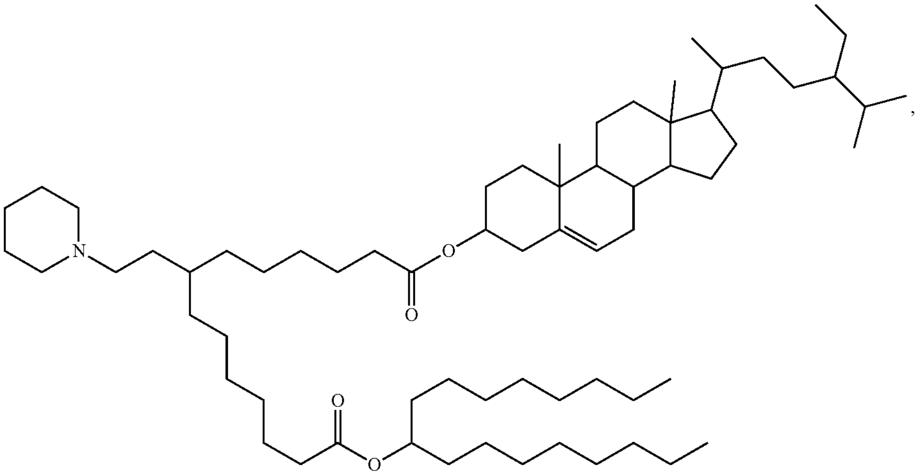
,
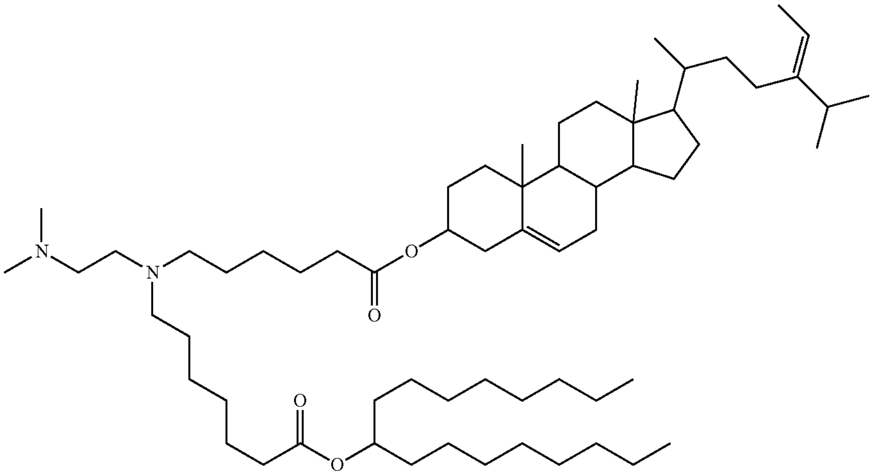
,
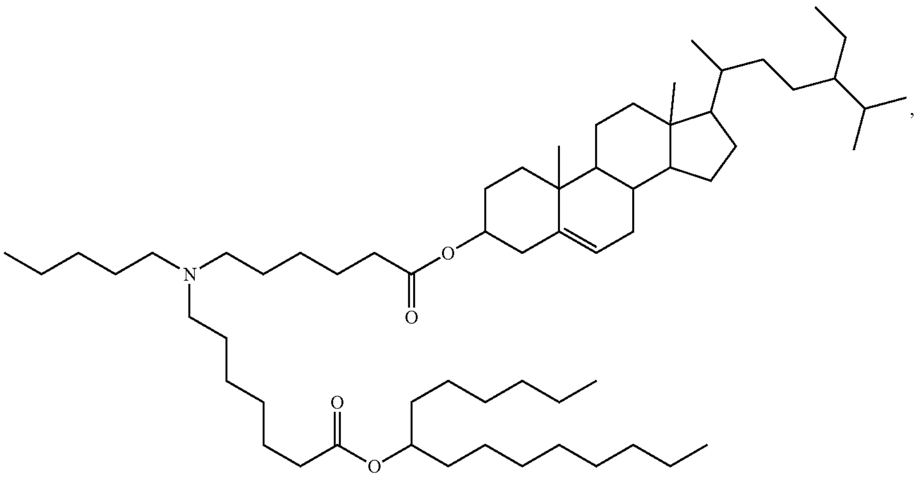
, -continued
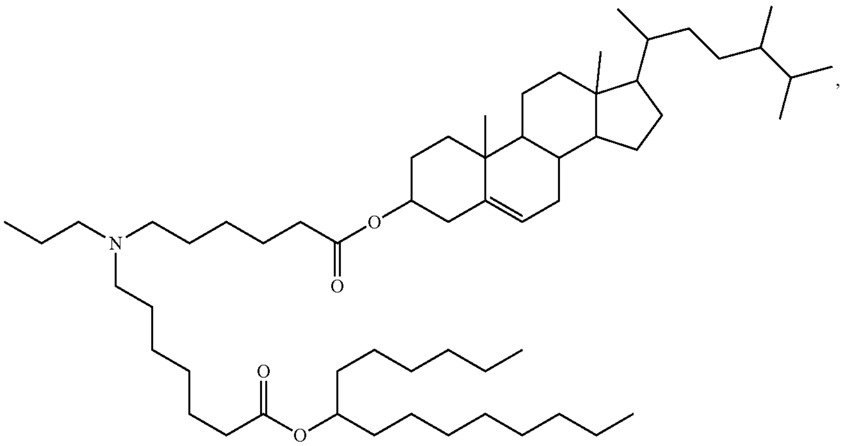
,
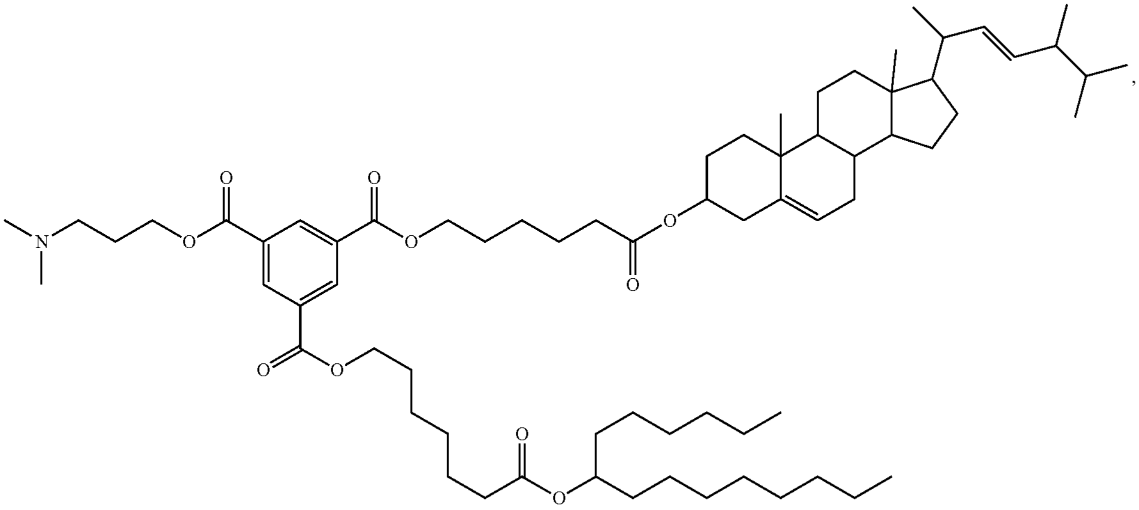
,
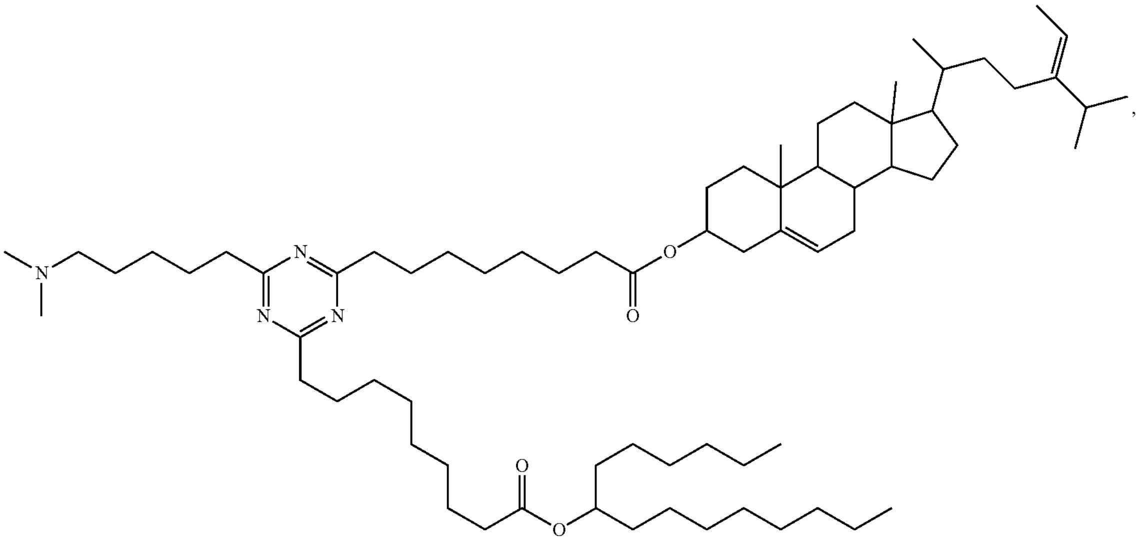
, -continued
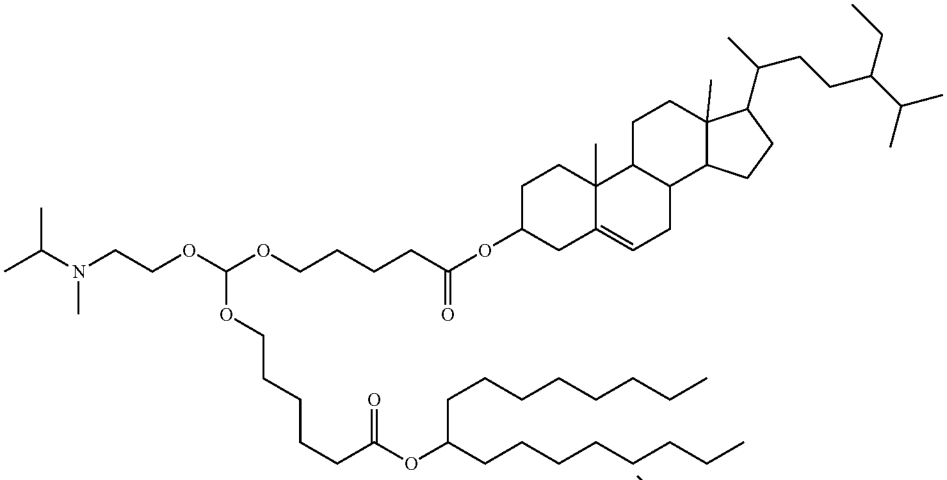
,
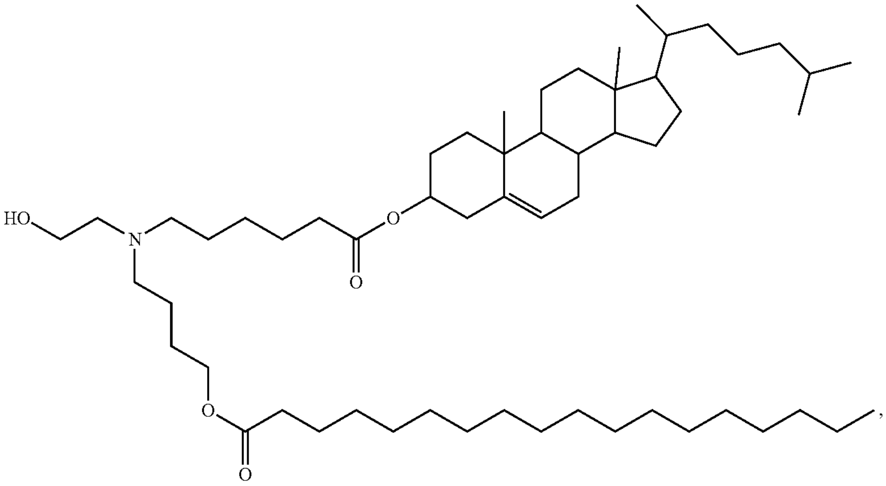
,
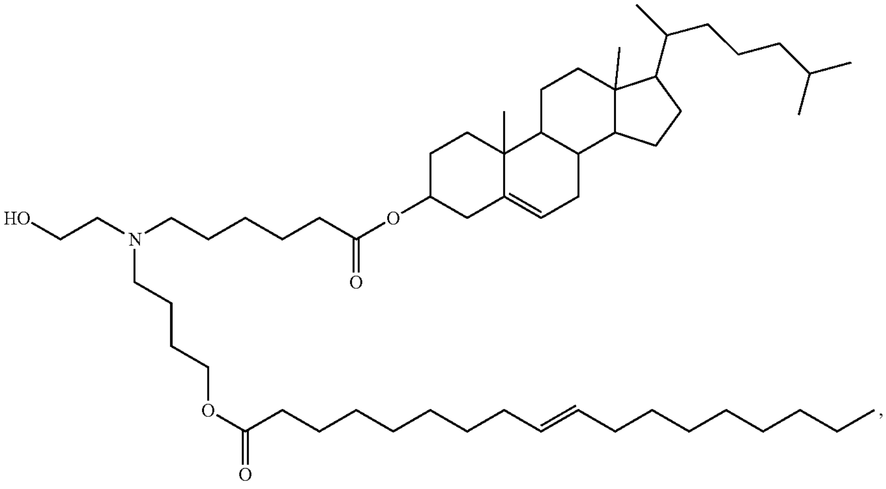
, -continued
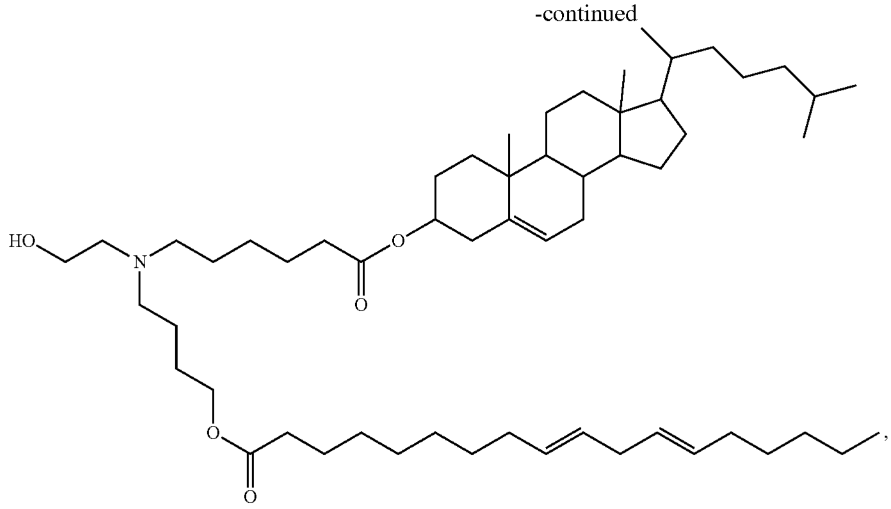
,
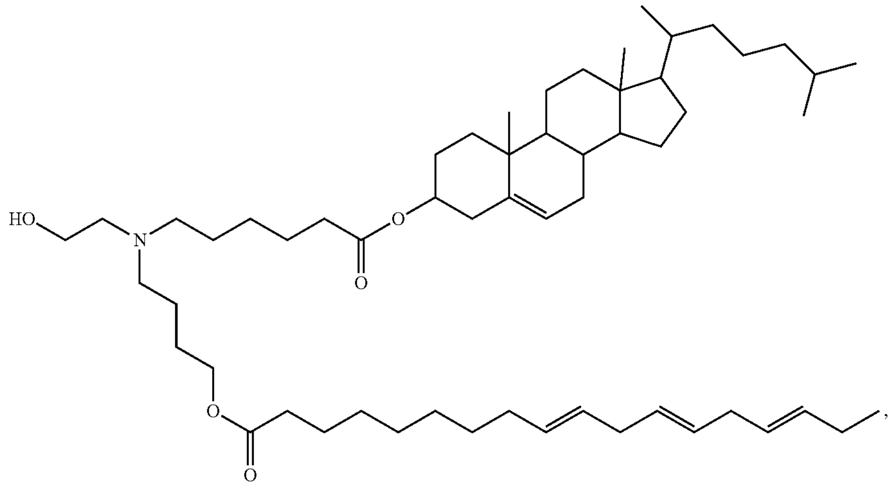
,
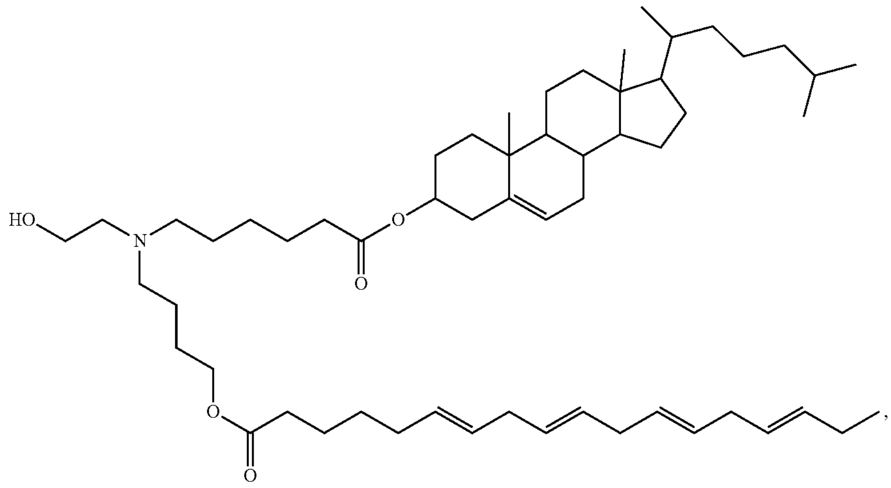
, -continued
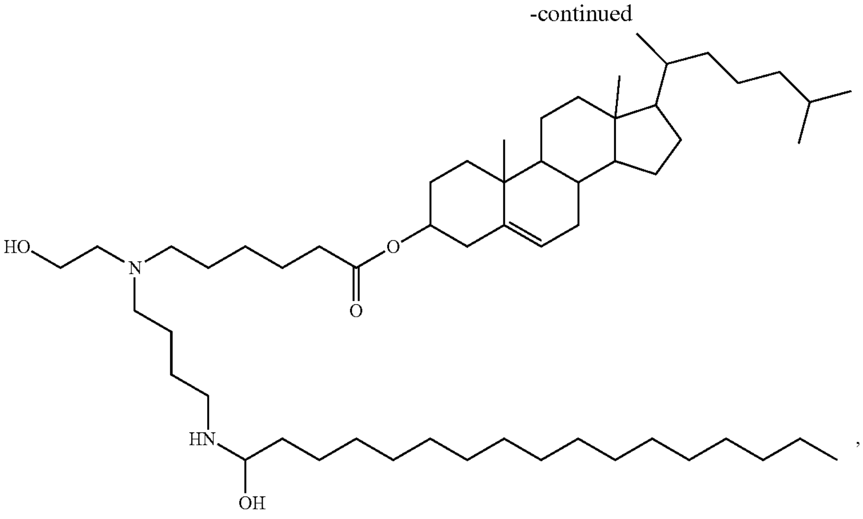
,
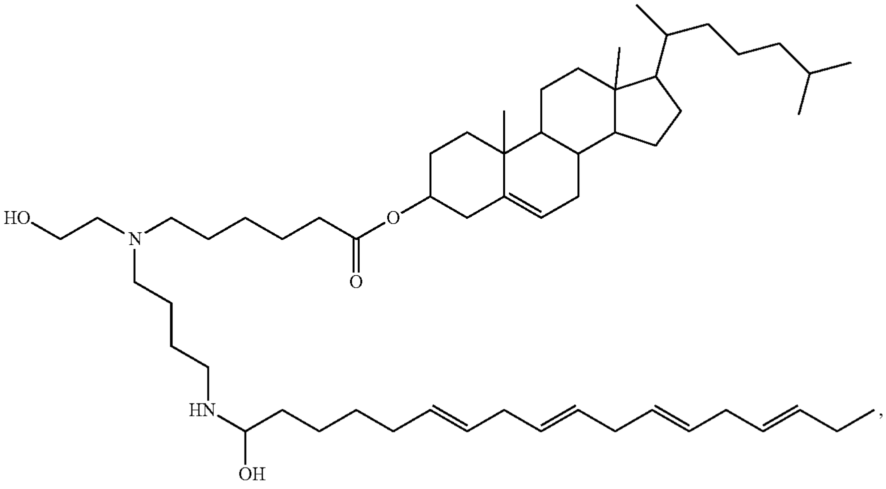
,
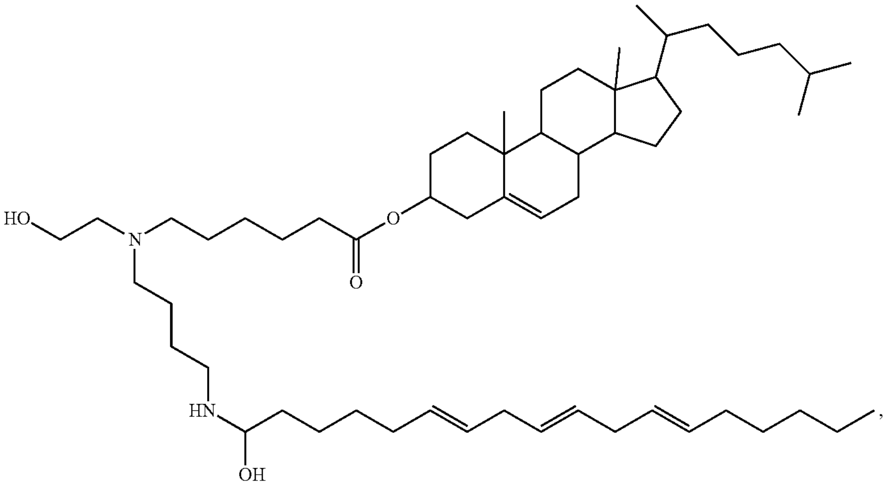
, -continued
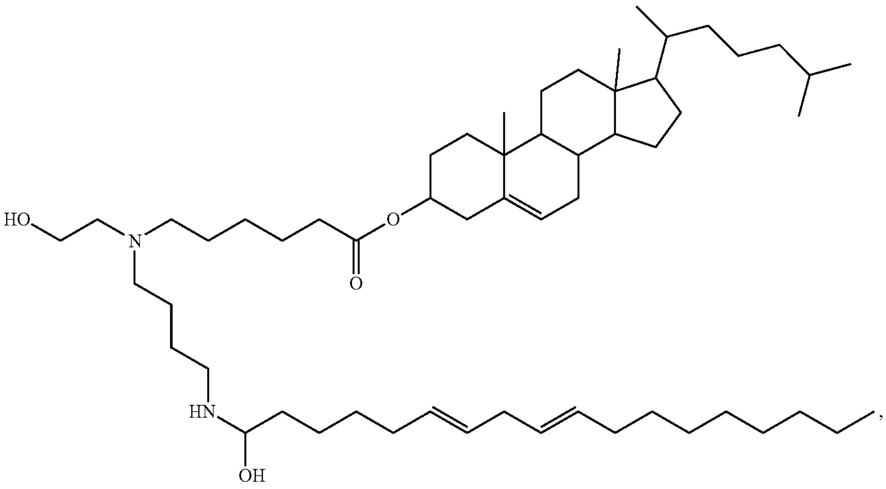
,
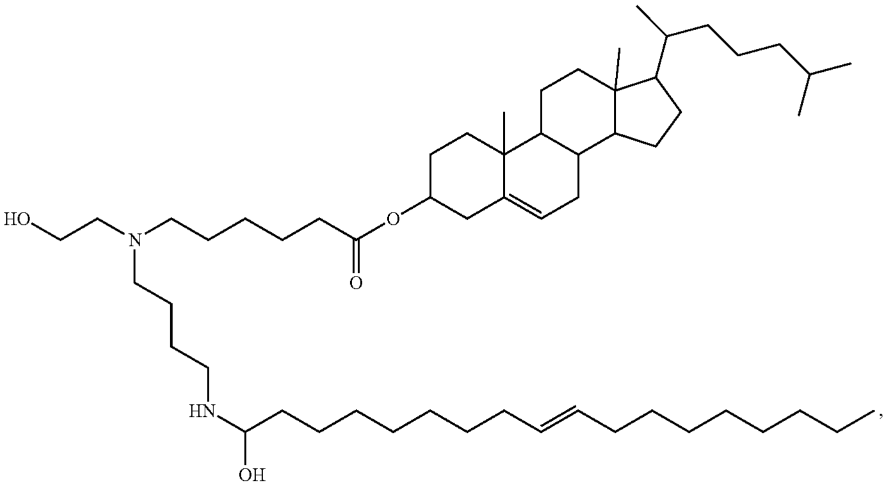
,
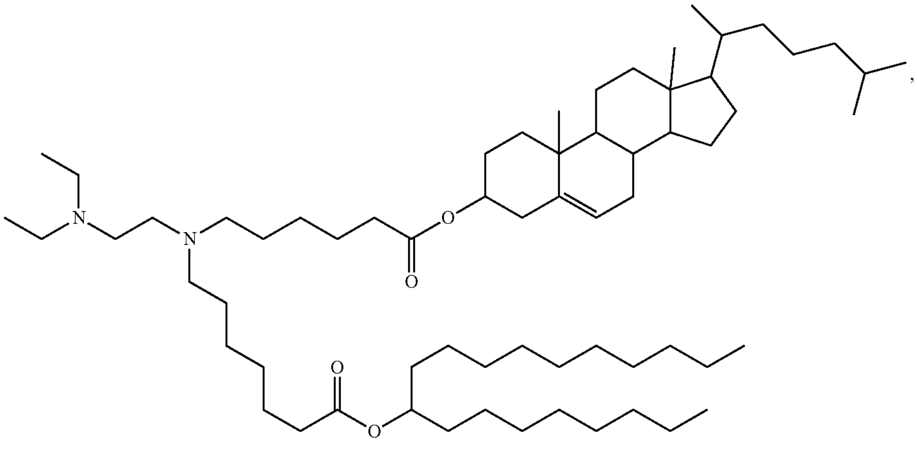
, -continued
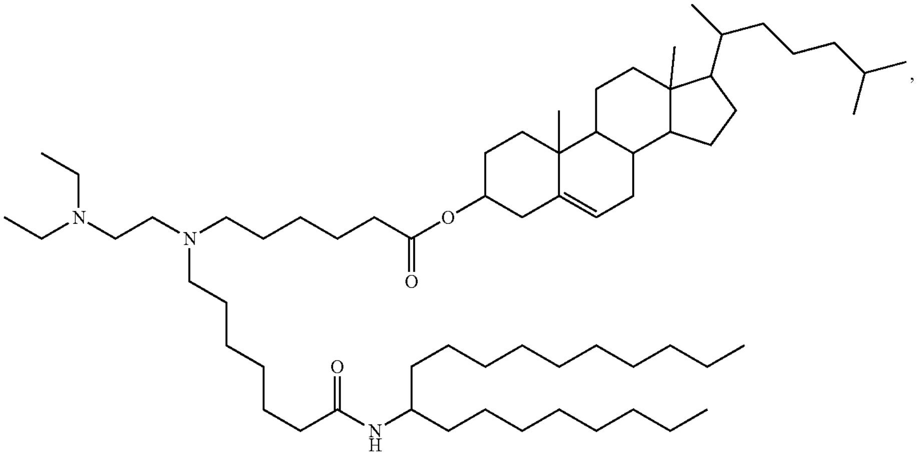
,
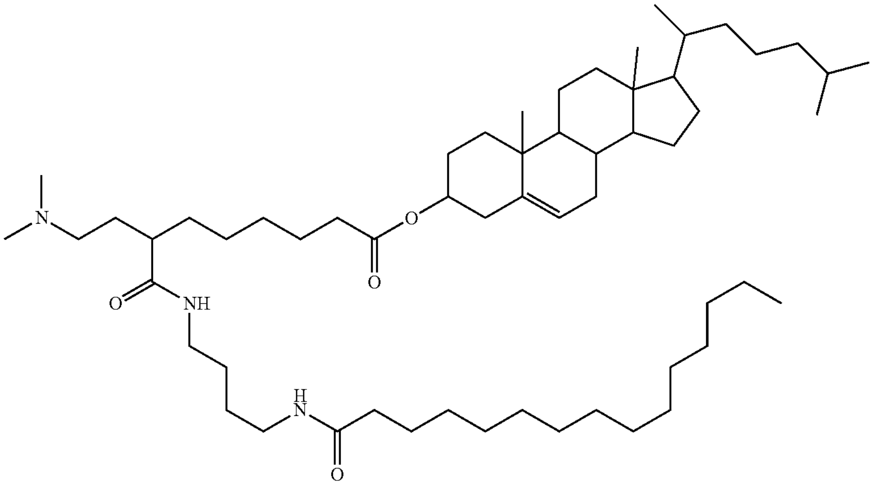
,
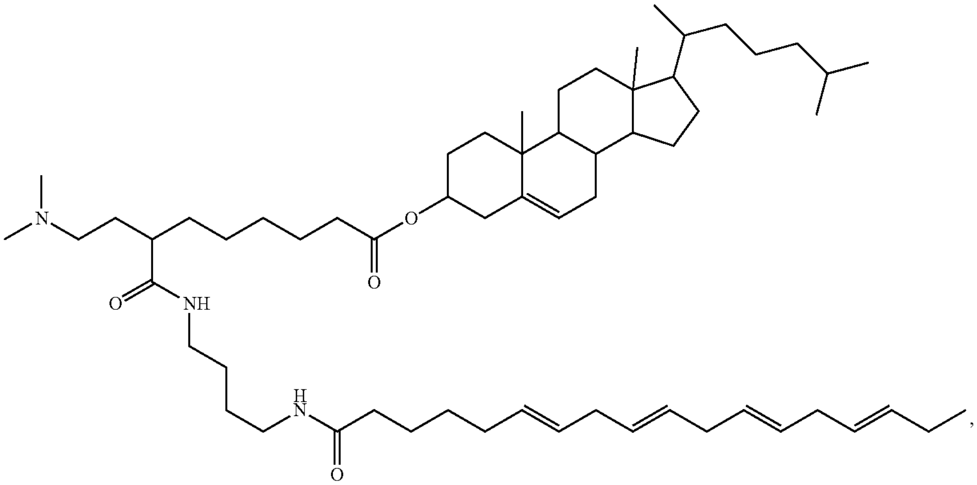
,

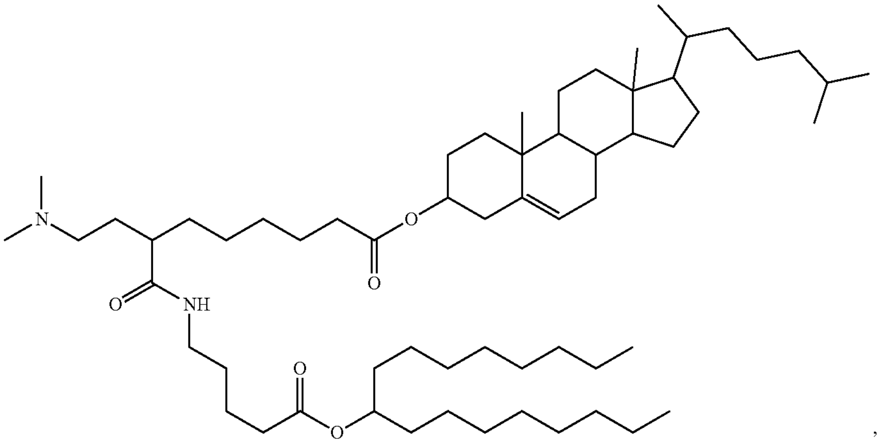
,
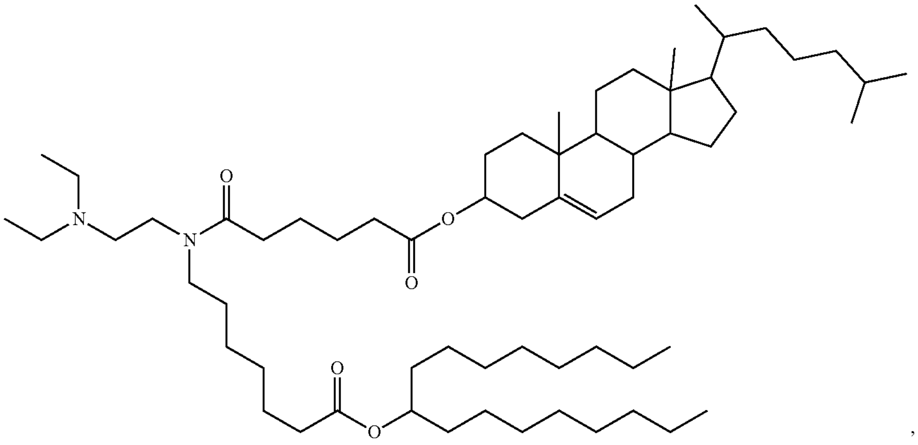
,
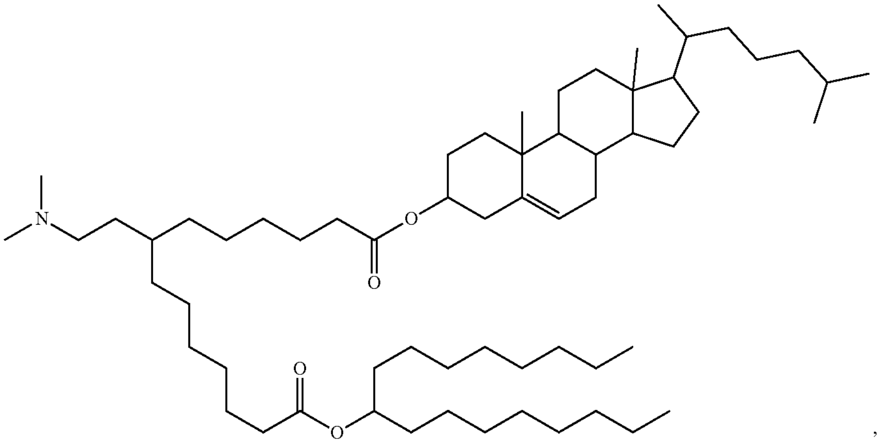
,

-continued
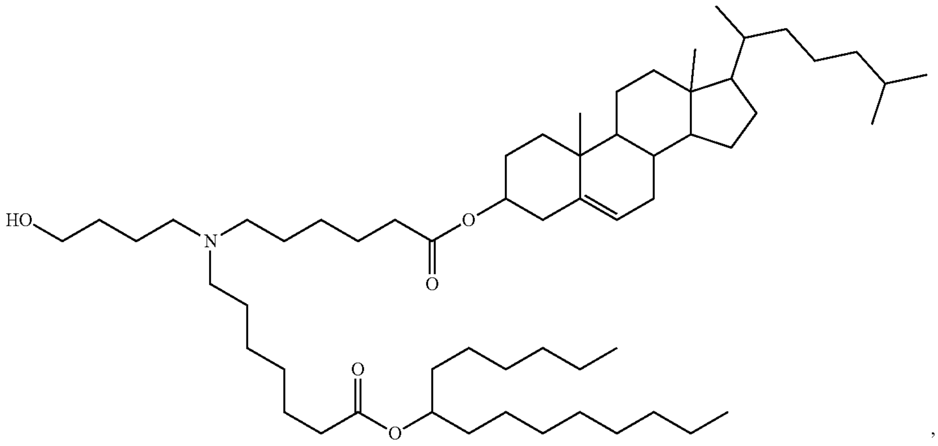
,
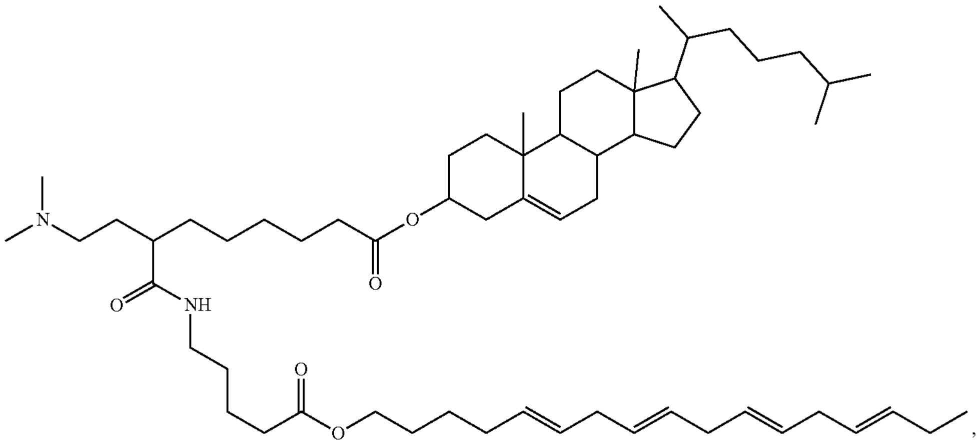
,
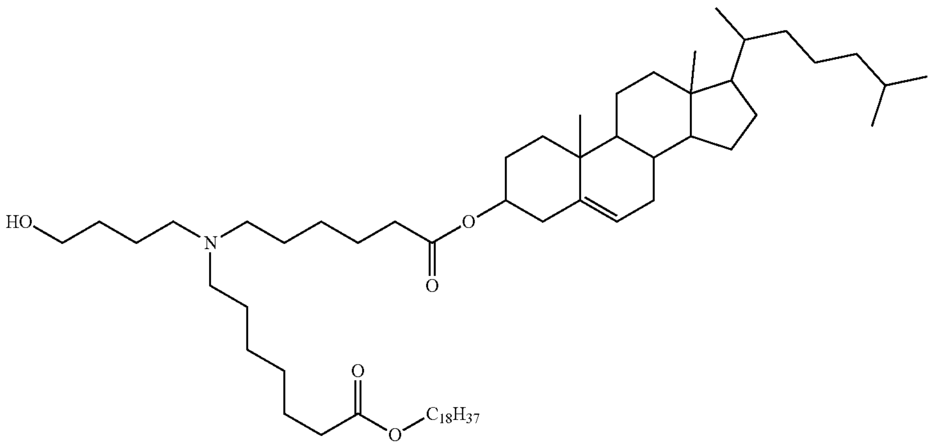
,

-continued
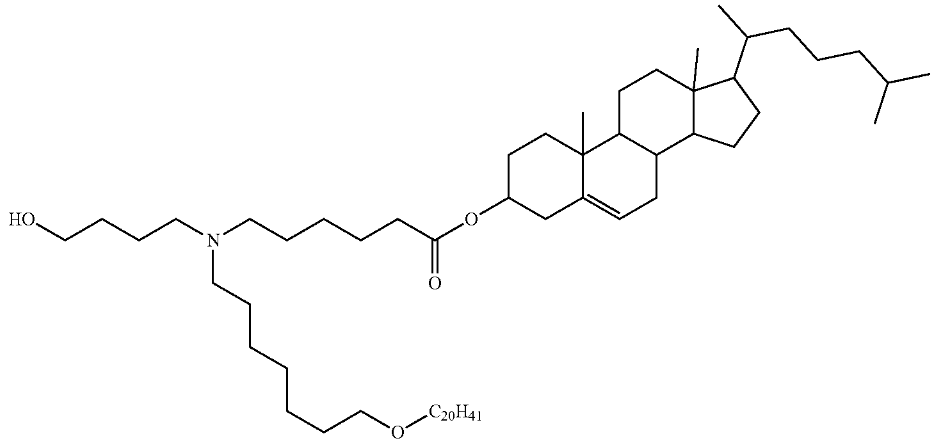
,
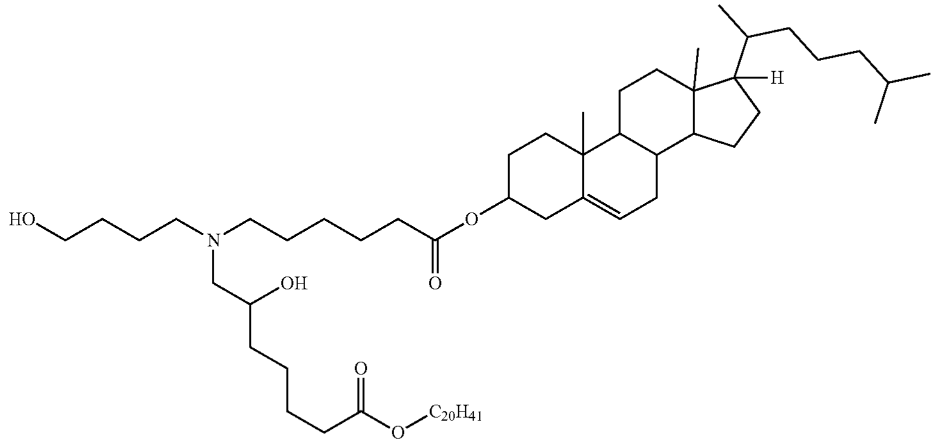
,
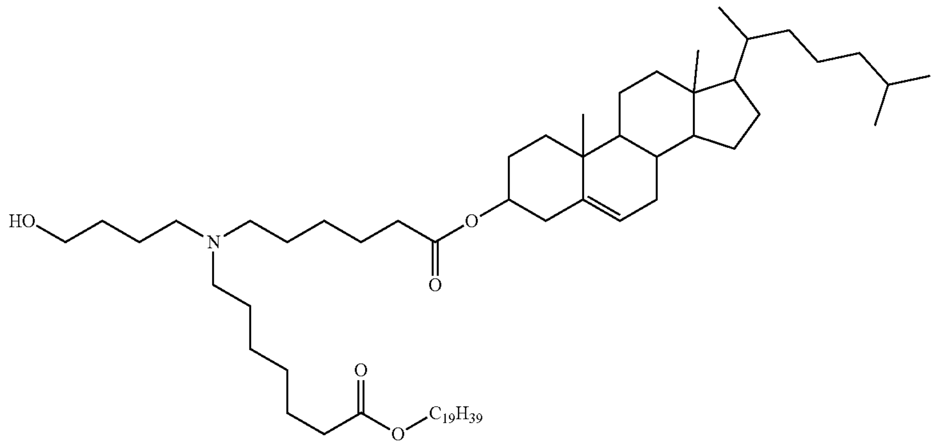
,

-continued
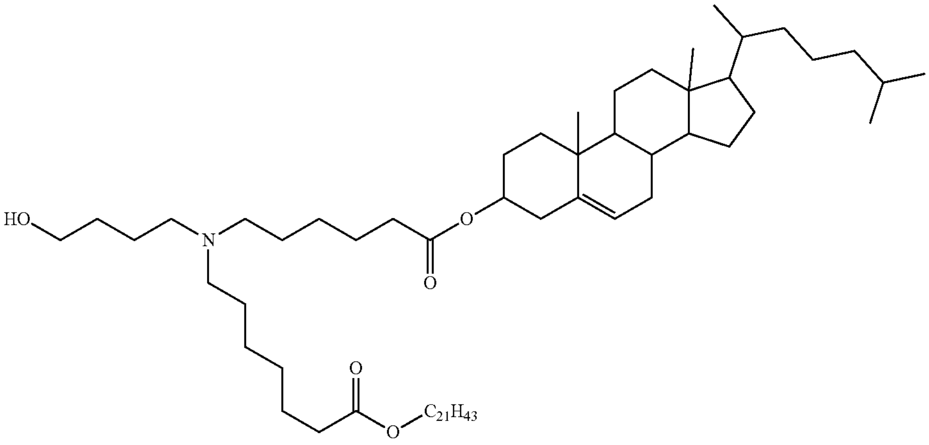
,
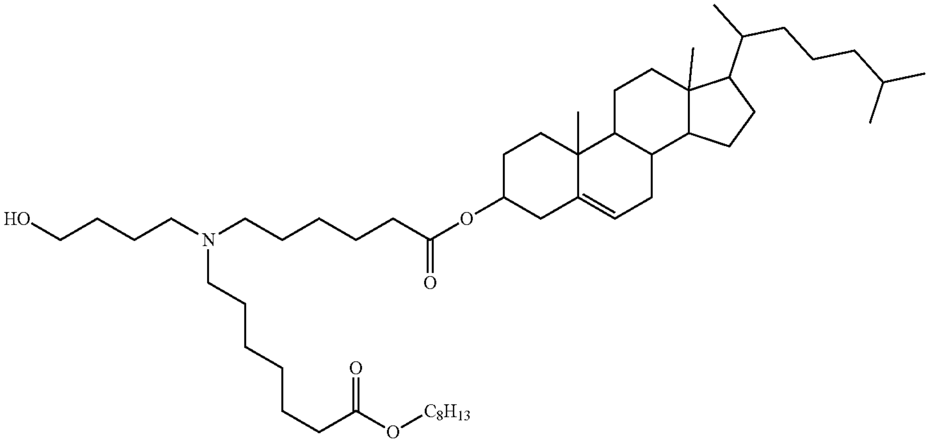
,
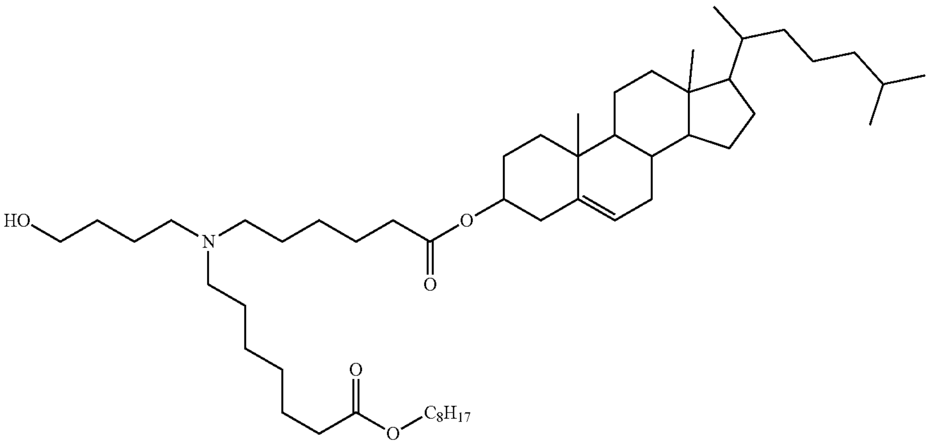
,

-continued
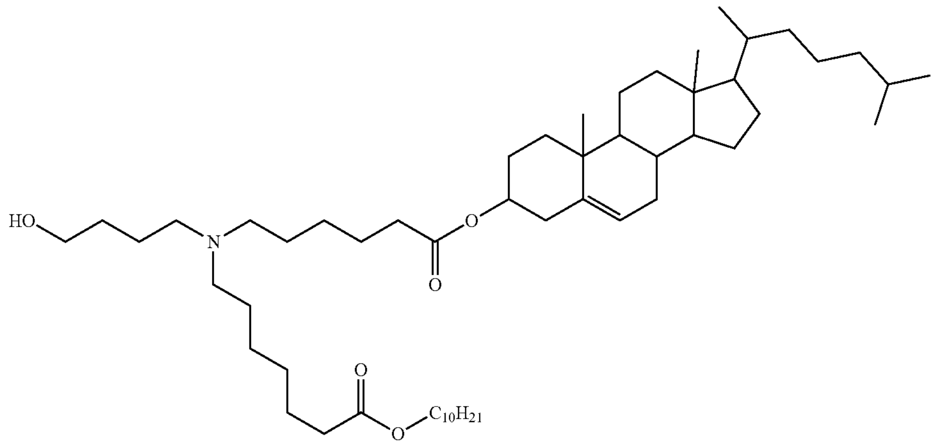
,
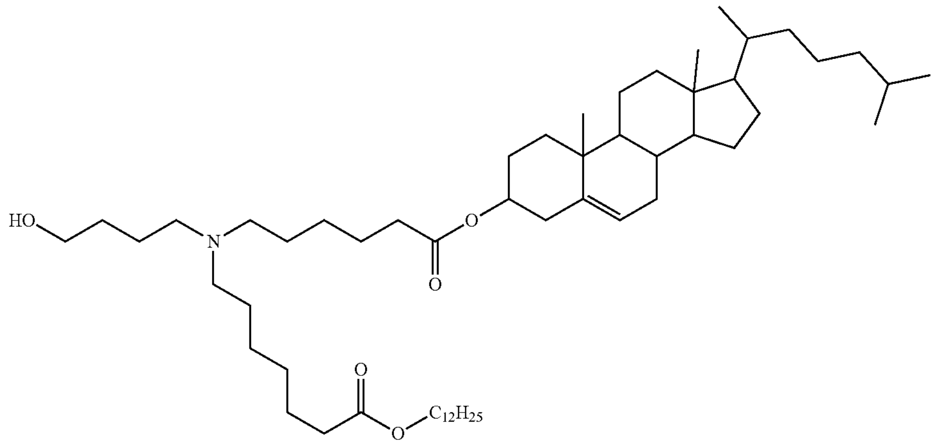
,
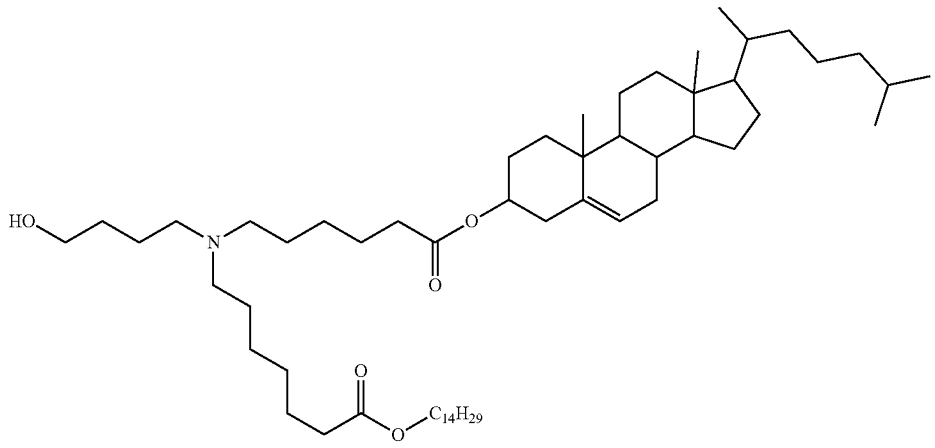
,

-continued
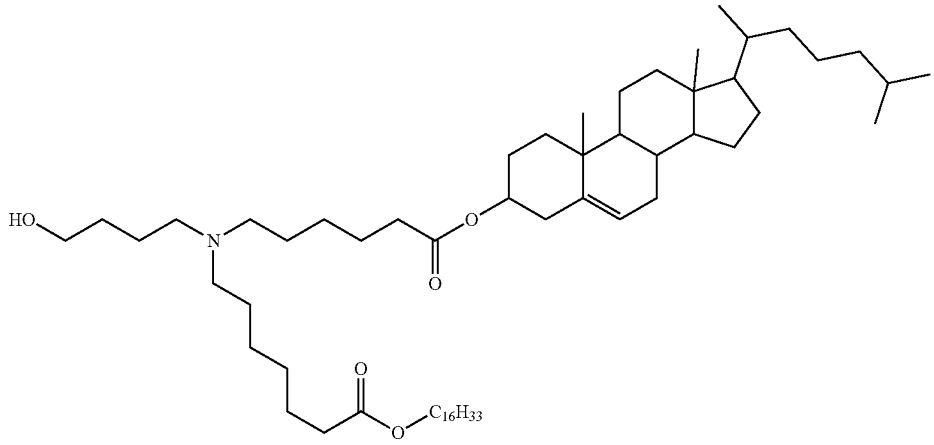
,
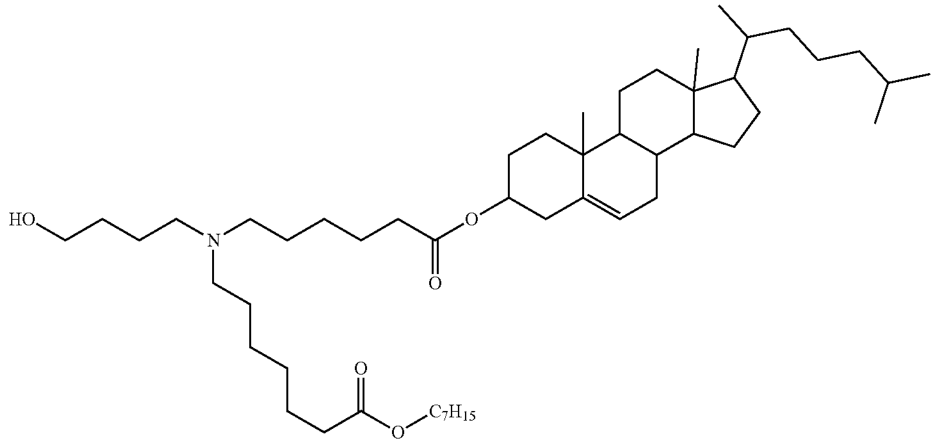
,
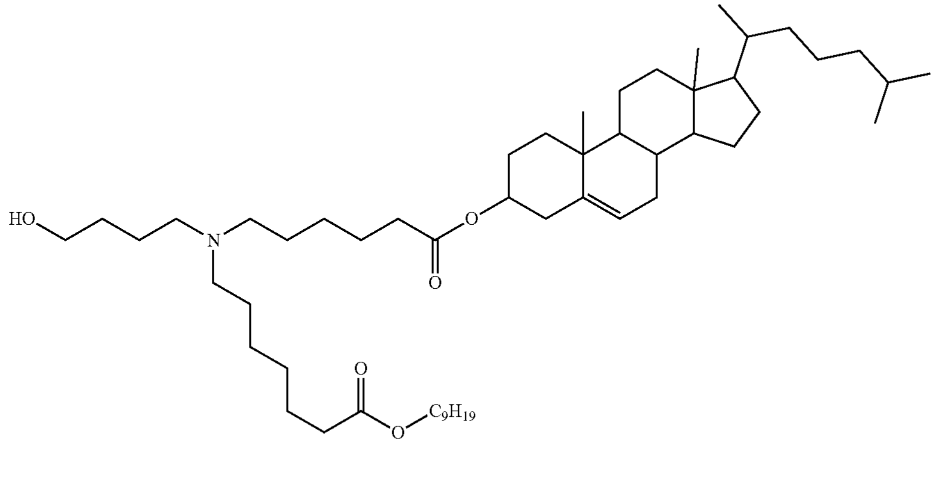
,

-continued
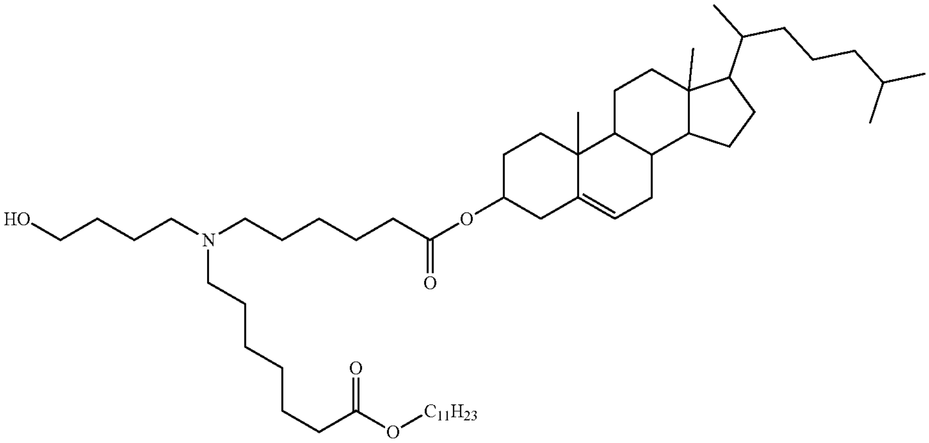
,
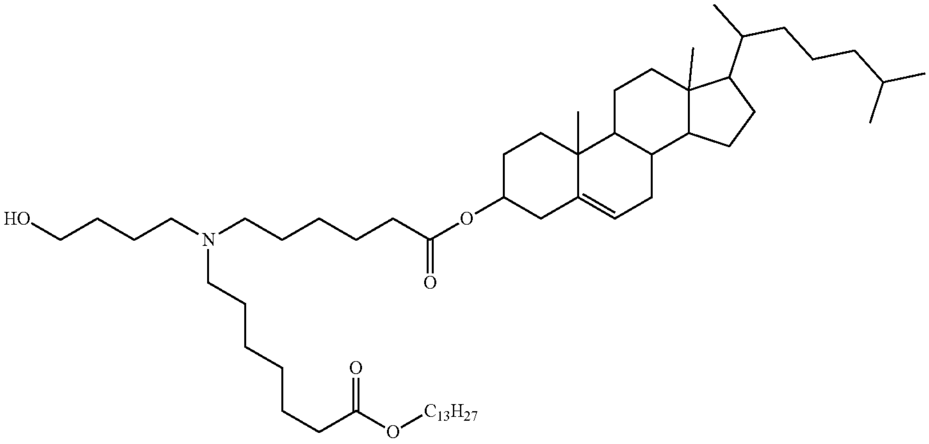
,
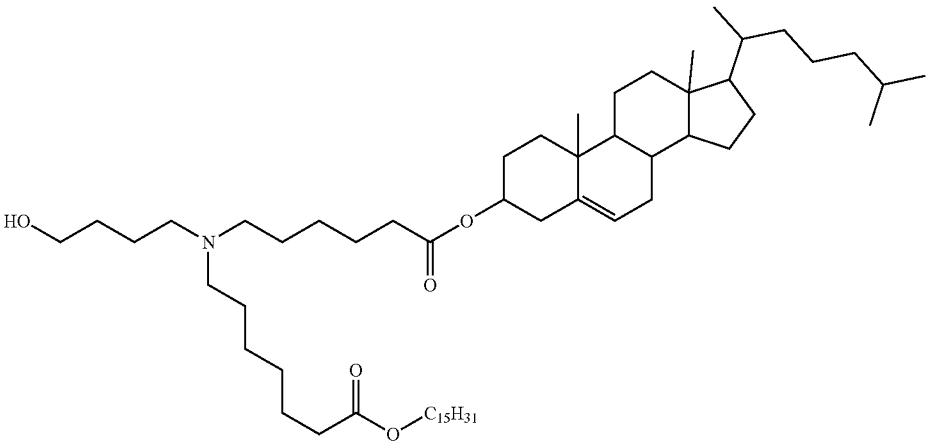
,

-continued
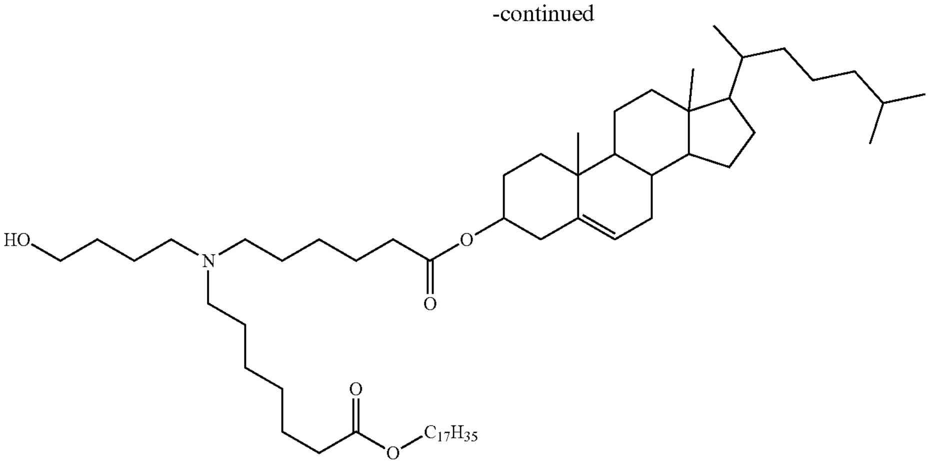
,
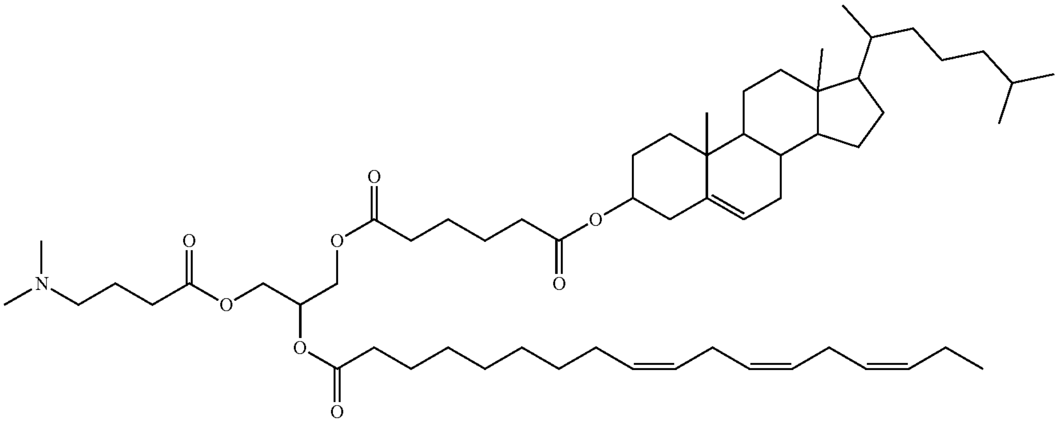
,
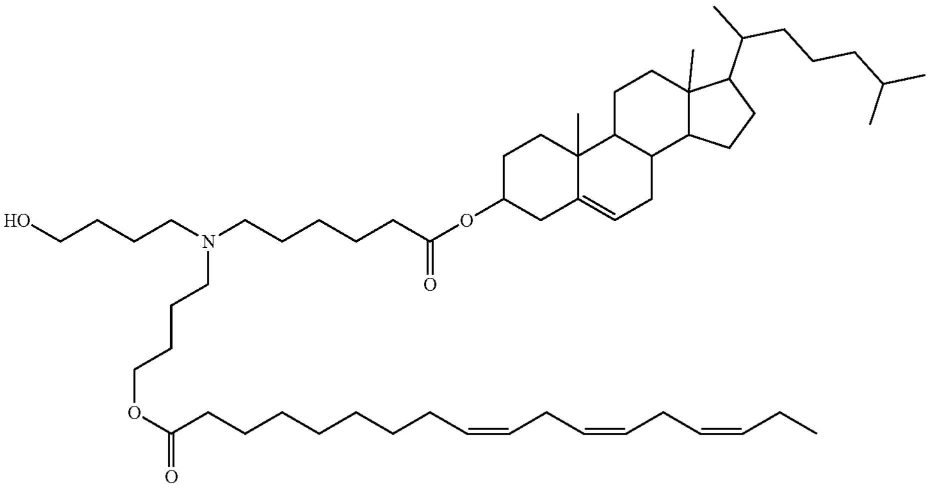
,
or pharmaceutically acceptable salts thereof.

In some embodiments, the compounds of Formula Y, I, Ia, or II-V can be:
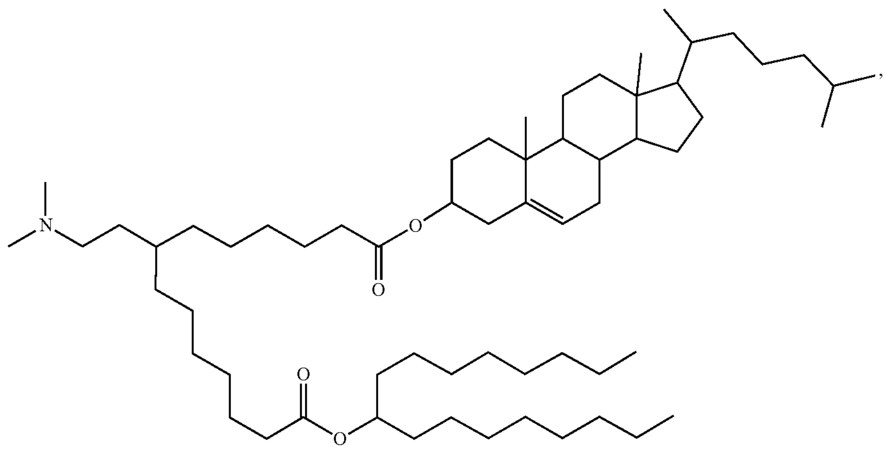
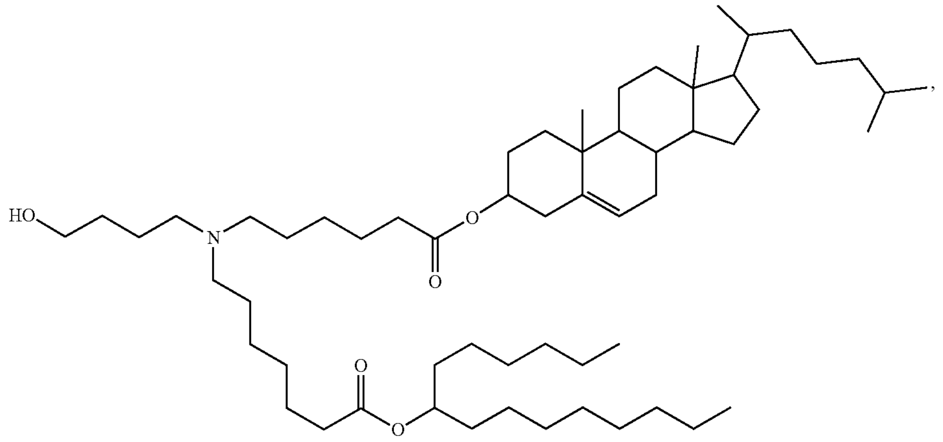
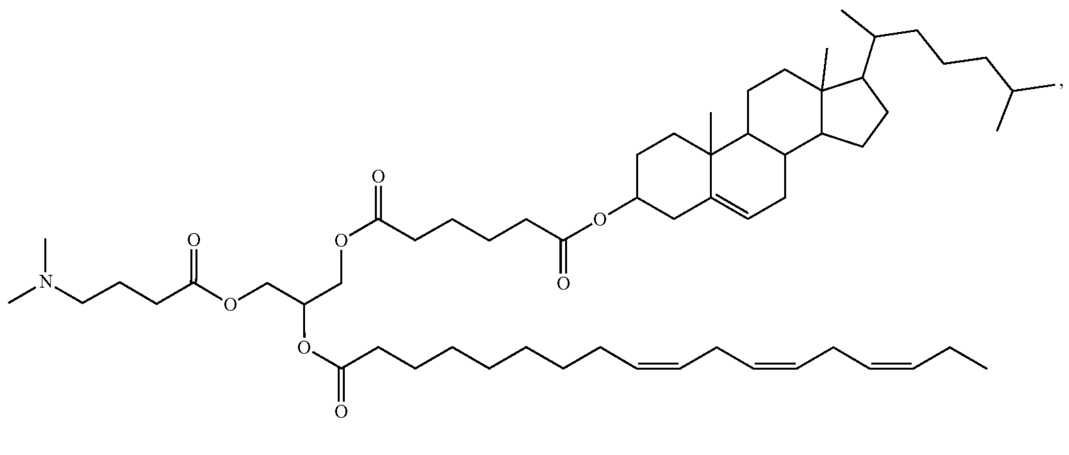

-continued
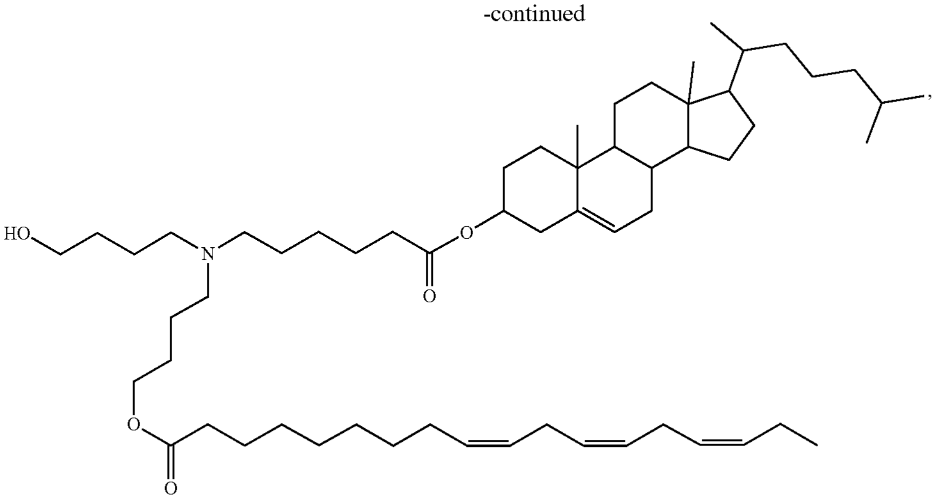
,
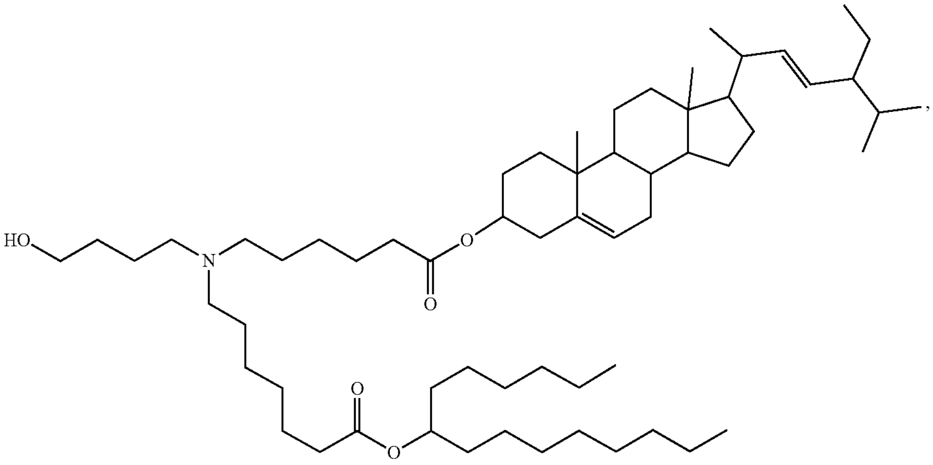
,
or pharmaceutically acceptable salts thereof.
In some embodiments, the compounds of Formula Y, I, Ia, or II-V can be:
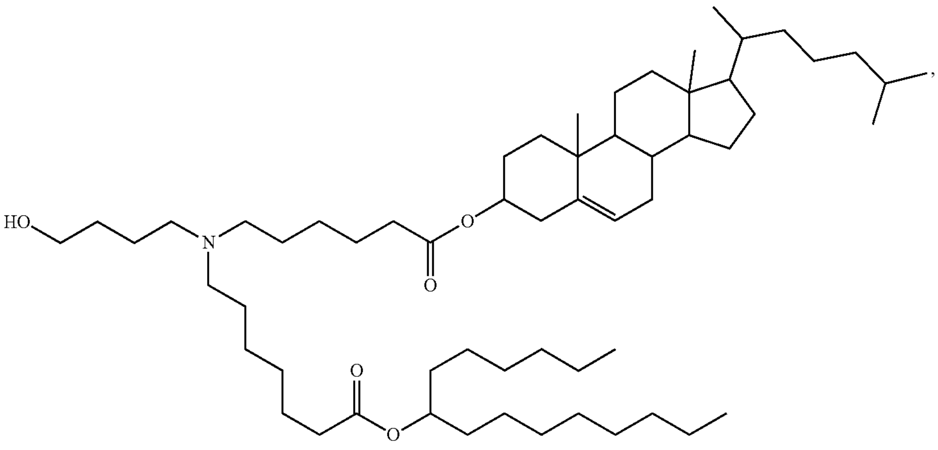
, -continued
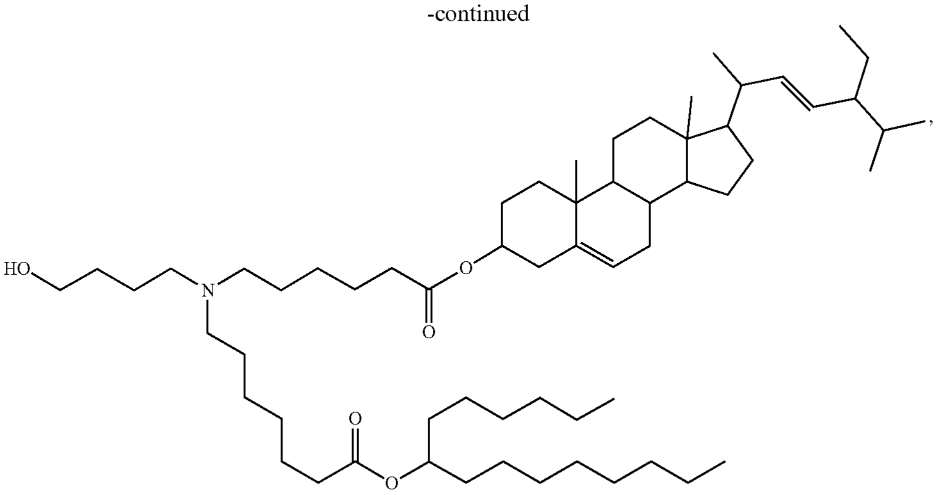
or pharmaceutically acceptable salts thereof, or any combination thereof.
In some embodiments, the compound of Formula Y, I, Ia, or II-V can be:
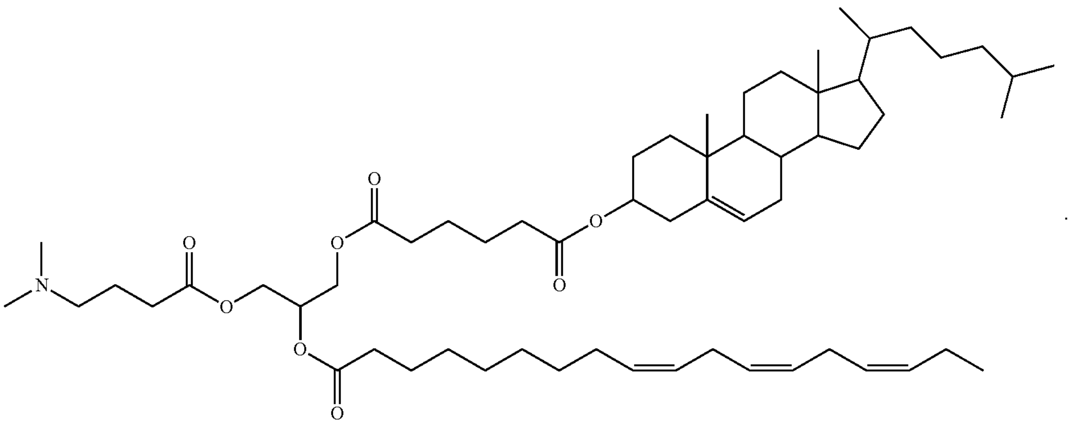 [SMILES: CC/C=C\C/C=C\C/C=C\CCCCCCCC(=O)OC(COC(=O)CCCCC(=O)OC1CCC2(C)C(=CCC3C2CCC2(C)C(C(C)CCCC(C)C)CCC32)C1)COC(=O)CCCN(C)C]
In some embodiments, the compound of Formula Y, I, Ia, or II-V can be:
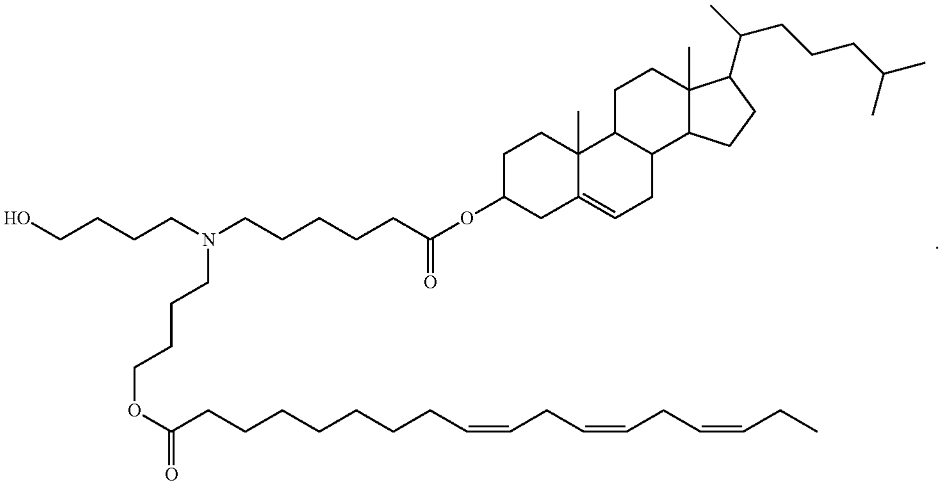 [SMILES: CC/C=C\C/C=C\C/C=C\CCCCCCCC(=O)OCCCCN(CCCCO)CCCCCC(=O)OC1CCC2(C)C(=CCC3C2CCC2(C)C(C(C)CCCC(C)C)CCC32)C1]

In some embodiments, the compound of Formula Y, I, Ia, or II-V can be:
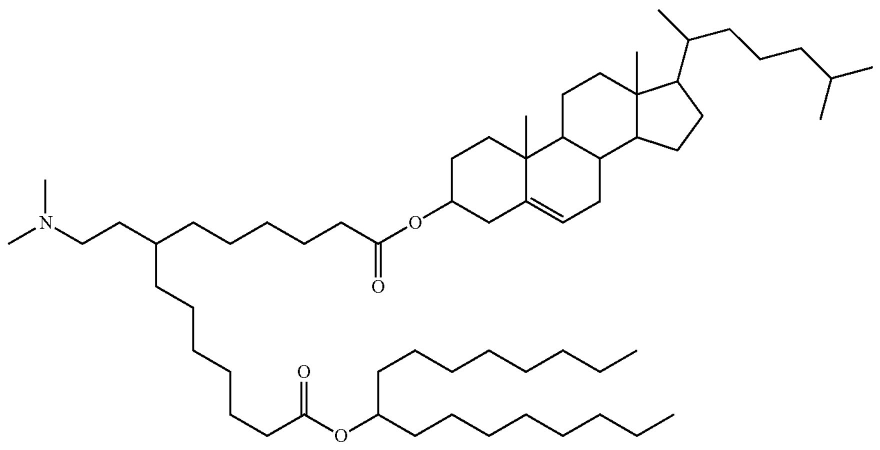 [SMILES: CCCCCCCCC(CCCCCCCC)OC(=O)CCCCCCC(CCCCCC(=O)OC1CCC2(C)C(=CCC3C2CCC2(C)C(C(C)CCCC(C)C)CCC32)C1)CCN(C)C]
or pharmaceutically acceptable salts thereof.
In some embodiments, the compound of Formula Y, I, Ia, or II-V can be:
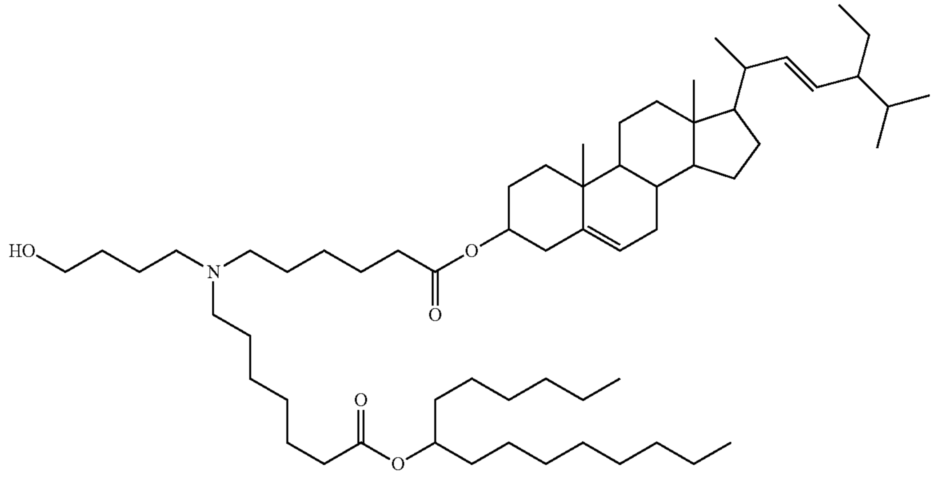

In some embodiments, the compound of Formula Y, I, Ia, or II-V can be:

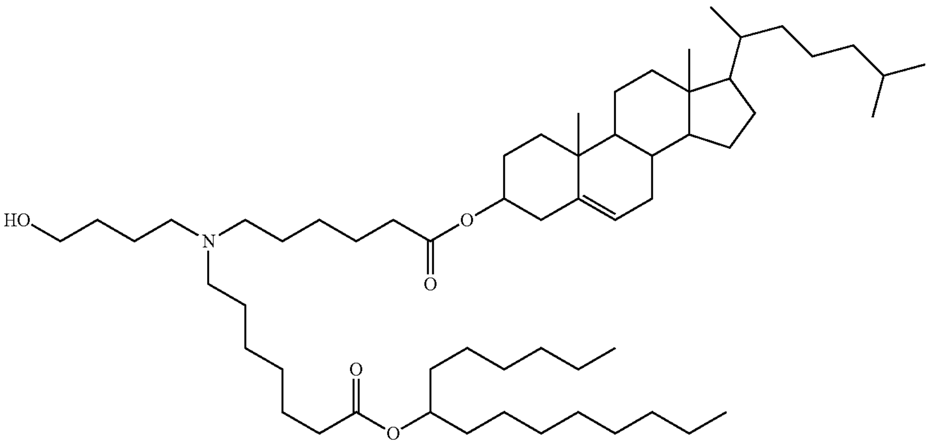 [SMILES: CCCCCCCCC(CCCCCC)OC(=O)CCCCCCN(CCCCO)CCCCCC(=O)OC1CCC2(C)C(=CCC3C2CCC2(C)C(C(C)CCCC(C)C)CCC32)C1]

or pharmaceutically acceptable salts thereof.

Described herein are compositions including a compound of Formula Y, I, Ia, II, III, IV, aV, or any combination thereof; and an active agent.

Compositions

Compositions, as described herein, include a compound of Formula Y, I, Ia, II, III, IV, V, or any combination thereof, and an active agent. The compositions can further include an excipient of some sort may be useful in a variety of medical and non-medical applications. For example, pharmaceutical compositions described herein may be useful in the delivery of an effective amount of an agent to a subject in need thereof. Compositions described herein may be useful for non-medical applications, e.g., such as an emulsion or emulsifier, useful, for example, as a food component, for extinguishing fires, for disinfecting surfaces, for oil cleanup, etc.

In some embodiments, the composition can be a lipid nanoparticle dispersion, a liposomal formulation, a lipid emulsion, or any combination thereof including a compound of Formula Y, I, Ia, II, III, IV, V, or any combination thereof.

In one aspect, the disclosure provides a composition including: a lipid nanoparticle, including a compound of Formula Y, I, Ia, II, III, IV, V, or any combination thereof; and an active agent.

In certain embodiments, the composition can include an agent, as described herein. For example, in certain embodiments, the agent is any chemical compound to be administered to a subject may be delivered using the particles or nanoparticles described herein. The agent may be an organic molecule (e.g., a therapeutic agent, a drug), inorganic molecule, small molecule, organometallic compound, metal, nucleic acid, protein, amino acid, peptide, polypeptide, polynucleotide, targeting agent, isotopically labeled organic or inorganic molecule, vaccine, immunological agent, or an agent useful in bioprocessing. In certain embodiments, the agent is a polynucleotide. In some embodiments, the agent includes an mRNA encoding at least one antigenic polypeptide or an immunogenic fragment thereof capable of inducing an immune response to the antigenic polypeptide.

In some embodiments, the mRNA encoding at least one antigenic polypeptide or an immunogenic fragment thereof capable of inducing an immune response to the antigenic polypeptide is encapsulated by the nanoparticle.

In some aspects, disclosed herein is a pharmaceutical composition comprising a pharmaceutically acceptable carrier and a nanoparticle comprising a compound of Formula I, Ia, II, III, IV, V, or any combination thereof; and an mRNA encoding at least one antigenic polypeptide or an immunogenic fragment thereof capable of inducing an immune response to the antigenic polypeptide.

Nanoparticles

Described herein are lipid nanoparticles including 20% to 80% of a compound described herein (e.g., a compound of Formula I, Ia, II, III, IV, V, or any combination thereof); greater than 0% to 5% polyethylene glycol-lipid; greater than 0% to 40% helper lipids; 0% to 80% sterol; and an active agent encapsulated in the nanoparticle.

Described herein are also composition including an effective amount of a lipid nanoparticle described herein and a pharmaceutically acceptable carrier.

In one aspect, the disclosure provides a nanoparticle comprising: a compound of A, I, Ia II, III, IV, V, or any combination thereof; and optionally a helper lipid; a polyethylene glycol-lipid; a sterol, or any combination thereof; and an active agent encapsulated in the nanoparticle.

In one aspect, the disclosure provides a nanoparticle comprising: a compound of A, I, Ia II, III, IV, V, or any combination thereof; and a helper lipid; a polyethylene glycol-lipid; and/or a sterol; and an active agent encapsulated in the nanoparticle.

In one aspect, the disclosure provides a nanoparticle comprising: a compound of A, I, Ia II, III, IV, V, or any combination thereof; a helper lipid; a polyethylene glycol-lipid; and a sterol; and an active agent encapsulated in the nanoparticle.

In one aspect, the disclosure provides a nanoparticle comprising: a compound of Formula Y; and a helper lipid; a polyethylene glycol-lipid; and/or a sterol; and an active agent encapsulated in the nanoparticle.

In one aspect, the disclosure provides a nanoparticle comprising: a compound of Formula I; and a helper lipid; a polyethylene glycol-lipid; and/or a sterol; and an active agent encapsulated in the nanoparticle.

In one aspect, the disclosure provides a nanoparticle comprising: a compound of Formula Ia; and a helper lipid; a polyethylene glycol-lipid; and/or a sterol; and an active agent encapsulated in the nanoparticle.

In one aspect, the disclosure provides a nanoparticle comprising: a compound of Formula II; and a helper lipid; a polyethylene glycol-lipid; and/or a sterol; and an active agent encapsulated in the nanoparticle.

In one aspect, the disclosure provides a nanoparticle comprising: a compound of Formula III; and a helper lipid; a polyethylene glycol-lipid; and/or a sterol; and an active agent encapsulated in the nanoparticle.

In one aspect, the disclosure provides a nanoparticle comprising: a compound of Formula IV; and a helper lipid; a polyethylene glycol-lipid; and/or a sterol; and an active agent encapsulated in the nanoparticle.

In one aspect, the disclosure provides a nanoparticle comprising: a compound of Formula V; and a helper lipid; a polyethylene glycol-lipid; and/or a sterol; and an active agent encapsulated in the nanoparticle.

The various compounds of Formula Y, I, Ia, II, III, IV, or V are described in the Compounds section above. In some embodiments, the nanoparticle comprises a compound of Formula Y, I, Ia II, III, IV, V, or any combination thereof in a molar ratio of from 20% to 80%; and an active agent encapsulated in the nanoparticle.

In some embodiments, the nanoparticle comprises a helper lipid. In some embodiments, the helper lipid can be a non-cationic lipid. In some embodiments, the non-cationic lipid can include, but is not limited to, 1,2-dioleoyl-sn-glycero-3-phosphoethanolamine (DOPE), 1-palmitoyl-2-oleoyl-sn-glycero-3-phosphoethanolamine (POPE), 1,2-distearoyl-sn-glycero-3-phosphocholine (DSPC), 1-stearoyl-2-oleoyl-sn-glycero-3-phosphoethanolamine (SOPE), 1,2-dipalmitoyl-sn-glycero-3-phosphocholine (DPPC), 1,2-dioleyl-sn-glycero-3-phosphotidylcholine (DOPC), 1,2-dipalmitoyl-sn-glycero-3-phosphoethanolamine (DPPE), 1,2-dimyristoyl-sn-glycero-3-phosphoethanolamine (DMPE), 1,2-Dimyristoyl-sn-glycero-3-phosphorylcholine (DMPC), 1,2-dioleoyl-5/7-glycero-3-phospho-(1'-rac-glycerol) (DOPG), 1-Palmitoyl-2-linoleoyl-sn-glycero-3-phosphocholine (PLPC), 1-Palmitoyl-2-oleoyl-sn-glycero-3-phosphocholine (POPC). 1-Stearoyl-2-myristoyl-sn-glycero-3-phosphocholine (SMPC), or combinations thereof. In one embodiment, the non-cationic lipid is 1,2-dioleoyl-sn-glycero-3-phosphoethanolamine (DOPE). In one embodiment, the non-cationic lipid is 1-palmitoyl-2-oleoyl-sn-glycero-3-phosphoethanolamine (POPE), In one embodiment, the non-cationic lipid is 1,2-distearoyl-sn-glycero-3-phosphocholine (DSPC). In one embodiment, the non-cationic lipid is 1-stearoyl-2-oleoyl-sn-glycero-3-phosphoethanolamine (SOPE). While several non-cationic lipids are described here, additional non-cationic lipids can be used in combination with the compounds disclosed herein.

In some embodiments, the helper lipid can be present in a molar ratio of at least 0%, (e.g., at least 5%, at least 10%, at least 20%, at least 30%, or at least 40%). In some embodiments, the helper lipid can be present in a molar ratio of 40% or less, (e.g., 30% or less, 20% or less, 10% or less, 5% or less, 1% or less, or 0.5% or less).

The helper lipid can be present in a molar ratio ranging from any of the minimum values described above to any of the maximum values described above. For example, in some embodiments, the helper lipid can be present in a molar ratio of from 0% to 40% (e.g., from greater than 0% to 30%, from greater than 0% to 20%, from greater than 0% to 10%, from greater than 0% to 5%, from greater than 0% to 1%, from greater than 0% to 0.5%, from 1% to 30%, from 1% to 20%, from 1% to 10%, from 1% to 5%, from 5% to 30%, from 5% to 20%, from 5% to 10%, from 10% to 30%, from 10% to 20%, from 20% to 30%, from 20% to 40%, or from 30% to 40%).

In some embodiments, the nanoparticle includes a polyethylene glycol-lipid (PEG-lipid). PEG-lipid is incorporated to form a hydrophilic outer layer and stabilize the particles. Nonlimiting examples of polyethylene glycol-lipids include PEG-modified lipids such as PEG-modified phosphatidylethanolamines, PEG-modified phosphatidic acids, PEG-modified ceramides, PEG-modified dialkylamines, PEG-modified diacylglycerols, and PEG-modified dialkylglycerols. Representative polyethylene glycol-lipids include DMG-PEG, DLPE-PEGs, DMPE-PEGs, DPPC-PEGs, and DSPE-PEGs. In one embodiment, the polyethylene glycol-lipid is 1,2-dimyristoyl-sn-glycerol, methoxypolyethylene glycol (DMG-PEG). In one embodiment, the polyethylene glycol-lipid is 1,2-dimyristoyl-sn-glycerol, methoxypolyethylene glycol-2000 (DMG-PEG2000). DMG-PEGXXXX means 1,2-dimyristoyl-sn-glycerol, methoxypolyethylene glycol-XXXX, wherein XXXX signifies the molecular weight of the polyethylene glycol moiety, e.g. DMG-PEG2000 or DMG-PEG5000.

In some embodiments, the polyethylene glycol-lipid can be present in a molar ratio of at least 0%, (e.g., at least 0.25%, at least 0.5%, at least 0.75%, at least 1%, at least 1.5%, at least 2%, at least 3%, at least 4%, or at least 5%). In some embodiments, the polyethylene glycol-lipid can be present in a molar ratio of 5% or less, (e.g., 4% or less, 3% or less, 2% or less, 1% or less, or 0.5% or less).

The polyethylene glycol-lipid can be present in a molar ratio ranging from any of the minimum values described above to any of the maximum values described above. For example, in some embodiments, the polyethylene glycol-lipid can be present in a molar ratio of from 0% to 5% (e.g., from greater than 0% to 4%, from greater than 0% to 3%, from greater than 0% to 2%, from greater than 0% to 1%, from greater than 0% to 0.5%, from 1% to 5%, from 1% to 4%, from 1% to 3%, from 1% to 2%, from 2% to 5%, 2% to 4%, 2% to 3%, from 3% to 5%, from 3% to 4%, or 4% to 5%). In one embodiment, the polyethylene glycol-lipid in a molar ratio of 0.75%.

In some embodiments, the nanoparticle includes a sterol. Sterols are well known to those skilled in the art and generally refers to those compounds having a perhydrocyclopentanophenanthrene ring system and having one or more OH substituents. Examples of sterols include, but are not limited to, cholesterol, campesterol, ergosterol, sitosterol, and the like.

In some embodiments, the sterol is selected from a cholesterol-based lipid. In some embodiments, the one or more cholesterol-based lipids are selected from cholesterol, PEGylated cholesterol, DC-Choi (N,N-dimethyl-N-ethylcarboxamidocholesterol), 1,4-bis(3-N-oleylamino-propyl) piperazine, or combinations thereof.

The sterol can be used to tune the particle permeability and fluidity base on its function in cell membranes. In one embodiment, the sterol is cholesterol.

In some embodiments, the sterol in a molar ratio of at least 0%, (e.g., at least 5%, at least 10%, at least 15%, at least 20%, at least 25%, at least 30%, at least 35%, at least 40%, at least 45%, at least 50%, at least 60%, at least 70%, or at least 80%). In some embodiments, the sterol in a molar ratio of 80% or less, (e.g., 70% or less, 60% or less, 50% or less, 40% or less, 30% or less, 20% or less, 10% or less, 5% or less, or 1% or less).

The sterol can be present in a molar ratio ranging from any of the minimum values described above to any of the maximum values described above. In some embodiments, the sterol can be present in a molar ratio of from 0% to 80%, (e.g., from greater than 0% to 70%, from greater than 0% to 60%, from greater than 0% to 50% from greater than 0% to 40%, from greater than 0% to 30%, from greater than 0% to 20%, from greater than 0% to 10%, from greater than 0% to 5%, from greater than 0% to 1%, from 5% to 70%, from 5% to 60%, from 5% to 50% from 5% to 40%, from 5% to 30%, from 5% to 20%, from 5% to 10%, from 10% to 70%, from 10% to 60%, from 10% to 50% from 10% to 40%, from 10% to 30%, from 10% to 20%, from 20% to 70%, from 20% to 60%, from 20% to 50%, from 20% to 40%, from 20% to 30%, from 30% to 70%, from 30% to 60%, from 30% to 50%, from 30% to 40%, from 40% to 70%, from 40% to 60%, from 40% to 50%, from 50% to 70%, from 50% to 60%, from 60% to 70% from 60% to 80%, from 70% to 80%, from 10% to 80%, from 20% to 80%, from 30% to 80%, from 40% to 80%, or from 50% to 80%. In some embodiment, the nanoparticle comprises a sterol in a molar ratio of 40%.

In some embodiment, the nanoparticle can include from 40% to 60% of a compound described herein; from 1% to 2% polyethylene glycol-lipid; from 8% to 12% helper lipids; from 35% to 40% sterol; and an active agent encapsulated in the nanoparticle.

In one embodiment, described are nanoparticles including 50% of a compound described herein; 1.5% polyethylene glycol-lipid; 10% helper lipids (e.g., DSPC); 38.5% sterol (e.g., cholesterol); and an active agent encapsulated in the nanoparticle.

In one embodiment, the disclosure provides a nanoparticle comprising:

a compound of Formula Y, I, Ia, II, III, IV, V, or any combination thereof; and
an active agent encapsulated in the nanoparticle.

In some embodiments, described are nanoparticles including:

a compound of Formula Y, I, Ia, II, III, IV, V or any combination thereof;
1,2-dioleoyl-sn-glycero-3-phosphoethanolamine (DOPE);
1,2-dimyristoyl-sn-glycerol, methoxypolyethylene glycol ($DMG-PEG_{2000}$);
cholesterol; and
an active agent encapsulated in the nanoparticle.

In one embodiment, the disclosure provides a nanoparticle comprising:

a compound of Formula Y, I, Ia, II, III, IV, V, or any combination thereof;
1-palmitoyl-2-oleoyl-sn-glycero-3-phosphoethanolamine (POPE);
1,2-dimyristoyl-sn-glycerol, methoxypolyethylene glycol ($DMG-PEG_{2000}$);
cholesterol; and
an active agent encapsulated in the nanoparticle.

In one embodiment, the disclosure provides a nanoparticle comprising:

a compound of Formula Y, I, Ia, II, III, IV, V, or any combination thereof;
1,2-distearoyl-sn-glycero-3-phosphocholine (DSPC);
1,2-dimyristoyl-sn-glycerol, methoxypolyethylene glycol ($DMG-PEG_{2000}$); and cholesterol.

In one embodiment, the disclosure provides a nanoparticle comprising:

a compound of Formula Y, I, Ia, II, III, IV, V, or any combination thereof;
1,2-dioleoyl-sn-glycero-3-phosphoethanolamine (DOPE);
1,2-distearoyl-sn-glycero-3-phosphoethanolamine-N-[amino(polyethylene glycol)-2000]($DSPE-PEG_{2000}$);
cholesterol; and
an active agent encapsulated in the nanoparticle.

In one embodiment, the nanoparticle can further include an active agent. In one embodiment, the nanoparticle can further include a therapeutic agent. In one embodiment, the nanoparticle can further include a diagnostic agent. In one embodiment, the nanoparticle can further include a prophylactic agent.

Active Agents

As used herein, an "active agent" refers to therapeutic agents, diagnostic agents, or prophylactic agents. As discussed herein, the therapeutic agents can be released from the disclosed compounds, compositions, and systems in a biologically active form.

It is further understood, that as used herein, the terms "therapeutic agents" refers to one or more therapeutic agents, active ingredients, or substances that can be used to treat a medical condition. Therapeutic agent includes any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins and minerals such as essential amino acids, calcium, iron, potassium, zinc, vitamin B12, and the like; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; an antimicrobial agents (including antibiotics, antiviral agents, antiparasitic, and anti-fungal agents), anti-inflammatory agents (including steroids and non-steroidal anti-inflammatory agents), anti-coagulant agents, ophthalmic agents, gastrointestinal drugs, antiplatelet agents, and antiseptic agents, steroidal agent, anti-neoplastic agent, anti-cancer agent, antigen, antibody (e.g., cetuximab, anti-CD24 antibody, panitumumab and bevacizumab), birth control agent, progestational agent, anti-cholinergic, nutritional agent, analgesics and analgesic combinations such as acetaminophen, acetylsalicylic acid, and the like; anesthetics such as lidocaine, xylocaine, and the like, anorexics such as dexadrine, phendimetrazine tartrate, and the like; anti-epileptics, local and general anesthetics, hypnotics, sedatives, antipsychotic agents, neuroleptic agents, antidepressants such as isocarboxazid, amoxapine, and the like; anxiolytics, antagonists, neuron blocking agents, anticholinergic and cholinomimetic agents, antimuscarinic and muscarinic agents, antiparkinsonian agents, anti-Alzheimer's agents, antiadrenergics, antiarrhythmics, antihypertensive agents, hormones such as insulin, progestins, estrogens, corticoids, glucocorticoids, androgens, and the like; and nutrients, antiarthritics such as methylprednisolone, ibuprofen, and the like; antiasthmatics such as terbutaline sulfate, theophylline, ephedrine, and the like; anticonvulsants such as phenyloin sodium, diazepam, and the like; antiallergenics, antihistamines such as diphenhydramine HCl, chlorpheniramine maleate, and the like; antinauseants, antineoplastics, antipruritics, antipyretics; antispasmodics such as belladonna alkaloids, dicyclomine hydrochloride, and the like; cardiovascular agents such as prazosin HCl, nitroglycerin, propranolol HCl, hydralazine HCl, pancrelipase, succinic acid dehydrogenase, and the like; vasoactive agent, cardiovascular preparations (including calcium channel blockers, beta-blockers, beta-agonists and antiarrythmics), antihypertensives, diuretics such as furosemide, spironolactone, and the like; vasodilators; central nervous system stimulants; cough and cold preparations; decongestants; diagnostics; bone growth stimulants and bone resorption inhibitors; muscle relaxants; psychostimulants; sedatives; tranquilizers such as thorazine, diazepam, chlorpromazine HCl, reserpine, chlordiazepoxide HCl, and the like; antiulcer drugs such as rantidine HCl, cimetidine HCl, and the like; anti-asthmatic agents, anti-diarrheals, anti-obesity agents, anti-thrombotic agents, anti-tussive agents, anti-uricemic agents, anti-anginal agents, appetite suppressants, expectorants, hyperglycemic agents, hypoglycemic agents, thyroid and anti-thyroid agents, tissue growth agents, uterine relaxants, immunomodulator, including, for example, cytokines, interleukins, interferon, colony stimulating factor, tumor necrosis factor, and the like; immunosuppressants such as rapamycin, tacrolimus, and the like; immunological agent; antigens, factors, growth factors, amino acids, peptides and proteins and fragments thereof (whether naturally occurring, chemically synthesized or recombinantly produced) such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxam®, Herceptin®, alpha-glucosidase, Cerazyme/Ceredose®, vasopressin, ACTH, human serum albumin, gamma globulin, structural proteins, blood product proteins, complex proteins, antigens or antigenic polypeptides, enzymes, antibodies, monoclonal antibodies, and the like; and nucleic acid molecules (polymeric forms of two or more nucleotides, polynucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. In certain embodiments of the present disclosure, the agent to be delivered may be a mixture of active agents.

Representative examples of antibiotics include amikacin, amoxicillin, ampicillin, atovaquone, azithromycin, aztreonam, bacitracin, carbenicillin, cefadroxil, cefazolin, cefdinir, cefditoren, cefepime, cefiderocol, cefoperazone, cefotetan, cefoxitin, cefotaxime, cefpodoxime, cefprozil, ceftaroline, ceftazidime, ceftibuten, ceftizoxime, ceftriaxone, chloramphenicol, colistimethate, cefuroxime, cephalexin, cephradine, cilastatin, cinoxacin, ciprofloxacin, clarithromycin, clindamycin, dalbavancin, dalfopristin, daptomycin, demeclocycline, dicloxacillin, doripenem, doxycycline, eravacycline, ertapenem, erythromycin, fidaxomicin, fosfomycin, gatifloxacin, gemifloxacin, gentamicin, imipenem, lefamulin, lincomycin, linezolid, lomefloxacin, loracarbef, meropenem, metronidazole, minocycline, moxifloxacin, nafcillin, nalidixic acid, neomycin, norfloxacin, ofloxacin, omadacycline, oritavancin, oxacillin, oxytetracycline, paromomycin, penicillin, pentamidine, piperacillin, plazomicin, quinupristin, rifaximin, sarecycline, secnidazole, sparfloxacin, spectinomycin, sulfamethoxazole, sulfisoxazole, tedizolid, telavancin, telithromycin, ticarcillin, tigecycline, tobramycin, trimethoprim, trovafloxacin, and vancomycin.

Representative examples of antiviral agents include, but are not limited to, abacavir, acyclovir, adefovir, amantadine, amprenavir, atazanavir, balavir, baloxavir marboxil, boceprevir, cidofovir, cobicistat, daclatasvir, darunavir, delavirdine, didanosine, docasanol, dolutegravir, doravirine, ecoliever, edoxudine, efavirenz, elvitegravir, emtricitabine, enfuvirtide, entecavir, etravirine, famciclovir, fomivirsen, fosamprenavir, forscarnet, fosnonet, famciclovir, favipravir, fomivirsen, foscavir, ganciclovir, ibacitabine, idoxuridine, indinavir, inosine, inosine pranobex, interferon type I, interferon type II, interferon type III, lamivudine, letermovir, letermovir, lopinavir, loviride, maraviroc, methisazone, moroxydine, nelfinavir, nevirapine, nitazoxanide, oseltamivir, peginterferon alfa-2a, peginterferon alfa-2b, penciclovir, peramivir, pleconaril, podophyllotoxin, pyramidine, raltegravir, remdesevir, ribavirin, rilpivirine, rimantadine, rintatolimod, molnupiravir, ritonavir, saquinavir, simeprevir, sofosbuvir, stavudine, tarabivirin, telaprevir, telbivudine, tenofovir alafenamide, tenofovir disoproxil, tenofovir, tipranavir, trifluridine, trizivir, tromantadine, umifenovir, valaciclovir, valganciclovir, vidarabine, zalcitabine, zanamivir, and zidovudine.

Representative examples of anticoagulant agents include, but are not limited to, heparin, warfarin, rivaroxaban, dabigatran, apixaban, edoxaban, enoxaparin, and fondaparinux.

Representative examples of antiplatelet agents include, but are not limited to, clopidogrel, ticagrelor, prasugrel, dipyridamole, dipyridamole/aspirin, ticlopidine, and eptifibatide.

Representative examples of antifungal agents include, but are not limited to, voriconazole, itraconazole, posaconazole, fluconazole, ketoconazole, clotrimazole, isavuconazonium, miconazole, caspofungin, anidulafungin, micafungin, griseofulvin, terbinafine, flucytosine, terbinafine, nystatin, and amphotericin b.

Representative examples of steroidal anti-inflammatory agents include, but are not limited to, hydrocortisone, dexamethasone, prednisolone, prednisone, triamcinolone, methylprednisolone, budesonide, betamethasone, cortisone, and deflazacort. Representative examples of non-steroidal anti-inflammatory drugs include ibuprofen, naproxen, ketoprofen, tolmetin, etodolac, fenoprofen, flurbiprofen, diclofenac, piroxicam, indomethacin, sulindax, meloxicam, nabumetone, oxaprozin, mefenamic acid, and diflunisal.

Other examples of active agents include chloroquine, hydrochloroquine, Pyridoxal phosphate, Vitamin D, and Vitamin C.

Representative examples of anticytokine or immunomodulatory agents, but are not limited to, tocilizumab, sarilumab, bevacizumab, fingolimod, imiquimod, and eculizumab.

Immunotherapeutic agent can include but are not limited to an anti-CD40 antibody, an anti-PDL1 antibody (e.g., atezolizumab, durvalumab, or avelumab), an anti-PD1 antibody, an anti-CTLA4 antibody, programmed death protein 1 (PD-1) inhibitor or programmed death protein ligand 1 or 2 inhibitor include, (e.g., nivolumab (BMS), pembrolizumab (Merck), pidilizumab (CureTech/Teva), AMP-244 (Amplimmune/GSK), BMS-936559 (BMS), and MEDI4736 (Roche/Genentech)), or a combination thereof.

Representative examples of contraceptives include, but are not limited to, progestins, estrogens, or any combination thereof. For example, suitable progestins include, but are not limited to, natural and synthetic compounds having progestational activity, such as, for example, progesterone, chlormadinone acetate, norethindrone, cyproterone acetate, norethindrone acetate, desogestrel, levonorgestrel, drospirenone, trimegestone, norgestrel, norgestimate, norelgestromin, etonogestrel, gestodene, and other natural and/or synthetic gestagens. For example suitable estrogens include, but are not limited to, natural and synthetic compounds having estrogenic activity, such as, for example, estradiol (17β-estradiol), 17α-estradiol, estriol, estrone, and their esters, such as the acetate, sulfate, valerate or benzoate esters of these compounds, including, for example, estradiol 17β-cypionate, estradiol 17-propionate, estradiol 3-benzoate, and piperazine estrone sulfate; ethinyl estradiol; conjugated estrogens (natural and synthetic); mestranol; agonistic anti-estrogens; and selective estrogen receptor modulators. Other examples of contraceptives include gonodotropin releasing hormone (GnRh) or anologs thereof such as deslorelin, avorelin, leuprolide, triptorelin, nafarelin, goserelin, buserelin, and fertirelin.

The term "steroid" refers to compounds belonging to or related to the following illustrative families of compounds: corticosteroids, mineralicosteroids, and sex steroids (including, for example, potentially androgenic or estrogenic or anti-androgenic and anti-estrogenic molecules). Included among these are, for example, prednisone, prednisolone, methyl-prednisolone, triamcinolone, fluocinolone, aldosterone, spironolactone, danazol (otherwise known as OPTINA), and others. In some embodiments, the therapeutic agent may comprise a steroid.

Exemplary cancer drugs or anti-cancer agents can include, but are not limited to, antimetabolite anti-cancer agents and antimitotic anti-cancer agents, and combinations thereof. Various antimetabolite and antimitotic anti-cancer agents, including single such agents or combinations of such agents, may be employed in the methods and compositions described herein.

Antimetabolic anti-cancer agents typically structurally resemble natural metabolites, which are involved in normal metabolic processes of cancer cells such as the synthesis of nucleic acids and proteins. The antimetabolites, however, differ enough from the natural metabolites such that they interfere with the metabolic processes of cancer cells. In the cell, antimetabolites are mistaken for the metabolites they resemble, and are processed by the cell in a manner analogous to the normal compounds. The presence of the "decoy" metabolites prevents the cells from carrying out vital functions and the cells are unable to grow and survive. For example, antimetabolites may exert cytotoxic activity by substituting these fraudulent nucleotides into cellular DNA, thereby disrupting cellular division, or by inhibition of critical cellular enzymes, which prevents replication of DNA.

In one aspect, therefore, the antimetabolite anti-cancer agent is a nucleotide or a nucleotide analog. In certain aspects, for example, the antimetabolite agent may comprise purine (e.g., guanine or adenosine) or analogs thereof, or pyrimidine (cytidine or thymidine) or analogs thereof, with or without an attached sugar moiety.

Suitable antimetabolite anti-cancer agents for use in the present disclosure may be generally classified according to the metabolic process they affect, and can include, but are not limited to, analogues and derivatives of folic acid, pyrimidines, purines, and cytidine. Thus, in one aspect, the antimetabolite agent(s) is selected from the group consisting of cytidine analogs, folic acid analogs, purine analogs, pyrimidine analogs, and combinations thereof.

In one particular aspect, for example, the antimetabolite agent is a cytidine analog. According to this aspect, for example, the cytidine analog may be selected from the group consisting of cytarabine (cytosine arabinodside), azacitidine (5-azacytidine), and salts, analogs, and derivatives thereof.

In another particular aspect, for example, the antimetabolite agent is a folic acid analog. Folic acid analogs or antifolates generally function by inhibiting dihydrofolate reductase (DHFR), an enzyme involved in the formation of nucleotides; when this enzyme is blocked, nucleotides are not formed, disrupting DNA replication and cell division. According to certain aspects, for example, the folic acid analog may be selected from the group consisting of denopterin, methotrexate (amethopterin), pemetrexed, pteropterin, raltitrexed, trimetrexate, and salts, analogs, and derivatives thereof.

In another particular aspect, for example, the antimetabolite agent is a purine analog. Purine-based antimetabolite agents function by inhibiting DNA synthesis, for example, by interfering with the production of purine containing nucleotides, adenine and guanine which halts DNA synthesis and thereby cell division. Purine analogs can also be incorporated into the DNA molecule itself during DNA synthesis, which can interfere with cell division. According to certain aspects, for example, the purine analog may be selected from the group consisting of acyclovir, allopurinol, 2-aminoadenosine, arabinosyl adenine (ara-A), azacitidine, azathiprine, 8-aza-adenosine, 8-fluoro-adenosine, 8-methoxy-adenosine, 8-oxo-adenosine, cladribine, deoxycoformycin, fludarabine, gancylovir, 8-aza-guanosine, 8-fluoro-guanosine, 8-methoxy-guanosine, 8-oxo-guanosine, guanosine diphosphate, guanosine diphosphate-beta-L-2-aminofucose, guanosine diphosphate-D-arabinose, guanosine diphosphate-2-fluorofucose, guanosine diphosphate fucose, mercaptopurine (6-MP), pentostatin, thiamiprine, thioguanine (6-TG), and salts, analogs, and derivatives thereof.

In yet another particular aspect, for example, the antimetabolite agent is a pyrimidine analog. Similar to the purine analogs discussed above, pyrimidine-based antimetabolite agents block the synthesis of pyrimidine-containing nucleotides (cytosine and thymine in DNA; cytosine and uracil in RNA). By acting as "decoys," the pyrimidine-based compounds can prevent the production of nucleotides, and/or can be incorporated into a growing DNA chain and lead to its termination. According to certain aspects, for example, the pyrimidine analog may be selected from the group consisting of ancitabine, azacitidine, 6-azauridine, bromouracil (e.g., 5-bromouracil), capecitabine, carmofur, chlorouracil (e.g. 5-chlorouracil), cytarabine (cytosine arabinoside), cytosine, dideoxyuridine, 3'-azido-3'-deoxythymidine, 3'-dideoxycytidin-2'-ene, 3'-deoxy-3'-deoxythymidin-2'-ene, dihydrouracil, doxifluridine, enocitabine, floxuridine, 5-fluorocytosine, 2-fluorodeoxycytidine, 3-fluoro-3'-deoxythymidine, fluorouracil (e.g., 5-fluorouracil (also known as 5-FU), gemcitabine, 5-methylcytosine, 5-propynylcytosine, 5-propynylthymine, 5-propynyluracil, thymine, uracil, uridine, and salts, analogs, and derivatives thereof. In one aspect, the pyrimidine analog is other than 5-fluorouracil. In another aspect, the pyrimidine analog is gemcitabine or a salt thereof.

In certain aspects, the antimetabolite agent is selected from the group consisting of 5-fluorouracil, capecitabine, 6-mercaptopurine, methotrexate, gemcitabine, cytarabine, fludarabine, pemetrexed, and salts, analogs, derivatives, and combinations thereof. In other aspects, the antimetabolite agent is selected from the group consisting of capecitabine, 6-mercaptopurine, methotrexate, gemcitabine, cytarabine, fludarabine, pemetrexed, and salts, analogs, derivatives, and combinations thereof. In one particular aspect, the antimetabolite agent is other than 5-fluorouracil. In a particularly preferred aspect, the antimetabolite agent is gemcitabine or a salt or thereof (e.g., gemcitabine HCl (Gemzar®)).

Other antimetabolite anti-cancer agents may be selected from, but are not limited to, the group consisting of acanthifolic acid, aminothiadiazole, brequinar sodium, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, Wellcome EHNA, Merck & Co. EX-015, fazarabine, fludarabine phosphate, N-(2'-furanidyl)-5-fluorouracil, Daiichi Seiyaku FO-152, 5-FU-fibrinogen, isopropyl pyrrolizine, Lilly LY-188011; Lilly LY-264618, methobenzaprim, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, tiazofurin, Erbamont TIF, tyrosine kinase inhibitors, Taiho UFT and uricytin, among others.

In one aspect, the antimitotic anti-cancer agent is a microtubule inhibitor or a microtubule stabilizer. In general, microtubule stabilizers, such as taxanes and epothilones, bind to the interior surface of the beta-microtubule chain and enhance microtubule assembly by promoting the nucleation and elongation phases of the polymerization reaction and by reducing the critical tubulin subunit concentration required for microtubules to assemble. Unlike mictrotubule inhibitors, such as the vinca alkaloids, which prevent microtubule assembly, the microtubule stabilizers, such as taxanes, decrease the lag time and dramatically shift the dynamic equilibrium between tubulin dimers and microtubule polymers towards polymerization. In one aspect, therefore, the microtubule stabilizer is a taxane or an epothilone. In another aspect, the microtubule inhibitor is a vinca alkaloid.

In some embodiments, the anti-cancer agent may comprise a taxane or derivative or analog thereof. The taxane may be a naturally derived compound or a related form, or may be a chemically synthesized compound or a derivative thereof, with antineoplastic properties. The taxanes are a family of terpenes, including, but not limited to paclitaxel (Taxol®) and docetaxel (Taxotere®), which are derived primarily from the Pacific yew tree, *Taxus brevifolia*, and which have activity against certain tumors, particularly breast and ovarian tumors. In one aspect, the taxane is docetaxel or paclitaxel. Paclitaxel is a preferred taxane and is considered an antimitotic agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions.

Also included are a variety of known taxane derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; deoxygenated paclitaxel compounds such as those described in U.S. Pat. No. 5,440,056; and taxol derivatives described in U.S. Pat. No. 5,415,869. As noted above, it further includes prodrugs of paclitaxel including, but not limited to, those described in WO 98/58927; WO 98/13059; and U.S. Pat. No. 5,824,701. The taxane may also be a taxane conjugate such as, for example, paclitaxel-PEG, paclitaxel-dextran, paclitaxel-xylose, docetaxel-PEG, docetaxel-dextran, docetaxel-xylose, and the like. Other derivatives are mentioned in "Synthesis and Anticancer Activity of Taxol Derivatives," D. G. I. Kingston et al., Studies in Organic Chemistry, vol. 26, entitled "New Trends in Natural Products Chemistry" (1986), Atta-ur-Rabman, P. W. le Quesne, Eds. (Elsevier, Amsterdam 1986), among other references. Each of these references is hereby incorporated by reference herein in its entirety.

Various taxanes may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267) (each of which is hereby incorporated by reference herein in its entirety), or obtained from a variety of commercial sources, including for example, Sigma-Aldrich Co., St. Louis, Mo.

Alternatively, the antimitotic anti-cancer agent can be a microtubule inhibitor; in one preferred aspect, the microtubule inhibitor is a vinca alkaloid. In general, the vinca alkaloids are mitotic spindle poisons. The vinca alkaloid agents act during mitosis when chromosomes are split and begin to migrate along the tubules of the mitosis spindle towards one of its poles, prior to cell separation. Under the action of these spindle poisons, the spindle becomes disorganized by the dispersion of chromosomes during mitosis, affecting cellular reproduction. According to certain aspects, for example, the vinca alkaloid is selected from the group consisting of vinblastine, vincristine, vindesine, vinorelbine, and salts, analogs, and derivatives thereof.

The antimitotic anti-cancer agent can also be an epothilone. In general, members of the epothilone class of compounds stabilize microtubule function according to mechanisms similar to those of the taxanes. Epothilones can also cause cell cycle arrest at the G2-M transition phase, leading to cytotoxicity and eventually apoptosis. Suitable epithiolones include epothilone A, epothilone B, epothilone C, epothilone D, epothilone E, and epothilone F, and salts, analogs, and derivatives thereof. One particular epothilone analog is an epothilone B analog, ixabepilone (Ixempra™).

In certain aspects, the antimitotic anti-cancer agent is selected from the group consisting of taxanes, epothilones, vinca alkaloids, and salts and combinations thereof. Thus, for example, in one aspect the antimitotic agent is a taxane. More preferably in this aspect the antimitotic agent is paclitaxel or docetaxel, still more preferably paclitaxel. In another aspect, the antimitotic agent is an epothilone (e.g., an epothilone B analog). In another aspect, the antimitotic agent is a vinca alkaloid.

Examples of cancer drugs that may be used in the present disclosure include, but are not limited to: thalidomide; platinum coordination complexes such as cisplatin (cis-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as sunitimib and imatinib.

Examples of additional cancer drugs include alkylating agents, antimetabolites, natural products, hormones and antagonists, and miscellaneous agents. Alternate names are indicated in parentheses. Examples of alkylating agents include nitrogen mustards such as mechlorethamine, cyclophosphainide, ifosfamide, melphalan sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, SFU), floxuridine (fluorodeoxyuridine, FUdR), cytarabine (cytosine arabinoside) and gemcitabine; purine analogs such as mercaptopurine (6-mercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel, protein bound paclitaxel (Abraxane) and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, histrelin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, rnedroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Alternate names and trade-names of these and additional examples of cancer drugs, and their methods of use including dosing and administration regimens, will be known to a person versed in the art.

In some aspects, the anti-cancer agent may comprise a chemotherapeutic agent. Suitable chemotherapeutic agents include, but are not limited to, alkylating agents, antibiotic agents, antimetabolic agents, hormonal agents, plant-derived agents and their synthetic derivatives, anti-angiogenic agents, differentiation inducing agents, cell growth arrest inducing agents, apoptosis inducing agents, cytotoxic agents, agents affecting cell bioenergetics i.e., affecting cellular ATP levels and molecules/activities regulating these levels, biologic agents, e.g., monoclonal antibodies, kinase inhibitors and inhibitors of growth factors and their receptors, gene therapy agents, cell therapy, e.g., stem cells, or any combination thereof.

According to these aspects, the chemotherapeutic agent is selected from the group consisting of cyclophosphamide, chlorambucil, melphalan, mechlorethamine, ifosfamide, busulfan, lomustine, streptozocin, temozolomide, dacarbazine, cisplatin, carboplatin, oxaliplatin, procarbazine, uramustine, methotrexate, pemetrexed, fludarabine, cytarabine, fluorouracil, floxuridine, gemcitabine, capecitabine, vinblastine, vincristine, vinorelbine, etoposide, paclitaxel, docetaxel, doxorubicin, daunorubicin, epirubicin, idarubicin, mitoxantrone, bleomycin, mitomycin, hydroxyurea, topotecan, irinotecan, amsacrine, teniposide, erlotinib hydrochloride and combinations thereof. Each possibility represents a separate aspect of the invention.

Anti-neoplastic agent can be selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Akynzeo (Netupitant and Palonosetron Hydrochloride), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, CARBOPLATIN-TAXOL, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Interferon Alfa-2b, Recombinant, Intron A (Recombinant Interferon Alfa-2b), Iodine I 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Netupitant and Palonosetron Hydrochloride, Neupogen (Filgrastim), Nexavar (Sorafenib Tosylate), Nilotinib, Nivolumab, Nolvadex (Tamoxifen Citrate), Nplate (Romiplostim), Obinutuzumab, Odomzo (Sonidegib), OEPA, Ofatumumab, OFF, Olaparib, Omacetaxine Mepesuccinate, Oncaspar (Pegaspargase), Ondansetron Hydrochloride, Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and Iodine I 131 Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Unituxin (Dinutuximab), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

Growth factors useful as therapeutic agents include, but are not limited to, transforming growth factor-α ("TGF-α"), transforming growth factors ("TGF-β"), platelet-derived growth factors ("PDGF"), fibroblast growth factors ("FGF"), including FGF acidic isoforms 1 and 2, FGF basic form 2 and FGF 4, 8, 9 and 10, nerve growth factors ("NGF") including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, and bone derived growth factors and mixtures thereof.

Immunoglobulins useful in the present disclosure include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Other molecules useful as anti-cancer agents include but are not limited to growth hormones, leptin, leukemia inhibitory factor (LIF), tumor necrosis factor alpha and beta, endostatin, thrombospondin, osteogenic protein-1, bone morphogenetic proteins 2 and 7, osteonectin, somatomedin-like peptide, osteocalcin.

Tumor antigens can be based on specific mutations (neoepitopes) and those expressed by cancer-germline genes (antigens common to tumors found in multiple patients, referred to herein as "traditional cancer antigens" or "shared cancer antigens"). In some embodiments, a traditional antigen is one that is known to be found in cancers or tumors generally or in a specific type of cancer or tumor. In some embodiments, a traditional cancer antigen is a non-mutated tumor antigen. In some embodiments, a traditional cancer antigen is a mutated tumor antigen.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Vaccines may comprise isolated proteins or peptides, inactivated organisms and viruses, dead organisms and viruses, genetically altered organisms or viruses, cell extracts, and RNA encoding at least one antigenic polypeptide or an immunogenic fragment thereof (e.g., an immunogenic fragment capable of inducing an immune response to the antigenic polypeptide). Active agents may be combined with interleukins, interferon, cytokines, and adjuvants such as cholera toxin, alum, Freund's adjuvant, etc. Prophylactic agents can include infection agents such as antigens of such bacterial organisms as *Streptococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as human Metapneumovirus (hMPV), human parainfluenza viruses (hPIV) types 1, 2, and 3 (hPIV1, hPIV2 and hPIV3, respectively), respiratory syncytial virus (RSV), measles virus (MeV), coronaviruses (e.g., MERS-CoV, SARS-CoV, SARS-CoV2, HCoV-OC43, HCoV-229E, HCoV-NL63, HCoV-NL, HCoV-NH, HCoV-HKU1), poxviruses (e.g., smallpox, monkeypox), African swine virus, influenza A and B, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In certain embodiments, the active agent is a polynucleotide. Polynucleotides or oligonucleotides that can be introduced according to the methods herein include DNA, cDNA, and RNA sequences of all types. For example, the polynucleotide can be double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA), self-amplify mRNA (saRNA), guide RNA (gRNA), cRNA and combinations thereof. The polynucleotides can also be DNA constructs, such as expression vectors, expression vectors encoding a desired gene product (e.g., a gene product homologous or heterologous to the subject into which it is to be introduced), and the like.

In some embodiments, the RNA (e.g., mRNA) may be used to induce a balanced immune response against an infection agent. In some embodiments, the RNA (e.g., mRNA) may be used to induce a balanced immune response against an viruses as Metapneumovirus such as human Metapneumovirus (hMPV), parainfluenza viruses such as human parainfluenza viruses (hPIV) types 1, 2, and 3 (hPIV1, hPIV2 and hPIV3, respectively), respiratory syncytial virus (RSV), measles virus (MeV), coronaviruses (e.g., MERS-CoV, SARS-CoV, SARS-CoV2, HCoV-OC43, HCoV-229E, HCoV-NL63, HCoV-NL, HCoV-NH, HCoV-HKU1), poxviruses (e.g., smallpox, monkeypox), African swine virus, influenza A and B, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like. In some embodiments, the RNA (e.g., mRNA) may be used to induce a balanced immune response against. In some embodiments, the RNA (e.g., mRNA) may be used to induce a balanced immune response against respiratory viruses. The term "respiratory viruses" refers herein to viruses causing respiratory diseases. For example, negative-sense, single-stranded RNA virus of the family Paramyxoviridae such as human Metapneumovirus (hMPV), human parainfluenza viruses (hPIV) types 1, 2, and 3 (hPIV1, hPIV2 and hPIV3, respectively), RSV, and Measles virus (MeV). Another example of respiratory viruses are coronaviruses. Coronaviruses are enveloped viruses with a positive-sense single-stranded RNA genome and with a nucleocapsid of helical symmetry. Coronaviruses are species of virus belonging to the subfamily Coronavirinae in the family Coronaviridae, in the order Nidovirales.

Representative examples of betacoronaviruses include, but are not limited to an embecovirus 1 (e.g., Betacoronavirus 1, Human coronavirus OC43, China *Rattus* coronavirus HKU24, Human coronavirus HKU1, Murine coronavirus), a hibecovirus (e.g., Bat Hp-betacoronavirus Zhejiang2013), a merbecovirus (e.g., Hedgehog coronavirus 1, Middle East respiratory syndrome-related coronavirus (MERS-CoV), *Pipistrellus* bat coronavirus HKU5, *Tylonycteris* bat coronavirus HKU4), a nobecovirus (e.g., Rousettus bat coronavirus GCCDCl, Rousettus bat coronavirus HKU9), a sarbecovirus (e.g., severe acute respiratory syndrome coronavirus (SARS-CoV), severe acute respiratory syndrome coronavirus 2 (SARS-CoV-2).

Representative examples of gammacoronaviruses include, but are not limited to, a cegacovirus (e.g., Beluga whale coronavirus SQ1) and an Igacovirus (e.g., Avian coronavirus (IBV)).

Representative examples of deltacoronaviruses include, but are not limited to, an andecovirus (e.g., Wigeon coronavirus HKU20), a buldecovirus (e.g., Bulbul coronavirus HKU11, Porcine coronavirus HKU15 (PorCoV HKU15), Munia coronavirus HKU13, White-eye coronavirus HKU16), a herdecovirus (e.g., Night heron coronavirus HKU19), and a moordecovirus (e.g., Common moorhen coronavirus HKU21).

In some embodiments, the coronavirus is a human coronavirus. Representative examples of human coronaviruses include, but are not limited to, human coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), severe acute respiratory syndrome coronavirus 2 (SARS-CoV-2), and Middle East respiratory syndrome-related coronavirus (MERS-CoV).

In some embodiments, the RNA (e.g., mRNA) polynucleotide having an open reading frame encoding at least one (e.g., at least 2, 3, 4 or 5) human Metapneumovirus (hMPV) antigenic polypeptide, human parainfluenza viruses (hPIV) types 1, 2, and 3 (hPIV1, hPIV2 and hPIV3, respectively) antigenic polypeptide, respiratory syncytial virus (RSV) antigenic polypeptide, measles virus (MeV) antigenic polypeptide, varicella-zoster antigenic polypeptide, influenza virus antigenic polypeptide, herpes simplex virus 1 (HSV1) antigenic polypeptide, herpes simplex virus 2 (HSV2) antigenic polypeptide, poxvirus (e.g., smallpox, monkeypox) antigenic polypeptide, African swine virus antigenic polypeptide, cytomegalovirus antigenic polypeptide, Epstein-Barr virus antigenic polypeptide, rotavirus antigenic polypeptide, rhinovirus antigenic polypeptide, adenovirus antigenic polypeptide, papillomavirus antigenic polypeptide, poliovirus antigenic polypeptide, mumps antigenic polypeptide, rabies antigenic polypeptide, rubella antigenic polypeptide, coxsackieviruses antigenic polypeptide, equine encephalitis antigenic polypeptide, Japanese encephalitis antigenic polypeptide, yellow fever antigenic polypeptide, Rift Valley fever antigenic polypeptide, hepatitis A, B, C, D, and E virus antigenic polypeptide, or coronaviruses (e.g., MERS-CoV, SARS-CoV, SARS-CoV2, HCoV-OC43, HCoV-229E, HCoV-NL63, HCoV-NL, HCoV-NH, HCoV-HKU1) antigenic polypeptide. Herein, use of the term "antigenic polypeptide" encompasses immunogenic fragments of the antigenic polypeptide (an immunogenic fragment that induces (or is capable of inducing) an immune response human Metapneumovirus (hMPV), human parainfluenza viruses (hPIV) types 1, 2, and 3 (hPIV1, hPIV2 and hPIV3, respectively), respiratory syncytial virus (RSV), measles virus (MeV), varicella-zoster, influenza virus, herpes simplex virus 1 (HSV1), herpes simplex virus 2 (HSV2), poxvirus (e.g., smallpox, monkeypox), African swine virus, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, or coronaviruses (e.g., MERS-CoV, SARS-CoV, SARS-CoV2, HCoV-OC43, HCoV-229E, HCoV-NL63, HCoV-NL, HCoV-NH, HCoV-HKU1), or any combination thereof.

In some embodiments, the agent is an RNA (e.g., mRNA) that can induce a balanced immune response against hMPV, PIV, RSV, MeV, and/or coronaviruses (e.g., MERS-CoV, SARS-CoV, SARS-CoV2, HCoV-OC43, HCoV-229E, HCoV-NL63, HCoV-NL, HCoV-NH and/or HCoV-HKU1), or any combination of two or more of the foregoing viruses, comprising both cellular and humoral immunity, without risking the possibility of insertional mutagenesis, for example.

In some embodiments, the nucleic acids disclosed herein can include at least one chemically modified nucleotide. In some embodiments, the at least one chemically modified nucleotide comprises a chemically modified nucleobase, a chemically modified ribose, a chemically modified phosphodiester linkage, or a combination thereof.

In one embodiment, the at least one chemically modified nucleotide is a chemically modified nucleobase.

In one embodiment, the chemically modified nucleobase is selected from 5-formylcytidine (5fC), 5-methylcytidine (5meC), 5-methoxycytidine (5moC), 5-hydroxycytidine (5hoC), 5-hydroxymethylcytidine (5hmC), 5-formyluridine (5fU), 5-methyluridine (5-meU), 5-methoxyuridine (5moU), 5-carboxymethylesteruridine (5camU), pseudouridine (Ψ), Ni-methylpseudouridine ($me^1Ψ$), $N^6$-methyladenosine ($me^6A$), or thienoguanosine ($^{th}G$).

In some embodiments, the chemically modified nucleobase is 5-methoxyuridine (5moU). In some embodiments, the chemically modified nucleobase is pseudouridine (Ψ). In some embodiments, the chemically modified nucleobase is $N^1$-methylpseudouridine ($me^1Ψ$).

The structures of these modified nucleobases are shown below:

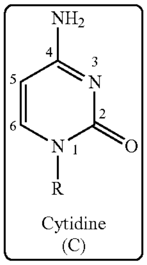
Cytidine (C)

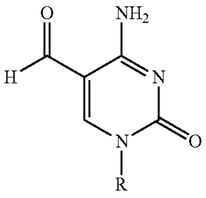
5-formylcytidine (5fC)

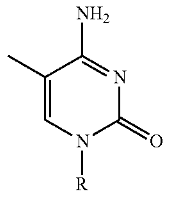
5-methylcytidine (5meC)

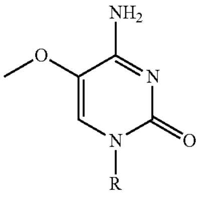
5-methoxycytidine (5moC)

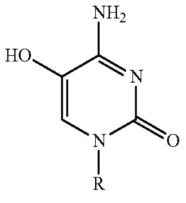
5-hydroxycytidine (5hoC)

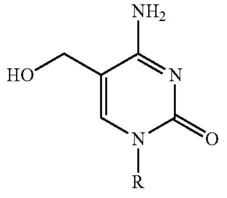
5-hydroxymethylcytidine (5hmC)

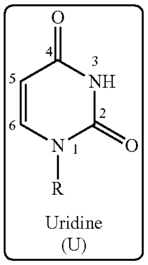
Uridine (U)

-continued

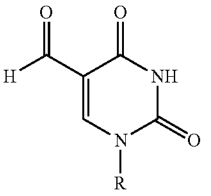

5-formyluridine (5fU)

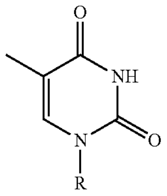

5-methyluridine (5meU)

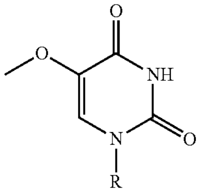

5-methoxy-uridine (5moU)

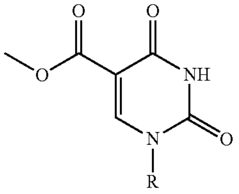

5-carboxy-methyl-esteruridine (5camU)

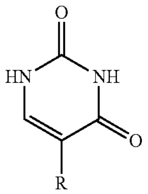

pseudouridine (Ψ)

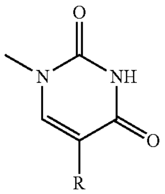

$N^1$-methylpseudo-uridine ($me^1Ψ$)

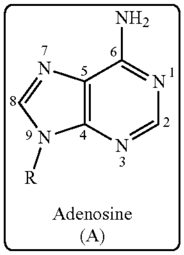

Adenosine (A)

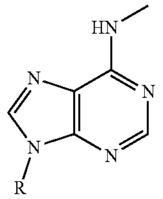

$N^8$ Methyladenosine ($me^6A$)

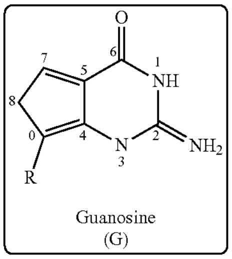

Guanosine (G)

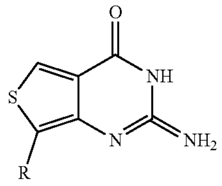

R-ribose.

Thienoguanosine ($^{th}G$)

In one embodiment, the at least one chemically modified nucleotide is a chemically modified ribose.

In one embodiment, the chemically modified ribose is selected from 2'-O-methyl (2'-O-Me), 2'-Fluoro (2'-F), 2'-deoxy-2'-fluoro-beta-D-arabino-nucleic acid (2'F-ANA), 4'-S, 4'-SFANA, 2'-azido, UNA, 2'-O-methoxy-ethyl (2'-O-ME), 2'-O-Allyl, 2'-O-Ethylamine, 2'-O-Cyanoethyl, Locked nucleic acid (LAN), Methylene-cLAN, N-MeO-amino BNA, or N-MeO-aminooxy BNA. In one embodiment, the chemically modified ribose is 2'-O-methyl (2'-O-Me). In one embodiment, the chemically modified ribose is 2'-Fluoro (2'-F).

The structures of these modified riboses are shown below:

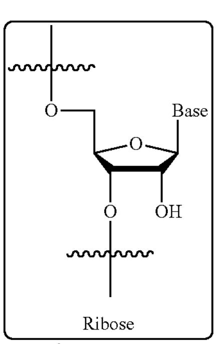

Ribose

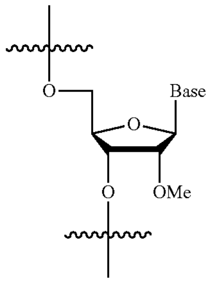

2'-O-methyl (2'-O-Me)

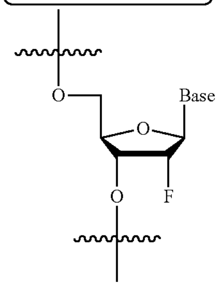

2'-Fluoro (2'-F)

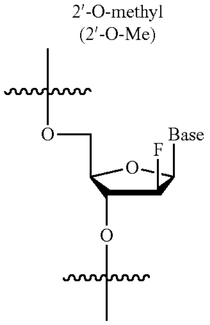

2'-deoxy-2'-fluoro-beta-D-arabino-nucleic acid (2'F-ANA)

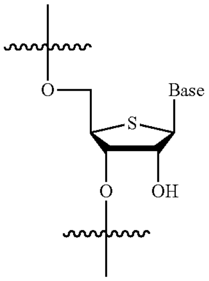

4'-S

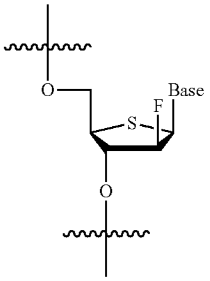

4'-SFANA

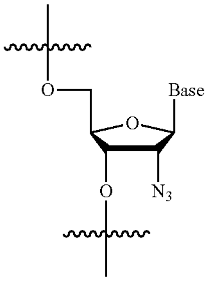

2'-azido

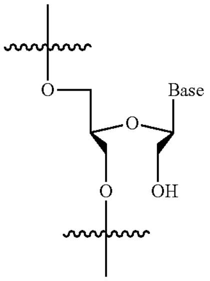

UNA

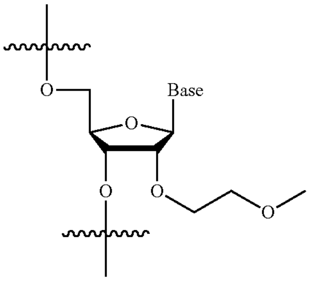

2'-O-methoxy-ethyl (2'-O-ME)

-continued

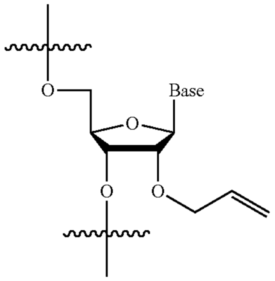

2′-O-Allyl

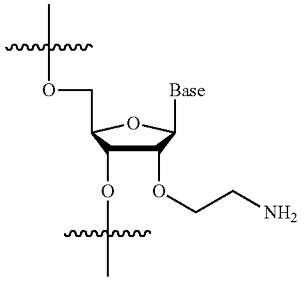

2′-O-Ethylamine

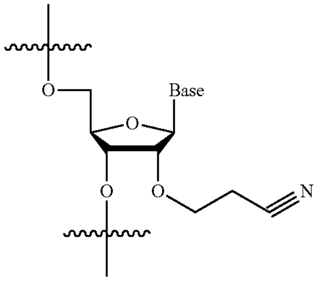

2′-O-Cyanoethyl

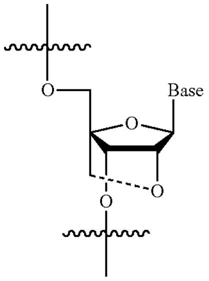

Locked nucleic acid (LAN)

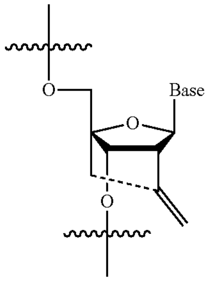

Methylene-cLAN

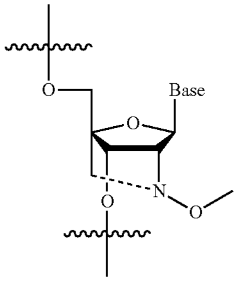

N-MeO-amino BNA

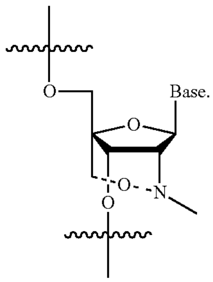

N-MeO-aminooxy BNA

In one embodiment, the at least one chemically modified nucleotide is a chemically modified phosphodiester linkage.

In one embodiment, the chemically modified phosphodiester linkage is selected from phosphorothioate (PS), boranophosphate, phosphodithioate (PS2), 3',5'-amide, N3'-phosphoramidate (NP), Phosphodiester (PO), or 2',5'-phosphodiester (2',5'-PO). In one embodiment, the chemically modified phosphodiester linkage is phosphorothioate.

The structures of these modified phosphodiester linkages are shown below:

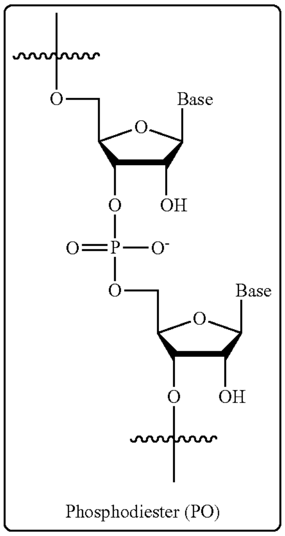

Phosphodiester (PO)

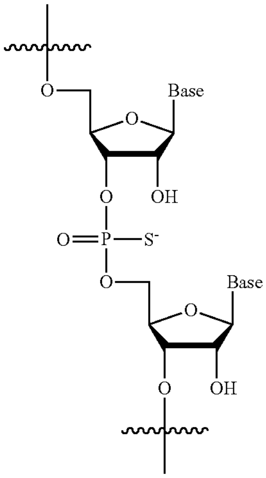

Phosphorothioate (PS)

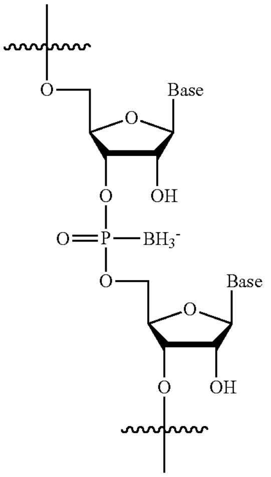

Boranophosphate

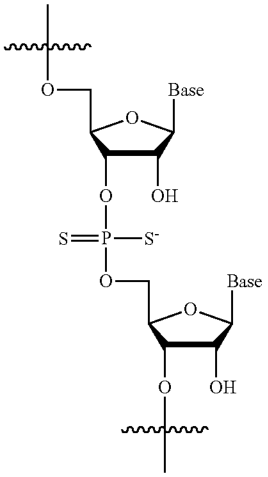

Phosphodithioate (PS2)

-continued

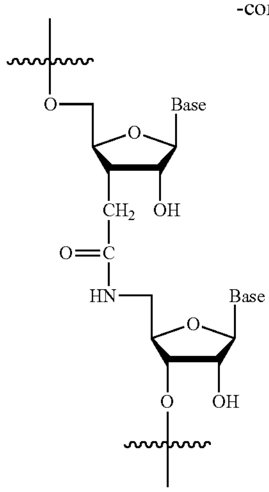

3′,5′-amide

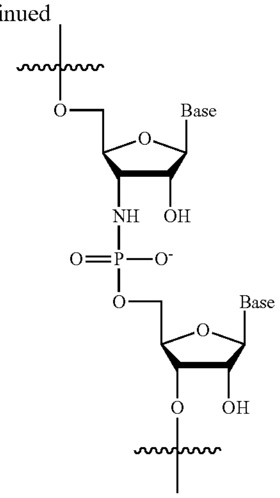

N3′-phosphoramidate (NP)

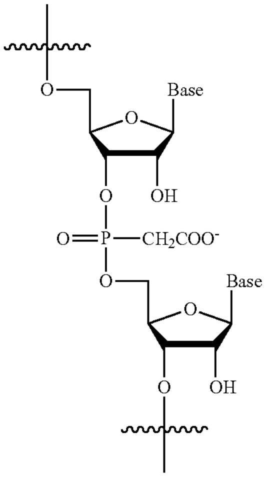

Phosphodiester (PO)

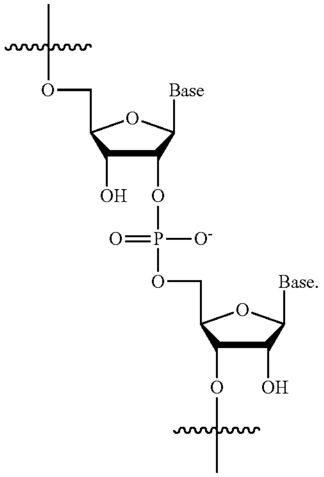

2′,5′-phosphodiester (2′,5′-PO)

In some embodiments, the mRNA can include a heterologous 5' untranslated region (5'UTR). In some embodiments, the mRNA can include a heterologous 3' untranslated region (3'UTR).

Methods

The composition of the present invention can be utilized as a composition for the diagnosis, prevention and treatment of a disease or disorder (e.g., an infection, of cancer, of pain, of depression, of an inflammatory disease, of an intestinal disease, of a brain disease, of an allergic disease, of arrhythmia, of hypertension, of an eye disease, of an endocrine disease, or of a cardiovascular disease), depending on the type of the active agent.

Described herein are methods for the delivery of an active agent (for example, a polynucleotide) into an organ, a tissue, and/or cell including: introducing into the organ, tissue and/or cell a composition or nanoparticle described herein including: a compound of Formula Y, I, Ia, II, III, IV, V or any combination thereof; and an active agent.

Described herein are methods for diagnosing, treating or preventing diseases comprising administering to a subject in need thereof an effective amount of a composition or nanoparticle described herein including a compound of Formula Y, I, Ia, II, III, IV, V or any combination thereof; and an active agent.

Described herein are methods for treating or preventing an infection comprising administering to a subject in need thereof an effective amount of a composition or nanoparticle described herein including a compound of Formula Y, I, Ia, II, III, IV, V or any combination thereof; and an active agent.

Described herein are methods for treating or preventing a respiratory infection comprising administering to a subject in need thereof an effective amount of a composition or nanoparticle described herein including a compound of Formula Y, I, Ia, II, III, IV, V or any combination thereof; and an active agent.

Described herein are also methods inducing an immune response against viruses, the method comprising administering to a subject in need thereof an effective amount of a composition or nanoparticle described herein including a compound of Formula Y, I, Ia, II, III, IV, V or any combination thereof; and an active agent.

Described herein are also methods inducing an immune response against respiratory viruses, the method comprising administering to a subject in need thereof an effective amount of a composition or a nanoparticle including a compound of Formula Y, I, Ia, II, III, IV, V or any combination thereof; and an active agent.

In some embodiments, provided herein are methods for the delivery of polynucleotides. In some embodiments, provided herein are methods for the delivery of polynucleotides (for example, mRNA) to provide expression of the polynucleotides (and translation to produce a protein) in a cell. In some embodiments, provided herein are methods for the delivery of polynucleotides (for example, mRNA) to induce an immune response in a subject.

In some embodiments, the methods for delivery of an active agent can introduce polynucleotide to a cell or tissue to express in vivo the encoded protein by the polynucleotide. In some embodiments, delivery of the active agent (e.g., polynucleotide) can correct a defect caused by a deficiency in that polynucleotide in the cell or tissue.

In some embodiments, the methods for delivery of an active agent can introduce a polynucleotide into a cell or tissue to regulate (e.g., turn off or decrease/increase) a specific gene expression. For example, delivery of an antisense mRNA or shRNA to tumor cells can regulate the protein expression encoded by the mRNA or shRNA.

In some embodiments, the methods for delivery of an active agent can introduce polynucleotide to a cell or tissue for cell reprogramming where the polynucleotide can be used to modulate cell behavior by expressing transcription factors or growth factors.

In some embodiments, the methods for delivery of an active agent can introduce a polynucleotide into a cell or tissue in vivo, for example to introduce "suicide genes" or drug sensitivity genes to tumor cells, allowing the cells to express prodrug activating enzyme, such as herpes simplex virus thymidine kinase, which can kill tumor cells upon exposure to a prodrug (e.g., acyclovir, ganciclovir, valcyclovir, or famciclovir).

In some embodiments, the methods for delivery of an active agent can introduce a polynucleotide into a cell or tissue to encode a polypeptide that evoke a specific immune response against a target cell. In some embodiments, the target cell can be a cancer cell, an infected cell, or any combination thereof. In some embodiments, the polynucleotide can encode an infection antigenic polypeptide, tumor antigen, cytokines (e.g., interferons, interleukins, colony stimulating factors), monoclonal antibodies, or antibody fragment (single chain fragment variable (scFv), fragment antigen binding ((Fab')2), intrabody, nanobody), or any combination thereof.

In some aspects, disclosed herein is a method of treating a cancer comprising administering to a subject in need thereof an effective amount of a composition or nanoparticle described herein including a compound of Formula Y, I, Ia, II, III, IV, V, or any combination thereof; and an active agent.

In some embodiments, the method for delivery of an active agent can include introducing a polynucleotide into a specific cell or tissue ex vivo to express a polypeptide encoded by the polynucleotide on the specific cell or tissue to generate a chimeric cell or tissue; and administering the chimeric cell or tissue to a subject for tumor treatment. In some embodiments, the specific cell can include CAR T cells, CAR-NK cells or other cells derived from a subject that can be used to for immunotherapy.

In some embodiments, the subject is a mammal. In some embodiments, the mammal is a human. In some embodiments, the subject is a veterinary patient.

In some embodiments, the compositions herein are used to treat both local and metastatic tumors.

In some embodiments, the compositions and methods described herein are useful for treating or preventing metastasis or recurrence of a cancer. In some embodiments, the compositions and methods described herein are useful for the prevention of recurrence of excised solid tumors. In some embodiments, the compositions and methods described herein are useful for the prevention of metastasis of excised solid tumors.

In one aspect, the methods described herein are used to treat cancer, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

In some embodiments, the compositions and methods described herein are useful in treating or preventing a cancer. In some cases, the cancer is a circulating cancer cell (circulating tumor cell). In some cases, the cancer is a metastatic cancer cell.

In some embodiments, the method further comprises administering an additional therapeutic agent. In some embodiments, the additional therapeutic agent comprises an additional immunotherapeutic agent, or an anti-neoplastic agent.

Also disclosed herein are methods of treating a disease or a condition such as an inflammation disorder (including an autoimmune disease) or lymphoid proliferative diseases, comprising administering to a subject in need thereof an effective amount of a compound, a combination of compounds, or a composition provided herein, or a pharmaceutically acceptable form thereof, or a pharmaceutical composition as provided herein.

Further disclosed herein are methods of treating a disease or a condition such as an inflammation disorder (including an autoimmune disease) or lymphoid proliferative diseases, comprising administering to a subject in need thereof an effective amount of a compound, a combination of compounds, or a composition provided herein, or a pharmaceutically acceptable form thereof, or a pharmaceutical composition as provided herein.

In one embodiment, provided herein is a method of treating an inflammation disorder, including autoimmune diseases in a subject. The method comprises administering to said subject a therapeutically effective amount of a compound, a combination of compounds, or a composition provided herein, or a pharmaceutically acceptable form thereof, or a pharmaceutical composition as provided herein. Examples of autoimmune diseases include but are not limited to acute disseminated encephalomyelitis (ADEM), Addison's disease, antiphospholipid antibody syndrome (APS), aplastic anemia, autoimmune hepatitis, autoimmune skin disease, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis (e.g., inflammatory alopecia), Chagas disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gout flare, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, polymyalgia rheumatic, reperfusion injury, regional enteritis, rheumatic fever, systemic lupus erythematosus, scleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), relapsing polychondritis (e.g., atrophic polychondritis and systemic polychondromalacia), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In one embodiment, provided herein is a method of treating an infection in a subject, the infection caused by an infection agent. The method comprises administering to said subject a therapeutically effective amount of a compound, a combination of compounds, or a composition provided herein, or a pharmaceutically acceptable form thereof, or a pharmaceutical composition as provided herein. The infection agents can include, but are not limited to, bacterial organisms as *Streptococcus pneumoniae, Haemophilus influenzae, Staphylococcus aureus, Streptococcus pyrogenes, Corynebacterium diphtheriae, Listeria monocyto-*

*genes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; viruses such as Metapneumovirus such as human Metapneumovirus (hMPV), parainfluenza viruses such as human parainfluenza viruses (hPIV) types 1, 2, and 3 (hPIV1, hPIV2 and hPIV3, respectively), respiratory syncytial virus (RSV), measles virus (MeV), coronaviruses (e.g., MERS-CoV, SARS-CoV, SARS-CoV2, HCoV-OC43, HCoV-229E, HCoV-NL63, HCoV-NL, HCoV-NH, HCoV-HKU1), poxviruses (e.g., smallpox, monkeypox), African swine virus, influenza A and B, human immunodeficiency virus (HIV), varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

In some embodiments, the infection can be a coronavirus infection. In one embodiment, the coronavirus infection is an infection of the upper and/or lower respiratory tract. The "upper respiratory tract" includes the mouth, nose, sinus, middle ear, throat, larynx, and trachea. The "lower respiratory tract" includes the bronchial tubes (bronchi) and the lungs (bronchi, bronchioles and alveoli), as well as the interstitial tissue of the lungs.

In another embodiment, the coronavirus infection is an infection of the gastrointestinal tract. The "gastrointestinal tract" may include any area of the canal from the mouth to the anus, including the mouth, esophagus, stomach, and intestines.

In yet another embodiment, the coronavirus infection is a renal infection.

It is understood and herein contemplated that the coronavirus infections disclosed herein can cause a pathological state associated with the coronavirus infection referred to herein as a "coronavirus disease." In some embodiments, the coronavirus disease is selected from a common cold, pneumonia, pneumonitis, bronchitis, severe acute respiratory syndrome (SARS), coronavirus disease 2019 (COVID-2019), Middle East respiratory syndrome (MERS), sinusitis, porcine diarrhea, porcine epidemic diarrhea, avian infections bronchitis, otitis and pharyngitis. In some embodiments, the coronavirus infection is a common cold. In some embodiments, the coronavirus infection is selected from SARS, COVID-19, and MERS. In a particular embodiment, the coronavirus infection is COVID-19. In another particular embodiment, the coronavirus infection is IBV, PorCoV HKU15, or PEDV.

Most patients identified with SARS were previously healthy adults aged 25-70 years. A few suspected cases of SARS have been reported among children under 15 years. The case fatality among persons with illness meeting the current World Health Organization case definition for probable and suspected cases of SARS is around 3%.

Other indications associated with coronavirus infections are described in Gralinski & Baric, 2015, *J. Pathol.* 235: 185-195 and Cavanagh, 2005, "Coronaviridae: a review of coronavirus and toroviruses", *Coronaviruses with Special Emphasis on First Insights Concerning SARS* 1, ed. By A. Schmidt, M. H. Wolff and O. Weber, Birkhauser Verlag Baser, Switzerland, each of which is incorporated herein by reference in their entirety.

The coronavirus causing the infection may be selected from an alphacoronavirus, a betacoronavirus, a gammacoronavirus, or a deltacoronavirus.

Eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

Endocrine disorders that may be treated according to the compositions and methods disclosed herein include thyroid disorders (e.g., hyperthyroidism, hypothyroidism, thyroiditis, goitre, diabetes, hypoglycemia, glucagonoma, calcium homeostasis disorders (e.g., parathyroid gland, osteoporosis, osteomalacia, rickets, sex hormone disorders (e.g, disorders of sex development, hypogonadism, disorders of puberty, menstrual function or fertility disorders).

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: Synthetic Scheme for Ionizable Lipid (Compound Target 1)

Described is the experimental procedure for synthesizing compound Target 1. The synthetic route for compound 1 is illustrated in FIG. 1.

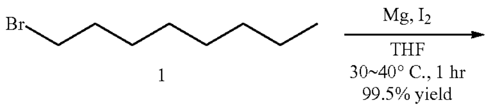

1

-continued

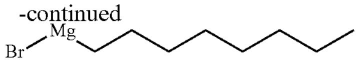

2

Procedure for preparation of compound 2: Charge Mg (48.5 g, 1.99 mol, 3.08 eq) and $I_2$ (20.0 mg, 78.8 μmol) into R1 (3.00 L three necked round bottom flask) at 30~40° C. under $N_2$. Charge compound 1 (125 g, 647 mmol, 113 mL, 1.00 eq) in THF (1.20 L) into R2 (2.00 L flask) at 30-40° C. Charge 5.00 mL of R2 into R1 at 30~40° C. An exothermic reaction is noticed, immediate decolorization is observed and the solution start refluxing. Charge the rest of R2 into R1 at 30~40° C. Stir R1 at 35° C. for 1 hr under $N_2$. An exothermic reaction is noticed and the color is turn to black brown. The mixture was used to next step without further purification. Compound 2 (140 g, 644 mmol, 99.5% yield) in THF (1.20 L) as a black brown liquid used to next step.

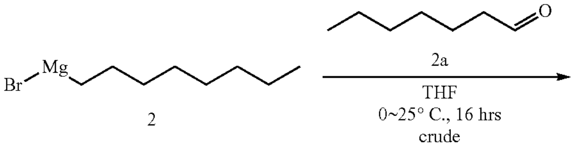

-continued

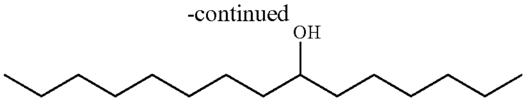

3

Procedure for preparation of compound 3: Charge compound 2 (141 g, 647 mmol, 146 mL, 1.40 eq) in THF (500 mL) to R1 (2.00 L three neck flask). Cool R1 to 0° C. Charge THF (400 mL) to R2 (1.00 L battle). Charge compound 2a (52.8 g, 462 mmol, 64.5 mL, 1.00 eq) into R2. Drop-wise the solution of R2 into R1 at 0° C. Stir R2 at 25° C. for 16 hrs. Charge the $H_2O$ (200 mL) into R2 (2.00 L barrel) at 25° C. Extract the reaction with ethyl acetate (800 mL*3) at 25° C. Dry the reaction with anhydrous $Na_2SO_4$ at 25° C. Concentrate organic phase below 40-50° C. to give a residue. The residue was purified by column chromatography to obtain compound 3 (129 g, 565 mmol, crude) as a white solid ($^1H$ NMR: 400 MHz, $CDCl_3$ δ 3.61-3.57 (m, 1H), 1.47-1.43 (m, 6H), 1.29-1.25 (m, 18H), 0.91-0.87 (m, 6H)).

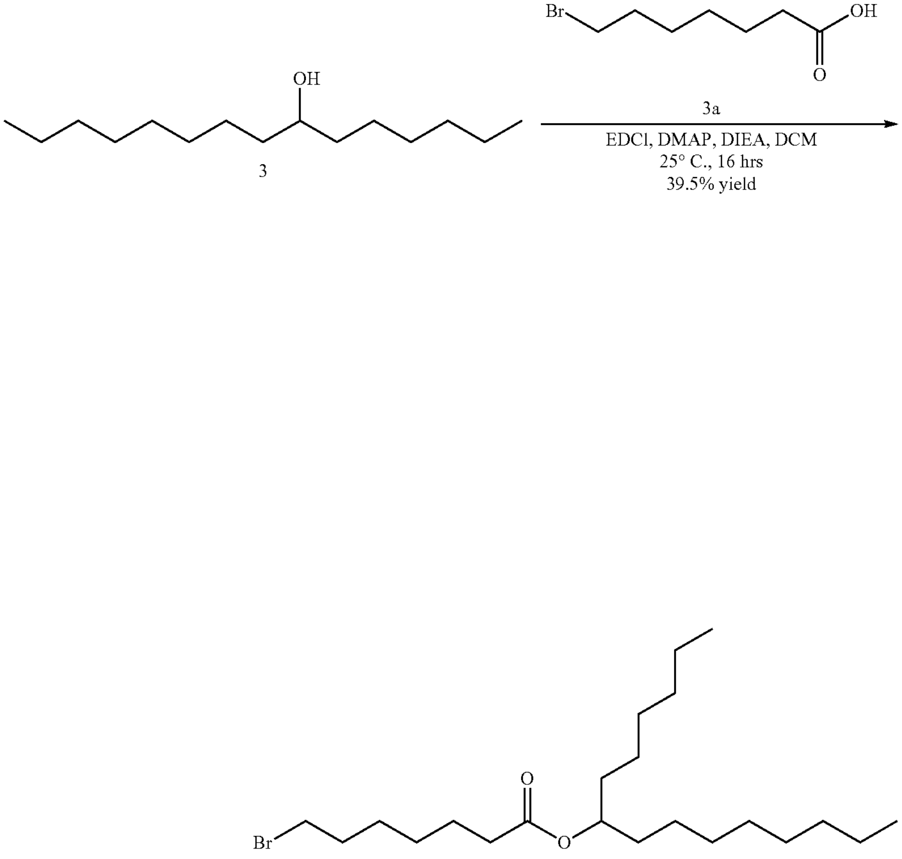

4

Procedure for preparation of compound 4: To a solution of compound 3 (50.0 g, 219 mmol, 1.10 eq) and compound 3a (41.6 g, 199 mmol, 1.00 eq) in 500 mL dichloromethane at 25° C., charge EDCI (49.6 g, 259 mmol, 1.30 eq), DIEA (103 g, 796 mmol, 139 mL, 4.00 eq) and DMAP (4.86 g, 39.8 mmol, 0.20 eq). Stir the mixture at 25° C. for 16 hrs. Charge 500 mL$H_2O$ into the mixture, and extract the reaction with dichloromethane (400 mL*3) at 25° C. Wash the reaction with saturated brine (300 mL*3) at 25° C. Dry the reaction with anhydrous $Na_2SO_4$ at 25° C. Concentrate organic phase below 40~50° C. to give a residue. The residue was purified by column chromatography to produce compound 4 (32.0 g, 78.7 mmol, 39.5% yield) as a colorless liquid ($^1$H NMR: 400 MHz, $CDCl_3$ δ 4.90-4.84 (m, 1H), 3.40 (t, J=6.8 Hz, 2H), 2.30 (t, J=7.2 Hz, 2H), 1.90-1.82 (m, 2H), 1.68-1.61 (m, 2H), 1.52-1.45 (m, 5H), 1.43-1.34 (m, 3H), 1.30-1.25 (m, 20H), 0.882 (t, J=6.4 Hz, 6H)).

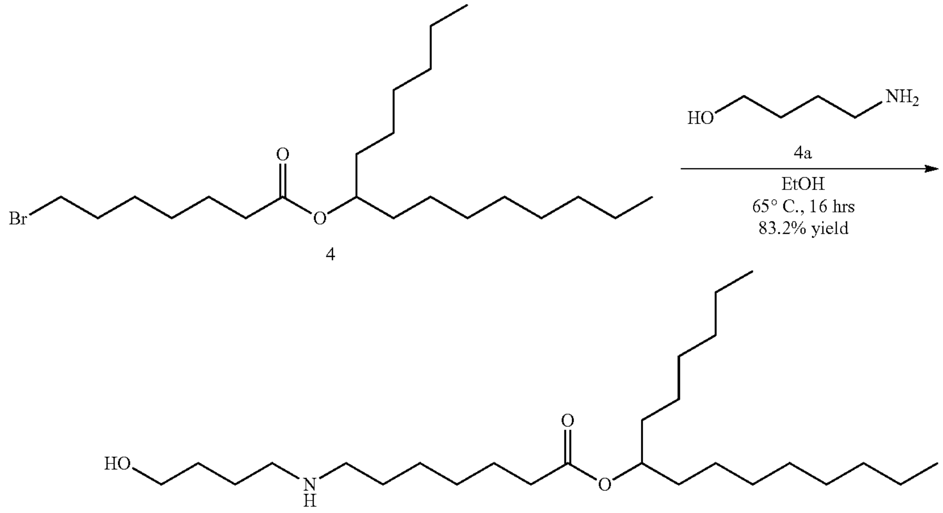

4

5

Procedure for preparation of compound 5: To a solution of compound 4 (32.0 g, 78.7 mmol, 1.00 eq) in 33 mL EtOH, charge compound 4a (210 g, 2.36 mol, 219 mL, 30.0 eq) into the solution at 25° C. Heat the mixture to 65° C. and stirred at 65° C. for 16 hrs. Cool down to 25° C. and charge 100 mL $H_2O$ into the mixture. Extract the reaction with ethyl acetate (60.0 mL*3), and wash the reaction with saturated brine (50.0 mL*3) at 25° C. Dry the reaction with anhydrous $Na_2SO_4$ at 25° C. Concentrate organic phase below 40~50° C. to give a residue. The residue was purified by column chromatography obtain compound 5 (16.4 g, 65.5 mmol, 83.2% yield) as a red oil (1H NMR: 400 MHz, $CDCl_3$ δ 4.89-4.83 (m, 1H), 3.58-3.56 (m, 2H), 2.66-2.62 (m, 2H), 2.55-2.52 (m, 2H), 2.25-2.19 (m, 2H), 1.64-1.53 (m, 6H), 1.44-1.42 (m, 6H), 1.28-1.25 (m, 7H), 1.19 (s, 17H), 0.89-0.86 (m, 6H)).

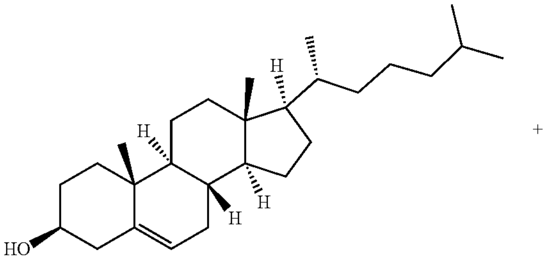

5c

+

-continued

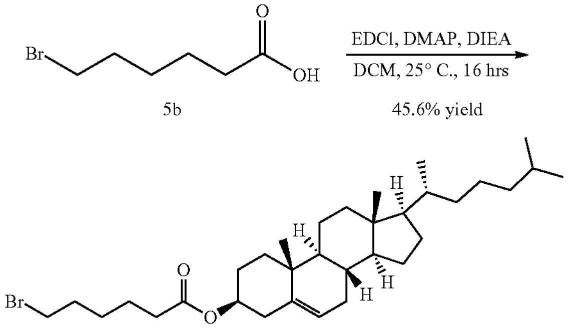

5b

5a

Procedure for preparation of compound 5a: To a solution of compound 5c (20.0 g, 51.7 mmol, 13.51 mL, 1.10 eq) in 400 mL DCM at 25° C., charge compound 5b (9.17 g, 47.0 mmol, 1.00 eq) into the solution. Then, charge EDCI (11.7 g, 61.1 mmol, 1.30 eq), DMAP (1.15 g, 9.40 mmol, 0.200 eq) and DIEA (24.3 g, 188 mmol, 32.8 mL, 4.00 eq) and stir the mixture at 25° C. for 16 hrs. Charge 300 mL $H_2O$ the mixture and extract the mixture with DCM (100 mL*3) at 25° C. Dry the reaction with anhydrous $Na_2SO_4$, and concentrate organic phase below 40-50° C. to give a residue.

The residue was purified by column chromatography to produce compound 5a (12.1 g, 21.5 mmol, 45.6% yield) as a white solid ($^1$H NMR: EC3947-13-P1A1, 400 MHz, $CDCl_3$ δ 5.38 (d, J=4.8 Hz, 1H), 4.67-4.59 (m, 1H), 3.44-3.38 (m, 2H), 2.34-2.29 (m, 4H), 2.03-2.00 (m, 2H), 1.66-1.51 (m, 4H), 1.50-1.48 (m, 6H), 1.35-1.33 (m, 5H), 1.27-1.13 (m, 7H), 1.03 (s, 3H), 0.92 (d, J=6.4 Hz, 3H), 0.089-0.087 (m, 6H), 0.07 (s, 3H)).

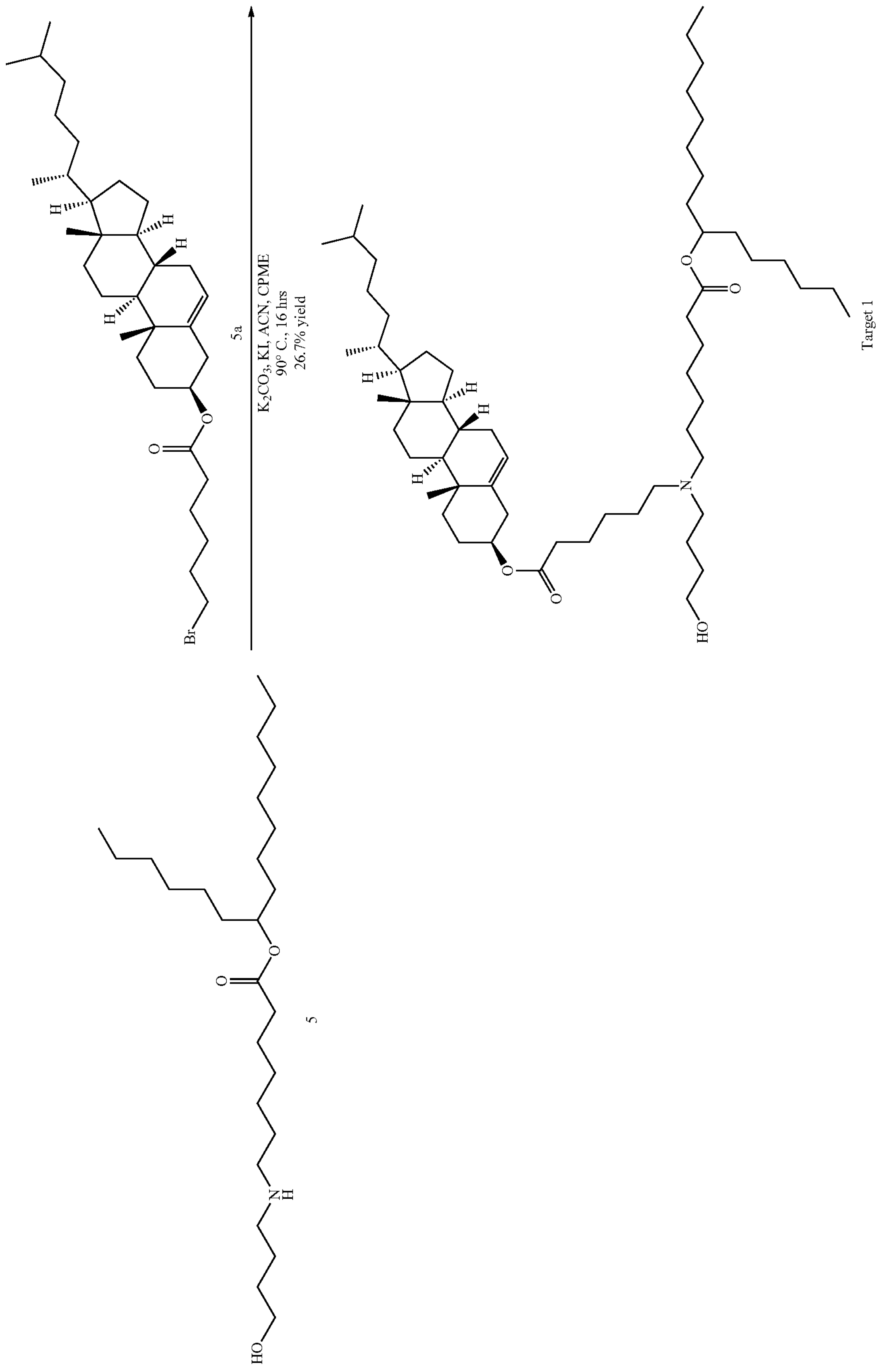
5
5a
$K_2CO_3$, KI, ACN, CPME
90° C., 16 hrs
26.7% yield
Target 1

Figure 2A:
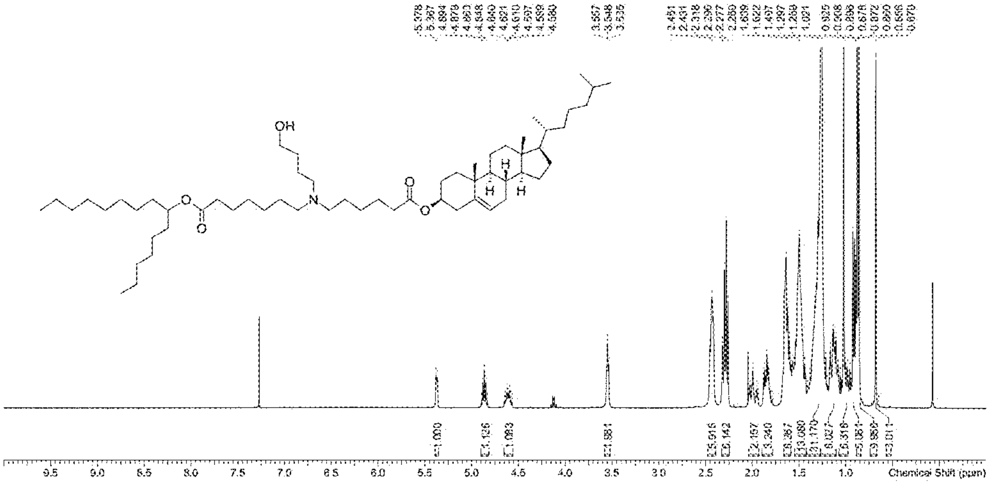
FIGS. 2A-2C show $^1$H NMR spectra (2A), mass spectra (2B), and HPLC spectra (2C) for compound Target 1.
Figure 2B:
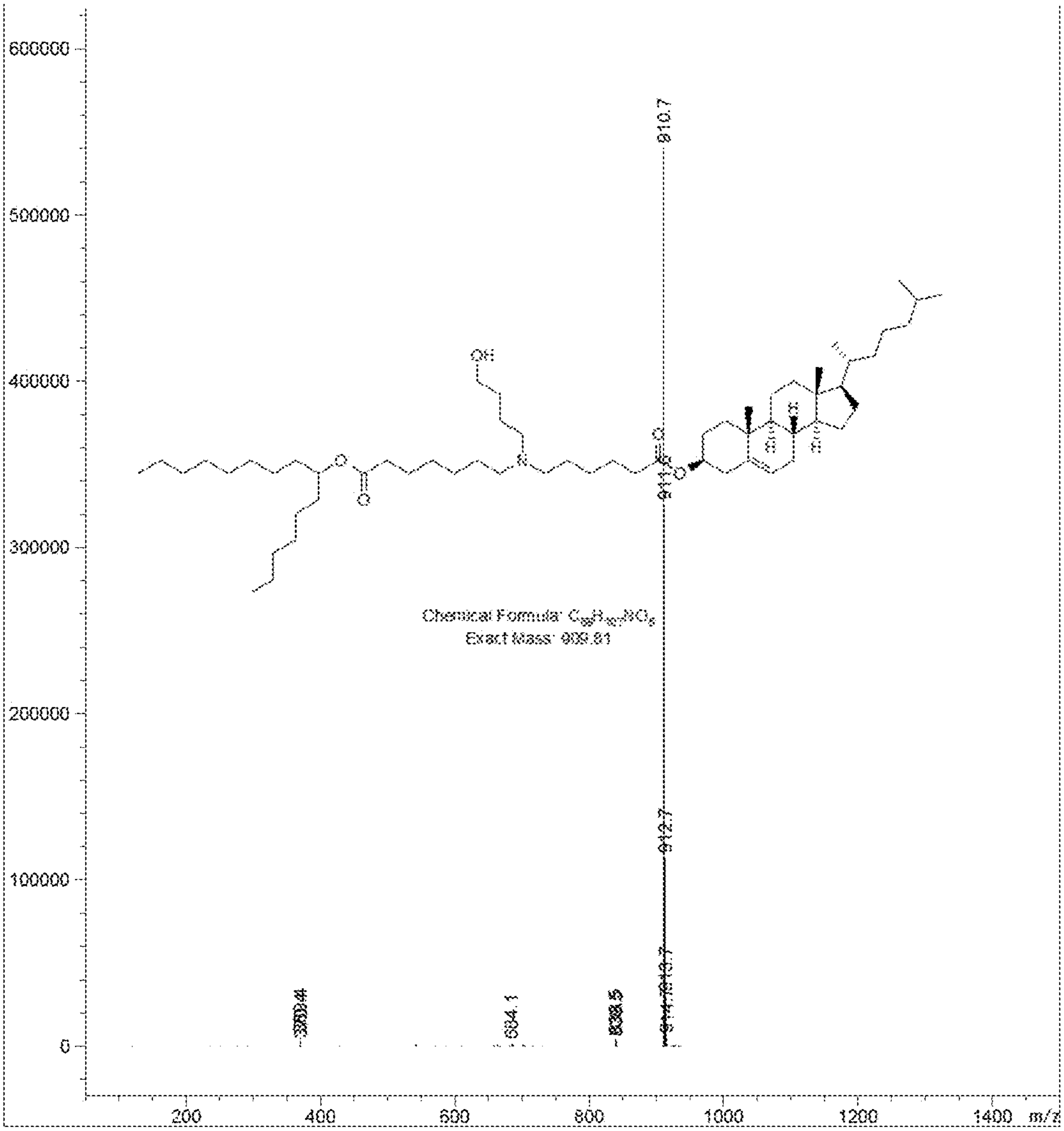
Figure 2C:
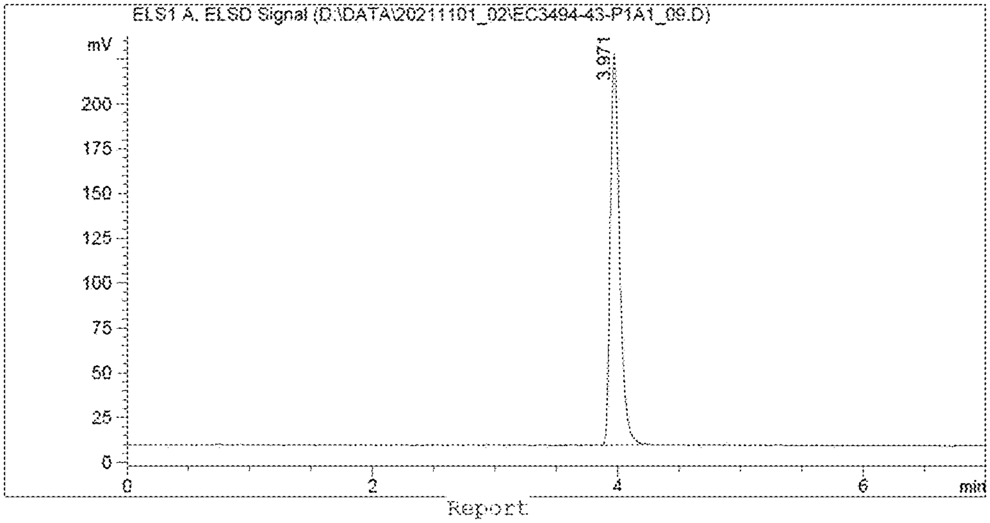

Procedure for preparation of lipid Target 1: To a solution of compound 6 (6.40 g, 14.9 mmol, 1.00 eq) in 140 mL ACN, charge compound 6a (8.43 g, 14.9 mmol, 1.00 eq) into the solution at 25° C. Charge $K_2CO_3$ (8.27 g, 59.9 mmol, 4.00 eq), KI (2.73 g, 16.5 mmol, 1.10 eq) and CPME (35.0 mL) into the solution. Heat the mixture to 90° C. and stir the mixture at 90° C. for 16 hrs. After cool to 25° C., the residue was dissolved with dichloromethane (100 mL) and filtered. The residue was purified by column chromatography to get compound Target 1 as a yellow oil (MS: m/z=910.7 (M+H)+, $^1$H NMR: 400 MHz, $CDCl_3$ δ 5.38 (d, J=4.0 Hz, 1H), 4.89-4.79 (m, 1H), 4.64-4.58 (m, 1H), 3.55 (d, J=8.0 Hz, 2H), 2.45-2.35 (m, 6H), 2.25-2.19 (m, 6H), 1.98-1.88 (m, 2H), 1.80-1.72 (m, 3H), 1.57-1.52 (m, 8H), 1.47-1.34 (m, 13H), 1.27-1.14 (m, 31H), 1.10-1.01 (m, 8H), 0.95-0.90 (m, 6H), 0.89-0.82 (m, 5H), 0.81-0.78 (m, 10H), 0.68 (s, 3H)). FIGS. 2A-2C show 1H NMR spectra (2A), mass spectra (2B), and HPLC spectra (2C) for compound Target 1.

Example 2: Synthetic Scheme for Ionizable Lipid (Compound Target 11)

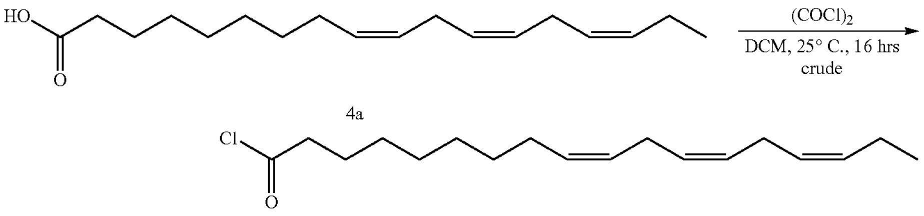

4a

4b

To a solution of compound 4a (10.0 g, 31.6 mmol, 1.00 eq) in DCM (270 mL) was added $(COCl)_2$ (27.2 g, 214 mmol, 18.8 mL, 6.80 eq) and DMF (231 mg, 3.16 mmol, 243 μL, 0.01 eq). The mixture was stirred at 25° C. for 16 hrs. Diluting a drop of reaction mixture with 3 drops of methanol to get a mixture and then the mixture was monitored by TLC. TLC (DCM:Methanol=10:1) showed compound 4a ($R_f$=0.30) was consumed completely and a new spot ($R_f$=0.80) was detected. Then the reaction mixture was concentrated in vacuum to give compound 4b (9.00 g, crude) as brown oil.

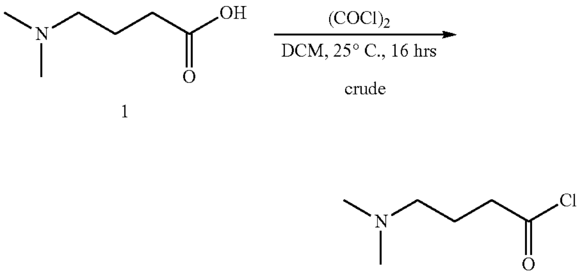

1

1b

To a solution of compound 1 (4.00 g, 30.4 mmol, 1.00 eq) in DCM (200 mL) was added $(COCl)_2$ (11.6 g, 91.4 mmol, 8.01 mL, 3.00 eq) and DMF (22.2 mg, 304 mol, 23.4 μL, 0.01 eq). The mixture was stirred at 25° C. for 16 hrs. Diluting a drop of reaction mixture with 3 drops of methanol to get a mixture and then the mixture was monitored by TLC. TLC (DCM:Methanol=10:1) showed compound 1 ($R_f$=0.00) was consumed completely and a new spot ($R_f$=0.50) was detected. Then the reaction mixture was concentrated in vacuum to give compound 1b (4.50 g, crude) as a brown solid.

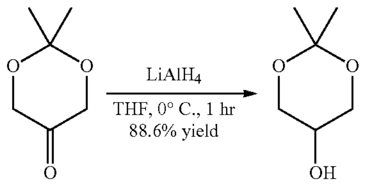

b1 b2

To a solution of compound b1 (20.0 g, 153 mmol, 1.00 eq) in THF (400 mL) was added $LiAlH_4$ (2.50 M, 61.4 mL, 1.00 eq) at 0° C. under $N_2$. The mixture was stirred at 25° C. for 1 hr under $N_2$. TLC (Petroleum ether:EtOAc=1:1) showed compound b1 ($R_f$=0.80) was consumed and a new spot ($R_f$=0.20) was detected. The reaction mixture was quenched with $Na_2SO_4 \cdot 10H_2O$ until a lot of white solids were produced and no gas was produced at 0° C. The solid was filtered, the filter cake was washed with DCM (3×100 mL). The combined filtrate was dried over anhydrous $Na_2SO_4$ and filtered. The filtrate was concentrated in vacuum to give compound b2 (18.0 g, 136 mmol, 88.6% yield) as colorless oil. $^1$H NMR: (400 MHz, DMSO-$d_6$) δ 4.94-4.91 (m, 1H), 3.80-3.74 (m, 2H), 3.52-3.44 (m, 3H), 1.33 (s, 3H), 1.27 (s, 3H).

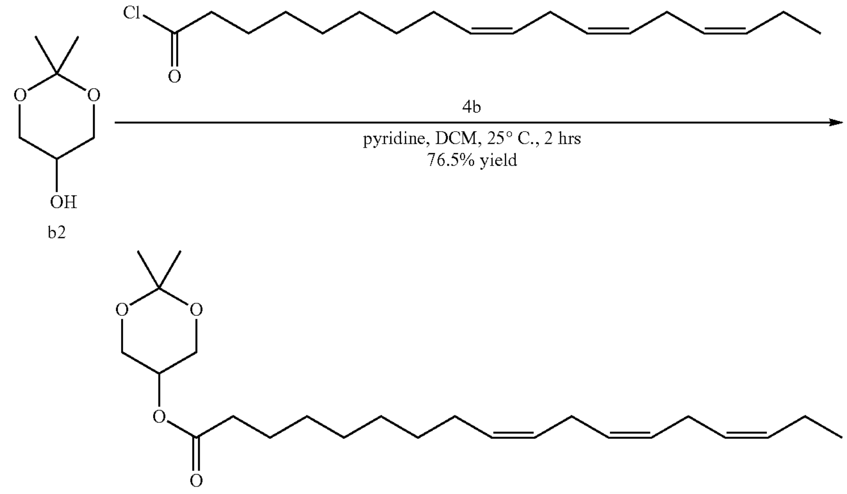

b2 b3

To a solution of compound b2 (4.00 g, 30.2 mmol, 1.00 eq) and pyridine (4.79 g, 60.5 mmol, 4.89 mL, 2.00 eq) in DCM (200 mL) was added compound 4b (8.99 g, 30.2 mmol, 1.00 eq). The mixture was stirred at 25° C. for 2 hrs. TLC (Petroleum ether:EtOAc=1:1) showed compound b2 ($R_f$=0.20) was consumed and a new spot ($R_f$=0.80) was detected. The reaction mixture was poured into 400 mL of water and then extracted with DCM (3×100 mL). The combined organic layers were washed with brine (100 mL), dried over $Na_2SO_4$ and filtered. The filtrate was concentrated in vacuum to get a residue. The residue was purified by column chromatography ($SiO_2$, Petroleum ether: EtOAc=100:1 to 5:1, $R_f$=0.40 (Petroleum ether:EtOAc=5: 1)) to give compound b3 (10.0 g, 23.1 mmol, 76.5% yield, 91.0% purity in LCMS at ELSD) as light yellow oil. $^1H$ NMR: (400 MHz, $CDCl_3$) δ 5.45-5.28 (m, 6H), 4.74-4.69 (m, 1H), 4.10 (dd, J=13.2, 3.6 Hz, 2H), 3.81 (dd, J=12.8, 3.6 Hz, 2H), 2.86-2.75 (m, 4H), 2.38 (t, J=7.6 Hz, 2H), 2.11-2.03 (m, 4H), 1.68-1.60 (m, 2H), 1.45 (s, 6H), 1.36-1.30 (m, 8H), 0.98 (t, J=7.6 Hz, 3H).

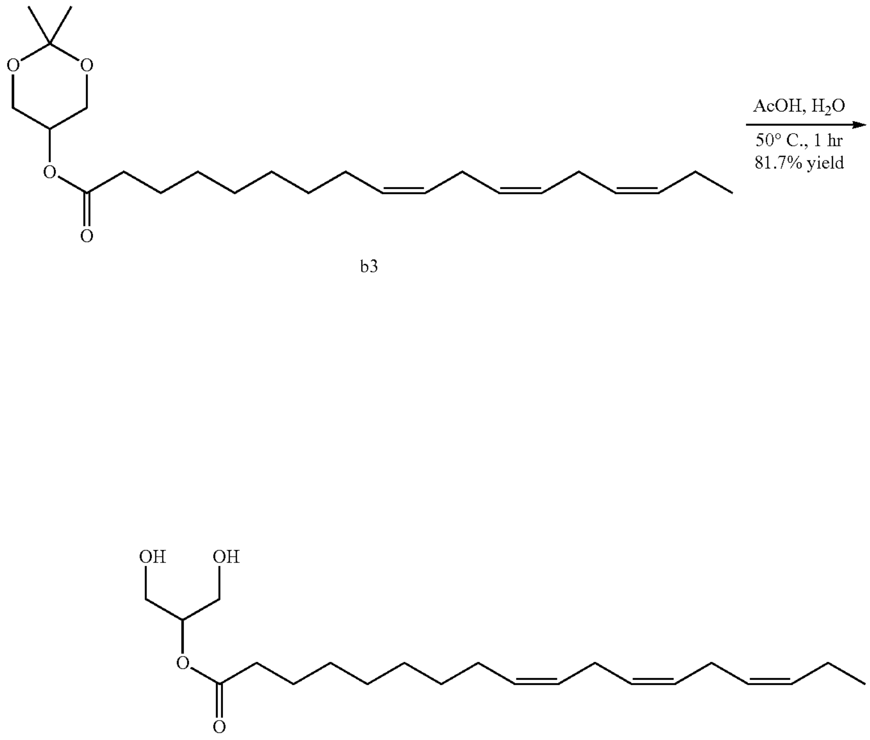

b3 b4

A solution of compound b3 (10.0 g, 23.1 mmol, 1.00 eq) in AcOH (80.0 mL) and $H_2O$ (20.0 mL) was stirred at 50° C. for 1 hr. TLC (Petroleum ether:EtOAc=1:1) showed compound b3 ($R_f$=0.80) was consumed and a new spot ($R_f$=0.20) was detected. The reaction mixture was concentrated in vacuum and then diluted with EtOAc (100 mL). The organic layer was washed with saturated $NaHCO_3$ solution (50.0 mL), water (50.0 mL) and brine (50.0 mL) in turn. Then the organic layer was dried over $Na_2SO_4$ and filtered. The filtrate was concentrated in vacuum to give compound b4 (7.00 g, 18.9 mmol, 81.7% yield, 95.4% purity in LCMS at ELSD) as yellow oil. $^1$H NMR: (400 MHz, DMSO-$d_6$) δ 5.40-5.24 (m, 6H), 4.73-4.67 (m, 2H), 4.02 (dd, J=14.4, 7.2 Hz, 1H), 3.53-3.39 (m, 4H), 2.81-2.71 (m, 4H), 2.30-2.24 (m, 2H), 2.08-2.00 (m, 4H), 1.55-1.47 (m, 2H), 1.30-1.24 (m, 8H), 0.92 (t, J=7.2 Hz, 3H).

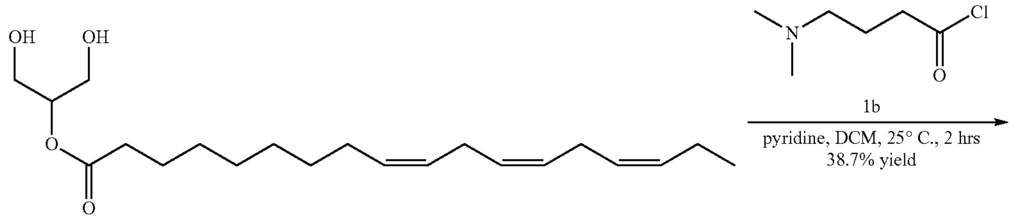

b4

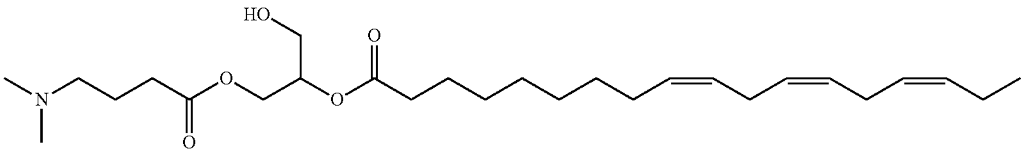

6

To a solution of compound b4 (7.00 g, 18.9 mmol, 1.00 eq) and pyridine (3.00 g, 37.8 mmol, 3.06 mL, 2.00 eq) in DCM (140 mL) was added a solution of compound 1b (2.27 g, 15.1 mmol, 0.80 eq) in DCM (20.0 mL). The mixture was stirred at 25° C. for 2 hrs. LCMS (EC15884-22-P1B1) showed most of compound b4 (Rt=2.118 mins) was consumed and desired mass (Rt=1.845 mins) was detected. The reaction mixture was poured into 200 mL of water and extracted with DCM (3×100 mL). The combined organic layers were washed with brine (100 mL), dried over $Na_2SO_4$ and filtered. The filtrate was concentrated in vacuum to get a residue. The residue was purified by column chromatography ($SiO_2$, Petroleum ether:EtOAc=100:1 to 5:1, $R_f$=0.40 (Petroleum ether:EtOAc=5:1)) to give compound 6 (3.50 g, 7.34 mmol, 38.7% yield, 97.7% purity in LCMS at ELSD) as yellow oil. $^1$H NMR: (400 MHz, $CDCl_3$) δ 5.41-5.28 (m, 6H), 5.11-5.04 (m, 1H), 4.37-4.30 (m, 1H), 4.25-4.18 (m, 1H), 4.16-4.06 (m, 2H), 2.84-2.74 (m, 4H), 2.61-2.51 (m, 2H), 2.47-2.42 (m, 2H), 2.40 (d, J=4.4 Hz, 6H), 2.36-2.30 (m, 2H), 2.11-2.01 (m, 4H), 1.97-1.86 (m, 2H), 1.65-1.57 (m, 2H), 1.34-1.28 (m, 8H), 0.96 (t, J=7.6 Hz, 3H).

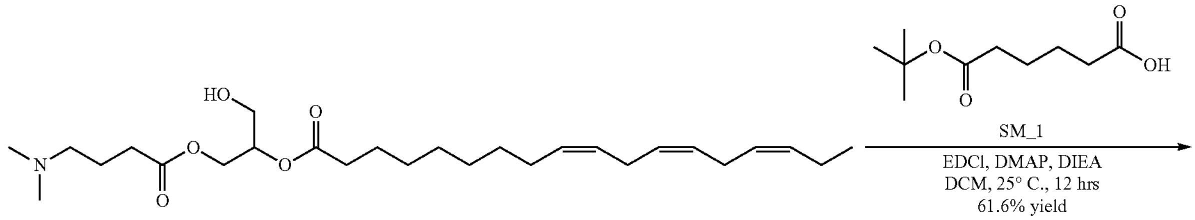

6

-continued

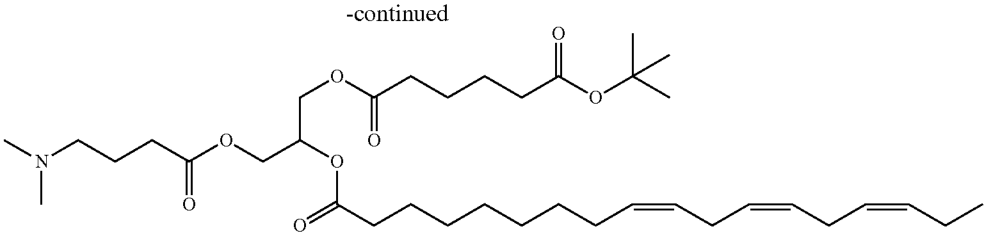

6d

To a solution of compound 6 (3.20 g, 6.71 mmol, 1.00 eq) in DCM (60.0 mL) was added compound SM_1 (1.63 g, 8.06 mmol, 1.20 eq), EDCI (1.93 g, 10.0 mmol, 1.50 eq), DIEA (3.47 g, 26.8 mmol, 4.68 mL, 4.00 eq) and DMAP (164 mg, 1.34 mmol, 0.20 eq). The mixture was stirred at 25° C. for 12 hrs. LCMS (EC15884-24-P1A1) showed compound 6 was consumed completely and desired mass (Rt=1.617 mins) was detected. The reaction mixture was concentrated in vacuum to get a residue. The residue was diluted with 50.0 mL of EtOAc. The organic layer was washed with $H_2O$ (50.0 mL), brine (50.0 mL), dried over $Na_2SO_4$ and filtered. The filtrate was concentrated in vacuum to get a residue. The residue was purified by column chromatography ($SiO_2$, DCM:Methanol=100:1 to 10:1, $R_f$=0.50 (DCM:Methanol=10:1)) to give compound 6d (3.00 g, 4.14 mmol, 61.6% yield, 89.6% purity in LCMS at ELSD) as yellow oil.

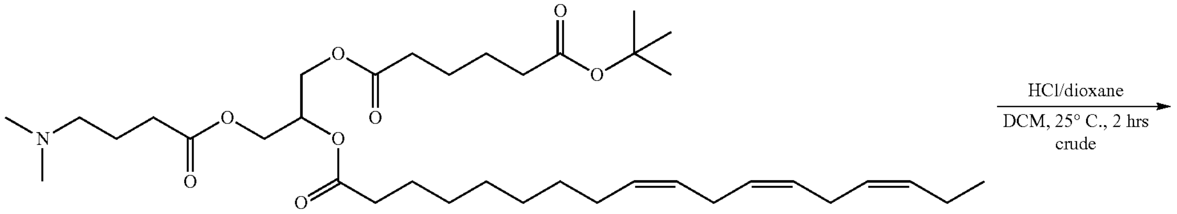

6d

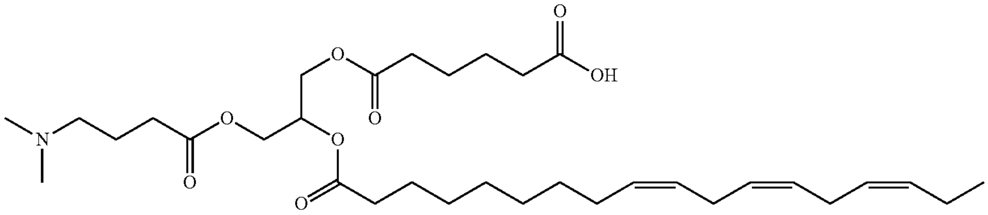

6c

To a solution of compound 6d (3.00 g, 4.14 mmol, 1.00 eq) in DCM (10.0 mL) was added HCV/dioxane (4.00 M, 30.0 mL, 29.0 eq). The mixture was stirred at 25° C. for 2 hrs. LCMS (EC15884-25-P1A1) showed compound 6d was consumed completely and desired mass (Rt=0.334 min) was detected. The reaction mixture was concentrated in vacuum to give compound 6c (2.46 g, crude) as yellow oil.

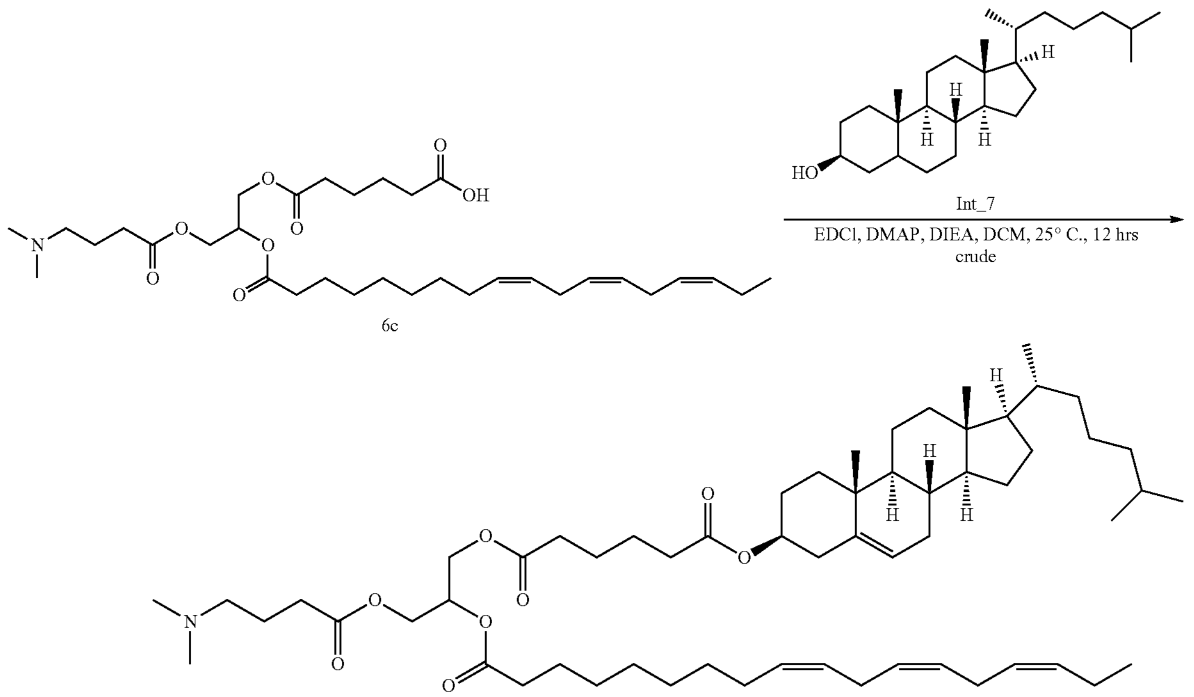

6c

To a solution of compound 6c (2.46 g, 4.14 mmol, 1.00 eq) in DCM (25.0 mL) was added Int_7 (2.40 g, 6.21 mmol, 1.62 mL, 1.50 eq), EDCI (1.03 g, 5.39 mmol, 1.30 eq), DIEA (2.68 g, 20.7 mmol, 3.61 mL, 5.00 eq) and DMAP (101 mg, 828 mol, 0.20 eq). The mixture was stirred at 25° C. for 12 hrs. LCMS (EC15884-26-P1A2) showed compound 6c was consumed completely and desired mass (Rt=2.090 mins) was detected. The reaction mixture was concentrated in vacuum to get a residue. The residue was diluted with 50.0 mL of EtOAc. The organic layer was washed with $H_2O$ (50.0 mL), brine (50.0 mL), dried over $Na_2SO_4$ and filtered. The filtrate was concentrated in vacuum to give Target 11 (4.00 g, crude) as yellow oil.

The crude Target 11 (4.00 g, crude) was purified by prep-HPLC (column: Welch Ultimate XB-CN 250*50*10 um; mobile phase: [EtOH+MeOH(4:1, neutral)]; gradient: 12%-100% B over 16 mins) and then by column chromatography ($SiO_2$, DCM:Methanol=100:0 to 50:1, $R_f$=0.35 (DCM:Methanol=10:1)) to give Target 11 (511.07 mg, 0.522 mmol, 98.3% purity, 12.5% yield) as yellow oil. $^1H$ NMR: (400 MHz, $CDCl_3$) δ 5.45-5.23 (m, 8H), 4.67-4.57 (m, 1H), 4.35-4.27 (m, 2H), 4.19-4.11 (m, 2H), 2.86-2.75 (m, 4H), 2.41-2.27 (m, 18H), 2.13-1.94 (m, 7H), 1.89-1.78 (m, 6H), 1.70-1.41 (m, 16H), 1.39-1.33 (m, 5H), 1.29-1.22 (m, 2H), 1.21-1.04 (m, 8H), 1.02 (s, 3H), 1.01-0.94 (m, 5H), 0.92 (d, J=6.4 Hz, 3H), 0.87 (d, J=6.8, 1.6 Hz, 6H), 0.68 (s, 3H).

Example 3: Synthetic Scheme for Ionizable Lipid (Compound Target 12)

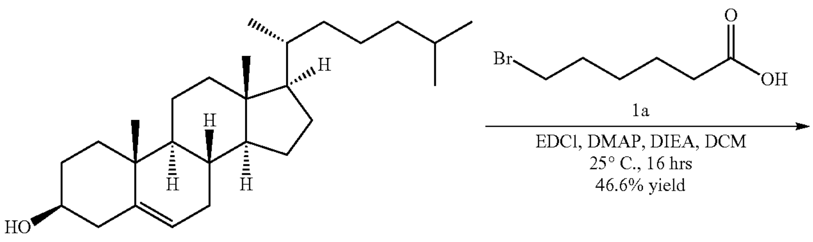

Int_7

-continued

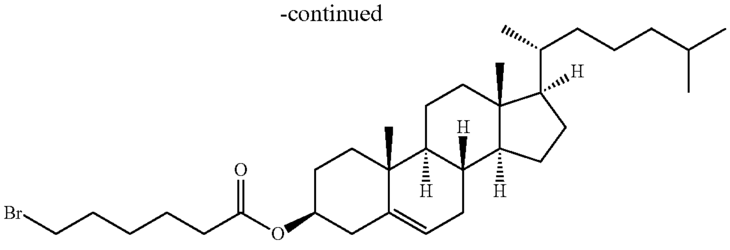

1

To a solution of compound Int_7 (11.0 g, 28.4 mmol, 7.43 mL, 1.10 eq) in DCM (220 mL) was added compound 1a (5.04 g, 25.8 mmol, 1.00 eq), EDCI (6.45 g, 33.6 mmol, 1.30 eq), DMAP (631 mg, 5.17 mmol, 0.20 eq) and DIEA (13.3 g, 103 mmol, 18.0 mL, 4.00 eq) at 25° C. The mixture was stirred at 25° C. for 16 hrs. TLC (Petroleum ether:Ethyl acetate=10:1) showed most of compound Int_7 ($R_f$=0.10) was consumed and a new spot ($R_f$=0.50) was formed. The reaction mixture was concentrated in vacuum to get a residue. The residue was purified by column chromatography ($SiO_2$, Petroleum ether:Ethyl acetate=100:1 to 10:1, $R_f$=0.50 (Petroleum ether:Ethyl acetate=10:1)) to give compound 1 (6.80 g, 12.0 mmol, 46.6% yield) as a white solid. $^1$H NMR: (400 MHz, $CDCl_3$) δ 5.38 (d, J=4.0 Hz, 1H), 4.67-4.56 (m, 1H), 3.41 (t, J=6.8 Hz, 2H), 2.36-2.27 (m, 4H), 2.05-1.94 (m, 2H), 1.93-1.81 (m, 5H), 1.70-1.58 (m, 4H), 1.55-1.46 (m, 6H), 1.45-1.27 (m, 5H), 1.23-1.05 (m, 8H), 1.02 (s, 3H), 1.01-0.95 (m, 2H), 0.92 (d, J=6.4 Hz, 3H), 0.87 (dd, J=6.4, 1.6 Hz, 6H), 0.68 (s, 3H).

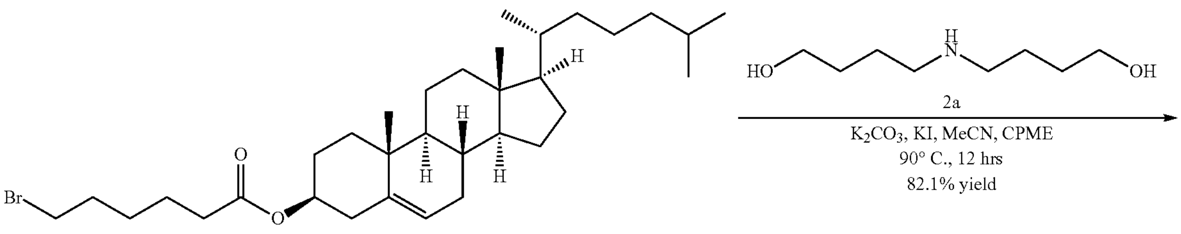

1

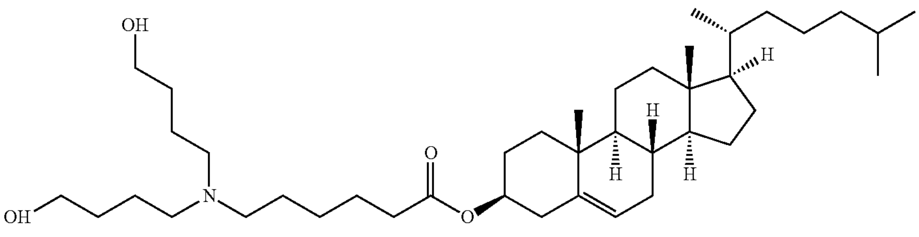

2

To a solution of compound 2a (1.14 g, 7.10 mmol, 1.00 eq) in ACN (60.0 mL) was added compound 1 (4.00 g, 7.10 mmol, 1.00 eq), $K_2CO_3$ (3.92 g, 28.3 mmol, 4.00 eq), KI (1.30 g, 7.81 mmol, 1.10 eq) and CPME (15.0 mL). The mixture was stirred at 90° C. for 12 hrs. LCMS (EC15884-12-P1B1) showed compound 1 was consumed completely and desired mass (Rt=1.825 mins) was detected. The reaction mixture was diluted with 100 mL of DCM and filtered. The filtrate was concentrated in vacuum to get a residue. The residue was purified by column chromatography ($SiO_2$, DCM:Methanol=100:1 to 5:1, $R_f$=0.35 (DCM:Methanol=10:1)) to give compound 2 (3.00 g, 4.41 mmol, 62.1% yield, 94.7% purity in LCMS at ELSD) as yellow oil. $^1$H NMR: (400 MHz, $CDCl_3$) δ 5.38 (d, J=4.0 Hz, 1H), 4.66-4.57 (m, 1H), 3.61 (t, J=5.6 Hz, 4H), 2.55-2.46 (m, 6H), 2.35-2.26 (m, 4H), 2.06-1.93 (m, 3H), 1.90-1.79 (m, 4H), 1.72-1.66 (m, 3H), 1.62-1.59 (m, 2H), 1.58-1.40 (m, 10H), 1.36-1.23 (m, 7H), 1.22-1.04 (m, 9H), 1.02 (s, 3H), 1.01-0.95 (m, 2H), 0.92 (d, J=6.4 Hz, 3H), 0.87 (dd, J=6.8, 2.0 Hz, 6H), 0.68 (s, 3H).

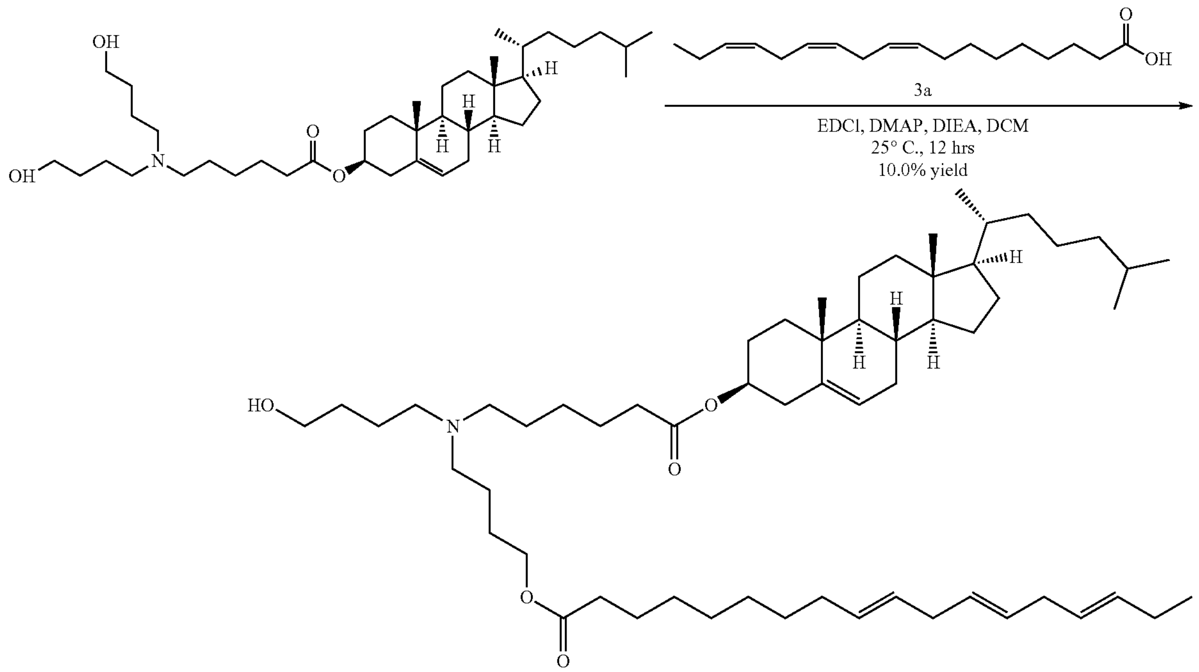

To a solution of compound 2 (2.00 g, 2.94 mmol, 1.00 eq) in DCM (20.0 mL) was added compound 3a (900 mg, 3.24 mmol, 1.10 eq), EDCI (732 mg, 3.82 mmol, 1.30 eq), DIEA (1.90 g, 14.7 mmol, 2.56 mL, 5.00 eq) and DMAP (71.8 mg, 588 mol, 0.20 eq). The mixture was stirred at 25° C. for 12 hrs. LCMS (EC15884-14-P1A2) showed most of compound 2 (Rt=1.814 mins) was consumed and desired mass (Rt=2.052 mins) was detected. The reaction mixture was concentrated in vacuum to get a residue. The residue was purified by prep-HPLC (column: Welch Ultimate XB-$NH_2$ 250*50*10 um; mobile phase: [EtOH+MeOH(4:1, neutral)]; B %:1%, isocratic elution mode) to give Target 12 (504.60 mg, 0.530 mmol, 18.0% yield, 95.0% purity in HPLC at ELSD) as off-white oil. $^1$H NMR: (400 MHz, $CDCl_3$) δ 5.44-5.28 (m, 7H), 4.66-4.57 (m, 1H), 4.07 (t, J=6.4 Hz, 2H), 3.60-3.54 (m, 2H), 2.85-2.75 (m, 4H), 2.55-2.43 (m, 6H), 2.34-2.26 (m, 7H), 2.13-1.94 (m, 7H), 1.90-1.79 (m, 4H), 1.69-1.43 (m, 28H), 1.30-1.20 (m, 4H), 1.19-1.05 (m, 8H), 1.02 (s, 3H), 1.01-0.94 (m, 5H), 0.92 (d, J=6.4 Hz, 3H), 0.87 (d, J=6.4, 1.6 Hz, 6H), 0.68 (s, 3H).

Example 4: Synthetic Scheme for Ionizable Lipid (Compound Target 13)

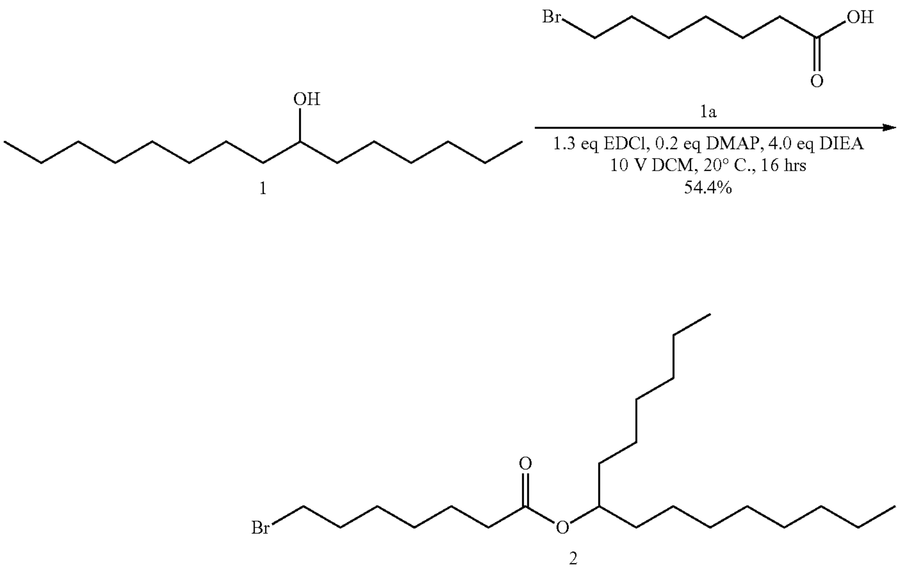

Charge compound 1 (30.0 g, 131 mmol, 1.00 eq) into R1 (1.00 L of three-bottomed flask) at 20° C. Charge DCM (350 mL) into R1 at 20° C. Charge compound 1a (27.4 g, 131 mmol, 1.00 eq) into R1 at 20° C. Charge DIEA (67.9 g, 525 mmol, 91.5 mL, 4.00 eq), DMAP (3.21 g, 26.2 mmol, 0.20 eq), EDCI (32.7 g, 170 mmol, 1.30 eq) into R1 at 20° C. Stir the mixture at 20° C. for 16 hrs. TLC (Petroleum ether:Ethyl acetate=20:1) showed the most of compound 1 ($R_f$=0.60) was consumed and a new main spot ($R_f$=0.50) was detected. Charge the $H_2O$ (300 mL) into R2 (1.00 L barrel) at 20° C. Charge the reaction into $R^2$ at 20° C. Extract the reaction with dichloromethane (300 mL*3) at 20° C. Wash the reaction with saturated brine (200 mL*2) at 20° C. Dry the reaction with anhydrous $Na_2SO_4$ at 20° C. Concentrate organic phase below 40~50° C. to give a residue. The residue was purified by column chromatography ($SiO_2$, Petroleum ether:Ethyl acetate=50:1 to 10:1, $R_f$=0.50). Compound 2 (30.0 g, 71.5 mmol, 54.4% yield) was obtained as a colorless liquid.

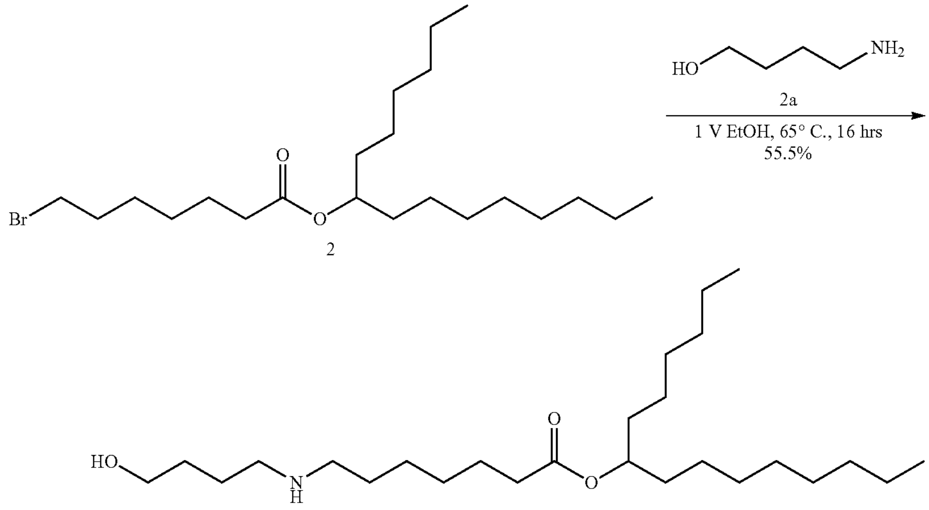

3

Charge compound 2 (30.0 g, 71.5 mmol, 1.00 eq) into R1 (250 mL of three-necked bottomed flask) at 20° C. Charge EtOH (30.0 mL) into R1 at 20° C. Charge compound 2a (191 g, 2.15 mol, 199 mL, 30.0 eq) into R1 at 20° C. Heat the mixture to 65° C. The mixture was stirred at 65° C. for 16 hrs. TLC (Dichloromethane:Methanol=5:1) showed the most of compound 2 ($R_f$=0.95) was consumed and a new main spot ($R_f$=0.20) was detected. Charge the $H_2O$ (100 mL) into R2 (250 mL barrel) at 20° C. Charge the reaction into R2 at 20° C. Extract the reaction with ethyl acetate (60.0 mL*3) at 20° C. Wash the reaction with saturated brine (50.0 mL*3) at 20° C. Dry the reaction with anhydrous $Na_2SO_4$ at 20° C. Concentrate organic phase below 40-50° C. to give a residue. The residue was purified by column chromatography ($SiO_2$, Dichloromethane:Methanol=50:1 to 10:1, $R_f$=0.20). Compound 3 (17.0 g, 39.7 mmol, 55.5% yield) was obtained as a light yellow oil

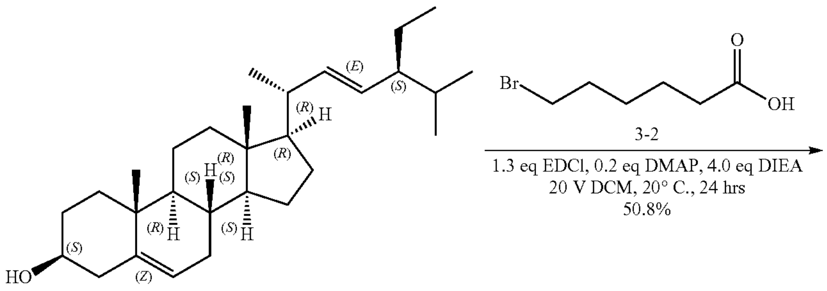

3-1

-continued

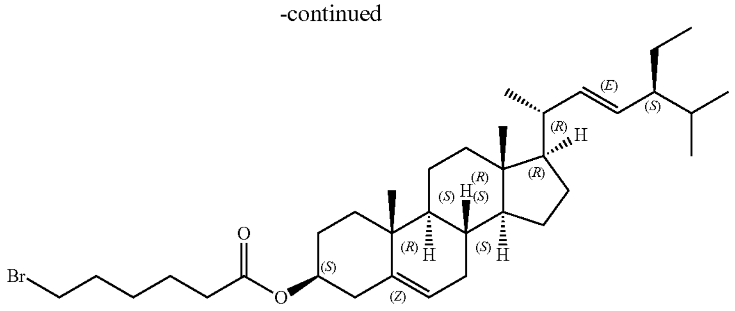

3-3

Charge compound 3-1 (5.00 g, 12.1 mmol, 1.10 eq) into R1 (2.00 L of three-bottomed flask) at 20° C. Charge DCM (100 mL) into R1 at 20° C. Charge compound 3-2 (2.15 g, 11.0 mmol, 1.00 eq) into R1 at 20° C. Charge EDCI (2.74 g, 14.3 mmol, 1.30 eq), DIEA (5.69 g, 44.0 mmol, 7.67 mL, 4.00 eq), DMAP (269 mg, 2.20 mmol, 0.20 eq) in R1 at 20° C. Stir the mixture at 20° C. for 20 hrs. TLC (Petroleum ether:Ethyl acetate=5:1) showed the most of compound 3-1 ($R_f$=0.30) was consumed and a new main spot ($R_f$=0.60) was detected. Charge the $H_2O$ (200 mL) into R2 (1.00 L barrel) at 20° C. Charge the reaction into R2 at 20° C. Extract the reaction with dichloromethane (200 mL*3) at 20° C. Dry the reaction with anhydrous $Na_2SO_4$ at 20° C. Concentrate organic phase below 40~50° C. to give a residue. The residue was purified by column chromatography ($SiO_2$, Petroleum ether:Ethyl acetate=20:1 to 1:3, $R_f$=0.60). Compound 3-3 (3.30 g, 5.60 mmol, 50.8% yield) was obtained as a white solid.

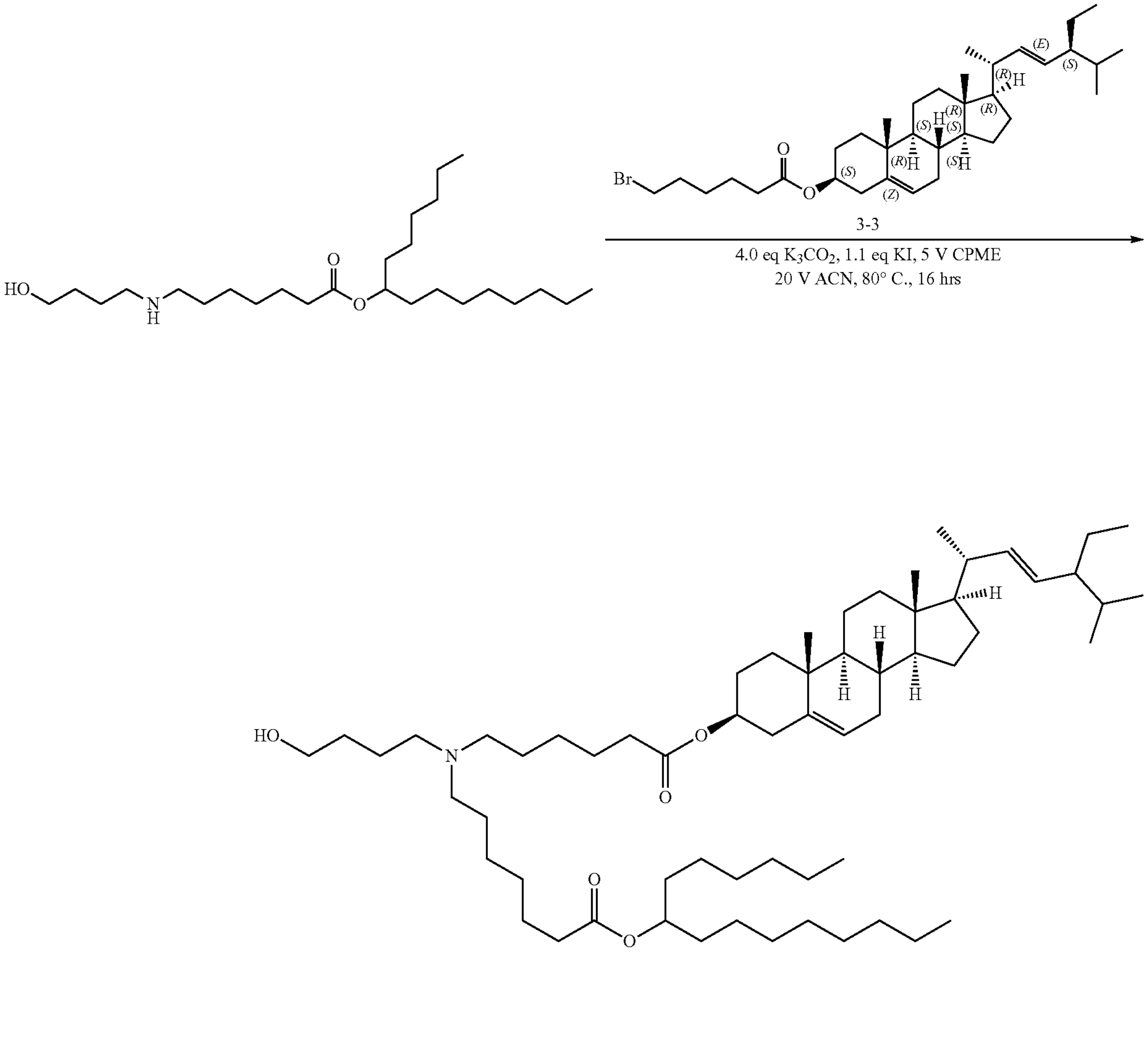

Charge compound 3-3 (1.50 g, 2.54 mmol, 1.00 eq) in R1 (500 mL three neck battle) at 20° C. Charge ACN (33.0 mL) into R1 at 20° C. Charge compound 3 (1.09 g, 2.54 mmol, 1.00 eq) into R1 at 20° C. Charge $K_2CO_3$ (1.41 g, 10.1 mmol, 4 eq), KI (464 mg, 2.80 mmol, 1.10 eq), CMPE (7.05 g, 70.4 mmol, 8.20 mL, 27.6 eq) in R1 at 20° C. Heat the mixture to 90° C. Stir the mixture at 90° C. for 16 hrs. TLC (Dichloromethane:Methanol=5:1) showed the most of reactant 1 ($R_f$=0.20) was consumed and a new main spot ($R_f$=0.50) was detected. Charge the $H_2O$ (100 mL) into R2 (1.00 L barrel) at 20° C. Charge the reaction into R2 at 20° C. Extract the reaction with Dichloromethane (100 mL*3) at 20° C. Dry the reaction with anhydrous $Na_2SO_4$ at 20° C. Concentrate organic phase below 40~50° C. to give a residue. The residue was purified by column chromatography ($SiO_2$, Dichloromethane:Methanol=50:1 to 10:1, $R_f$=0.50). Target 13 (1.04 g, 1.11 mmol, 43.5% yield) was obtained as a colorless oil.

Example 5: Lipid Nanoparticles for Nucleic Acid Delivery

Lipid nanoparticle (LNP) plays a key role in effectively protecting and delivering nucleic acid to cells for the application of prevention and therapeutics. Despite promising data from ongoing clinical trials, the clinical use of gene medicine requires the discovery and development of more efficient delivery systems. Described herein are nanoparticles for gene and drug delivery applications.

EGFP mRNA, Self-Amplifying mRNA, SARS-CoV-2 mRNA Lipid Nanoparticles (LNPs).

Lipid nanoparticle (LNP) formulations were prepared herein using either Target 1 (ARV-T1), Target 11 (ARV-T11), Target 12 (ARV-T12), Target 13 (ARV-T13) or commercially available SM-102 lipid for comparison. LNP formulations were prepared using lipids dissolved in ethanol at molar ratios of 50:10:38.5:1.5 (ionizable lipid:DSPC:cholesterol:PEG-lipid). The lipid mixture was combined with 100 mM sodium citrate buffer (pH 4.0) containing mRNA at a volume ratio of 3:1 (aqueous:ethanol) using a NanoAssemblr Ignite. Formulations were dialyzed against 10 mM Tris (pH 7.4) with 8% sucrose in Slide-A-Lyzer dialysis cassettes for at least 16 h and concentrated using Amicon ultra-centrifugal filters and then passed through a 0.22 μm filter and stored at 4° C. or −20° C. until use. The size, PDI, and charge were measured by dynamic light scattering while mRNA encapsulation efficiency was measured by Ribogreen assay spectrometrically using λex=480 nm and λem=535 nm.

Figure 3A:
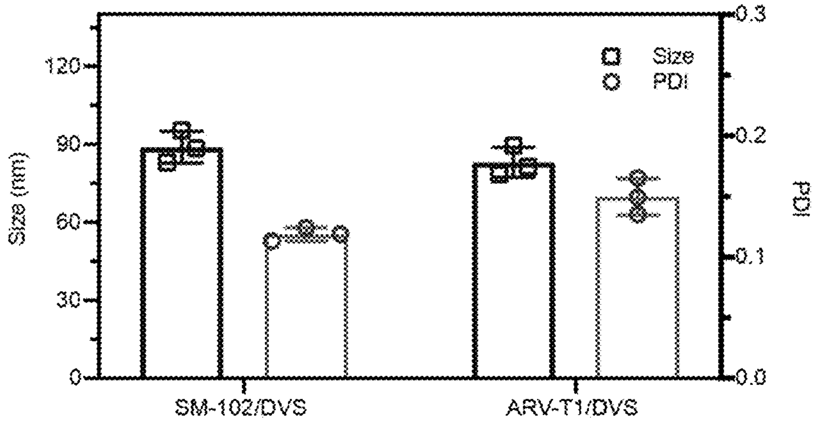
FIGS. 3A-3B show the characterization of SARS-CoV-2 mRNA lipid nanoparticles (LNPs). SM-102/DVS is formulated using commercially available SM-102 lipid, and ARV-T1 is formulated using Target 1 lipid (DVS: delta variant spike protein). Particle diameter and polydispersity index (PDI) of LNPs (3A). Surface charge (zeta potential) and mRNA encapsulation efficiency of SM-102 and ARV-T1 LNPs (3B).

FIG. 3A shows the particle diameter and polydispersity index (PDI) of the LNPs.

Figure 3B:
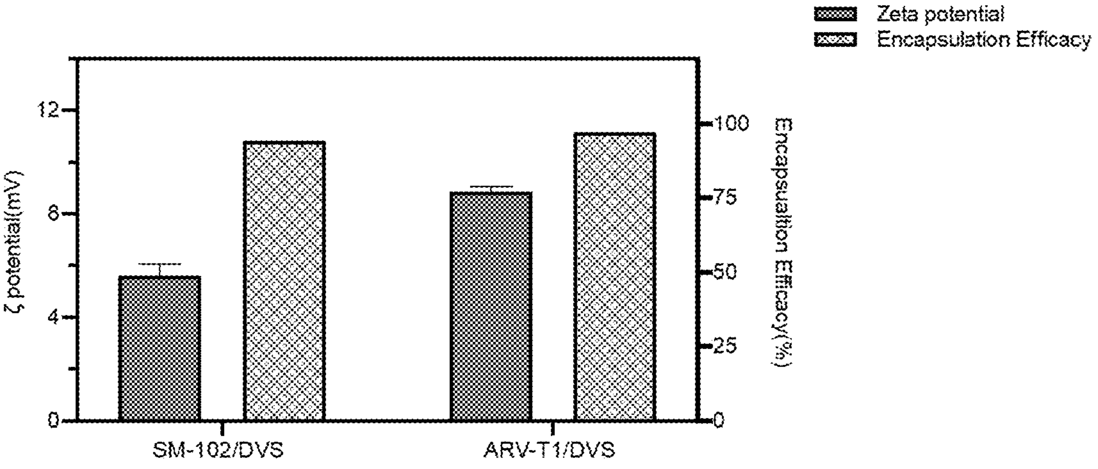

FIG. 3B shows the surface charge (zeta potential) and mRNA encapsulation efficiency of SM-102 and ARV-T1 LNPs.

Plasmid DNA Lipid Nanoparticles (LNPs).

Lipid nanoparticle (LNP) formulations were prepared herein using either Target 1 (ARV-T1), Target 11 (ARV-T11), Target 12 (ARV-T12), or Target 13 (ARV-T13) lipid. LNP formulations were prepared using lipids dissolved in ethanol with supplemented DOTAP (10% mole ratio) lipid. The lipid mixture was combined with 100 mM sodium citrate buffer (pH 4.0) containing mRNA at a volume ratio of 3:1 (aqueous:ethanol) using a NanoAssemblr Ignite. Formulations were dialyzed against 10 mM Tris (pH 7.4) with 8% sucrose in Slide-A-Lyzer dialysis cassettes for at least 16 h and concentrated using Amicon ultra-centrifugal filters and then passed through a 0.22 μm filter and stored at 4° C. or −20° C. until use. The size, PDI, and charge were measured by dynamic light scattering while mRNA encapsulation efficiency was measured by Ribogreen assay spectrometrically using λex=480 nm and λem=535 nm.

FIG. 3A shows the particle diameter and polydispersity index (PDI) of the LNPs.

FIG. 3B shows the surface charge (zeta potential) and mRNA encapsulation efficiency of SM-102 and ARV-T1 LNPs.

Figure 4:
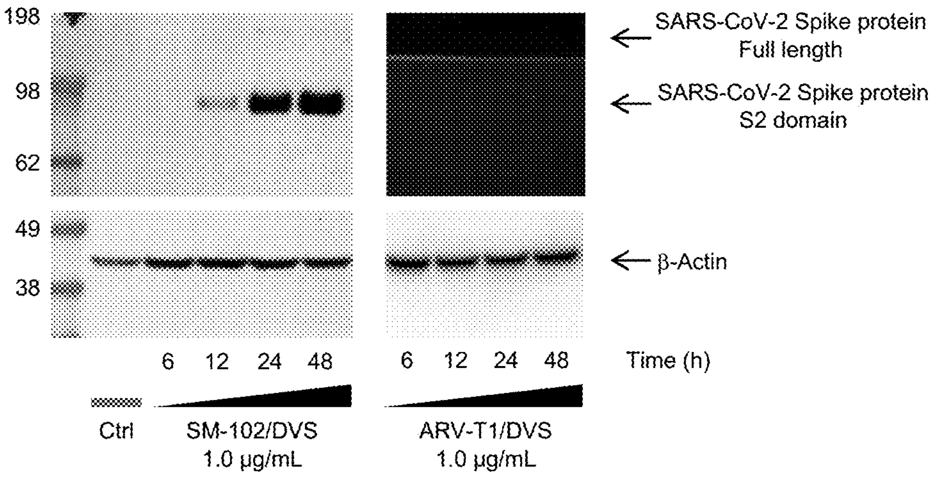
FIG. 4 shows in vitro expression of spike glycoprotein after transfecting cells with 1.0 μg DVS mRNA at 1.0 μg/mL mRNA over time in 293T cells.

In Vitro Studies 293T cells were transfected with an mRNA encoding a SARS-CoV-2 spike protein. FIG. 4 shows the in vitro expression of the spike protein after transfecting cells with 0.5 and 1.0 μg/mL mRNA over time.

Figure 5A:
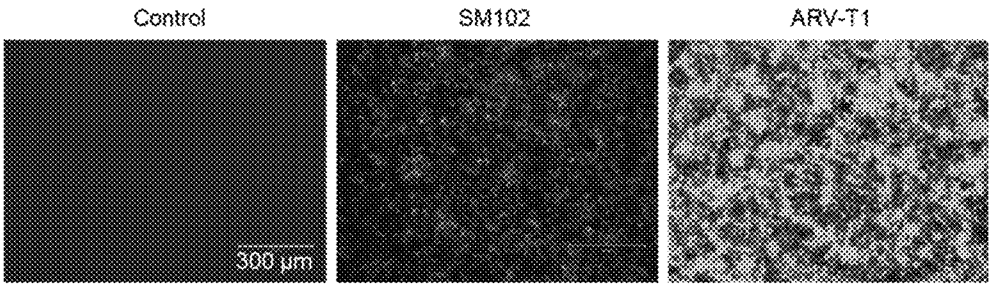
FIGS. 5A-5B show in vitro transfection efficiency of 1 μg GFP mRNA (1 μg/mL) using LNP deliver into BHK cells after 24 hours. (5A) Representative fluorescent images of BHK cells after transfection. (5B) Transfection efficacy analysis of GFP expression using flow cytometer. MFI denotes Mean Fluorescent Intensity.
Figure 5B:
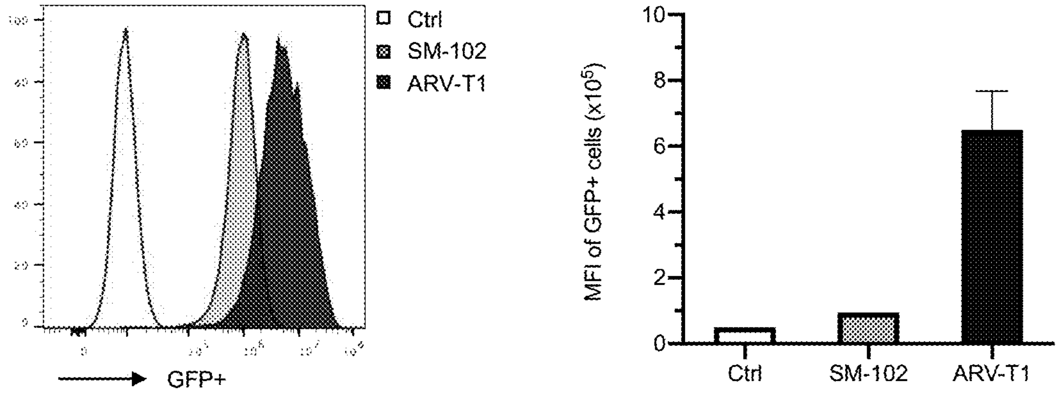

The transfection efficiency was studied by delivering GFP mRNA (1 μg/mL) using LNP deliver into BHK cells. The transfection efficiency was determined after 24 hours by imaging the BHK cells after transfection and analyzing the GFP expression using flow cytometry. The results of the study are shown in FIGS. 5A and 5B.

In Vivo Studies

Figure 6A:
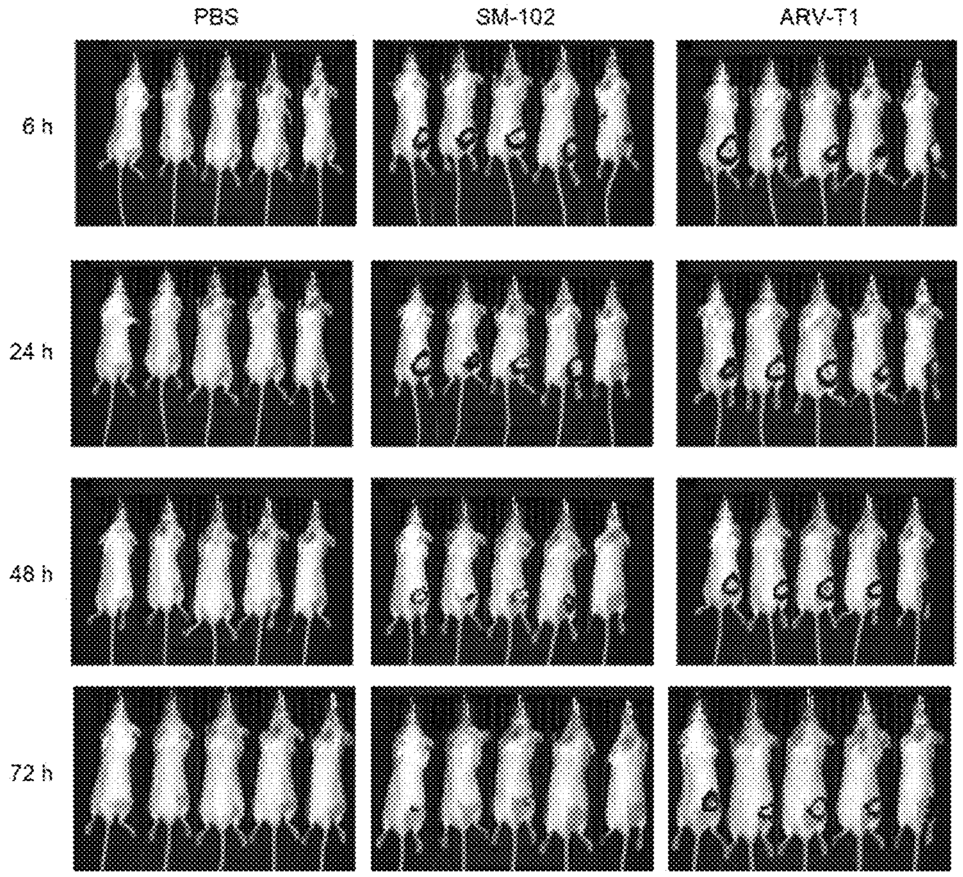
FIGS. 6A-6B show in vivo transfection efficiency of luciferase-expressing mRNA. LNPs were formulated with indicated ionizable lipids and 1 μg of formulated luciferase-expressing mRNA were injected intramuscularly. After administration, (6A) the representative imaging and (6B) the quantitative of the luciferase expression was determined by whole body bioluminescence imaging using an IVIS Spectrum in vivo imaging system at 6, 24, 48, and 72 hours, respectively.
Figure 6B:
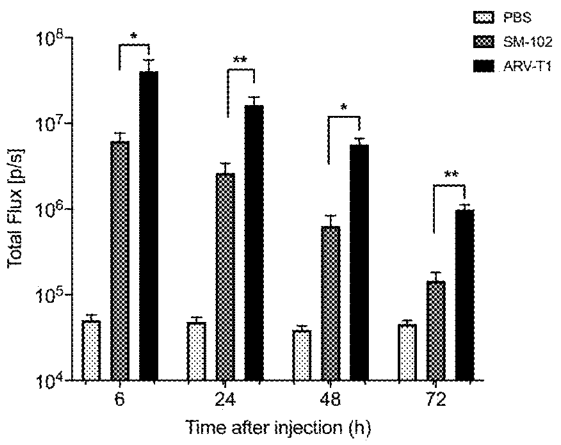

LNPs formulated with indicated ionizable lipids and 1 μg of Luciferase-expressing mRNA were injected intramuscularly. After administration, the luciferase expression was determined by whole body bioluminescence imaging using an IVIS Spectrum in vivo imaging system at 6, 24, 48, and 72 hours, respectively. Results of the in vivo transfection efficiency study of luciferase-expressing mRNA is shown in FIG. 6.

Figure 7A:
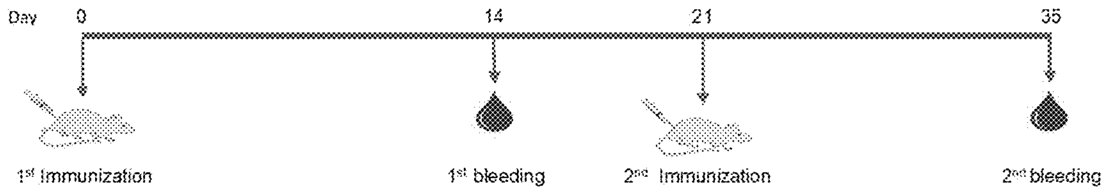
FIGS. 7A-7E show efficient elicited immunity in vivo. (7A) Experimental setup. mRNA encode full-length spike glycoprotein of SARS-CoV-2 (Delta variant) were formulated using Target 1 (ARV-T1) lipid. Commercially available lipid SM-102 was used as comparison. 1 μg of vaccine was injected intramuscularly as scheduled. (7B-7C) Spike-specific total IgG were evaluated on day 14 (7B) and day 35 (7C) after the first immunization. (7D) Neutralizing antibodies in the serum are evaluated by pseudotyped viruses. (7E) Antigen-specific T cell responses were evaluated by Elispot. Data were presented as Mean±SD. Statistical comparisons were analyzed using by one-way ANOVA with Tukey's multiple comparison test. *$p<0.05$, $p<0.01$, *$p<0.001$.
Figure 7B:
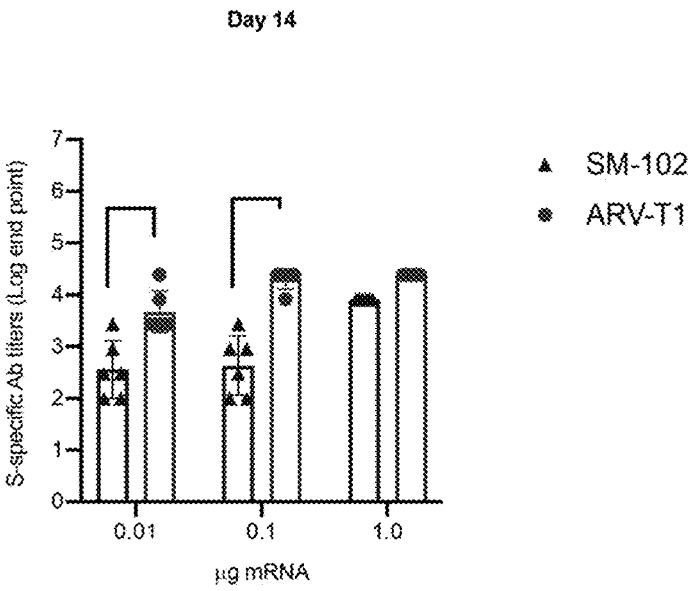
Figure 7C:
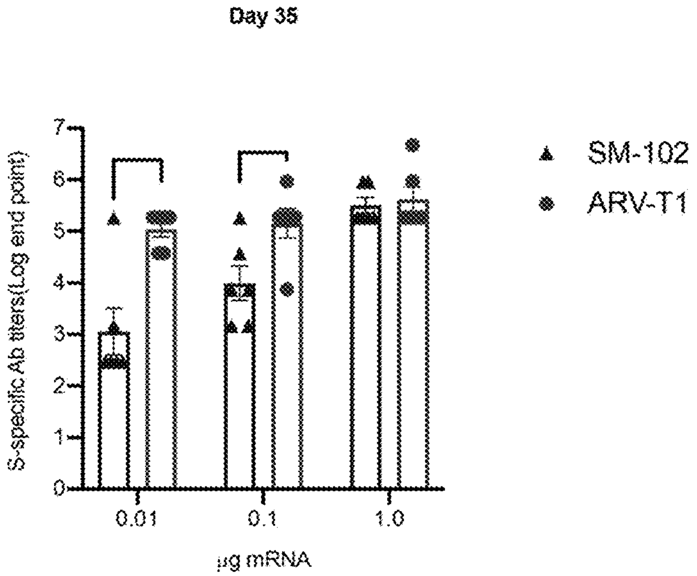
Figure 7D:
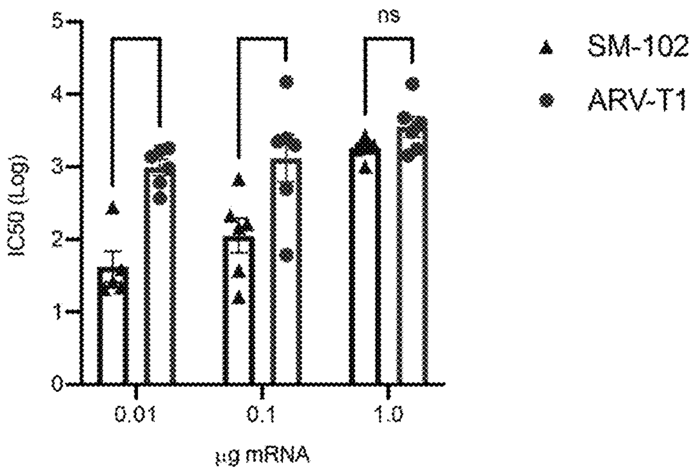
Figure 7E:
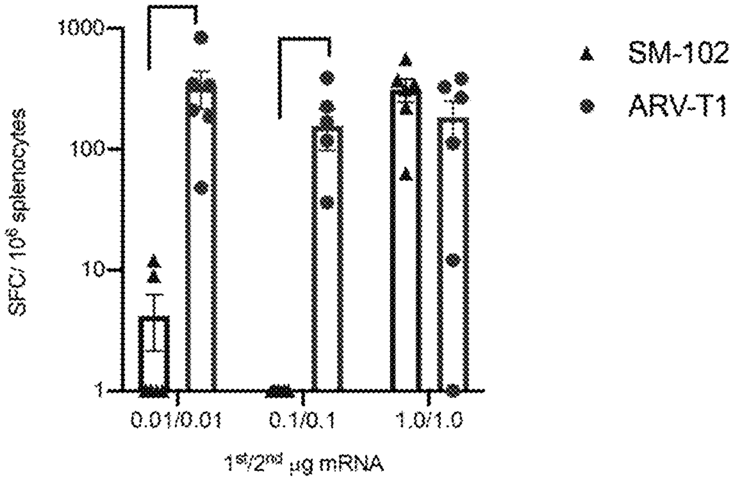
Figure 8A:
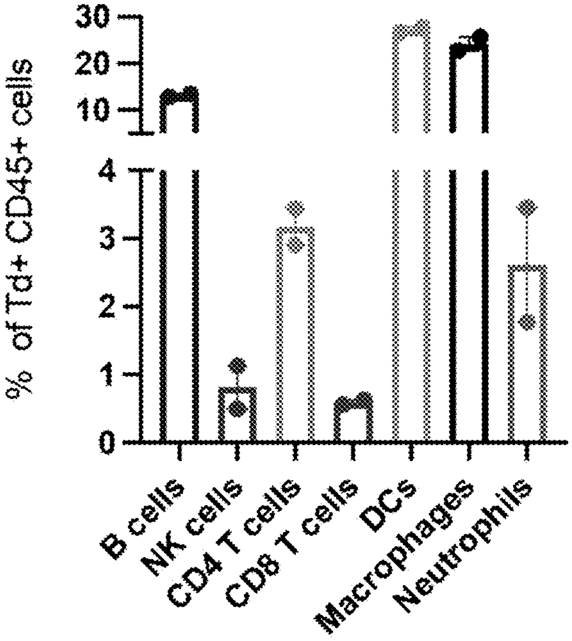
FIGS. 8A-8B show single-cell analysis of spleen cells from Ai14/Cre tdTomato reporter mice indicating that ARV-T1-based LNP can deliver mRNA to a variety of cells in vivo. A 10 μg of Cre mRNA formulated with ARV-T1 lipid was administered intravenously to A114 mouse. At 48 hours after injection, (8A) the percentage of $CD45^+$ splenic cells that are $tdTomato^+$ and (8B) the distribution of $CD45^+$ $tdTomato^+$splenic cells are determined by Flow Cytometer.
Figure 8B:
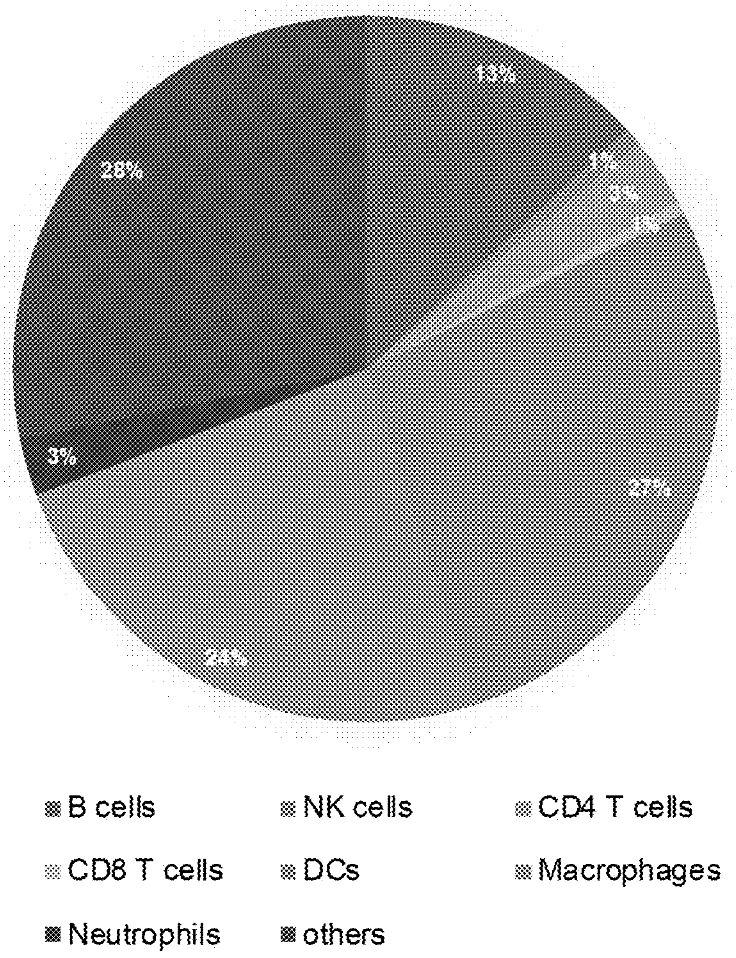
Figure 9A:
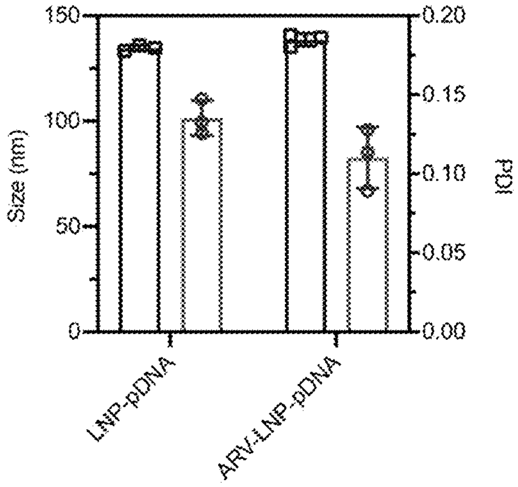
Figure 10E:
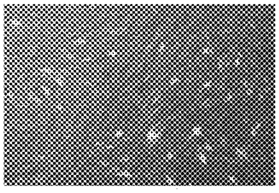
Figure 10F:
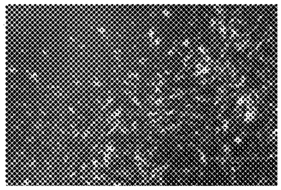
Figure 11:
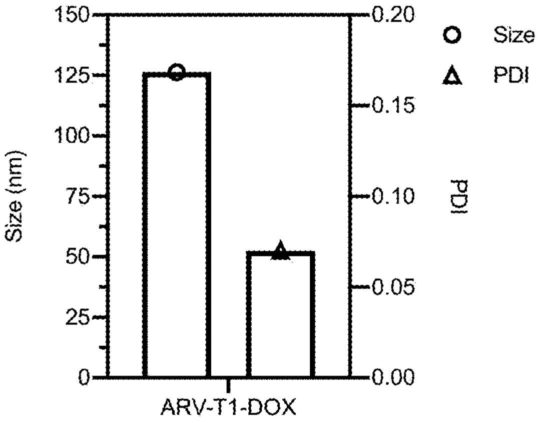
FIG. 11 is a graph of size and PDI characterization of a formulation of small molecular drug doxorubicin (DOX) using ARV-T1 LNP.
Figure 12:
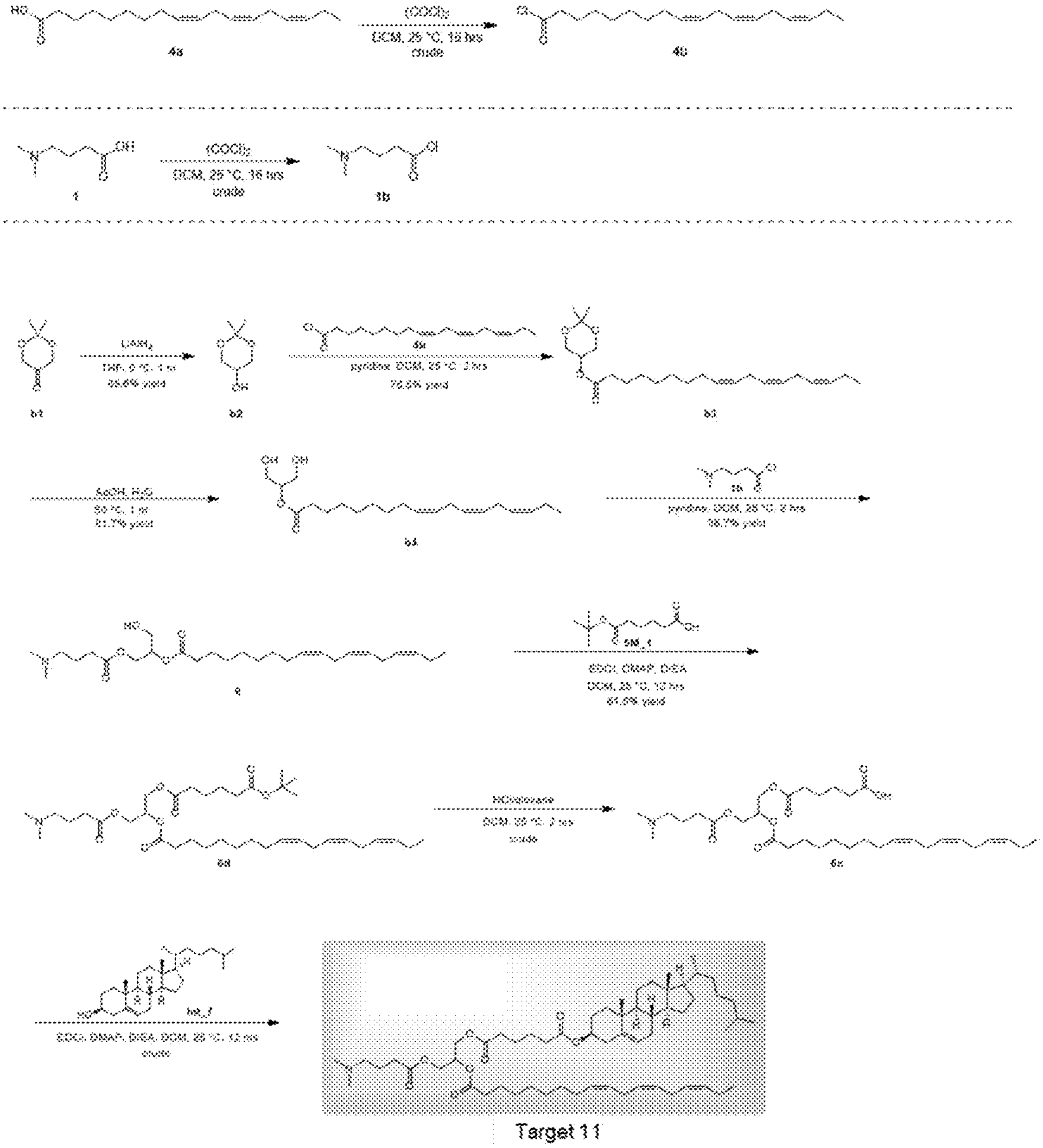
FIG. 12 illustrates a synthetic route for compound Target 11.
Figure 13A:
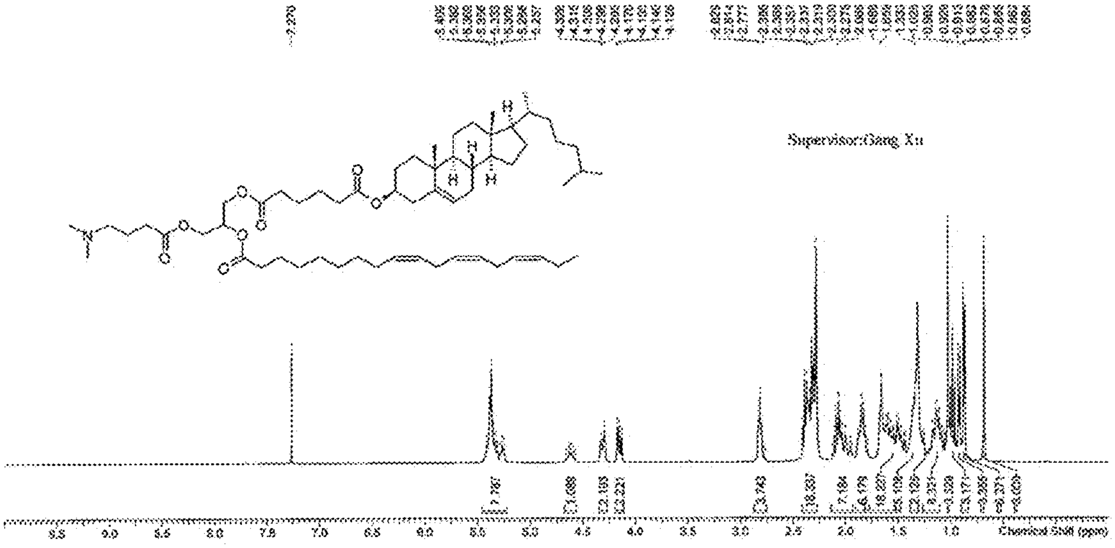
FIGS. 13A-13B show $^1$H NMR spectra (13A), mass spectra (13B) for compound Target 11.
Figure 13B:
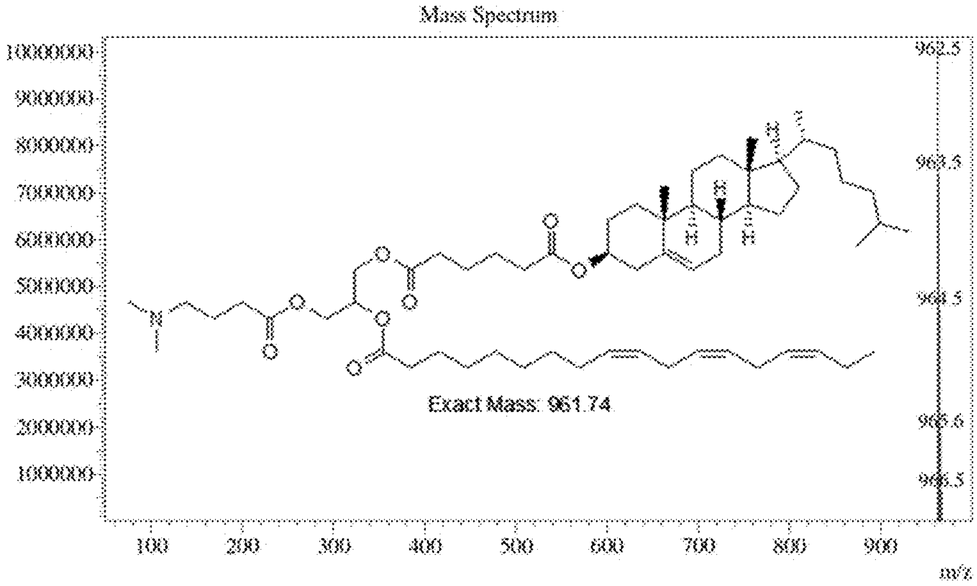
Figure 14A:
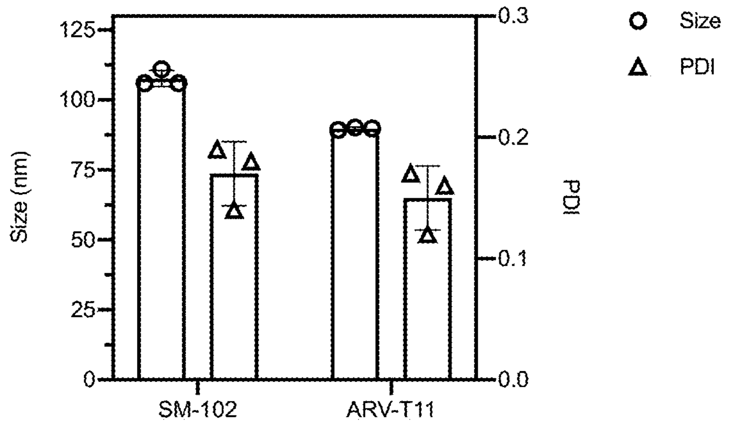
FIGS. 14A-14E show formulation of mRNA-LNP using ARV-T11 lipid and in vitro transfection efficiency of 1 μg GFP mRNA (1 μg/mL) using ARV-T11 LNP deliver into 293T cells after 24 hours. (14A) is a graph of size and PDI characterization of GFP mRNA ARV-T11 LNPs. (14B-14D) are representative fluorescent images of 293T cells after transfection (14B) control, (14C) SM-102, and (14D) ARV-T11. (14E) is an graph of the transfection efficacy analysis of GFP expression using flow cytometer.
Figure 14B:
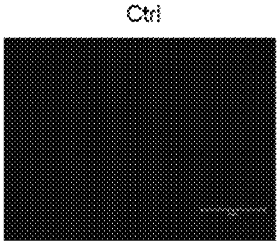
Figure 14C:
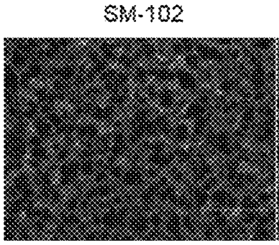
Figure 14D:
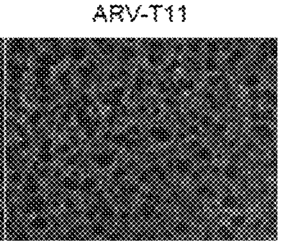
Figure 14E:
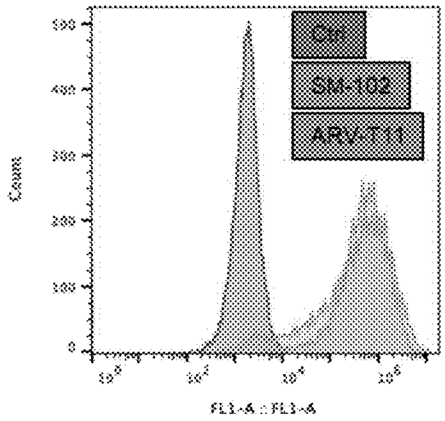
Figure 15:
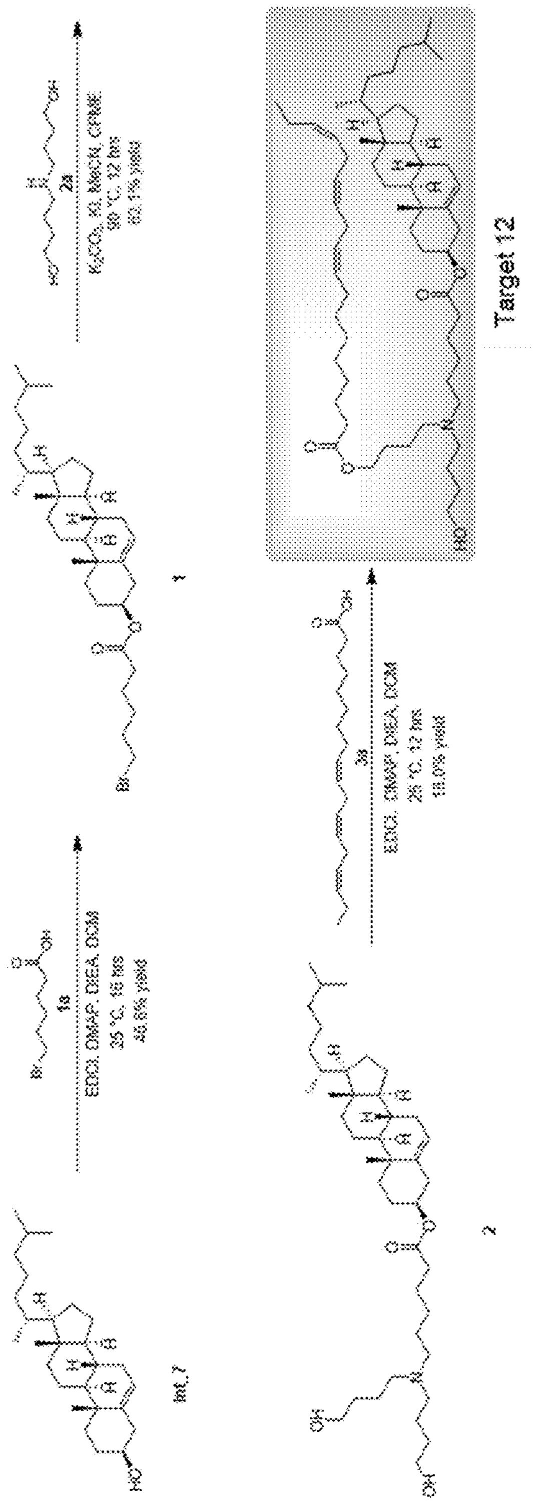
FIG. 15 illustrates a synthetic route for compound Target 12.
Figure 16A:
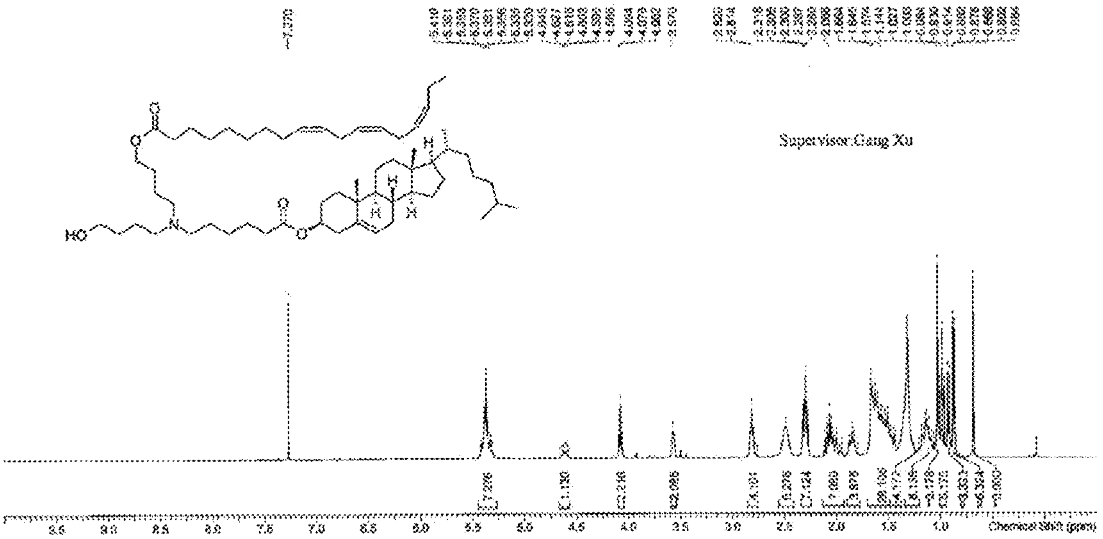
Figure 16B:
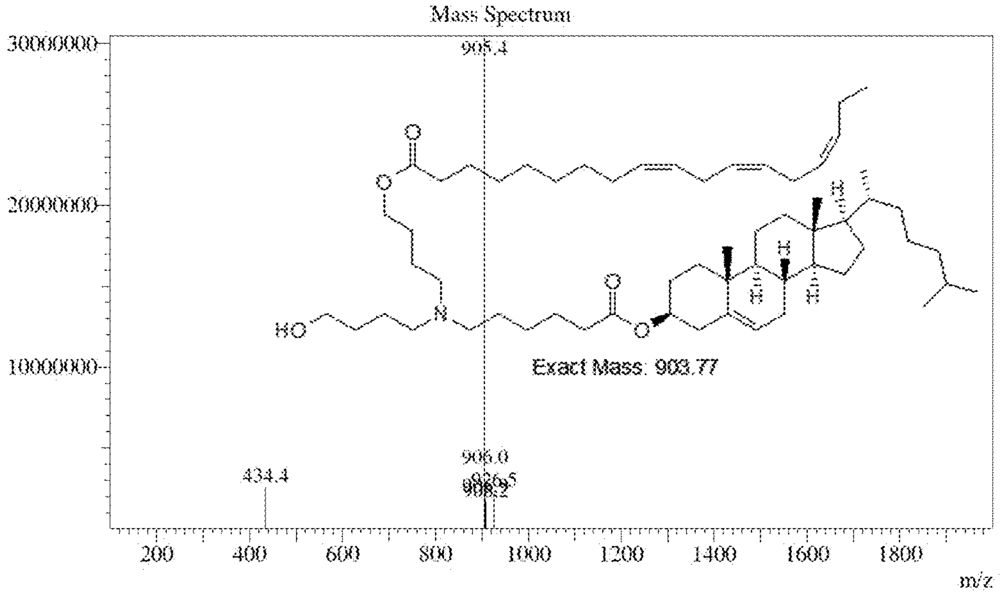
Figure 17E:
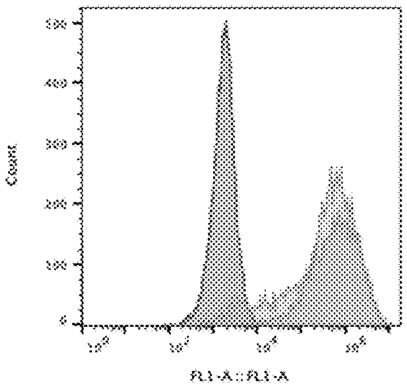
Figure 18:
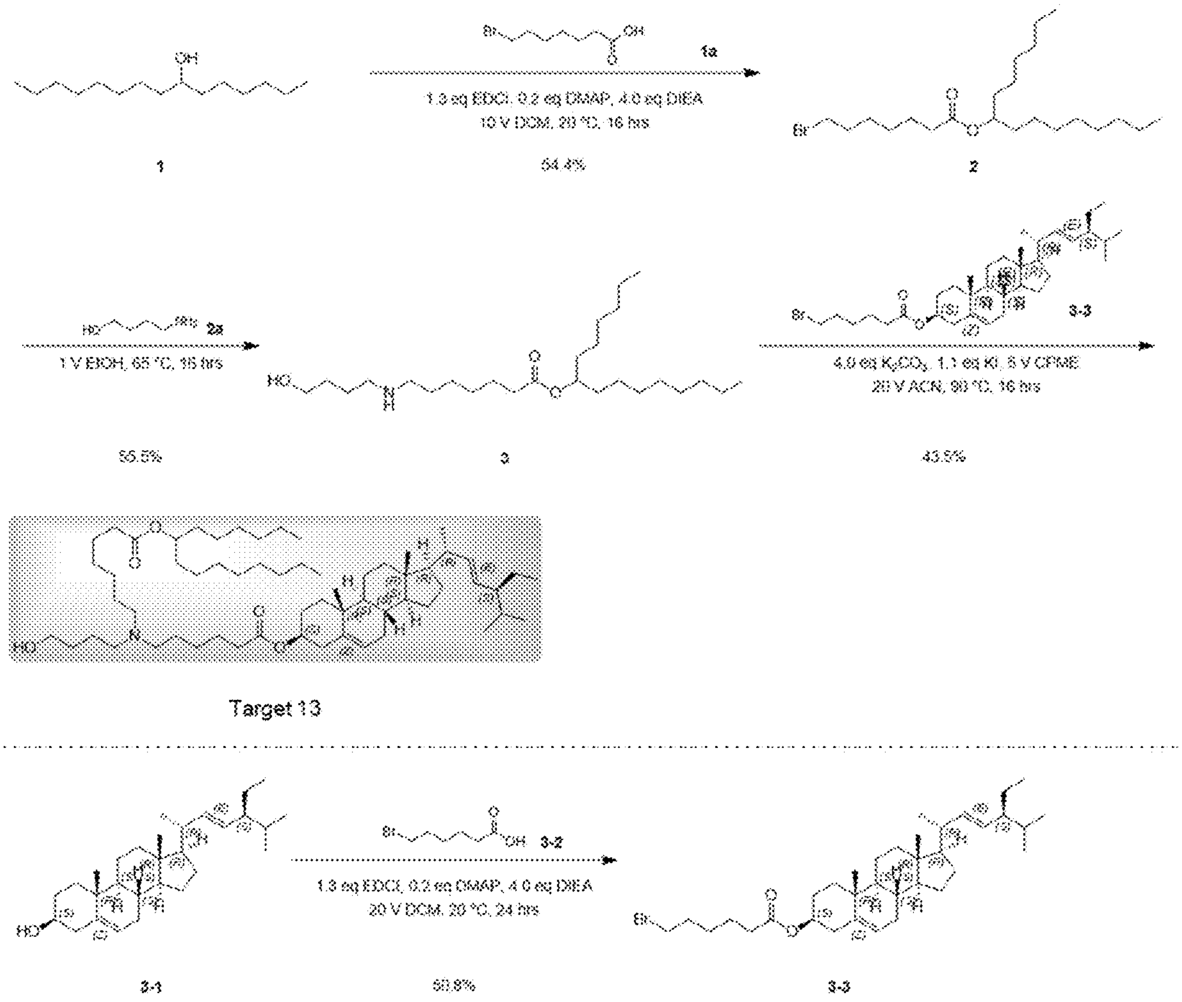
FIG. 18 illustrates a synthetic route for compound Target 13.
Figure 19A:
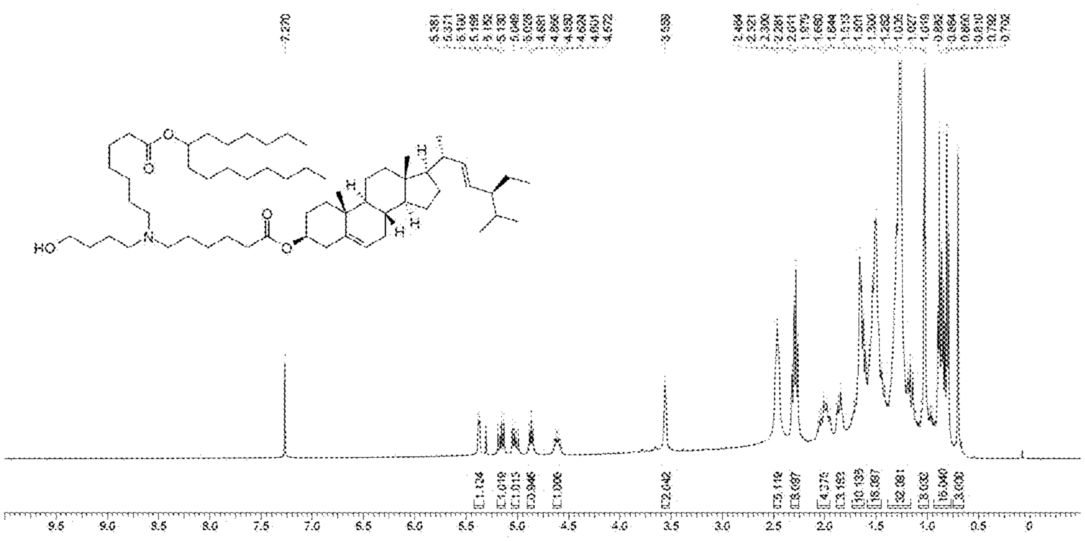
FIGS. 19A-19C show $^1$H NMR spectra (19A), mass spectra (19B), and HPLC spectra (19C) for compound Target 13.
Figure 19B:
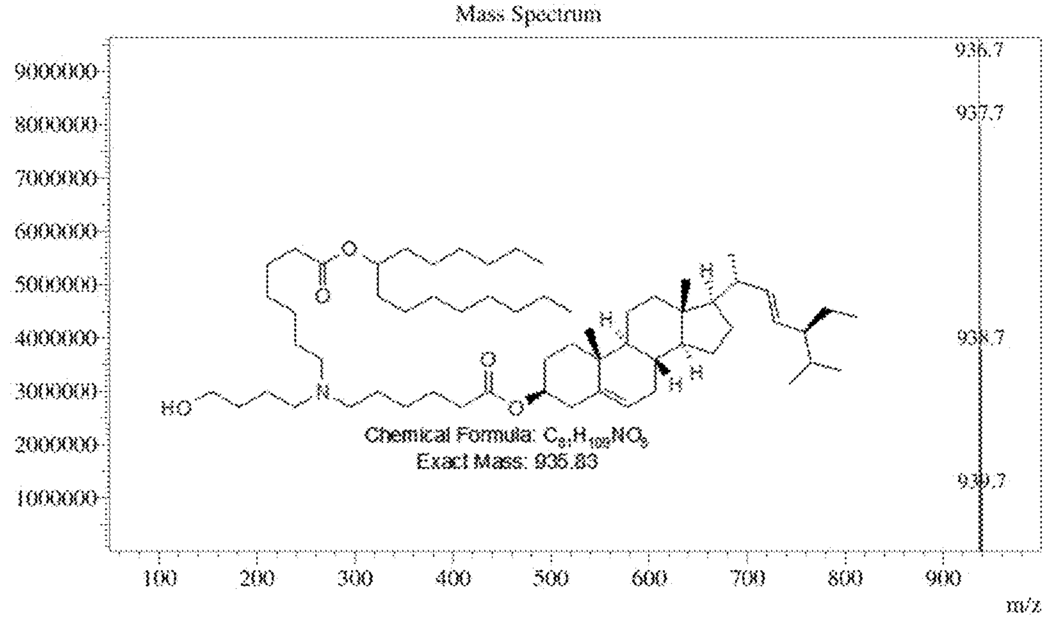
Figure 19C:
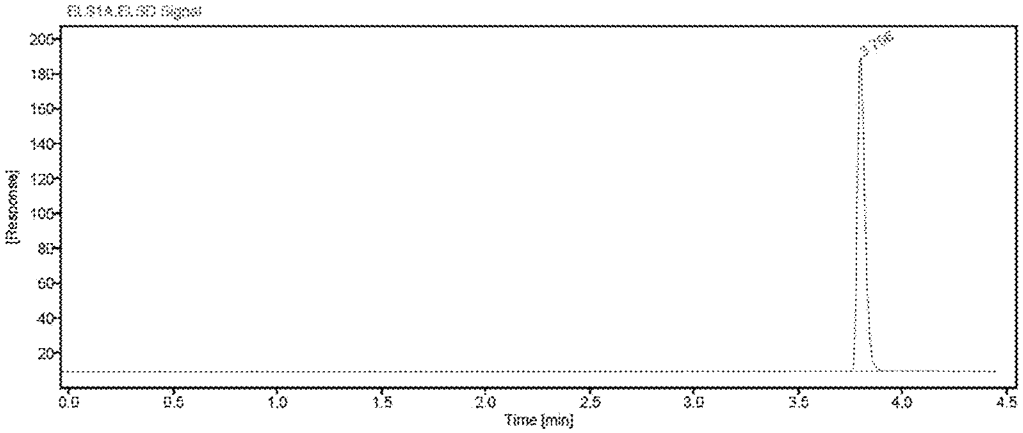
Figure 20A:
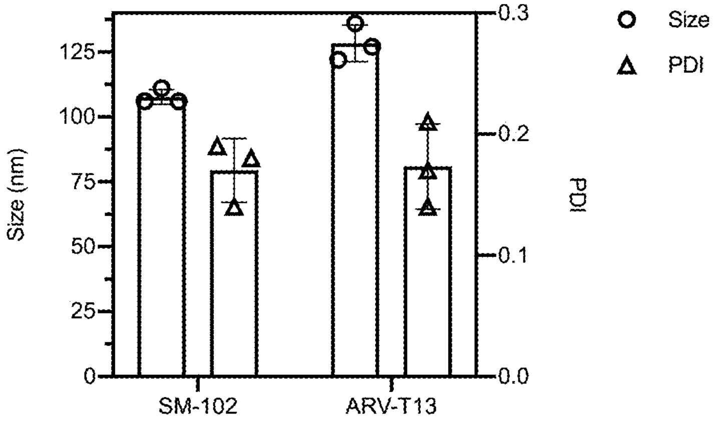
FIGS. 20A-20E show formulation of mRNA-LNP using ARV-T13 lipid and in vitro transfection efficiency of 1 μg GFP mRNA (1 μg/mL) using ARV-T13 LNP deliver into 293T cells after 24 hours. (20A) is a graph of size and PDI characterization of GFP mRNA ARV-T13 LNPs. (20B-20D) are representative fluorescent images of 293T cells after transfection (20B) control, (20C) SM-102, and (20D) ARV-T12. (20E) is a graph of the transfection efficacy analysis of GFP expression using flow cytometer.
Figures 20B, 20C, 20D:
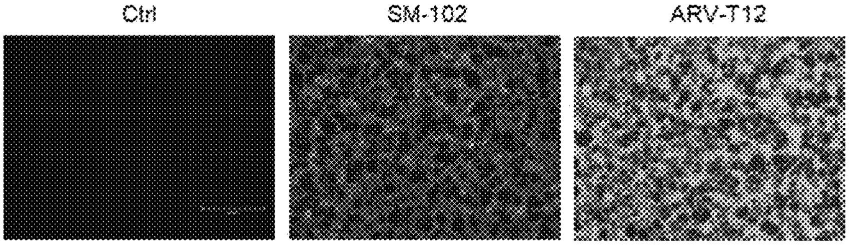
Figure 20E:
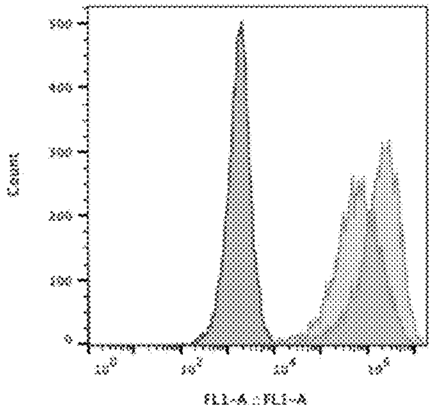

1 μg of a vaccine formulated with Target 1 lipid (ARV-T1) and mRNA encoding full-length spike glycoprotein of SARS-CoV-2 (Delta variant) was injected intramuscularly as scheduled. A formulation comprising commercially available lipid SM-102 and mRNA encoding full-length spike glycoprotein of SARS-CoV-2 (Delta variant) was prepared and used as comparison. Total Spike-specific total IgG were evaluated on day 14 and 35 after the first immunization results are shown in FIGS. 7B and 7C. Neutralizing antibodies in the serum are evaluated by pseudotyped viruses results are shown in FIG. 7D. Antigen-specific T cell responses were evaluated by Elispot results are shown in FIG. 7E. Data was presented as Mean±SD. Statistical comparisons were analyzed using by one-way ANOVA with Tukey's multiple comparison test. *$p<0.05$, **$p<0.01$. The results demonstrate efficient elicited immunity in vivo.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A compound defined by the structure below

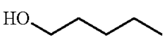

-continued

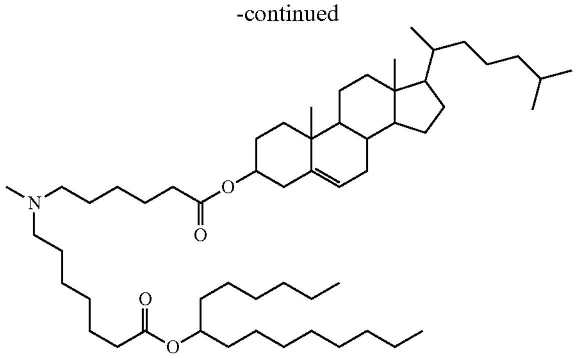

or pharmaceutically acceptable salts thereof.

2. A composition comprising the compound of claim 1 and an active agent, wherein the active agent is a diagnostic, prophylactic, or therapeutic agent.

3. The composition of claim 2, wherein the active agent comprises a nucleic acid.

4. The composition of claim 3, wherein the nucleic acid comprises double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA), self-amplify mRNA (saRNA), guide RNA (gRNA), cRNA, or any combination thereof.

5. The composition of claim 3, wherein the nucleic acid comprises mRNA that encodes at least one Metapneumovirus (hMPV) antigenic polypeptide, parainfluenza viruses (hPIV) types 1, 2, and 3 (hPIV1, hPIV2 and hPIV3, respectively) antigenic polypeptide, respiratory syncytial virus (RSV) antigenic polypeptide, measles virus (MeV) antigenic polypeptide, varicella-zoster antigenic polypeptide, influenza virus antigenic polypeptide, herpes simplex virus 1 (HSV1) antigenic polypeptide, herpes simplex virus 2 (HSV2) antigenic polypeptide, poxvirus (e.g., smallpox, monkeypox) antigenic polypeptide, African swine fever virus antigenic polypeptide, cytomegalovirus antigenic polypeptide, Epstein-Barr virus antigenic polypeptide, rotavirus antigenic polypeptide, rhinovirus antigenic polypeptide, adenovirus antigenic polypeptide, papillomavirus antigenic polypeptide, poliovirus antigenic polypeptide, mumps antigenic polypeptide, rabies antigenic polypeptide, rubella antigenic polypeptide, coxsackieviruses antigenic polypeptide, equine encephalitis antigenic polypeptide, Japanese encephalitis antigenic polypeptide, yellow fever antigenic polypeptide, Rift Valley fever antigenic polypeptide, hepatitis A, B, C, D, and E virus antigenic polypeptide, or coronaviruses (e.g., MERS-CoV, SARS-CoV, SARS-CoV2, HCoV-OC43, HCoV-229E, HCoV-NL63, HCoV-NL, HCoV-NH, HCoV-HKU1) antigenic polypeptide, or any combination thereof.

6. The composition of claim 3, wherein the nucleic acid comprises mRNA that encodes a tumor antigen, a cytokine, a monoclonal antibody, an antibody fragment, or any combination thereof.

7. The composition of claim 2, wherein the composition comprises a lipid nanoparticle dispersion, a liposomal formulation, a lipid emulsion, or any combination thereof.

8. The composition of claim 7, wherein the composition comprises a lipid nanoparticle dispersion comprising a population of lipid nanoparticles dispersed in a carrier, wherein the lipid nanoparticles comprise 20% to 80% of the compound of claims 1, 0% to 5% pegylated lipids; 0% to 40% helper lipids; 0% to 80% sterol; and the active agent encapsulated in the nanoparticles.

9. The composition of claim 8, wherein the active agent comprises a nucleic acid.

10. The composition of claim 9, wherein the nucleic acid comprises double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA), self-amplify mRNA (saRNA), guide RNA (gRNA), cRNA, or any combination thereof.

11. The composition of claim 9, wherein the nucleic acid comprises mRNA that encodes at least one Metapneumovirus (hMPV) antigenic polypeptide, parainfluenza viruses (hPIV) types 1, 2, and 3 (hPIV1, hPIV2 and hPIV3, respectively) antigenic polypeptide, respiratory syncytial virus (RSV) antigenic polypeptide, measles virus (MeV) antigenic polypeptide, varicella-zoster antigenic polypeptide, influenza virus antigenic polypeptide, herpes simplex virus 1 (HSV1) antigenic polypeptide, herpes simplex virus 2 (HSV2) antigenic polypeptide, poxvirus (e.g., smallpox, monkeypox) antigenic polypeptide, African swine fever virus antigenic polypeptide, cytomegalovirus antigenic polypeptide, Epstein-Barr virus antigenic polypeptide, rotavirus antigenic polypeptide, rhinovirus antigenic polypeptide, adenovirus antigenic polypeptide, papillomavirus antigenic polypeptide, poliovirus antigenic polypeptide, mumps antigenic polypeptide, rabies antigenic polypeptide, rubella antigenic polypeptide, coxsackieviruses antigenic polypeptide, equine encephalitis antigenic polypeptide, Japanese encephalitis antigenic polypeptide, yellow fever antigenic polypeptide, Rift Valley fever antigenic polypeptide, hepatitis A, B, C, D, and E virus antigenic polypeptide, or coronaviruses (e.g., MERS-CoV, SARS-CoV, SARS-CoV2, HCoV-OC43, HCoV-229E, HCoV-NL63, HCoV-NL, HCoV-NH, HCoV-HKU1) antigenic polypeptide, or any combination thereof.

* * * * *